United States Patent [19]
Bock et al.

[11] Patent Number: 5,665,719
[45] Date of Patent: Sep. 9, 1997

[54] BENZOXAZINONE AND BENZOPYRIMIDINONE PIPERIDINYL TOCOLYTIC OXYTOCIN RECEPTOR ANTAGONISTS

[75] Inventors: Mark G. Bock, Hatfield; Ben E. Evans, Lansdale; Peter D. Williams, Harleysville; Roger M. Freidinger, Lansdale; Douglas J. Pettibone, Chalfont; Doug W. Hobbs; Paul S. Anderson, both of Lansdale, all of Pa.

[73] Assignee: Merck & Co., Inc., Rahway, N.J.

[21] Appl. No.: 470,693

[22] Filed: Jun. 6, 1995

Related U.S. Application Data

[63] Continuation of PCT/US94/07784, Jul. 14, 1994, which is a continuation-in-part of Ser. No. 92,840, Jul. 16, 1993, abandoned.

[51] Int. Cl.[6] .......... C07D 401/02; C07D 403/02; A61K 31/54; A61K 31/545
[52] U.S. Cl. .......... 514/227.8; 514/228.2; 514/230.5; 514/230.8; 514/249; 514/258; 514/259; 514/301; 514/312; 514/314; 514/318; 544/90; 544/91; 544/92; 544/257; 544/283; 544/284; 544/105; 544/353; 544/58.5; 544/58.6; 544/58.2; 544/350; 546/158; 546/157; 546/165; 546/112
[58] Field of Search .......... 544/90–92, 257, 544/283, 284, 105; 546/158; 514/230.5, 312, 227.8, 228.2, 230.8, 249, 258, 259, 301, 314, 318

[56] References Cited

U.S. PATENT DOCUMENTS

| | | | |
|---|---|---|---|
| 4,087,425 | 5/1978 | Garcia et al. | 544/383 |
| 4,147,870 | 4/1979 | Garcia et al. | 544/383 |
| 4,344,945 | 8/1982 | Teranishi et al. | 424/248.52 |
| 5,091,387 | 2/1992 | Evans et al. | 514/278 |
| 5,204,349 | 4/1993 | Bock et al. | 514/253 |
| 5,225,402 | 7/1993 | Ogawa et al. | 514/312 |
| 5,300,513 | 4/1994 | Ogawa et al. | 514/312 |
| 5,356,904 | 10/1994 | Freidinger et al. | 514/312 |
| 5,436,254 | 7/1995 | Ogawa et al. | 514/312 |

FOREIGN PATENT DOCUMENTS

| | | |
|---|---|---|
| 0382185 | 8/1990 | European Pat. Off. |
| 0384843 | 8/1990 | European Pat. Off. |
| 0450761 | 10/1991 | European Pat. Off. |
| 0470514 | 2/1992 | European Pat. Off. |
| 0469984A2 | 2/1992 | European Pat. Off. |
| 0486280 | 5/1992 | European Pat. Off. |
| 2 081 346 | 12/1970 | France . |
| 2 292 477 | 10/1975 | France . |
| 94/01113 | 1/1994 | WIPO . |
| 94/07496 | 4/1994 | WIPO . |

OTHER PUBLICATIONS

Klein et al., Chemical Abstracts, vol. 81, AB. No. 81:77, 786r (1974).
Klein et al., Chemical Abstracts, vol. 84, AB. No. 84:105, 358 (1976).
Takai et al., Chemical and Pharmaceutical Bulletin, vol. 33, No. 3, (1985).
Kyowa Hakko Kogyo Co. Ltd., Chemical Abstracts, vol. 98, AB No. 98:179,406k, (1983) JP 57,192,383 (1982).
Kyowa Hakko Kogyo Co. Ltd., Chemical Abstracts, vol. 97, AB No. 97:182,449m, JP 82,59,889 (1982).
Lobbezoo, et al., Journal of Medicinal Chemistry, vol. 24, No. 7, pp. 777–782 (1981).
Ogawa, et al., Journal of Medicinal Chemistry, vol. 36, No. 14, pp. 2011–2017 (1993).

(List continued on next page.)

*Primary Examiner*—Matthew V. Grumbling
*Attorney, Agent, or Firm*—Mary A. Appollina; Melvin Winokur

[57] ABSTRACT

Compounds of the formula

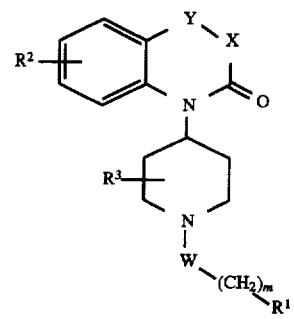

X is —O—, —NH— and —NR$^8$—; Y is —CH$_2$—, —CHR$^8$— and —C(R$^8$)$_2$—; R$^1$ is camphor-10-yl, C$_{1-5}$ alkoxyl, styryl, hydroxystyryl, furyl, unsubstituted or substituted thienyl, naphthyl, indolyl, tetrahydronaphthyl, unsubstituted, mono- or di-substituted pyridyl, pyrazinyl, unsubstituted or substituted cyclohexyl where the substituent is R$^4$, and unsubstituted or substituted phenyl where the substituents on phenyl are R$^5$, R$^6$ and R$^7$; R$^2$ is hydrogen, C$_{1-5}$ alkoxy, C$_{1-5}$ alkyl, amino, C$_{1-5}$ alkylcarbonylamino, nitro or halogen; R$^3$ is hydrogen, C$_{1-5}$ alkoxycarbonyl, cyano or carbamoyl; R$^4$ is one to two of hydrogen, oxo, hydroxy, C$_{1-5}$ alkoxy, C$_{1-5}$ alkoxycarbonylamino-C$_{1-5}$ alkyl and amino-C$_{1-5}$ alkyl; R$^5$, R$^6$ are each independently selected from hydrogen, halogen, C$_{1-5}$ alkyl, hydroxyl and C$_{1-5}$ alkoxy; R$^7$ is

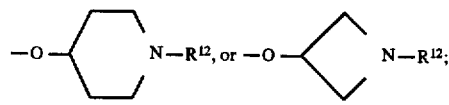

W is CO or SO$_2$; and m is an integer from 0 to 1. Such compounds as useful as oxytocin and vasopressin receptor antagonists.

20 Claims, No Drawings

OTHER PUBLICATIONS

Yamamura, et al., Science, vol. 252, No. 5005, pp. 572–574 (1991).

J. Pharm. Exp. Ther., vol. 264, No. 1, pp. 308–314, by Pettibone et al., entitled Identification of an Orally Active, Nonpeptidyl Oxytocin Antagonist, 1985.

J. Med. Chem., vol. 35, No. 21, pp. 3919–3927, by Evans et al., entitled Orally Active, Nonpeptide Oxytocin Antagonists, 1978.

Chemical abstracts, Vo. 78, No. 5, 5 Feb. 1973, abstract No. 29818u, p. 510, col. L.

Chemical abstracts, vol. 86, No. 5, 31 Jan. 1977, abstract No. 29877c p. 376, col. R.

BENZOXAZINONE AND BENZOPYRIMIDINONE PIPERIDINYL TOCOLYTIC OXYTOCIN RECEPTOR ANTAGONISTS

FIELD OF THE INVENTION

This application is a continuation of prior application PCT/US94/07784, filed 14 Jul. 1994, which is a continuation-in-part of prior application U.S. Ser. No. 08/092,840, filed Jul. 16, 1993, now abandoned the contents of which are hereby incorporated by reference.

The present invention provides novel compounds, novel compositions, methods of their use and methods of their manufacture, such compounds generally pharmacologically useful as agents in obstetric and gynecologic therapy. The aforementioned pharmacologic activities are useful in the treatment of mammals. More specifically, the compounds of the present invention can be used in the treatment of preterm labor, stopping labor preparatory to Caesarean delivery, and in the treatment of dysmenorrhea. At the present time, there is a need in the area of obstetric and gynecologic therapy for such agents.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and ethanol. Ritodrine, the leading $\beta_2$-adrenergic agonist, causes a number of cardiovascular and metabolic side effects in the mother, including tachycardia, increased renin secretion, hyperglycemia (and reactive hypoglycemia in the infant). Other $\beta_2$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

It has been proposed that a selective oxytocin antagonist would be the ideal tocolytic agent. In the last few years, evidence has accumulated to strongly suggest that the hormone oxytocin may be a physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part as a result of a well-documented increase in the number of oxytocin receptors in this tissue. This "up-regulation" of oxytocin receptors and enhanced uterine sensitivity appears to be due to trophic effects of rising plasma levels of estrogen towards term. By blocking oxytocin, one would block both the direct (contractile) and indirect (enhanced prostaglandin synthesis) effects of oxytocin on the uterus. A selective oxytocin blocker, or antagonist, would likely be more efficacious for treating preterm labor than current regimens. In addition, since oxytocin at term has major effects only on the uterus, such an oxytocin antagonizing compound would be expected to have few, if any, side effects.

The compounds of the present invention can also be useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist can be more efficacious for treating dysmenorrhea than current regimens. An additional use for the present invention is for the stoppage of labor preparatory to Caesarean delivery.

It is, therefore, a purpose of this invention to provide substances which more effectively antagonize the function of oxytocin in disease states in animals, preferably mammals, especially in humans. It is another purpose of this invention to prepare novel compounds which more selectively inhibit oxytocin. It is still another purpose of this invention to provide a method of antagonizing the functions of oxytocin in disease states in mammals. It is also a purpose of this invention to develop a method of preventing or treating oxytocin-related disorders of preterm labor and dysmenorrhea by antagonizing oxytocin.

It has now been found that compounds of the present invention are antagonists of oxytocin and bind to the oxytocin receptor. When the oxytocin receptor is bound by the compounds of the present invention, oxytocin is antagonized by being blocked from its receptor and thus being unable to exert its biologic or pharmacologic effects. These compounds are useful in the treatment and prevention of oxytocin-related disorders of animals, preferably mammals and especially humans. These disorders are primarily preterm labor and dysmenorrhea. The compounds would also find usefulness for stoppage of labor preparatory to Caesarean delivery. Additionally, such compounds are useful in inducing contraception in mammals inasmuch as oxytocin antagonists have now been shown to inhibit the release of oxytocin-stimulated luteinizing hormone (LH) by anterior pituitary cells.

Compounds of the present invention are also inhibitors of vasopressin and can bind to the vasopressin receptor. These compounds are useful in inducing vasodilation, treating hypertension, inducing diuresis and inhibiting platelet agglutination

SUMMARY OF THE INVENTION

The compounds and their pharmaceutically acceptable salts and esters of the present invention are those of the general structural formula

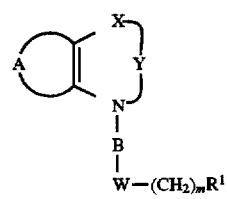

wherein

Y is $CH_2$, $C=O$, $C=S$, $C=N-H$ or $C=N-CH_3$;

X is selected from the group consisting of —O—, —NH—, —$NR^8$—, —$(CH_2)_q$—O—, —$C(R^8)_2$—O—, —$C(R^8)_2$—$CH_2$—, —$CH(R^{11})$—O—, —$CH(R^{11})$—$CH_2$, —C(O)—$CH_2$—, —$CH_2$—NH—, —$CH_2$—$NR^8$—, —O—$CH_2$—, —$C(R^8)=N$—, —$N=C(R^8)$—, —NH—$CH_2$—, —$NR^8$—$CH_2$—, —$(CH_2)_p$—, —CH=CH—, —C(OH)=CH—, —S— and —$S(O)_m$—$CH_2$—;

"A" represents a fused aromatic or heteroaromatic ring such that the bicyclic ring system containing the A ring is selected from the group consisting of

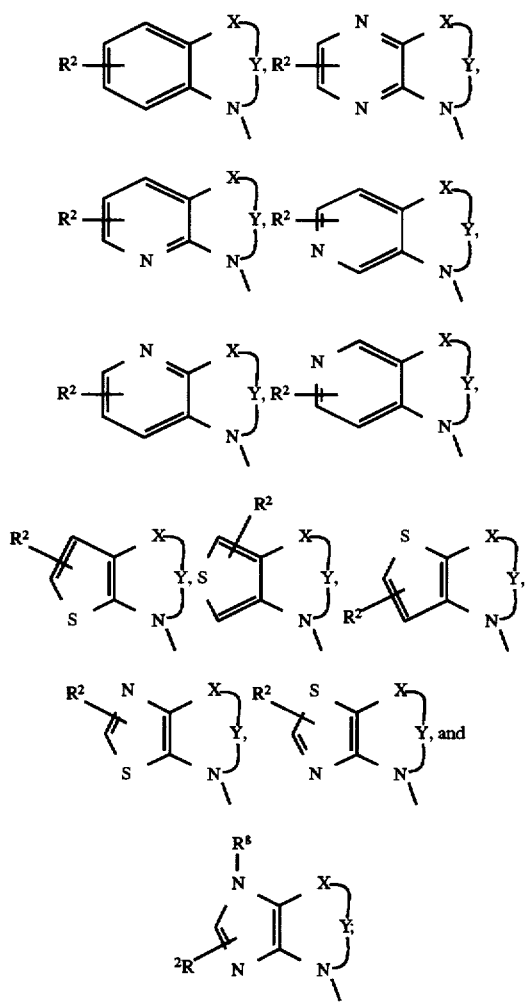

B is a heterocyclic or heterobicyclic ring selected from the group consisting of

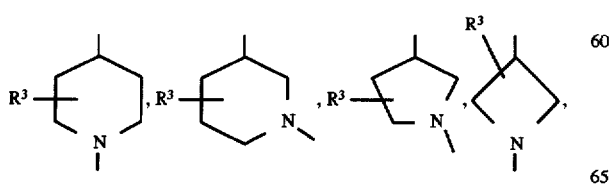

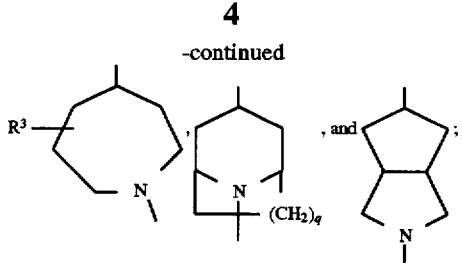

W is —$CH_2$—, —CO—, —COO—, —$CONR^8$—, —$C(=NR^8)$—, —C(O)—$CH(R^{10})$—, —$C(=NCH_2Ph)$— or —$SO_2$—;

$R^1$ is selected from the group consisting of camphor-10-yl, $C_{1-5}$ alkoxyl, styryl, hydroxystyryl, furyl, thienyl, pyrrolyl, naphthyl, indolyl, tetrahydronaphthyl, unsubstituted, mono- or di-substituted pyridyl where said substituent on said pyridyl are each independently selected from $C_{1-5}$ alkyl, $C_{1-5}$ alkoxy, halogen, hydroxyl or $R^7$, pyrazinyl, quinolinyl, substituted thienyl where said substituent is selected from the group consisting of $C_{1-5}$ alkoxycarbonyl, $C_{1-5}$ alkylcarbonyl, carboxyl and pyridyl, $C_{1-5}$ alkyl-substituted pyrrolyl, unsubstituted or substituted cyclohexyl where said substituent is $R^4$, and unsubstituted or substituted phenyl where said substituents are one or more of $R^5$, $R^6$ or $R^7$;

$R^2$ is selected from the group consisting of hydrogen, hydroxyl, $C_{1-5}$ alkoxyl, $C_{1-5}$ alkyl, amino, $C_{1-5}$ alkylcarbonylamino, nitro, methanesulfonylamino, trifluoromethyl and halogen;

$R^3$ is selected from the group consisting of hydrogen, amino, $C_{1-5}$ alkyl, $C_{1-5}$ alkoxycarbonyl, hydroxy-$C_{1-10}$ alkyl, methylthio-$C_{1-10}$ alkyl, methylsulfonyl-$C_{1-10}$ alkyl, methylsulfonyl, cyano, carbamoyl and carboxy;

$R^4$ is independently one or two members of the group consisting of hydrogen, oxo, hydroxyl, $C_{1-5}$ alkoxyl, $C_{1-5}$ alkoxycarbonylamino-$C_{1-5}$ alkyl and amino-$C_{1-5}$ alkyl;

$R^5$ and $R^6$ are each independently selected from the group consisting of hydrogen, halogen, phenyl, hydroxyphenyl, phenoxy, hydroxyphenoxy, phenyl-$C_{1-5}$ alkyl, $C_{1-10}$ alkyl, trifluoromethyl, $C_{3-6}$ cycloalkyl, cyano, carboxy-$C_{1-5}$ alkyl, $C_{1-10}$ alkoxy-$C_{1-5}$ alkyl, $C_{1-10}$ alkoxycarbonyl-$C_{1-5}$ alkyl, $C_{1-10}$ alkoxycarbonyl-$C_{2-6}$ alkenyl, mono- or di-$C_{1-10}$ alkylamino-$C_{1-5}$ alkyl, cyano-$C_{1-5}$ alkyl, halo-$C_{1-5}$ alkyl, —$S(O)m$—$CH_3$, —$NO_2$, hydroxyl, hydroxy-$C_{1-5}$ alkyl, $C_{1-10}$ alkoxyl, substituted $C_{1-5}$ alkoxy in which the alkyl group of said alkyloxy substitutent is substituted with a $C_{2-6}$ alkenyl group, substituted $C_{1-5}$ alkoxy in which the alkyl group of said alkyloxy substitutent is substituted with a $C_{2-6}$ alkynyl group, $C_{3-6}$ cycloalkyloxy, $C_{3-6}$ cycloalkyl-$C_{1-5}$ alkoxy, trifluoromethoxy, carboxy, $C_{1-10}$ alkoxycarbonyl, $C_{1-10}$ alkylcarbonyl, —$N(R^{13})_2$ and —NH—$COR^{14}$;

$R^7$ is selected from the group consisting of hydrogen, $C_{1-5}$ alkoxy, carboxyl, amino-$C_{2-5}$ alkoxy, —CO—$R^{16}$,

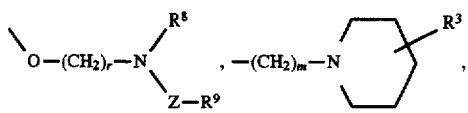

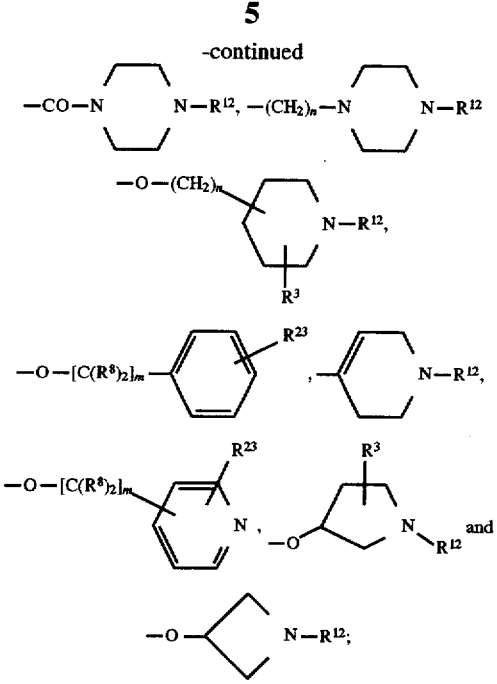

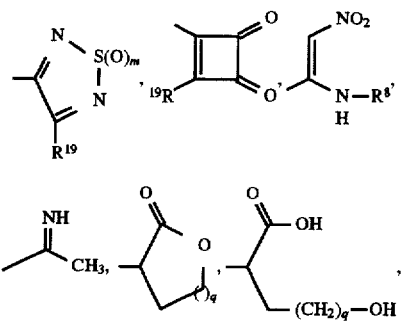

R⁸ is independently selected from hydrogen or $C_{1-5}$ alkyl;

R⁹ is selected from the group consisting of Het, amino, $-N(R^8)-(CH_2)_q-CO-R^{14}$, $C_{1-5}$ alkoxyl, mono- or di-$C_{1-10}$ alkylamino-$C_{1-5}$ alkyl, mono- or di-$C_{1-10}$ alkylamino-$C_{2-6}$ alkylamino, unsubstituted $C_{1-5}$ alkyl and substituted $C_{1-5}$ alkyl where said substitutent is selected from the group consisting of carboxyl, hydroxyl, amino, methylsulfonyl, $-N(R^8)_2$, $-NHR^8$, $C_{1-5}$ alkoxycarbonyl, $C_{1-10}$ alkoxycarbonylamino and Het;

R¹⁰ is selected from the group consisting of hydrogen, hydroxyl, $C_{1-5}$ alkoxycarbonyl, $C_{1-5}$ alkoxycarbonylamino, hydroxy-$C_{1-5}$ alkyl, amino, $-N(R^8)_2$, $-NHR^8$, cyano, $C_{1-5}$ alkyl and $C_{1-5}$ alkoxy;

R¹¹ is selected from the group consisting of $C_{1-5}$ alkyl, trifluoromethyl and unsubstituted, mono-, di- or tri-substituted phenyl wherein said substituents on said phenyl are independently selected from the group consisting of $C_{1-5}$ alkyl, $C_{1-10}$ alkoxyl, halogen and trifluoromethyl;

R¹² is selected from the group consisting of hydrogen, $C_{1-10}$ alkyl, $C_{3-6}$ cycloalkyl, $C_{3-6}$ cycloalkyl-$C_{1-5}$ alkyl, $C_{2-6}$ alkenyl, $C_{2-6}$ alkynyl, $C_{1-10}$ alkoxycarbonyl, $C_{1-5}$ alkylcarbonyl, tetrazolyl, cyano, 4-tetrahydropyranyl, 4-tetrahydrothiopyranyl, 4-piperidinyl, N-($C_{1-10}$ alkoxycarbonyl)-4-piperidinyl, N-($C_{1-5}$ alkyl)-4-piperidinyl, 2-pyrimidinyl optionally substituted with one to two members of the group consisting of halogen, carbamoyl, carboxyl, cyano, 5-tetrazolyl, aminothiocarbonyl, $-C(NHR^{18})=NR^{17}$, amino-$C_{1-5}$-alkyl, and mono- or di-$C_{1-10}$-alkylamino-$C_{1-5}$-alkyl,

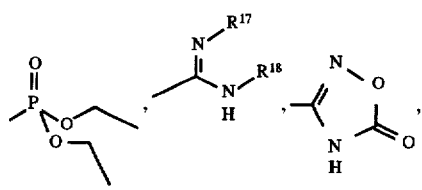

$-SO_2-R^{15}$, $-CO-R^{16}$, unsubstituted or substituted pyridyl wherein said substituent on said pyridyl is selected from hydrogen, halogen, $C_{1-10}$ alkoxycarbonyl, carboxy, nitro or amino, and mono- or di-substituted $C_{1-10}$ alkyl wherein said substituents on said $C_{1-10}$ alkyl are independently selected from the group consisting of hydroxyl, $C_{1-10}$ alkoxycarbonyl, carboxyl, hydroxyl, $C_{1-5}$ alkoxyl, cyano, methylsulfonyl, aminocarbonyl, imidazolyl, tetrazolyl, morpholinyl, piperazinyl, benzodioxanyl, quinolinyl, isoquinolinyl, furyl, furopyridyl, thienyl, 5-halo-2-thienyl, 3,5-dimethyl-4-isoxazolyl, pyrazinyl, $C_{1-5}$ akyl-substituted pyrazinyl, pyrimidinyl, pyridazinyl, thiazolyl, $C_{1-10}$ alkyl-substituted thiazolyl, oxadiazolyl, phenyl-substituted oxadiazolyl, chlorophenyl-substituted thiazolyl, benzimidazolyl, thienopyridyl, mono or di-chlorothienopyridyl, furopyridyl, uracil, unsubstituted, mono-, or di-substituted pyridyl wherein said substituents on said pyridyl are independently selected from hydrogen, halogen, $C_{1-10}$ alkoxy, $_{1-10}$ alkyl, amino-$C_{1-5}$ alkyl, mono or di-$C_{1-5}$ alkylamino-$C_{1-5}$ alkyl, $C_{1-10}$ alkylcarbonyl, $C_{1-10}$ alkoxycarbonyl, carboxy, nitro, hydroxy, hydroxy $C_{1-5}$ alkyl, $C_{1-5}$ alkoxy-$C_{1-5}$ alkyl or amino, mono-, or di-substituted pyridyl-N-oxide wherein said substituents on said pyridyl-N-oxide are independently selected from hydrogen, halogen, $C_{1-10}$ alkoxy, $C_{1-10}$ alkyl, amino-$C_{1-5}$ alkyl, mono or di-$C_{1-5}$ alkylamino-$C_{1-5}$ alkyl, $C_{1-10}$ alkylcarbonyl, $C_{1-10}$ alkoxycarbonyl, carboxy, nitro, hydroxy, hydroxy $C_{1-5}$ alkyl, $C_{1-5}$ alkoxy-$C_{1-5}$ alkyl or amino, and unsubstituted, mono-or di-substituted phenyl wherein said substituents on said phenyl are independently selected from hydrogen, halogen, hydroxyl, $C_{1-10}$ alkoxyl, $C_{1-10}$ alkoxycarbonyl, cyano or carboxyl;

R¹³ is independently selected from the group consisting of hydrogen, $C_{1-5}$ alkyl and $C_{1-5}$ alkylsulfonyl;

R¹⁴ is selected from the group consisting of $C_{1-5}$ alkyl, $C_{1-5}$ alkoxyl, amino-$C_{1-5}$ alkyl, phenyl and benzimidazolyl;

R¹⁵ is selected from the group consisting of amino, $C_{1-10}$ alkoxycarbonylamino, amino-$C_{2-10}$ alkylamino, mono- or di-$C_{1-10}$ alkylamino-$C_{2-10}$ alkylamino, 3-azetidinyl, 1-benzyl-3-azetidinyl, 1-($C_{1-10}$ alkyl)-3-azetidinyl, unsubstituted or 1-substituted piperidinyl in which said substituent on said piperidinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, unsubstituted or 1-substituted 3-pyrrolidinyl in which said substituent on said pyrrolidinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, unsubstituted or 4-substituted 1-piperazinyl in which said substituent on said piperazinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, 1-($C_{3-6}$ cycloalkyl)-4-piperazinyl, mono- or di-$C_{1-10}$ alkylamino-$C_{2-10}$ alkylamino, vinyl, pyridyl, unsubstituted or substituted phenyl wherein said substitutent on said phenyl is selected from $C_{1-5}$ alkyl, nitro, amino, $C_{1-10}$ alkoxycarbonyl or carboxy, and unsubstituted or substituted $C_{1-10}$ alkyl wherein said substituent on said alkyl is selected from halogen, $R^{20}$, carboxy, cyano, $C_{1-10}$ alkoxycarbonyl, azido, acetamidinyl, guanido, morpholino, pyrrolidinyl, piperidinyl, 2,2,6,6-tetramethyl-1-piperidinyl, hydroxy-pyrrolidinyl, tetrazolyl, piperazinyl, $C_{1-5}$ alkoxy-$C_{1-5}$ alkyl-substituted 1-pyrrolidinyl, 3-($C_{1-5}$ alkoxy)-1-pyrrolidinyl, 4-($C_{1-5}$ alkoxy-$C_{2-5}$ alkyl)-1-piperazinyl, 1-($C_{1-10}$ alkyl)-4-piperazinyl, N-tetrahydroisoquinolinyl, aza-cycloheptyl, mono- or di-substituted 1-piperidinyl wherein said substitutents on said piperidinyl are independently selected from $C_{1-5}$ alkyl, hydroxyl, $C_{1-5}$ alkoxy, cyano, phenyl, 1-piperidinyl, trihalomethyl, spiro-cyclopropyl, or spiro-cyclopentyl, mono- or di-substituted 1-pyrrolidinyl wherein said substitutents on said pyrrolidinyl are independently selected from $C_{1-5}$ alkyl, trihalomethyl, spiro-cyclopropyl, or spiro-cyclopentyl, $C_{3-8}$ cycloalkyl wherein said cycloalkyl is optionally substituted with carboxy, nitro, amino, mono- or di-$C_{1-5}$ alkylamino, $R^{20}$, 1-pyrrolidinyl, 4-morpholinyl, 1-piperidinyl, 4-($C_{1-5}$ alkyl)-1-piperidinyl, or 4,4-di-($C_{1-5}$ alkyl)-1-piperidinyl, or unsubstituted, mono- or di-substituted amino wherein said substituents on said amino are independently selected from benzyl, $C_{1-10}$ alkyl, hydroxy-$C_{2-10}$ alkyl, $C_{1-10}$ alkoxy-$C_{2-10}$ alkyl, $C_{3-8}$ cycloalkyl, carboxy-$C_{1-10}$ alkyl, $C_{1-10}$ alkoxycarbonyl-$C_{1-10}$ alkyl, $C_{3-6}$ cycloalkyl-substituted-$C_{1-10}$ alkyl or allyl;

$R^{16}$ is selected from the group consisting of hydrogen, Het, 1-($C_{1-10}$ alkoxycarbonyl)-4-piperidinyl, imidazolyl, unsubstituted or 1-substituted piperidinyl in which said substituent on said piperidinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, unsubstituted or 1-substituted 3-pyrrolidinyl in which said substituent on said pyrrolidinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, unsubstituted or 4-substituted 1-piperazinyl in which said substituent on said piperazinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, pyridyl, 1-($C_{3-6}$ cycloalkyl)-4-piperazinyl, trihalomethyl, $C_{1-10}$ alkoxycarbonyl, carboxyl, phenylamino, vinyl, $C_{1-10}$ alkoxycarbonylamino, methylsulfonylamino, trihalomethyl-sulfonylamino, amino, guanido, propargylamino, mono- or di-$C_{1-10}$ alkylamino-$C_{2-10}$ alkylamino, $C_{1-10}$ alkylamino, cyanoamino, $C_{1-10}$ alkoxycarbonyl-$C_{1-10}$ alkylamino, $C_{1-10}$ alkoxycarbonyl-$C_{1-10}$ alkylamino-$C_{1-10}$ alkyl, carboxy-$C_{1-10}$ alkylamino-$C_{1-10}$ alkyl, unsubstituted, mono- or di-substituted phenyl wherein said substituents on said phenyl are independently selected from halogen, amino-$C_{1-10}$ alkyl, mono- or di-$C_{1-10}$ alkylamino-$C_{2-10}$ alkylamino, $C_{1-10}$ alkoxycarbonyl, carboxyl, $C_{1-10}$ alkoxyl, 1-($C_{1-10}$ alkoxycarbonyl)-4-piperidinyloxy or 4-piperidinyloxy, and mono- or di-substituted $C_{1-10}$ alkyl wherein said substituents on said alkyl are independently selected from halogen, $R^{20}$, azido, guanido, acetamidinyl, $C_{1-10}$ alkoxycarbonyl, carboxy, carboxymethoxy, carboxy-$C_{1-10}$ alkylcyclopentyl, $C_{1-10}$ alkoxycarbonylamino, amino, cyano, methylsulfonyl, imidazolyl, morpholinyl, azetidinyl, pyrrolidinyl, piperazinyl, piperidinyl, 2,2,6,6-tetramethyl-1-piperidinyl, 3-hydroxy-1-pyrrolidinyl, $C_{1-5}$ alkoxy-$C_{1-5}$ alkyl-substituted 1-pyrrolidinyl, 1-($C_{1-10}$ alkyl)-4-piperazinyl, piperidinyl, N-tetrahydroisoquinolinyl, aza-cycloheptyl, mono- or di-substituted 1-piperidinyl wherein said substitutents on said piperidinyl are independently selected from $C_{1-5}$ alkyl, hydroxyl, $C_{1-5}$ alkoxyl, cyano, or spiro-cyclopentyl, $C_{3-8}$ cycloalkyl wherein said cycloalkyl is optionally substituted with nitro, amino, mono- or di-$C_{1-5}$ alkylamino, $R^{20}$, 1-pyrrolidinyl, or 1-piperidinyl, unsubstituted, mono- or di-substituted amino wherein said substituents on said amino are independently selected from benzyl, $C_{1-10}$ alkyl, hydroxy-$C_{2-10}$ alkyl, $C_{1-10}$ alkoxy-$C_{2-10}$ alkyl, $C_{3-6}$ cycloalkyl, $C_{1-5}$ alkoxycarbonyl-$C_{1-10}$ alkyl, carboxy-$C_{1-10}$ alkyl or $C_{3-8}$ cycloalkyl-substituted $C_{1-10}$ alkyl, $C_{1-10}$ alkoxycarbonyl, carboxy, carboxymethoxy, carboxy-$C_{1-10}$ alkylcyclopentyl, $C_{1-10}$ alkoxycarbonylamino, cyano, methylsulfonyl, imidazolyl, morpholinyl, azetidinyl, or 1-($C_{1-10}$ alkyl)-4-piperazinyl;

$R^{17}$ is selected from the group consisting of hydrogen, hydroxyl, cyano, $C_{1-10}$ alkylsulfonyl, trihalomethylsulfonyl, $C_{1-10}$ alkylcarbonyl and trihalomethylcarbonyl;

$R^{18}$ is selected from the group consisting of hydrogen, $C_{1-10}$ alkyl, mono- or di-$C_{1-10}$ alkylamino-$C_{2-10}$ alkyl and $C_{3-6}$ cycloalkyl;

$R^{19}$ is selected from the group consisting of $C_{1-10}$ alkoxy, hydroxyl, mono- or di-$C_{1-10}$ alkylamino-$C_{2-10}$ alkylamino and di-$C_{1-10}$ alkylamino-$C_{1-10}$ alkyl;

$R^{20}$ is

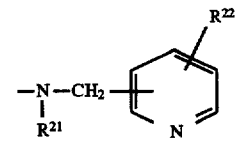

$R^{21}$ is selected from the group consisting of hydrogen, $C_{1-10}$ alkyl, and $C_{3-8}$ cycloalkyl; and $R^{22}$ is independently one to two members from the group consisting of hydrogen, $C_{1-5}$ alkyl, halogen, $C_{1-5}$ alkoxylcarbonyl, $C_{1-5}$ alkoxy, and carboxy.

$R^{23}$ is selected from the group consisting of hydrogen, cyano, amino, $C_{1-5}$ alkylcarbonylamino, halogen, halomethyl, —CHO, nitro, carboxy, $C_{1-5}$ alkoxycarbonyl, and unsubstituted or substituted $C_{1-5}$ alkyl wherein said substituent on said alkyl is selected from amino, mono- or di-$C_{1-5}$ alkylamino, cyano, $C_{1-5}$ alkoxycarbonyl, carboxy, piperazinyl, 4-[$C_{1-5}$ alkoxycarbonyl]-1-piperazinyl, 4-($C_{1-5}$ alkylcarbonyl)-1-piperazinyl, piperidinyl or substituted piperidinyl wherein said substituent on said piperidine is selected from hydroxyl, $C_{1-5}$ alkoxycarbonyl or carboxyl;

Het is selected from the group consisting of imidazolyl, piperidinyl, $C_{1-5}$ alkyl-substituted piperidinyl, piperazinyl, $C_{1-5}$ alkyl-substituted piperizinyl, $C_{1-5}$ alkoxycarbonyl-substituted piperazinyl, morpholinyl, tetrazolyl, $C_{1-5}$ alkylcarbonyl-substituted piperidinyl, $C_{1-5}$ alkoxycarbonyl-substituted piperidinyl, pyrrolidinyl, $C_{1-5}$ alkyl-substituted pyrrolidinyl, and pyridyl;

Z is —CO— or —$SO_2$—;

m is an integer of from 0 to 2;

n is an integer of from 0 to 3;

p is an integer of from 1 to 4;

q is an integer from 1 to 2; and r is an integer of from 2 to 4;

provided that when the A containing bicyclic ring system is

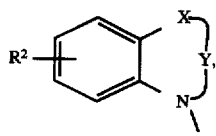

and Y is —C=O, and X is —$(CH_2)_2$—, —CH=CH—, —$C(R^8)_2$—$CH_2$—, —$CH(R^{11})$—$CH_2$ or —C(OH)=CH—, then $R^1$ is substituted phenyl wherein $R^7$ is

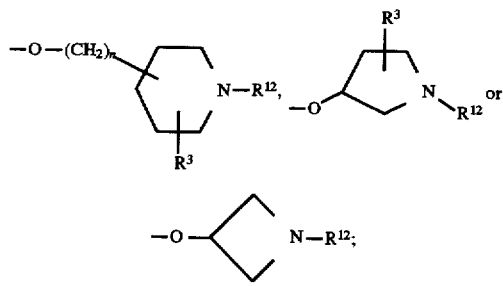

and the pharmaceutically acceptable salts thereof.

In one embodiment of the invention are the compounds wherein

X is selected from the group consisting of —O—, —$(CH_2)_q$—O—, —$C(R^8)_2$—O—, —$CH(R^{11})$—O—, —C(O)—$CH_2$—, —O—$CH_2$—, —$(CH_2)_p$—, —CH=CH— and —$S(O)_m$—$CH_2$—;

A represents a fused aromatic ring such that the bicyclic ring system containing the A ring is

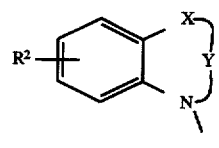

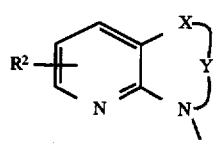

-continued

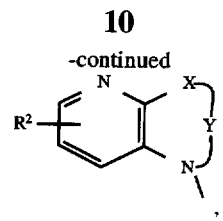

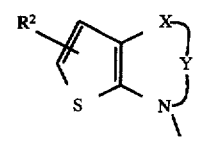

and,

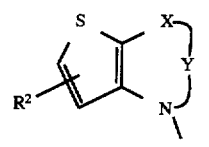

W is selected from —$CH_2$—, —CO—, —$CONR^8$—, —C(=$NR^8$)—, —C(O)—$CH(R^{10})$— or —$SO_2$—;

$R^1$ is selected from the group consisting of camphor-10-yl, $C_{1-5}$ alkoxyl, styryl, hydroxystyryl, furyl, thienyl, indolyl, tetrahydronaphthyl, unsubstituted, mono- or di-substituted pyridyl where said substituent on said pyridyl are each independently selected from $C_{1-5}$ alkyl, $C_{1-5}$ alkoxy, halogen, hydroxyl or $R^7$, pyrazinyl, substituted thienyl where said substituent on said thienyl is selected from $C_{1-5}$ alkoxycarbonyl, carboxy or pyridyl, $C_{1-5}$ alkyl-substituted pyrrolyl, unsubstituted or substituted cyclohexyl where said substituent is $R^4$, and unsubstituted or substituted phenyl where said substituents are one or more of $R^5$, $R^6$ or $R^7$;

$R^2$ is selected from the group consisting of hydrogen, $C_{1-5}$ alkoxyl, $C_{1-5}$ alkyl, amino, $C_{1-5}$ alkylcarbonylamino, nitro and halogen;

$R^3$ is selected from the group consisting of hydrogen, $C_{1-5}$ alkoxycarbonyl, cyano and carbamoyl;

$R^5$ and $R^6$ are each independently selected from the group consisting of hydrogen, halogen, hydroxyphenyl, hydroxyphenoxy, phenyl-$C_{1-5}$ alkyl, $C_{1-5}$ alkyl, cyano, $C_{1-5}$ alkoxy-$C_{1-5}$ alkyl, $C_{1-5}$ alkoxycarbonyl-$C_{1-5}$ alkyl, $C_{1-10}$ alkoxycarbonyl-$C_{2-6}$ alkenyl, mono- or di-$C_{1-10}$ alkylamino-$C_{1-5}$ alkyl, cyano-$C_{1-5}$ alkyl, halo-$C_{1-5}$ alkyl, —$S(O)_m$—$CH_3$, —$NO_2$, hydroxyl, hydroxy-$C_{1-5}$ alkyl, $C_{1-5}$ alkoxyl, substituted $C_{1-5}$ alkoxy in which the alkyl group of said alkyloxy substituent is substituted with a $C_{2-6}$ alkenyl group, substituted $C_{1-5}$ alkoxy in which the alkyl group of said alkyloxy substituent is substituted with a $C_{2-6}$ alkynyl group, $C_{3-6}$ cyloalkyl-$C_{1-5}$ alkoxy, trifluoromethoxy, carboxy, $C_{1-5}$ alkoxycarbonyl, $C_{1-5}$ alkylcarbonyl, —$N(R^{13})_2$ and —NH—$COR^{14}$;

$R^7$ is selected from the group consisting of hydrogen, $C_{1-5}$ alkoxy, amino-$C_{2-5}$ alkoxy, —CO—$R^{16}$,

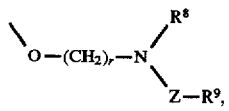

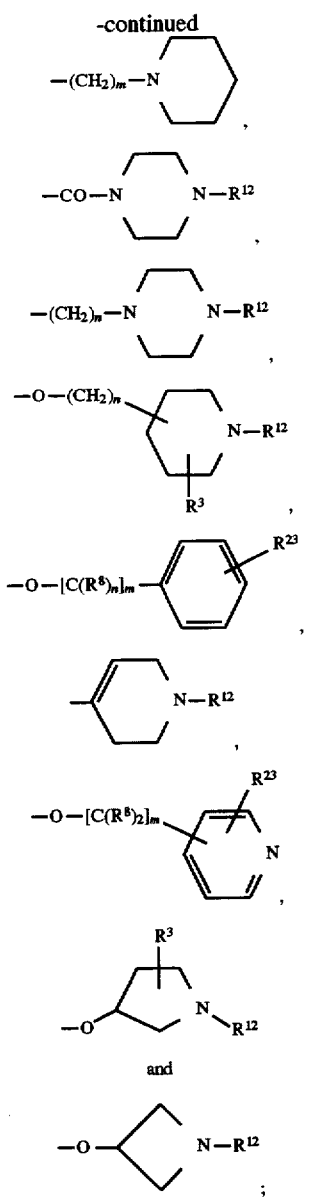

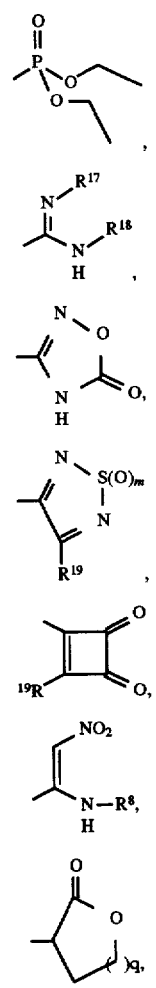

$R^9$ is selected from the group consisting of Het, —N($R^8$) —(CH$_2$)$_q$—CO—$R^{14}$, C$_{1-5}$ alkoxyl, unsubstituted C$_{1-5}$ alkyl and substituted C$_{1-5}$ alkyl where said substitutent is selected from the group consisting of amino, C$_{1-10}$ alkoxycarbonylamino and Het;

$R^{10}$ is selected from the group consisting of hydroxyl, C$_{1-5}$ alkoxycarbonylamino, hydroxy-C$_{1-5}$ alkyl, amino and C$_{1-5}$ alkoxyl;

$R^{11}$ is selected from the group consisting of C$_{1-5}$ alkyl and unsubstituted phenyl;

$R^{12}$ is selected from the group consisting of hydrogen, C$_{1-10}$ alkyl, C$_{3-6}$ cycloalkyl-substituted C$_{1-5}$ alkyl, C$_{1-5}$ alkoxycarbonyl, C$_{1-5}$ alkylcarbonyl, tetrazolyl, cyano, 4-tetrahydropyranyl, 4-tetrahydrothiopyranyl, 2-pyrimidinyl optionally substituted with one to two members of the group consisting of halogen, carbamoyl, carboxyl, cyano, 5-tetrazolyl, aminothiocarbonyl, —C(NHR$^{18}$)=NR$^{17}$, amino-C$_{1-5}$-alkyl, and mono- or di-C$_{1-10}$-alkylamino-C$_{1-5}$-alkyl, —SO$_2$—R$^{15}$, —CO—R$^{16}$, unsubstituted or substituted 2-pyridyl wherein said substituent on said pyridyl is selected from halogen, C$_{1-5}$ alkoxycarbonyl, carboxy, nitro or amino, and mono-substituted C$_{1-5}$ alkyl wherein the substituent on said alkyl is selected from the group consisting of C$_{1-10}$ alkoxycarbonyl, carboxy, cyano, methylsulfonyl, aminocarbonyl, imidazolyl, benzodioxanyl, quinolinyl, furyl, furopyridinyl, thienyl, 5-halo-2-thienyl, 3,5-dimethyl-4-isoxazolyl, pyrazinyl, C$_{1-5}$ alkyl-substituted pyrazinyl, thiazolyl, C$_{1-5}$ alkyl-substituted thiazolyl, oxadiazolyl, phenyl-substituted oxadiazolyl, chlorophenyl-substituted thiazolyl, benzimidazolyl, uracil, unsubstituted, mono-, or disubstituted pyridyl in which said substituents on said pyridyl are independently selected from hydrogen, halogen, C$_{1-10}$ alkoxyl, C$_{1-10}$ alkyl, amino-C$_{1-5}$ alkyl, mono- or di-C$_{1-5}$ alkylamino-C$_{1-5}$ alkyl, C$_{1-10}$ alkylcarbonyl, C$_{1-10}$ alkoxycarbonyl, carboxy, hydroxy, hydroxy-C$_{1-5}$ alkyl, C$_{1-5}$ alkoxy-C$_{1-5}$ alkyl or amino, mono-, or disubstituted pyridyl-N-oxide in which said substituents on said pyridyl-N-oxide are independently selected from hydrogen, halogen, C$_{1-10}$ alkoxyl, C$_{1-10}$ alkyl, amino-C$_{1-5}$ alkyl, mono- or di-C$_{1-5}$ alkylamino-C$_{1-5}$ alkyl, C$_{1-10}$ alkylcarbonyl, C$_{1-10}$ alkoxycarbonyl, carboxy, hydroxy, hydroxy-C$_{1-5}$ alkyl, C$_{1-5}$ alkoxy-C$_{1-5}$ alkyl or amino, and unsubstituted, mono- or di-substituted phenyl wherein said substituents on said phenyl are independently selected from halogen, hydroxy, C$_{1-10}$ alkoxy, C$_{1-10}$ alkoxycarbonyl, cyano or carboxy;

$R^{13}$ is selected from hydrogen or C$_{1-5}$ alkylsulfonyl;

$R^{14}$ is selected from the group consisting of $C_{1-5}$ alkyl, $C_{1-5}$ alkoxy, amino-$C_{1-5}$ alkyl and benzimidazolyl;

$R^{15}$ is selected from the group consisting of amino, $C_{1-10}$ alkoxycarbonylamino, unsubstituted or 1-substituted piperidinyl in which said substituent on said piperidinyl is selected from the group consisting of benzyl, $C_{1-5}$ alkoxycarbonyl, $C_{1-5}$ alkyl, hydroxy-$C_{2-5}$ alkyl, $C_{2-5}$ alkoxy-$C_{2-5}$ alkyl, pyridylmethyl, or $C_{1-5}$ alkylpyridylmethyl, unsubstituted or 1-substituted 3-pyrrolidinyl in which said substituent on said pyrrolidinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, unsubstituted or 4-substituted 1-piperazinyl in which said substituent on said piperazinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, 1-($C_{3-6}$ cycloalkyl)-4-piperazinyl, mono- or di-$C_{1-10}$ alkylamino-$C_{2-10}$ alkylamino, vinyl, unsubstituted or substituted phenyl wherein said substitutent on said phenyl is selected from $C_{1-5}$ alkyl, nitro, amino or $C_{1-10}$ alkoxycarbonyl, and unsubstituted or substituted $C_{1-10}$ alkyl wherein said substituent on said alkyl is selected from the group consisting of halogen, $R^{20}$, carboxy, $C_{1-10}$ alkoxycarbonyl, azido, acetamidinyl, guanido, morpholino, pyrrolidinyl, piperidinyl, 2,2,6,6-tetramethyl-1-piperi-dinyl, 3-hydroxy-1-pyrrolidinyl, $C_{1-5}$ alkoxy-$C_{1-5}$ alkyl-substituted 1-pyrrolidinyl, 3-($C_{1-5}$ alkoxy)-1-pyrrolidinyl, 4-($C_{1-5}$ alkoxy-$C_{2-5}$ alkyl)-1-piperazinyl, 1-($C_{1-10}$ alkyl)-4-piperazinyl, N-tetrahydroisoquinolinyl, aza-cycloheptyl, mono- or di-substituted 1-piperidinyl wherein said substitutents on said piperidinyl are independently selected from $C_{1-5}$ alkyl, hydroxyl, $C_{1-5}$ alkoxyl, cyano, phenyl, 1-piperidinyl, spiro-cyclopropyl or spiro-cyclopentyl, $C_{3-8}$ cycloalkyl wherein said cycloalkyl is optionally substituted with nitro, amino, mono- or di-$C_{1-5}$ alkylamino, $R^{20}$, 1-pyrrolidinyl, or 1-piperidinyl, unsubstituted, mono- or di-substituted amino wherein said substituents on said amino are independently selected from benzyl, $C_{1-10}$ alkyl, hydroxy-$C_{2-10}$ alkyl, $C_{1-10}$ alkoxy-$C_{2-10}$ alkyl, $C_{3-8}$ cycloalkyl, $C_{1-5}$ alkoxycarbonyl-$C_{1-10}$ alkyl, carboxy-$C_{1-10}$ alkyl or $C_{3-6}$ cycloalkyl-substituted $C_{1-10}$ alkyl;

$R^{16}$ is selected from the group consisting of hydrogen, unsubstituted or 1unsubstituted piperidinyl in which said substituent on said piperidinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, unsubstituted or 1-substituted 3-pyrrolidinyl in which said substituent on said pyrrolidinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, imidazolyl, $C_{1-10}$ alkoxycarbonyl, carboxyl, 1-($C_{1-10}$ alkyl)-4-piperidinyl, phenylamino, vinyl, $C_{1-10}$ alkoxycarbonylamino, amino, guanidino, propargylamino, mono- or di-$C_{1-10}$ alkylamino-$C_{2-10}$ alkylamino, $C_{1-10}$ alkylamino, $C_{1-10}$ alkoxycarbonyl-$C_{1-10}$ alkylamino, unsubstituted, mono- or di-substituted phenyl wherein said substituents on said phenyl are independently selected from $C_{1-10}$ alkoxycarbonyl, carboxyl, $C_{1-10}$ alkoxy, 1-($C_{1-10}$ alkoxycarbonyl)-4-piperidinyloxy or 4-piperidinyloxy, and mono- or di-substituted $C_{1-10}$ alkyl wherein said substituents on said alkyl are independently selected from halogen, $R^{20}$, azido, guanido, acetamidinyl, $C_{1-10}$ alkoxy-carbonyl, carboxy, carboxymethoxy, carboxy-$C_{1-10}$ alkylcyclopentyl, $C_{1-10}$ alkoxycarbonylamino, amino, cyano, methylsulfonyl, imidazolyl, morpholinyl, azetidinyl, pyrrolidinyl, piperidinyl, 2,2,6,6-tetramethyl-1-piperidinyl, 3-hydroxy-1-pyrrolidinyl, $C_{1-5}$ alkoxy-$C_{1-5}$ alkyl-substituted 1-pyrrolidinyl, 1-($C_{1-10}$ alkyl)-4-piperazinyl, N-tetrahydroisoquinolinyl, aza-cycloheptyl, mono- or di-substituted 1-piperidinyl wherein said substitutents on said piperidinyl are independently selected from $C_{1-5}$ alkyl, hydroxyl, $C_{1-5}$ alkoxyl, cyano, or spirocyclopentyl, $C_{3-8}$ cycloalkyl wherein said cycloalkyl is optionally substituted with nitro, amino, mono- or di-$C_{1-5}$ alkylamino, $R^{20}$, 1-pyrrolidinyl, or 1-piperidinyl, unsubstituted, mono- or di-substituted amino wherein said substituents on said amino are independently selected from benzyl, $C_{1-10}$ alkyl, hydroxy-$C_{2-10}$ alkyl, $C_{1-10}$ alkoxy-$C_{1-10}$ alkyl, $C_{3-6}$cycloalkyl, $C_{1-5}$ alkoxycarbonyl-$C_{1-10}$ alkyl, carboxy-$C_{1-10}$ alkyl or $C_{3-8}$ cycloalkyl-substituted $C_{1-10}$ alkyl, $C_{1-10}$ alkoxycarbonyl, carboxy, carboxymethoxy, carboxy-$C_{1-10}$ alkylcyclopentyl, $C_{1-10}$ alkoxycarbonylamino, cyano, methylsulfonyl, imidazolyl, morpholinyl, azetidinyl, or 1-($C_{1-10}$ alkyl)-4-piperazinyl;

$R^{17}$ is selected from the group consisting of hydrogen, hydroxyl, cyano, $C_{1-10}$ alkylsulfonyl and trihalomethylcarbonyl;

$R^{18}$ is selected from the group consisting of hydrogen, $C_{1-10}$ alkyl and mono- or di-$C_{1-10}$ alkylamino-$C_{2-20}$ alkyl;

$R^{19}$ is selected from the group consisting of $C_{1-10}$ alkoxy, hydroxyl and mono- or di-$C_{1-10}$ alkylamino-$C_{2-10}$ alkylamino;

$R^{21}$ is hydrogen;

$R^{22}$ is $C_{1-5}$ alkyl; and

Het is selected from the group consisting of imidazolyl, piperidinyl, piperazinyl, $C_{1-5}$ alkoxycarbonyl-substituted piperazinyl and $C_{1-5}$ alkylcarbonyl-substituted piperidinyl.

In one class of the invention are the compounds wherein A represents a fused aromatic ring such that the bicyclic ring system containing the A ring is

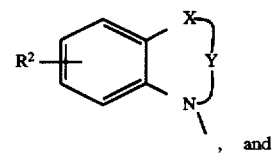

, and

B is a heterocyclic or heterobicyclic ring selected from the group consisting of

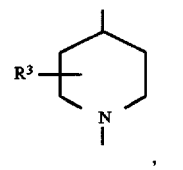

,

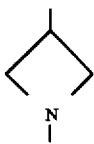

,

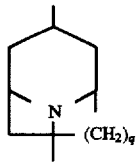

, and

In a subclass are the compounds of the formula

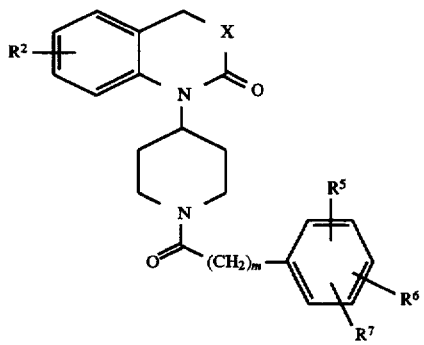

wherein

X is —CH$_2$— or —O—;

m is an integer from 0 to 1;

R$^2$ is selected from the group consisting of hydrogen, C$_{1-5}$ alkyl and halogen;

R$^5$ and R$^6$ are each independently selected from the group consisting of hydrogen, halogen, C$_{1-5}$ alkyl, hydroxyl and C$_{1-5}$ alkoxyl;

R$^7$ is selected from

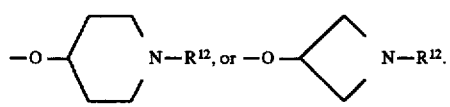

Illustrative of the subclass are the compounds of the formula

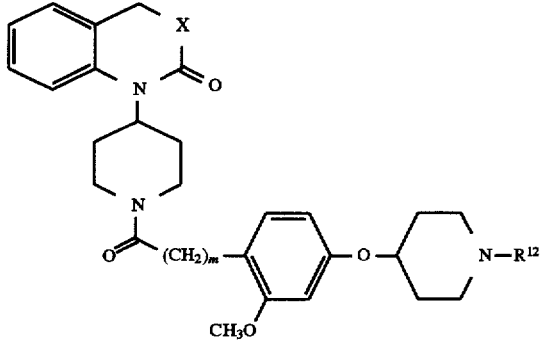

wherein

X is —CH$_2$— or —O—;

m is an integer from 0 to 1;

R$^{12}$ is hydrogen, unsubstituted C$_{1-10}$ alkyl, 'SO$_2$—R$^{15}$ and substituted C$_{1-5}$ alkyl wherein the substituent on said alkyl is selected from the group consisting of hydroxyl, C$_{1-5}$ alkoxyl, imidazolyl, benzodioxanyl, quinolinyl, furyl, furopyridinyl, thienyl, 5-halo-2-thienyl, 3,5-dimethyl-4-isoxazolyl, pyrazinyl, C$_{1-5}$ alkyl-substituted pyrazinyl, thiazolyl, C$_{1-5}$ alkyl-substituted thiazolyl, oxadiazolyl, phenyl-substituted oxadiazolyl, pyrazinyl, pyrimidinyl, chlorophenyl-substituted thiazolyl, benzimidazolyl, uracil, unsubstituted, mono-, or disubstituted pyridyl in which said substituents on said pyridyl are independently selected from hydrogen, halogen, C$_{1-10}$ alkoxyl, C$_{1-10}$ alkyl, amino-C$_{1-5}$ alkyl, mono- or di-C$_{1-5}$ alkylamino-C$_{1-5}$ alkyl, C$_{1-10}$ alkylcarbonyl, C$_{1-10}$ alkoxycarbonyl, carboxy, amino, hydroxy, hydroxy-C$_{1-5}$ alkyl, or C$_{1-5}$ alkoxy-C$_{1-5}$ alkyl, mono-, or disubstituted pyridyl-N-oxide in which said substituents on said pyridyl-N-oxide are independently selected from hydrogen, halogen, C$_{1-10}$ alkoxyl, C$_{1-10}$ alkyl, amino -C$_{1-5}$ alkyl, mono- or di-C$_{1-5}$ alkylamino-C$_{1-5}$ alkyl, C$_{1-10}$ alkylcarbonyl, C$_{1-10}$ alkoxycarbonyl, carboxy, amino, hydroxy, hydroxy-C$_{1-5}$ alkyl, or C$_{1-5}$ alkoxy-C$_{1-5}$ alkyl, and unsubstituted, mono-, or di-substituted phenyl wherein said substituents on said phenyl are independently selected from halogen, cyano, C$_{1-10}$ alkoxy, hydroxy, C$_{1-10}$ alkoxycarbonyl or carboxy;

R$^{15}$ is selected from the group consisting of unsubstituted or 1-substituted 3-pyrrolidinyl in which said substituent on said pyrrolidinyl is selected from the group consisting of benzyl, C$_{1-5}$ alkyl, hydroxy-C$_{2-5}$ alkyl, C$_{1-5}$ alkoxy-C$_{2-5}$ alkyl, pyridylmethyl, or C$_{1-5}$ alkylpyridylmethyl, unsubstituted or 4-substituted 1-piperazinyl in which said substituent on said piperazinyl is selected from the group consisting of benzyl, C$_{1-5}$ alkoxycarbonyl, C$_{1-5}$ alkyl, hydroxy-C$_{2-5}$ alkyl, C$_{1-5}$ alkoxy-C$_{2-5}$ alkyl, pyridylmethyl, or C$_{1-5}$ alkylpyridylmethyl, mono- or di-C$_{1-10}$ alkylamino -C$_{2-10}$ alkylamino, and substituted C$_{1-10}$ alkyl wherein said substituent on said alkyl is selected from the group consisting of R$^{20}$, carboxy, C$_{1-10}$ alkoxycarbonyl, guanido, acetamidinyl, morpholino, pyrrolidinyl, piperidinyl, 2,2,6,6-tetramethyl-1-piperidinyl, 3-hydroxy-1-pyrrolidinyl, C$_{1-5}$ alkoxy-C$_{1-5}$ alkyl-substituted 1-pyrrolidinyl, 3-(C$_{1-5}$ alkoxy)-1-pyrrolidinyl, 4-(C$_{1-5}$ alkoxy-C$_{2-5}$ alkyl)-1-piperazinyl, 1-(C$_{1-10}$ alkyl)-4-piperazinyl, N-tetrahydroisoquinolinyl, aza-cycloheptyl, mono- or di-substituted 1-piperidinyl wherein said substitutents on said piperidinyl are independently selected from $C_{1-5}$ alkyl, hydroxyl, $C_{1-5}$ alkoxyl, cyano, phenyl, 1-piperidinyl, spiro-cyclopropyl or spiro-cyclopentyl, $C_{3-8}$ cycloalkyl wherein said cycloalkyl is substituted with amino, mono- or di-$C_{1-5}$ alkylamino, 1-pyrrolidinyl, 1-piperidinyl, or $R^{20}$, and unsubstituted, mono- or di-substituted amino wherein said substituents on said amino are independently selected from $C_{1-10}$ alkyl, hydroxy-$C_{2-10}$ alkyl, $C_{1-10}$ alkoxy-$C_{2-10}$ alkyl, $C_{3-8}$ cycloalkyl, $C_{1-5}$ alkoxycarbonyl-$C_{1-10}$ alkyl, carboxy-$C_{1-10}$ alkyl or $C_{3-6}$ cycloalkyl-substituted $C_{1-10}$ alkyl.

Exemplifying the invention are the compounds selected from the group consisting of

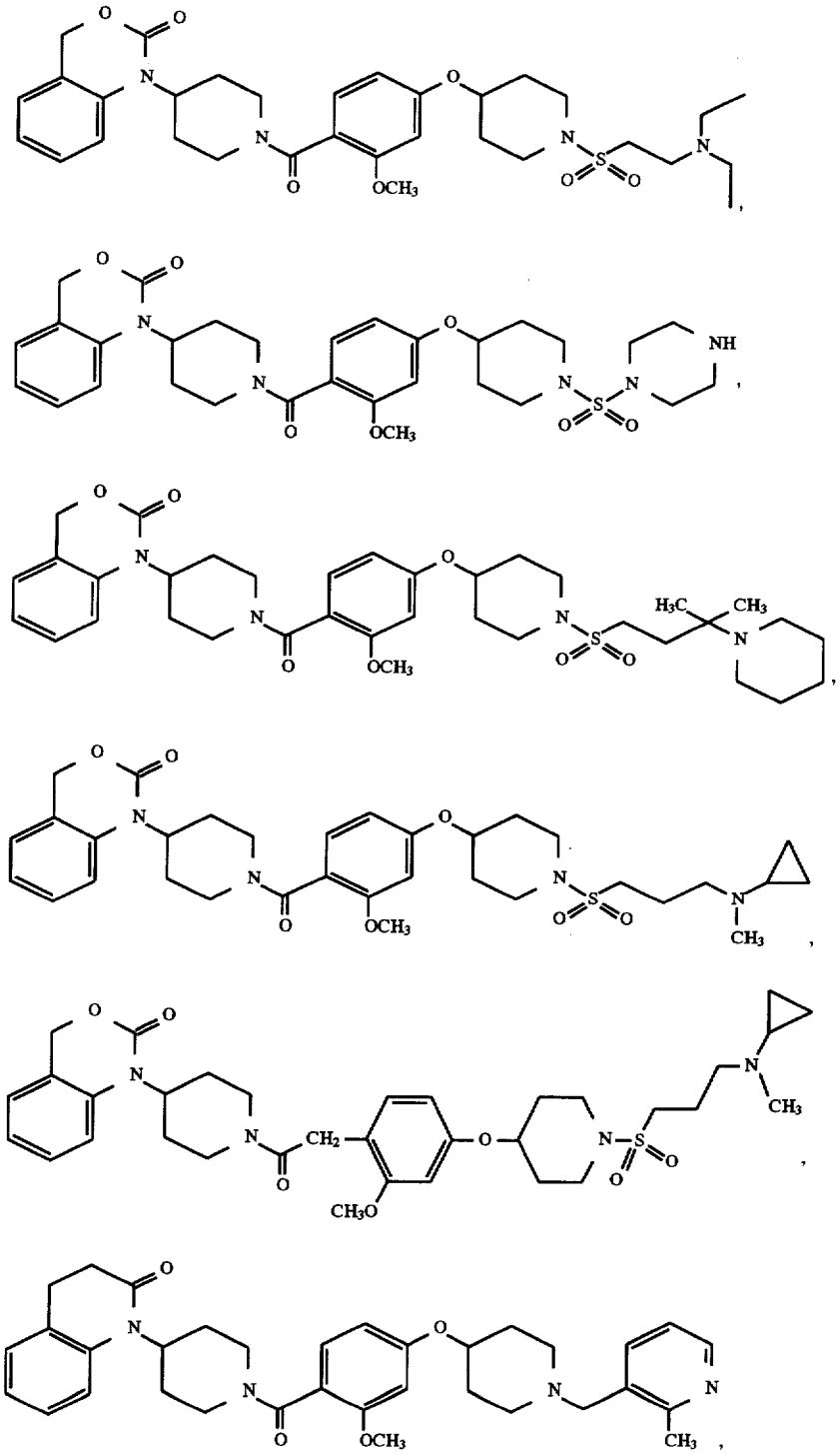

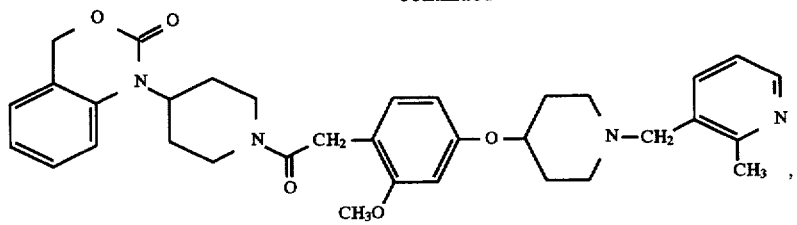

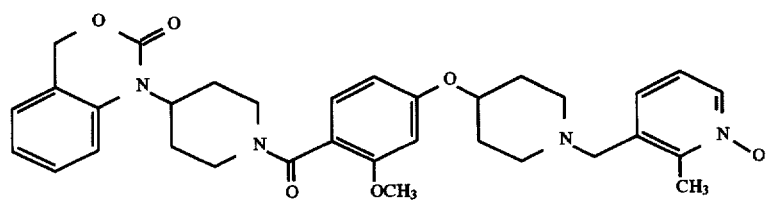

and

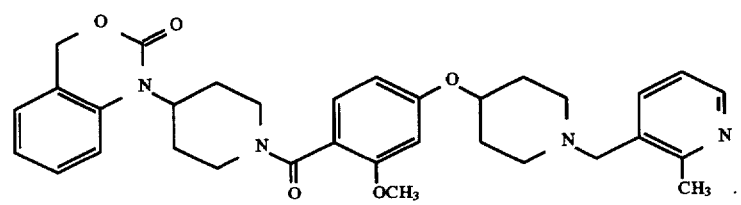

A further illustration of the invention are the compounds selected from the group consisting of

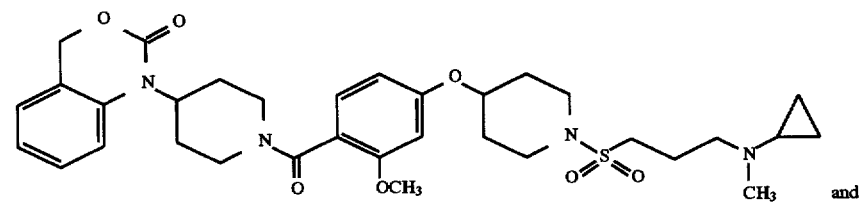

and

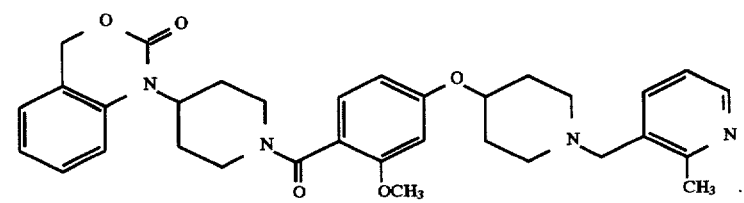

More specifically exemplifying the invention is a pharmaceutically acceptable salt of a compound of the instant invention wherein the salt is selected from the group consisting of hydrochloride, tartrate and sulfate.

An example of the invention is a pharmaceutical composition comprising a pharmaceutically acceptable carrier and a pharmacologically effective amount of a compound of the instant invention sufficient to prevent preterm labor in a mammal in need thereof.

A further example of the invention is a method of antagonizing oxytocin from binding to its receptor site in a mammal, comprising the step of administering to said mammal a pharmacologically effective amount of a compound of the instant invention.

More particularly illustrating the invention is a method of preventing preterm labor in a mammal in need thereof, comprising the step of administering to said mammal a pharmacologically effective amount of a compound of the instant inventions.

A further illustration of the invention is a method of stopping labor preparatory to cesarian delivery in a mammal in need thereof, comprising the step of administering to said mammal a pharmacologically effective amount of a compound of the instant invention.

More particularly exemplifying the invention is a method of treating dysmenorrhea in a mammal in need thereof, comprising the step of administering to said mammal a pharmacologically effective amount of a compound of the instant invention.

Another example of the invention is a method of antagonizing vasopressin from binding to its receptor site in a mammal, comprising the step of administering to said mammal a pharmacologically effective amount of a compound of the instant invention.

Another illustration of the invention is a method of inducing vasodilation in a mammal in need thereof, comprising the step of administering to said mammal a pharmacologically effective amount of a compound of the instant invention.

More specifically illustrating the invention is a method of treating hypertension in a mammal in need thereof, comprising the step of administering to said mammal a pharmacologically effective amount of a compound of the instant invention.

A further example of the invention is a method of inducing diuresis in a mammal in need thereof, comprising the step of administering to said mammal a pharmacologically effective amount of a compound of the instant invention.

Further illustrating the invention is a method of inhibiting platelet agglutination in a mammal in need thereof, comprising the step of administering to said mammal a pharmacologically effective amount of a compound of the instant invention.

Further exemplifying the invention is a method of causing contraception in a mammal in need thereof, comprising the step of administering to said mammal a pharmacologically effective amount of a compound of the instant invention.

A further illustration of the invention is a method of improving fertility rates in a farm animal, comprising the step of administering to the farm animal a pharmacologically effective amount of a compound of the instant invention.

Salts and esters encompassed within the term "pharmaceutically acceptable salts and esters" refer to non-toxic salts of the compounds of this invention which are generally prepared by reacting the free base with a suitable organic or inorganic acid. Representative salts and esters include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate ,Tosylate, Triethiodide and Valerate.

The compounds of the present invention, may have asymmetric centers and occur as racemates, racemic mixtures and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

The term "pharmacologically effective amount" shall mean that amount of a drug or pharmaceutical agent that will elicit the biological or medical response of a tissue, system, animal or human that is being sought by a researcher or clinician.

The term "alkyl" shall mean straight or branched chain alkanes of one to ten total carbon atoms, or any number within this range.

The term "lower alkyl" shall mean straight or branched chain alkanes of one to five total carbon atoms, or any number within this range.

The term "lower cycloalkyl" shall mean cycloalkanes of three to six carbon atoms (i.e., cyclopropane, cyclobutane, cyclopentane and cyclohexane).

Whenever the term "alkyl" or its prefix root appears in a name of a substituent (e.g. aralkoxyaryloxy) it shall be interpreted as including those limitations given above for "alkyl". Designated numbers of carbon atoms (e.g. $C_{1-10}$) shall refer independently to the number of carbon atoms in an alkyl or cyclic alkyl moiety or to the alkyl portion of a larger substituent in which alkyl appears as its prefix root.

The term "halogen" shall include iodine, bromine, chlorine and fluorine.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "Caesarean delivery" shall mean incision through the abdominal and uterine walls for delivery of a fetus.

The term "substituted" shall be deemed to include multiple degrees of substitution by a named substitutent.

Where multiple substituent moieties are disclosed or claimed, the substituted compound can be independently substituted by one or more of the disclosed or claimed substituent moieties, singly or plurally.

The ability of the compounds of the present invention to antagonize oxytocin makes these compounds useful as pharmacologic agents for mammals, especially for humans, for the treatment and prevention of disorders wherein oxytocin may be involved. Examples of such disorders include preterm labor and especially dysmenorrhea. These compounds may also find usefulness for stoppage of labor preparatory to Cesarean delivery.

The compounds of the present invention also bind to the vasopressin receptor and are therefore useful as vasopressin antagonists. Vasopressin antagonists are useful in the treatment or prevention of disease states involving vasopressin disorders, including their use as diuretics and their use in congestive heart failure.

In addition, the compounds of the instant invention are useful for improving fertility rates in farm animals. In certain farm animals (sheep, cattle, swine, goats), the secretion of oxytocin from the ovary and/or pituitary acts on the uterine endometrium to stimulate the secretion of prostaglandins which in ram, causes the regression of the corpus luteum of the ovary. In the cycling animal, destruction of the corpus luteum removes the source of progesterone that is key to the preparation of the uterus for pregnancy. In the animal where fertilization has occurred, the conceptus secretes a factor that antagonizes the action of oxytocin to induce luteolysis, resulting in the continued secretion of progesterone. The maintenance of a functioning corpus luteum is obligatory to the initiation of pregnancy. An oxytocin antagonist given at this critical period supplements the natural signal from the conceptus to prolong corpus luteal function. The result is to increase pregnancy rates by enhancing the chances of impregnation through a reduction in embryonic loss.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.1–6.0 gm/day orally. Intravenously, the most preferred doses will range from 0.1 to about 10 mg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drag component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The compounds of of the present invention can be prepared readily according to the following Examples or modifications thereof using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these Examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Abbreviations used in the Examples are as follows:
BOP=benzotriazol-1-yloxytris(dimethylamino) phosphonium hexafluorophosphate
DCM=dichloromethane
DIEA=diisopropylethylamine
DMF=dimethylformamide
EtOAc=ethyl acetate
EtOH=ethanol
EDC=1-ethyl-3-(3-dimethylaminopropyl)carbodiimide
FAB MS=fast atom bombardment mass spectroscopy
HOAc=acetic acid
HOBT=1-hydroxybenzotriazole
HPLC=high pressure liquid chromatography
MeOH=methanol
NMR=nuclear magnetic resonance
THF=tetrahydrofuran
TLC=thin layer chromatography All solvents were reagent grade and stored over 4 Å molecular sieves. THF was distilled from $CaH_2$-$NaBH_4$ under inert atmosphere. Dioxane was dried and freed of peroxides by passage through a column of activity I neutral alumina.

Uniplate silica gel GF TLC plates (10×20 cm, 250 microns) were purchased from Analtech, Inc. Determination of reaction pH was estimated by spotting an aliquot from the reaction mixture on wetted E. Merck pH sticks. $^1$H NMR spectra were measured at 300 MHz on a Varian XL-300, at 400 MHz on a Varian XL-400, and at 360 MHz on a Nicolet NT-360 using $(CH_3)_4Si$ as an internal standard. Fast atom bombardment mass spectra (FAB MS) were obtained on a VG-ZAB-HF spectrometer using xenon as the reagent gas.

Analytical HPLC were run on a Spectra Physics SP4270/ 8800 instrument using the following conditions:
Column: Vydac $C_{18}$, 0.21×15 cm
Mobile Phases A=0.1% by volume TFA in $H_2O$
B=0.1% by volume TFA in acetonitrile
Method A: Gradient T=0 min, 95% A, 5% B T=15 min, 0% A, 100% B Method B: Gradient T=0 min, 95% A, 5% B T=30 min, 0% A, 100% B
Method C: Gradient T=0 min, 85% A, 15% B T=30 min, 5% A, 95% B
Flow=2.0 mL/min
UV detection at 215 um
Preparative reverse phase HPLC purifications utilized the following conditions:
Column: 5×30 cm $C_{18}$ Waters DeltaPak Prep Cartridge
Mobile Phases: A=0.1% TFA in $H_2O$, B=0.1% TFA in acetonitrile
Gradient: T=0 min, 95% A, 5% B, T=45 min, 0% A, 100% B
Flow=40 mL/min, UV Detection at 220 nm
The fractions containing product were combined and the solvents were removed by lyophilization.

Pressurized silica gel column chromatography (flash chromatography) using 230–400 mesh silica gel was performed according to the method of Still, Kahn, and Mitra (J. Org. Chem. (1978) vol. 43, p.2923).

EXAMPLE 1

1-((1-(2,4,6-Trimethoxybenzoyl)piperidin-4-yl)-1,2-dihydro-4(H)-3,1-benzoxazin-2-one

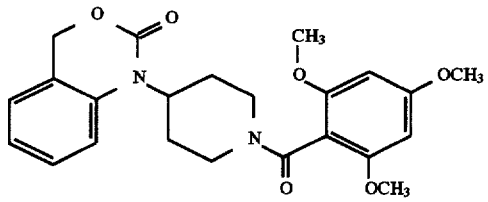

Step 1:

To a stirred, 0° C. solution of 4-piperidinone hydrochloride hydrate (50 g; 0.33 mol) in DMF (500 mL) was added di-t-butyldicarbonate (64 g; 0.29 mol) followed by a dropwise addition of DIEA (63 mL; 0.36 mol). After the addition of DIEA was complete, the reaction was allowed to gradually warm to ambient temperature over 4 h and stirring was continued for 20 h. The DMF was removed under reduced pressure and the residue was dissolved in EtOAc (1000 mL) and washed with 5% aqueous citric acid (2×500 mL), water (250 mL), and saturated aqueous $NaHCO_3$ (500 mL). The EtOAc layer was dried ($Na_2SO_4$), filtered, and the EtOAc was removed under reduced pressure. The residue was boiled in ether (ca. 250 mL) until the solid had dissolved. Cooling gave N-t-butyloxycarbonyl-4-piperidinone as white crystals (47 g; 80% yield).

Step 2:

N-t-butyloxycarbonyl-4-piperidinone (20 g, 0.10 mol) from Step 1, 2-aminobenzyl alcohol (13 g, 0.11 mol), and acetic acid (14 mL, 0.22 mol) were dissolved in dry toluene (500 mL). The solution was refluxed under inert atmosphere with azeotropic removal of water for 16 h. The solution was cooled to ambient temperature and to it was added $NaBH_3CN$ (14 g, 0.22 mol) and dry THF (200 mL). The reaction was stirred at ambient temperature for 24 h. The reaction was concentrated under reduced pressure and the residue was dissolved in EtOAc (750 mL). The EtOAc layer was washed with saturated aqueous $NaHCO_3$ (4×500 mL) and brine (250 mL). The EtOAc layer was dried ($MgSO_4$), filtered, and the solvent was removed under reduced pressure. The residue was purified by pressurized silica gel column chromatography, using a gradient elution of 15–30% EtOAc-hexanes. 1-t-Butyloxycarbonyl-4-((2-hydroxymethyl)phenylamino)-piperidine was obtained as a gum (24 g, 78% yield).

Step 3:

1-t-Butyloxycarbonyl-4-((2-hydroxymethyl) phenylamino)piperidine (24 g, 78 mmol) from Step 2 was dissolved in dry THF (250 mL) and cooled to 0° C. To the solution was added DIEA (41 mL, 0.24 mol) and triphosgene (8.54 g, 28.8 mmol). The reaction was stirred at 0° C. for 1 h, and then at ambient temperature for 72 h. Ether (250 mL) was added, the mixture was cooled to 0° C. for 3 h and then filtered to remove the hydrochloride salt of DIEA. The filtrate solvents were removed under reduced pressure and the residue was dissolved in EtOAc (750 mL). The EtOAc solution was washed with 5% aqueous citric acid (2×500 mL), water (250 mL), and saturated aqueous $NaHCO_3$ (2×500 mL). The EtOAc layer was dried ($MgSO_4$), filtered, and the solvent was removed under reduced pressure. The residue was boiled in ether (ca. 200 mL) until the solid had dissolved. Cooling overnight gave 1-((1-t-butyloxycarbonyl)piperidin-4-yl)-1,2-dihydro-4(H)-3,1-benzoxazin-2-one as off-white crystals (19 g; 75% yield).

Step 4:

A stirred solution of 1-((1-t-Butyloxycarbonyl)-piperidin-4-yl)-1,2-dihydro-4(H)-3,1-benzoxazin-2-one (19 g, 57 mmol) from Step 4 in EtOAc (500 mL) was cooled to 0° C. HCl gas was bubbled through the solution for 30 min. Stirring was continued at 0° C. for 1 h, during which time a precipitate had formed, and then at ambient temperature for 1 h. The stirred suspension was cooled to 0° C. and cold ether (250 mL) was added. After 1 h at 0° C., the solid was collected by filtration. The solid was dried under reduced pressure for 18 h, giving the hydrochloride salt of 1-(4-piperidinyl)-1,2-dihydro-4(H)-3,1-benzoxazin-2-one as an off-white solid (14 g, 91% yield).

Step 5:

To a solution of the hydrochloride salt of 1-(4-piperidinyl)-1,2-dihydro-4(H)-3,1-benzoxazin-2-one (150 mg, 0.559 mmol) from Step 4 in DMF (10 mL) was added DIEA (0.30 mL, 1.7 mmol), HOBT (92 mg, 0.60 mmol), EDC (140 mg, 0.73 mmol), and 2,4,6-trimethoxybenzoic acid (130 mg, 0.62 mmol). The reaction was stirred at ambient temperature for 48 h and the solvent was removed under reduced pressure. The residue was dissolved in EtOAc (50 mL) and washed with saturated aqueous $NaHCO_3$ (3×50 mL). The EtOAc layer was dried ($MgSO_4$), filtered, and the solvent was removed under reduced pressure. The residue was purified by pressurized silica gel column chromatography using a gradient elution of 1–3% MeOH-$CHCl_3$. The title compound was obtained as a white solid (167 mg, 70% yield).

Analysis calculated for ($C_{23}H_{26}N_2O_6$, 0.6 $H_2O$) C, 63.17; H, 6.27; N, 6.41 Found C, 63.13; H, 5.98; N, 6.14 TLC: $R_f$=0.37 (98:2 $CHCl_3$:MeOH) HPLC (method A): retention time 7.77 min FAB MS: m/z 427 ($M^+$+H)

EXAMPLE 2

1-((1-(2-methylthiobenzoyl)piperidin-4-yl)-1,2-dihydro-4(H)-3,1-benzoxazin-2-one

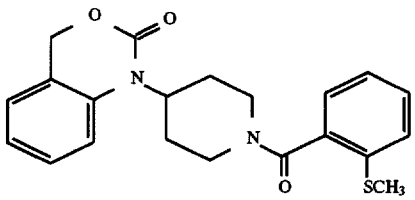

The title compound was prepared by the procedure of Step 5 in Example 1 using 2-methylthiobenzoic acid in place of 2,4,6-trimethoxybenzoic acid. The crude product was purified by preparative reverse phase HPLC. The title compound was obtained as a white solid by lyophilization (80% yield).

Analysis calculated for ($C_{21}H_{22}N_2O_3S$, 0.5 TFA, 0.2 $H_2O$) C, 59.63; H, 5.21; N, 6.32 Found C, 59.59; H, 5.15; N, 6.44 HPLC (method A): retention time 8.09 min FAB MS: m/z 383 (M$^+$+H)

EXAMPLE 3

1-((1-(2-Pyridylcarbonyl)piperidin-4-yl)-1,2-dihydro-4(H)-3,1-benzoxazin-2-one

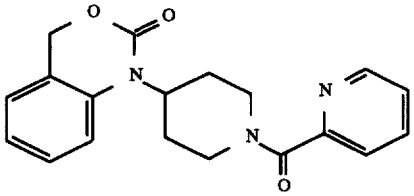

The title compound was prepared by the procedure of Step 5 in Example 1 using pyridine-2-carboxylic acid in place of 2,4,6-trimethoxybenzoic acid. The crude product was purified by pressurized silica gel column chromatography using a gradient elution of 1–3% MeOH-CHCl$_3$. The title compound was obtained as a white solid after lyophilization from dioxane (74% yield).

Analysis calculated for ($C_{19}H_{19}N_3O_3$, 0.2 dioxane, 0.2 $H_2O$) C, 66.31; H, 5.90; N, 11.72 Found C, 66.32; H, 5.86; N, 11.72 TLC: R$_f$=0.38 (97:3 DCM:MeOH) HPLC (method A): retention time 5.73 min FAB MS: m/z 338 (M$^+$+H)

EXAMPLE 4

1-((1-(2-Indolecarbonyl)piperidin-4-yl)-1,2-dihydro-4(H)-3,1-benzoxazin-2-one

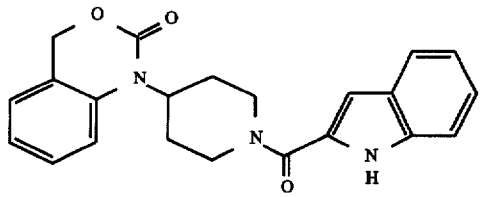

The title compound was prepared by the procedure of Step 5 in Example 1 using indole-2-carboxylic acid in place of 2,4,6-trimethoxybenzoic acid. The crude product was purified by pressurized silica gel column chromatography using 1:1 EtOAc:hexane as eluant. The title compound was obtained as a white solid after trituration from ether and filtration (82% yield).

Analysis calculated for ($C_{22}H_{21}N_3O_3$, 0.15 ether) C, 70.22; H, 5.87; N, 10.87 Found C, 69.85; H, 5.70; N, 10.96 TLC: R$_f$=0.30 (1:1 EtOAc:hexane) HPLC (method A): retention time 8.42 min FAB MS: m/z 376 (M$^+$+H)

EXAMPLE 5

1-((1-(2-Benzylbenzoyl)piperidin-4-yl)-1,2-dihydro-4(H)-3,1-benzoxazin-2-one

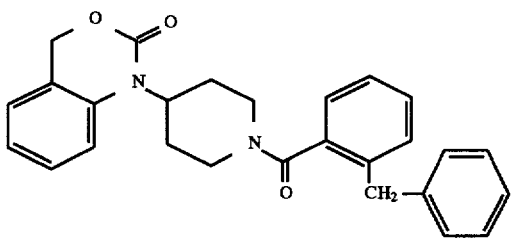

The title compound was prepared by the procedure of Step 5 in Example 1 using 2-benzylbenzoic acid in place of 2,4,6-trimethoxybenzoic acid. The crude product was purified by pressurized silica gel column chromatography using 1:1 EtOAc:hexane as eluant. The title compound was obtained as a white solid after lyophilization from dioxane (85% yield).

Analysis calculated for ($C_{27}H_{26}N_2O_3$, 0.15 dioxane, 0.5 $H_2O$) C, 75.22; H, 6.24; N, 6.36 Found C, 75.24; H, 6.12; N, 6.09 TLC: R$_f$=0.30 (1:1 EtOAc:hexane) HPLC (method A): retention time 9.58 min FAB MS: m/z 427 (M$^+$+H)

EXAMPLE 6

1-((1-(2-(1,2,3,4-Tetrahydronaphthyl)carbonyl)piperidin-4-yl)-1,2-dihydro-4(H)-3,1-benzoxazin-2-one

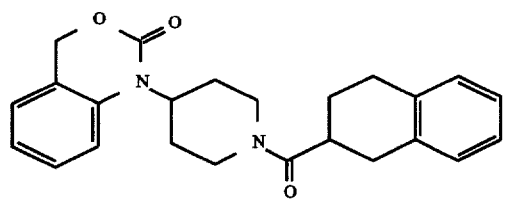

The title compound was prepared by the procedure of Step 5 in Example 1 using 1,2,3,4-tetrahydronaphthalene-2-carboxylic acid in place of 2,4,6-trimethoxybenzoic acid. The crude product was purified by pressurized silica gel column chromatography using 1:1 EtOAc:hexane as eluant. The title compound was obtained as a whim solid after lyophilization from dioxane (82% yield).

Analysis calculated for (C$_{24}$H$_{26}$N$_2$O$_3$, 0.45 dioxane) C, 72.03; H, 6.94; N, 6.51 Found C, 72.14; H, 6.72; N, 6.47 TLC: R$_f$=0.38 (3:2 EtOAc:hexane) HPLC (method A): retention time 8.99 min FAB MS: m/z 391 (M$^+$+H)

EXAMPLE 7

1-(1-(Cinnamoyl)piperidin-4-yl)-1,2-dihydro-4(H)-3,1-benzoxazin-2-one

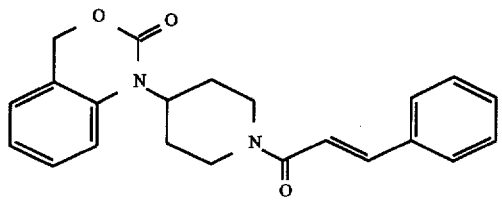

The title compound was prepared by the procedure of Step 5 in Example 1 using cinnamic acid in place of 2,4,6-trimethoxybenzoic acid. The crude product was purified by pressurized silica gel column chromatography using 1:1 EtOAc:hexane as eluant. The title compound was obtained as a foam from EtOAc (86% yield).

Analysis calculated for(C$_{22}$H$_{22}$N$_2$O$_3$, 0.3 EtOAc) C, 71.65; H, 6.32; N, 7.20 Found C, 71.49; H, 6.19; N, 7.53 TLC: R$_f$=0.25 (3:2 EtOAc:hexane) HPLC (method A): retention time 8.27 min FAB MS: m/z 389 (M$^+$+H)

EXAMPLE 8

1-(1-(4-Oxocyclohexylcarbonyl)piperidin-4-yl)-1,2-dihydro-4(H)-3,1-benzoxazin-2-one

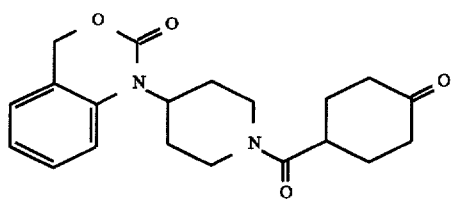

The title compound was prepared by the procedure of Step 5 in Example 1 using cyclohexanone-4-carboxylic acid in place of 2,4,6-trimethoxybenzoic acid. The crude product was purified by pressurized silica gel column chromatography using a gradient elution of 1–4% MeOH:CHCl$_3$. The title compound was obtained as a foam from EtOAc (77% yield).

Analysis calculated for (C$_{20}$H$_{24}$N$_2$O$_4$, 0.45 EtOAc) C, 66.10; H, 7.02; N, 7.07 Found C, 65.85; H, 6.78; N, 7.45 TLC: R$_f$=0.53 (95:5 MeOH:CHCl$_3$) HPLC (method A): retention time 5.95 min FAB MS: m/z 357 (M$^+$+H)

EXAMPLE 9

1-(1-(4-((5-Benzimidazolylcarbonyl)amino)phenylacetyl)piperidin-4-yl)-1,2-dihydro-4(H)-3,1-benzoxazin-2-one

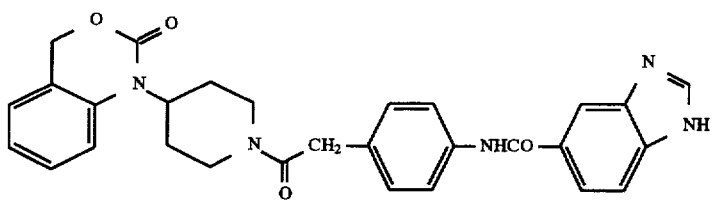

The title compound was prepared by the procedure of Step 5 in Example 1 using 4-((5-benzimidazolylcarbonyl)amino)phenylacetic acid in place of 2,4,6-trimethoxybenzoic acid. The crude product was purified by pressurized silica gel column chromatography using a gradient elution of 1–4% A:CHCl$_3$, where the A solvent is 10% NH$_4$OH:MeOH. The title compound was obtained as a white solid by lyophilization from dioxane (68% yield).

Analysis calculated for (C$_{29}$H$_{27}$N$_5$O$_4$, 0.85 dioxane, 1.25 H$_2$O) C, 64.11; H, 6.03; N, 11.49 Found C, 64.08; H, 5.68; N, 11.49 TLC: R$_f$=0.30 (98:2:0.2 CHCl$_3$:MeOH:NH$_4$OH) HPLC (method A): retention time 5.96 min FAB MS: m/z 510 (M$^+$+H)

EXAMPLE 10

1-(1-(4-(7,7-Dimethyl-2-oxo[2.2.1]bicycloheptan-1-ylmethylsulfonyl)piperidin-4-yl)-1,2-dihydro-4(H)-3,1-benzoxazin-2-one

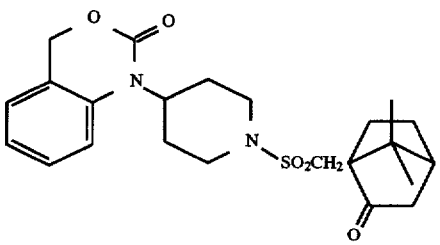

To a 0° C. stirred solution of the hydrochloride salt of 3-(4-piperidinyl)benzoxazin-2-one from Example 1, Step 4

(150 mg, 0.559 mmol) in CHCl₃ (20 mL) was added camphor-10-sulfonyl chloride (154 mg, 0.616 mmol) and DIEA (0.30 mL, 1.7 mmol). The reaction was warmed to ambient temperature and stirred for 1 h. The solvent was removed under reduced pressure. The residue was dissolved in EtOAc (50 mL) and washed with saturated aqueous NaHCO₃ (3×50 mL). The EtOAc layer was dried (MgSO₄), filtered, and the solvent was removed under reduced pressure. The residue was purified by pressurized silica gel column chromatography using 1:1 EtOAc:hexanes as eluant. The title compound was obtained as a white solid by lyophilization from dioxane (207 mg, 83% yield).

Analysis calculated for($C_{23}H_{30}N_2O_5S$, 0.1 dioxane) C, 61.71; H, 6.82; N, 6.15 Found C, 61.73; H, 6.83; N, 5.81 TLC: $R_f$=0.35 (1:1 EtOAc:hexanes) HPLC (method A): retention time 8.83 min FAB MS: m/z 456 ($M^+$+H)

EXAMPLE 11

1-(1-(4-(3-(t-Butyloxycarbonylamino)propoxy)-2-methoxybenzoyl)piperidin-4-yl)-1,2-dihydro-4(H)-3,1-benzoxazin-2-one

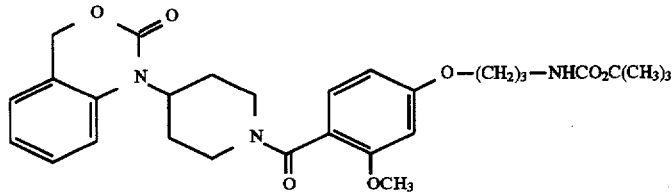

Step 1:

To a 0° C. stirred solution of 2,4-dihydroxybenzoic acid methyl ester (5 g, 30 mmol) in dry DMF (100 mL) was added sodium hydride (1.2 g of a 60% suspension in mineral oil, 30 mmol). After 1 h, the solution was warmed to ambient temperature and stirred for 1 h. To the solution was added N-t-butyloxycarbonyl-3-bromopropylamine (10.6 g, 45 mmol). The reaction was stirred at ambient temperature for 24 and the solvent was removed under reduced pressure. The residue was dissolved in EtOAc (250 mL) and washed with water (2×200 mL) and brine (100 mL). The EtOAc layer was dried (MgSO₄), filtered, and the solvent was removed under reduced pressure. The residue was purified by pressurized silica gel column chromatography using 1:4 EtOAc:hexanes as eluant. The product-containing fractions were pooled and the solvent was removed under reduced pressure. The resulting oil crystallized from ether to give 4-(3-(t-butyloxycarbonylamino)propyloxy)-2-hydroxybenzoic acid methyl ester (51% yield).

Step 2:

To a 0° C. solution of 4-(3-(t-butyloxycarbonylamino) propyloxy)-2-hydroxybenzoic acid methyl ester (3.0 g, 9.2 mmol) from Step 1 in dry DMF (25 mL) was added sodium hydride (0.39 g of a 60% suspension in mineral oil, 9.7 mmol). The reaction was stirred at 0° C. for 1 h, when iodomethane (1.0 mL, 16 mmol) was added. The reaction was then warmed to ambient temperature. After 24 h, acetic acid (1 mL) was added and the solvent was removed under reduced pressure. The residue was dissolved in EtOAc (150 mL) and washed with saturated aqueous NaHCO₃ (3×100 mL). The EtOAc layer was dried (MgSO₄), filtered, and the solvent was removed under reduced pressure. The residue was purified by pressurized silica gel column chromatography using 3:7 EtOAc:hexanes as eluant. 4-(3-(t-Butyloxycarbonylamino)propyloxy)-2-methoxybenzoic acid methyl ester was obtained as an oil (85% yield).

Step 3:

4-(3-(t-Butyloxycarbonylamino)-propyloxy)-2-methoxybenzoic acid methyl ester (2.63 g, 7.76 mmol) from Step 2 was dissolved in MeOH (25 mL) and heated with 1N NaOH (15 mL, 15 mmol)) at 50° C. for 18 h. The reaction was cooled to ambient temperature and 5% aqueous citric acid (10 mL) was added. The mixture was extracted with EtOAc (3×75 mL). The combined EtOAc phases were washed with water (2×50 mL) and brine (50 mL), dried (MgSO₄), filtered, and the solvent was removed under reduced pressure to give 4-(3-(t-butyloxycarbonylamino) propyloxy)-2-methoxybenzoic acid as a white foam (95% yield).

Step 4:

4-(3-(t-Butyloxycarbonylamino)-propyloxy)-2-methoxybenzoic acid was coupled to the hydrochloride salt of 1-(4-piperidinyl)-1,2-dihydro-4(H)-3,1-benzoxazin-2-one using the EDC/HOBT procedure described in Step 5 of Example 1. The crude product was purified by pressurized silica gel column chromatography using a gradient elution of 1–4% MeOH-CHCl₃. The title compound was obtained as a white foam by evaporation of a DCM solution under reduced pressure (86% yield).

Analysis calculated for ($C_{29}H_{37}N_3O_7$, 0.45 $CH_2Cl_2$) C, 61.21; H, 6.61; N, 7.27 Found C, 61.17; H, 6.56; N, 7.37 TLC: $R_f$=0.34 (3:97 MeOH:CHCl₃) HPLC (method A): retention time 8.96 min FAB MS: m/z 540 ($M^+$+H)

EXAMPLE 12

1-(1-(4-(3-Aminopropoxy)-2-methoxybenzoyl) piperidin-4-yl)-1,2-dihydro-4(H)-3,1-benzoxazin-2-one

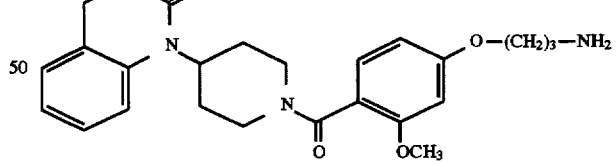

1-(1-(4-(3-(t-Butyloxycarbonylamino)propoxy)-2-methoxybenzoyl)piperidin-4-yl)-1,2-dihydro-4(H)-3,1-benzoxazin-2-one from Example 11 was N-deprotected with HCl gas in EtOAc using the procedure of Example 1, Step 4. The hydrochloride salt of the title compound was obtained as a white solid (92% yield). A portion of the sample was converted to the free base by partitioning between CHCl₃ and saturated aqueous NaHCO₃. The free base of the title compound was obtained as a foam by evaporation of a CHCl₃ solution under reduced pressure.

Analysis calculated for ($C_{24}H_{29}N_3O_5$ 0.9 CHCl₃) C, 54.67; H, 5.51; N, 7.68 Found C, 54.61; H, 5.67; N, 7.81

TLC: $R_f$=0.29 (97:3:0.3 CHCl$_3$:MeOH:NH$_4$OH) HPLC (method A): retention time 5.93 min FAB MS: m/z 440 (M$^+$+H)

EXAMPLE 13

1-(1-(4-(3-((N-t-Butyloxycarbonyl-4-piperidinylcarbonyl)amino)propoxy)-2-methoxybenzoyl)piperidin-4-yl)-1,2-dihydro-4(H)-3,1-benzoxazin-2-one

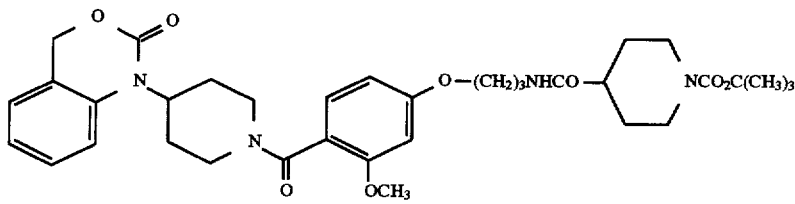

N-t-Butoxycarbonylpiperidine-4-carboxylic acid was coupled to 1-(1-(4-(3-minopropoxy)-2-methoxybenzoyl)piperidin-4-yl)-1,2-dihydro-4(H)-3,1-benzoxazin-2-one from Example 12 using the EDC/HOBT procedure of Step 5 in Example 1. The crude product was purified by pressurized silica gel column chromatography using a gradient elution of 2–5% MeOH-CHCl$_3$. The title compound was obtained as a white powder by lyophilization from dioxane (90% yield).

Analysis calculated for (C$_{35}$H$_{46}$N$_4$O$_8$ 0.3 dioxane, 0.65 H$_2$O) C, 63.11; H, 7.27; N, 8.13 Found C, 63.12; H, 6.99; N, 8.11 TLC: $R_f$=0.39 (97:3 CHCl$_3$:MeOH) HPLC (method A): retention time 8.60 min FAB MS: m/z 651 (M$^+$+H)

EXAMPLE 14

1-(1-(4-(3-(4-Piperidinylcarbonylamino)propoxy)-2-methoxybenzoyl)piperidin-4-yl)-1,2-dihydro-4(H)-3,1-benzoxazin-2-one

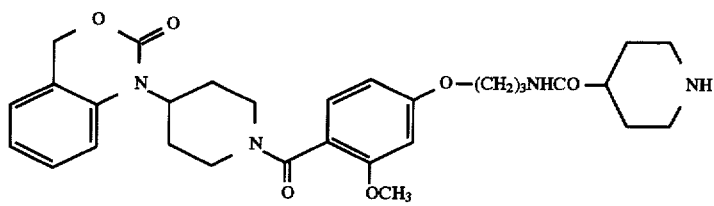

1-(1-(4-(3-((N-t-Butyloxycarbonyl-4-piperidinylcarbonyl)amino)propoxy)-2-methoxybenzoyl)piperidin-4-yl)-1,2-dihydro-4(H)- 3,1-benzoxazin-2-one from Example 13 was N-deprotected with HCl gas in EtOAc using the procedure given in Step 4 of Example 1. The hydrochloride salt of the title compound was obtained as a white solid (90% yield).

Analysis calculated for(C$_{30}$H$_{38}$N$_4$O$_6$, 2.05 HCl, 2.5 EtOAc) C, 56.81; H, 7.16; N, 6.63 Found C, 56.86; H, 7.31; N, 6.57 TLC: $R_f$=0.27 (80:20:2 CHCl$_3$:MeOH:NH$_4$OH) HPLC (method A): retention time 6.24 min FAB MS: m/z 551 (M$^+$+H)

EXAMPLE 15

1-(1-(4-(3-(4-Piperidinylcarbonylamino)propoxy)-6-methoxy-3-chlorobenzoyl)piperidin-4-yl)-1,2-dihydro-4(H)-3,1-benzoxazin-2-one

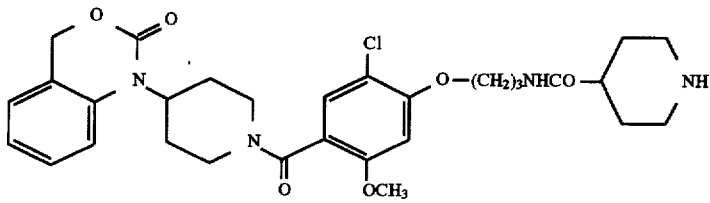

1-(1-(4-(3-((N-t-Butyloxycarbonyl-4-piperidinylcarbonyl)amino)propoxy)-2-methoxybenzoyl)piperidin-4-yl)-1,2-dihydro-4(H)-3,1-benzoxazin-2-one from Example 13 was N-deprotected with HCl gas in EtOAc using the procedure given in Step 4 of Example 1. The anticipated product, 1-(1-(4-(3-(4-piperidinylcarbonylamino)propoxy)-2-methoxybenzoyl)piperidin-4-yl)-1,2-dihydro-4(H)-3,1 -benzoxazin-2-one (Example 14) was obtained along with an equal amount of the title compound due to contamination of the HCl gas with chlorine gas. The two products were separated by pressurized silica gel column chromatography using a gradient elution of 10–20% A-CHCl$_3$, where solvent A was 10% NH$_4$OH-MeOH. The title compound was the faster eluting of the two-component mixture. The title compound was obtained as a foam by evaporation of a MeOH solution under reduced pressure.

Analysis calculated for($C_{30}H_{37}ClN_4O_6$, 1.6 $SiO_2$) C, 52.89; H, 5.47; N, 8.22 Found C, 53.10; H, 5.08; N, 8.53 TLC: $R_f$=0.25 (80:20:2 DCM:MeOH:$NH_4OH$) HPLC (method A): retention time 6.57 min FAB MS: m/z 585, 587 ($M^+$+H)

EXAMPLE 16

1-(1-(4-(3-((4-Imidazolylmethylcarbonyl)amino) propoxy)-2-methoxybenzoyl)piperidin-4-yl)-1,2-dihydro-4(H)-3,1-benzoxazin-2-one

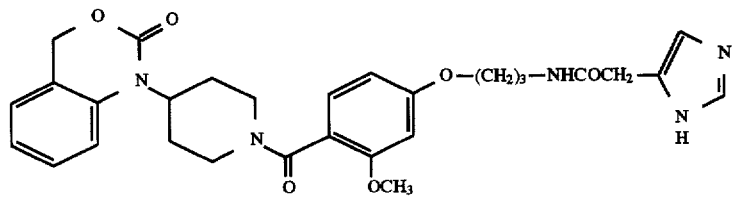

4-Imidazoleacetic acid hydrochloride was coupled to 1-(1-(4-(3-minopropoxy)-2-methoxybenzoyl)piperidin-4-yl)-1,2-dihydro-4(H)-3,1-benzoxazin-2-one from Example 12 using the EDC/HOBT procedure of Step 5 in Example 1. The crude product was purified by pressurized silica gel column chromatography using a gradient elution of 1–4% A-$CHCl_3$, where solvent A is 10% MeOH-$NH_4OH$. The title compound was obtained as a white powder by lyophilization from dioxane (74% yield).

Analysis calculated for ($C_{29}H_{33}N_5O_6$, 0.7 dioxane, 2.15 $H_2O$) C, 58.93; H, 6.67; N, 10.81 Found C, 58.92; H, 6.28; N, 10.59 TLC: $R_f$=0.32 (97:3:0.3 $CHCl_3$:MeOH:$NH_4OH$) HPLC (method A): retention time 6.06 min FAB MS: m/z 548 ($M^+$+H)

EXAMPLE 17

1-(1-(4-(3-((Methylsulfonyl)amino)propoxy)-2-methoxybenzoyl)piperidin-4-yl)-1,2-dihydro-4(H)-3,1-benzoxazin-2-one

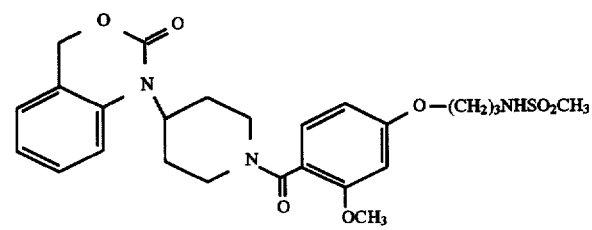

To a 0° C. stirred solution of 1-(1-(4-(3-aminopropoxy)-2-methoxybenzoyl)piperidin-4-yl)-1,2-dihydro-4(H)-3,1-benzoxazin-2-one from Example 12 (150 mg, 0.342 mmol) and DIEA (0.089 mL, 0.51 mmol) in DCM (10 mL) was added methanesulfonyl chloride (0.032 mL, 0.41 mmol). The solution was warmed to ambient temperature and stirred for 18 h. The solvent was removed under reduced pressure and the residue was dissolved in EtOAc and washed with saturated aqueous $NaHCO_3$. The EtOAc layer was dried ($MgSO_4$), filtered, and the solvent was removed under reduced pressure. The residue was purified by pressurized silica gel column chromatography using a gradient elution of 1–4% MeOH-DCM. The title compound was obtained as a white powder by lyophilization from dioxane (74% yield).

Analysis calculated for ($C_{25}H_{31}N_3O_7S$, 0.55 dioxane) C, 57.71; H, 6.30; N, 7.42 Found C, 58.10; H, 6.34; N, 7.16 TLC: $R_f$=0.41 (97:3 DCM:MeOH) HPLC (method A): retention time 7.14 min FAB MS: m/z 518 ($M^+$+H)

EXAMPLE 18

1-(1-(4-(3-(Acetylamino)propoxy)-2-methoxybenzoyl)piperidin-4-yl)-1,2-dihydro-4(H)-3,1-benzoxazin-2-one

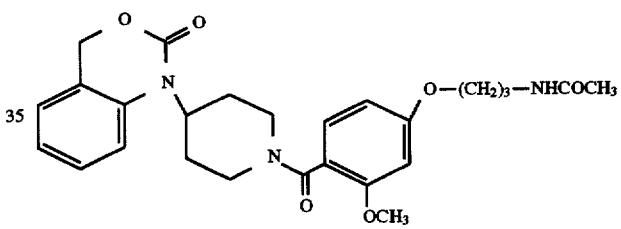

To a solution of 1-(1-(4-(3-aminopropoxy)-2-methoxybenzoyl)piperidin-4-yl)-1,2-dihydro-4(H)-3,1-benzoxazin-2-one from Example 12 (150 mg, 0.342 mmol) and DIEA (0.089 mL, 0.51 mmol) in DCM (10 mL) was added acetic anhydride (0.048 mL, 0.51 mmol). The solution was stirred at ambient temperature for 18 h. The solvent was removed under reduced pressure and the residue was dissolved in EtOAc and washed with saturated aqueous $NaHCO_3$. The EtOAc layer was dried ($MgSO_4$), filtered, and the solvent was removed under reduced pressure. The residue was purified by pressurized silica gel column chromatography using a gradient elution of 1–4% MeOH-$CHCl_3$. The title compound was obtained as a white powder by lyophilization from dioxane (90% yield).

Analysis calculated for ($C_{26}H_{31}N_3O_6$, 0.45dioxane, 0.6 $H_2O$) C, 62.76; H, 6.78; N, 7.90 Found C, 62.70; H, 6.81; N, 7.91 TLC: $R_f$=0.43 (96:4 $CHCl_3$:MeOH) HPLC (method A): retention time 6.80 min FAB MS: m/z 482 ($M^+$+H)

EXAMPLE 19

1-(1-(4-(3-((1-(t-Butyloxybarbonyl)piperazin-4-ylcarbonyl)amino)propoxy)-2-methoxybenzoyl) piperidin-4-yl)-1,2-dihydro-4(H)-3,1-benzoxazin-2-one

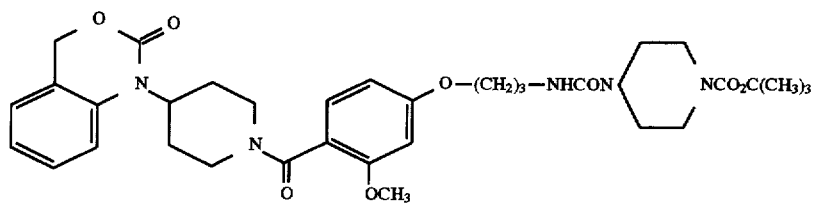

Step 1:

To a stirred 0° C. solution of 1-(1-(4-(3-aminopropoxy)-2-methoxybenzoyl)piperidin-4-yl)-1,2-dihydro-4(H)-3,1-benzoxazin-2-one from Example 12 (400 mg, 0.911 mmol) and DIEA (0.175 mL, 1.00 mmol) in DCM (60 mL) was added p-nitrophenylchloroformate (2.02 mg, 1.00 mmol). The solution was stirred at 0° C. for 1 h and then at ambient temperature for 1 h. The solvent was removed under reduced pressure and the residue was dissolved in EtOAc (150 mL) and washed with 5% aqueous citric acid (75 mL) and brine (75 mL). The EtOAc layer was dried (MgSO$_4$), filtered, and the solvent was removed under reduced pressure to give 1-(1-(4-(3-(p-nitrophenoxycarbonylamino)propoxy)-2-methoxybenzoyl)piperidin-4-yl)-1,2-dihydro-4(H)-3,1-benzoxazin-2-one as a foam.

Step 2:

To a solution of N-t-butyloxycarbonylpiperazine (183 mg, 0.983 mmol) and DIEA (0.348, 2.00 mL) in DMF (50 mL) was added 1-(1-(4-(3-(p-nitrophenoxycarbonylamino)propoxy)-2-methoxybenzoyl)piperidin-4-yl)-1,2-dihydro-4(H)-3,1-benzoxazin-2-one (540 mg, 0.894 mmol) from Step 1 above. The reaction was stirred at ambient temperature for 24 h. The solvent was removed under reduced pressure. The residue was dissolved in EtOAc (150 mL) and washed with saturated aqueous NaHCO$_3$ (4×75 mL). The crude product was purified by pressurized silica gel column chromatography using a gradient elution of 1–4% MeOH-DCM. The title compound was obtained as a foam by evaporation of a DCM solution under reduced pressure (90% yield).

Analysis calculated for (C$_{34}$H$_{45}$N$_5$O$_8$, 1.5 CH$_2$Cl$_2$) C, 54.72; H, 6.21; N, 8.99 Found C, 54.73; H, 6.08; N, 9.30 TLC: R$_f$=0.46 (96:4 DCM:MeOH) HPLC (method A): retention time 8.46 min FAB MS: m/z 652 (M$^+$+H)

EXAMPLE 20

1-(1-(4-(3-((1-Piperazinylcarbonyl)amino)propoxy)-2-methoxybenzoyl)piperidin-4-yl)-1,2-dihydro-4(H)-3,1-benzoxazin-2-one

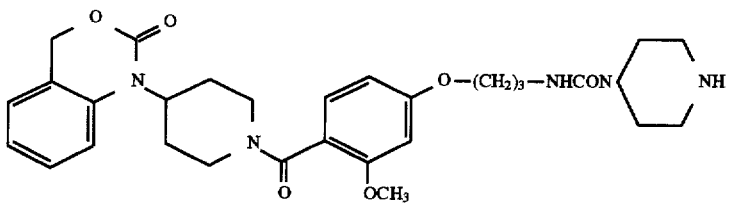

1-(1-(4-(3-((1-(t-Butyloxybarbonyl)piperazin-4-yl-carbonyl)amino)propoxy)-2-methoxybenzoyl)piperidin-4-yl)-1,2-dihydro-4(H)-3,1-benzoxazin-2-one from Example 19 was N-deprotected with HCl gas in EtOAc using the procedure given in Step 4 of Example 1. The HCl salt of the title compound was obtained as a white solid (91% yield).

Analysis calculated for (C$_{29}$H$_{37}$N$_5$O$_6$, 2.05 HCl, 2.35 EtOAc) C, 55.34; H, 6.98; N, 8.45 Found C, 55.29; H, 7.03; N, 8.45 TLC: R$_f$=0.26 (85: 15:1.5 DCM:MeOH:NH$_4$OH) HPLC (method A): retention time 6.00 min FAB MS: m/z 552 (M$^+$+H)

EXAMPLE 21

1-(1-(4-(3-((N-Ethoxycarbonylmethyl-N-methylaminocarbonyl)amino)propoxy)-2-methoxybenzoyl)piperidin-4-yl)-1,2-dihydro-4(H)-3,1-benzoxazin-2-one

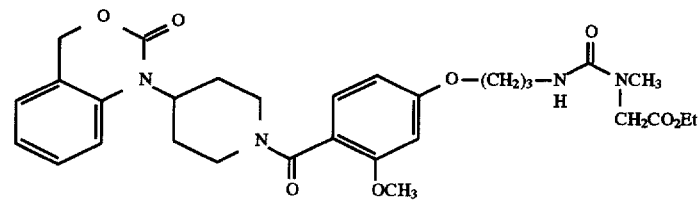

To a solution of sarcosine ethyl ester (58 mg, 0.497 mmol) and DIEA (0.174 mL, 1.00 mmol) in DMF (15 mL) was added 1-(1-(4-(3-(p-nitrophenoxycarbonylamino)propoxy)-2-methoxybenzoyl)piperidin-4-yl)-1,2-dihydro-4(H)-3,1-benzoxazin-2-one (250 mg, 0.414 mmol) from Step 1 in Example 19. The reaction was stirred at ambient temperature for 24 h. The solvent was removed under reduced pressure. The residue was dissolved in EtOAc (150 mL) and washed with saturated aqueous NaHCO$_3$ (4×75 mL). The crude product was purified by pressurized silica gel column chromatography using a gradient elution of 1–4% MeOH- DCM. The title compound was obtained as a foam by evaporation of a DCM solution under reduced pressure (86% yield).

Analysis calculated for ($C_{30}H_{38}N_4O_8$, 0.85 $CH_2Cl_2$) C, 56.58; H, 6.11; N, 8.56 Found C, 56.61; H, 6.04; N, 8.74 TLC: $R_f$=0.50 (96:4 DCM:MeOH) HPLC (method A): retention time 7.56 min FAB MS: m/z 583 ($M^+$+H)

EXAMPLE 22

1-(1-(4-(3-(1-Methylimidazoline-2,4-dione-3-yl)propoxy)-2-methoxybenzoyl)piperidin-4-yl)-1,2-dihydro-4(H)-3,1-benzoxazin-2-one

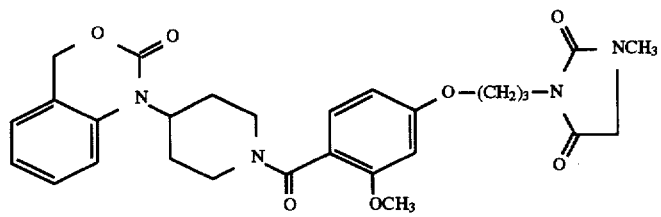

To a stirred, 0° C. solution of 1-(1-(4-(3-((N-ethoxycarbonylmethyl-N-methylaminocarbonyl)amino)propoxy)-2-methoxybenzoyl)piperidin-4-yl)-1,2-dihydro-4(H)-3,1-benzoxazin-2-one (186 mg, 0.320 mmol) from Example 21 in MeOH (30 mL) was added NaH (19 mg of a 60% suspension in mineral oil, 0.48 mmol). The reaction was stirred at 0° C. for 1 h and at ambient temperature for 24 h. Acetic acid (1 mL) was added and the solvents were removed under reduced pressure. The crude product was purified by pressurized silica gel column chromatography using a gradient elution of 1–3% MeOH-DCM. The title compound was obtained as a foam by evaporation of a DCM solution under reduced pressure (80% yield).

Analysis calculated for ($C_{28}H_{32}N_4O_7$, 1.05 $CH_2Cl_2$) C, 55.75; H, 5.49; N, 8.95 Found C, 55.80; H, 5.26; N, 9.25 TLC: $R_f$=0.42 (97:3 DCM:MeOH) HPLC (method A): retention time 7.11 min FAB MS: m/z 537 ($M^+$+H)

EXAMPLE 23

1-(1-(4-(3-(Acetylamino)propoxy)benzoyl)piperidin-4-yl)-1,2-dihydro-4(H)-3,1-benzoxazin-2-one

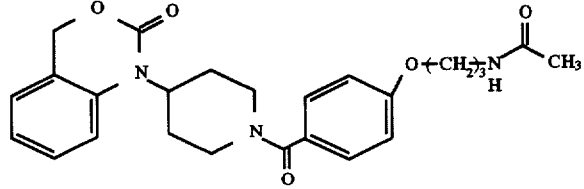

1-(1-(4-(3-(t-Butyloxycarbonylamino)propoxy)benzoyl)piperidin-4-yl)-1,2-dihydro-4(H)-3,1-benzoxazin-2-one was prepared beginning with ethyl 4-hydroxybenzoate using the procedures given in Steps 1, 3, and 4 of Example 11. 1-(1-(4-(3-(t-Butyloxycarbonylamino)propoxy)benzoyl)piperidin-4-yl)-1,2-dihydro-4(H)-3,1-benzoxazin-2-one was N-deprotected with HCl gas in EtOAc by the procedure of Step 4 of Example 1 to give 3-(1-(4-(3-aminopropoxy)benzoyl)piperidin-4-yl)benzoxazin-2-one, which was acetylated by the procedure of Example 18. The crude product was purified by pressurized silica gel column chromatogra-phy using a gradient elution of 1–4% MeOH-DCM. The title compound was obtained as a white solid by lyophilization from dioxane (89% yield).

Analysis calculated for ($C_{25}H_{29}N_3O_5$, 0.25 dioxane, 1.2 $H_2O$) C, 63.06; H, 6.80; N, 8.49 Found C, 63.01; H, 6.40; N, 8.40 TLC: $R_f$=0.38 (96:4 DCM:MeOH) HPLC (method A): retention time 6.60 min FAB MS: m/z 452 ($M^+$+H)

EXAMPLE 24

1-(1-(4-(3-(N-Methyl(acetylamino))propoxy)benzoyl)piperidin-4-yl)-1,2-dihydro-4(H)-3,1-benzoxazin-2-one

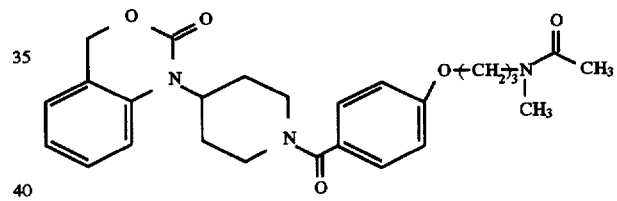

To a strirred, 0° C. solution of 1-(1-(4-(3-(acetylamino)propoxy)benzoyl)piperidin-4-yl)-1,2-dihydro-4(H)-3,1-benzoxazin-2-one (80 mg, 0.18 mmol) from Example 23 and iodomethane (0.010 mL, 0.62 mmol) in dry DMF (3 mL) was added sodium hydride (15 mg of a 60% suspension in mineral oil, 0.38 mmol). The reaction was stirred at 0° C. for 1 h and at ambient temperature for 24 h. Acetic acid (0.2 mL) was added and the solvent was removed under reduced pressure. The residue was dissolved in EtOAc (50 mL) and washed with saturated aqueous $NaHCO_3$ (25 mL). The EtOAc layer was dried ($MgSO_4$), filtered, and the solvent was removed under reduced pressure. The residue was purified by pressurized silica gel column chromatography using a gradient elution of 1–4% MeOH-DCM. The title compound was obtained as a white solid by lyophilization from dioxane (68% yield).

Analysis calculated for ($C_{26}H_{31}N_3O_5$, 0.7 dioxane) C, 65.60; H, 7.00; N, 7.97 Found C, 65.57; H, 6.90; N, 8.28 TLC: $R_f$=0.41 (97:3 DCM:MeOH) HPLC (method A): retention time 7.08 min FAB MS: m/z 466 ($M^+$+H)

EXAMPLE 25

1-(1-(4-(N-t-Butoxycarbonyl-4-piperidinyloxy)-2-methoxybenzoyl)piperidin-4-yl)-1,2-dihydro-4(H)-3,1-benzoxazin-2-one

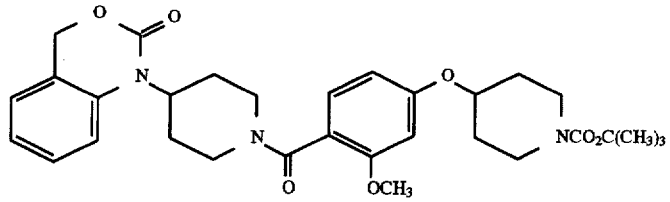

Step 1:

To a strirred, 0° C. solution of triphenylphosphine (57.2 g, 0.218 mol) and 2,4-dihydroxybenzoic acid methyl ester (29.2 g, 0.174 mol) in dry THF (200 mL) was added a solution of N-t-butyloxy-4-piperidinol (35 g, 0.174 mol) and diethylazodicarboxylate (32.9 mL, 0.209 mol) in dry THF (150 mL) dropwise over a period of 2 h. The resulting solution was slowly warmed to ambient temperature over 6 h and stirred for an additional 16 h. The solvent was removed under reduced pressure and the residue was dissolved in EtOAc (500 mL) and washed with 10% aqueous $Na_2CO_3$ (3×250 mL), water (150 mL), and brine (150 mL). The EtOAc layer was dried ($MgSO_4$), filtered, and the solvent was removed under reduced pressure. The residue was purified by pressurized silica gel column chromatography using a gradient elution of 10–25% EtOAc-hexane. 4-(N-t-Butoxycarbonyl-4-piperidinyloxy)-2-hydroxybenzoic acid methyl ester was obtained as a waxy solid (51% yield).

Step 2:

4-(N-t-Butoxycarbonyl-4-piperidinyloxy)-2-hydroxybenzoic acid methyl ester from Step 1 was methylated with iodomethane and sodium hydride in DMF using the procedure in Step 2 of Example 11. The crude product was purified by pressurized silica gel column chromatography using a gradient elution of 20–40% EtOAc-hexane. 4-(N-t-Butoxycarbonyl-4-piperidinyloxy)-2-methoxybenzoic acid methyl ester was obtained as an oil (88% yield).

Step 3:

4-(N-t-Butoxycarbonyl-4-piperidinyloxy)-2-methoxybenzoic acid methyl ester from Step 2 was saponified to the carboxylic acid with aqueous NaOH in MeOH using the procedure of Step 3 in Example 11. 4-(N-t-Butoxycarbonyl-4-piperidinyloxy)-2-methoxybenzoic acid was obtained as a foam by evaporation of a DCM solution under reduced pressure (95% yield).

Step 4:

4-(N-t-Butoxycarbonyl-4-piperidinyloxy)-2-methoxybenzoic acid was coupled to the hydrochloride salt of 1-(4-piperidinyl)1,2-dihydro-4(H)-3,1-benzoxazin-2-one using the EDC/HOBT procedure given in Step 5 of Example 1. The crude product was purified by pressurized silica gel column chromatography using a gradient elution of 1–4% MeOH-DCM. The title compound was obtained as a white foam by evaporation of a DCM solution under reduced pressure (88% yield).

Analysis calculated for ($C_{31}H_{39}N_3O_7$, 0.35 $CH_2Cl_2$, 0.1 $H_2O$) C, 63.04; H, 6.73; N, 7.04 Found C, 63.05; H, 6.77; N, 7.20 TLC: $R_f$=0.15 (98:2 DCM:MeOH) HPLC (method A): retention time 10.06 min FAB MS: m/z 566 ($M^+$+H)

EXAMPLE 26

1-(1-(4-(4-Piperidinyloxy)-2-methoxybenzoyl)piperidin-4-yl)-1,2-dihydro-4(H)-3,1-benzoxazin-2-one

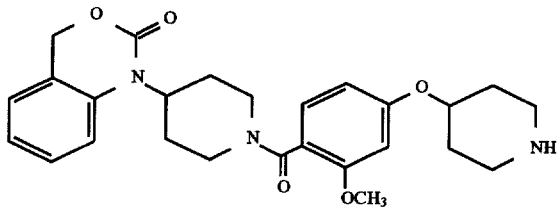

1-(1-(4-(N-t-Butoxycarbonyl-4-piperidinyloxy)-2-methoxybenzoyl)piperidin-4-yl)-1,2-dihydro-4(H)-3,1-benzoxazin-2-one from Example 25 (5.0 g, 8.8 mmol) was treated with 4N HCl in dioxane (40 mL) at ambient temperature for 1 h. The dioxane was evaporated under reduced pressure and the residue was triturated in EtOAc-ether and filtered. The solid was dried in vacuo for 24 h to give the hydrochloride salt of the title compound (93%). A small portion of this material was purified to greater than 99% homogeneity by preparative reverse phase HPLC to give, after lyophilization, the TFA salt of the title compound.

Analysis calculated for ($C_{26}H_{31}N_3O_5$, 1.35 TFA, 0.25 $H_2O$) C, 55.24; H, 5.31; N, 6.73 Found C, 55.27; H, 5.29; N, 6.70 TLC: $R_f$=0.33 (90:10:0.5 DCM:MeOH:$NH_4OH$) HPLC (method A): retention time 6.14 min FAB MS: m/z 466 ($M^+$+H)

EXAMPLE 27

1-(1-(4-(4-(N-Acetyl)piperidinyloxy)-2-methoxybenzoyl)piperidin-4-yl)-1,2-dihydro-4(H)-3,1-benzoxazin-2-one

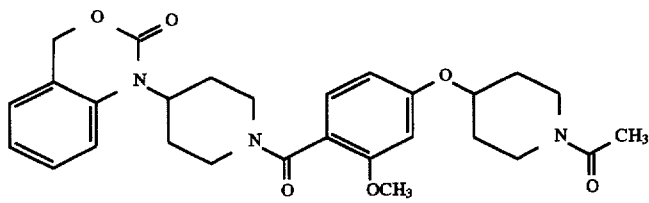

The hydrochloride salt of 1-(1-(4-(piperidinyloxy)-2-methoxybenzoyl)piperidin-4-yl)-1,2-dihydro-4(H)-3,1-benzoxazin-2-one was acetylated with acetic anhydride and DIEA in DCM using the procedure given in Example 18. The crude product was purified by pressurized silica gel column chromatography using a gradient elution of 2–5% MeOH-DCM. The title compound was obtained as a white solid by lyophilization from acetonitrile-$H_2O$ (89% yield).

Analysis calculated for ($C_{28}H_{33}N_3O_6$, 0.05 $CH_3CN$, 1.4 $H_2O$) C, 63.06; H, 6.77; N, 7.99 Found C, 63.11; H, 6.44; N, 7.95 TLC: $R_f$=0.XX (95:5 DCM:MeOH) HPLC (method A): retention time 7.35 min FAB MS: m/z 507 ($M^++H$)

EXAMPLE 28

1-(1-(4-(4-(N-Methylsulfonyl)piperidinyloxy)-2-methoxybenzoyl)piperidin-4-yl)-1,2-dihydro-4(H)-3,1-benzoxazin-2-one

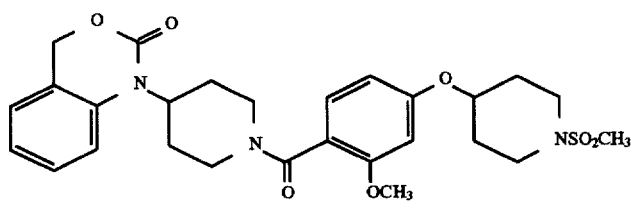

The hydrochloride salt of 1-(1-(4-(piperidinyloxy)-2-methoxybenzoyl)piperidin-4-yl)-1,2-dihydro-4(H)-3,1-benzoxazin-2-one was mesylated with methanesulfonyl chloride and DIEA in DCM using the procedure given in Example 17. The crude product was purified by preparative reverse phase HPLC. The title compound was obtained as a white solid by lyophilization (80% yield).

Analysis calculated for ($C_{27}H_{33}N_3O_6S$, 1.3 TFA, 0.25 $H_2O$) C, 51.05; H, 5.04; N, 6.03 Found C, 51.04; H, 5.03; N, 6.40 TLC: $R_f$=0.28 (95:5:0.5 DCM:MeOH:$NH_4OH$) HPLC (method A): retention time 8.30 min FAB MS: m/z 544 ($M^++H$)

EXAMPLE 29

1-(1-(4-(1-(4-(t-Butoxycarbonylamino)butanoyl)-4-piperidinyloxy)-2-methoxybenzoyl)piperidin-4-yl)-1,2-dihydro-4(H)-3,1-benzoxazin-2-one

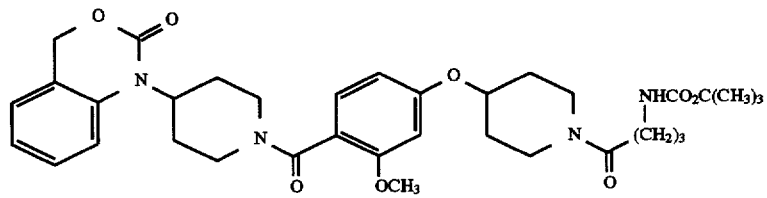

4-(N-t-Butyloxycarbonylamino)butyric acid was coupled to the hydrochloride salt of 1-(1-(4-(4-piperidinyloxy)-2-methoxybenzoyl)piperidin-4-yl)-1,2-dihydro-4(H)-3,1-benzoxazin-2-one using the EDC/HOBT procedure given in Step 5 of Example 1. The crude product was purified by pressurized silica gel column chromatography using a gradient elution of 2–5% MeOH-DCM. The title compound was obtained as a white foam by evaporation of a DCM solution under reduced pressure (90% yield).

Analysis calculated for ($C_{35}H_{46}N_4O_8$, 0.25 $CH_2Cl_2$) C, 63.00; H, 6.97; N, 8.34 Found C, 63.04; H, 7.20; N, 8.28 TLC: $R_f$=0.30 (94:4 DCM:MeOH) HPLC (method A): retention time 8.54 min FAB MS: m/z 651 ($M^+$+H)

EXAMPLE 30

1-(1-(4-(1-(4-Aminobutanoyl)-4-piperidinyloxy)-2-methoxybenzoyl)piperidin-4-yl)-1,2-dihydro-4(H)-3,1-benzoxazin-2-one

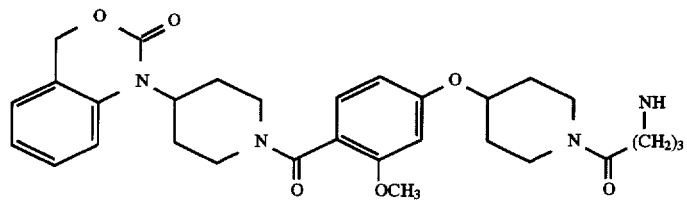

1-(1-(4-(1-(4-(t-Butoxycarbonylamino)butanoyl)-4-piperidinyloxy)-2-methoxybenzoyl)piperidin-4-yl)-1,2-dihydro-4(H)-3,1-benzoxazin-2-one (100 mg, 0.154 mmol) from Example 29 was dissolved in DCM (2 mL) and to the solution was added TFA (2 mL). After 1 h at ambient temperature, the solvents were evaporated under reduced pressure. The residue was purified by preparative reverse phase HPLC. The TFA salt of the title compound was obtained as a white solid by lyophilization (90% yield).

Analysis calculated for ($C_{30}H_{38}N_4O_6$, 1.9 TFA, 0.05 $H_2O$) C, 52.84; H, 5.25; N, 7.29 Found C, 52.85; H, 5.21; N, 7.44 TLC: $R_f$=0.10 (90:10:0.5 DCM:MeOH:$NH_4OH$) HPLC (method A): retention time 6.18 min FAB MS: m/z 551 ($M^+$+H)

EXAMPLE 31

1-(1-(4-(1-t-Butyloxycarbonyl-3-piperidinylmethoxy)benzoyl)piperidin-4-yl)-1,2-dihydro-4(H)-3,1-benzoxazin-2-one

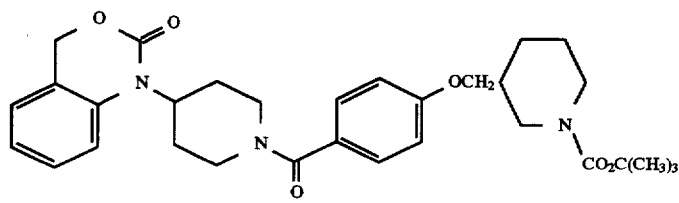

Step 1:
N-t-Butyloxycarbonyl-3-piperidinylmethanol was etherified with ethyl 4-hydroxybenzoate using the DEAD/triphenylphosphine procedure given in Step 1 of Example 25. The crude product was purified by pressurized silica gel column chromatography using a gradient elution of 10–25% EtOAc-hexanes. 4-(N-t-Butyloxycarbonyl-3-piperidinylmethoxy)benzoic acid ethyl ester was obtained as an oil (58% yield).

Step 2:
4-(N-t-Butyloxycarbonyl-3-piperidinylmethoxy)benzoic acid ethyl ester was saponified with aqueous NaOH in MeOH using the procedure given in Step 3 of Example 11.

4-(N-t-Butyloxycarbonyl-3-piperidinylmethoxy)benzoic acid was obtained as a foam by evaporation of a DCM solution (94% yield).

Step 3:
4-(N-t-Butyloxycarbonyl-3-piperidinylmethoxy)benzoic acid was coupled to the hydrochloride salt of 1-(4-piperidinyl)-1,2-dihydro-4(H)-3,1-benzoxazin-2-one using the EDC/HOBT procedure described in Step 5 of Example 1. The crude product was purified by pressurized silica gel column chromatography using a gradient elution of 1–4% MeOH-DCM. The title compound was obtained as a white foam by evaporation of a DCM solution under reduced pressure (87% yield).

Analysis calculated for ($C_{31}H_{39}N_3O_6$, 1.1 $CH_2Cl_2$) C, 59.95; H, 6.46; N, 6.53 Found C, 59.54; H, 6.65; N, 7.05 TLC: $R_f$=0.24 (97:3 DCM:MeOH) HPLC (method A): retention time 10.55 min FAB MS: m/z 550 ($M^+$+H)

EXAMPLE 32

1-(1-(4-(3-Piperidinylmethoxy)benzoyl)piperidin-4-yl)-1,2-dihydro-4(H)-3,1-benzoxazin-2-one

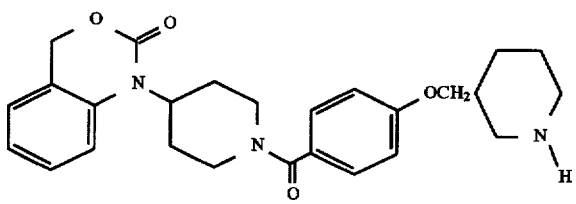

1-(1-(4-(N-t-Butyloxycarbonyl-3-piperidinylmethoxy)benzoyl)piperidin-4-yl)-1,2-dihydro-4(H)-3,1-benzoxazin-2-one from Example 31 was deprotected with HCl gas in EtOAc using the procedure given in Step 4 of Example 1. The hydrochloride salt of the title compound was obtained as a white solid.

Analysis calculated for ($C_{26}H_{31}N_3O_4$, 1.75 HCl, 0.5 EtOAc) C, 60.33; H, 6.65; N, 7.54 Found C, 60.32; H, 6.74; N, 7.61 TLC: $R_f$=0.XX (90:10:1 DCM:MeOH:$NH_4OH$) HPLC (method A): retention time 6.49 min FAB MS: m/z 450 ($M^+$+H)

EXAMPLE 33

1-(1-(4-(N-Acetyl-3-piperidinylmethoxy)benzoyl)
piperidin-4-yl)-1,2-dihydro-4(H)-3,1-benzoxazin-2-
one

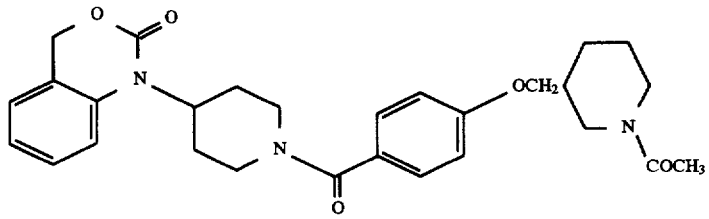

The hydrochloride salt of 1-(1-(4-(3-piperidinylmethoxy)
benzoyl)piperidin-4-yl)-1,2-dihydro-4(H)-3,1-benzoxazin-
2-one from Example 32 was acetylated with acetic anhydride and DIEA in DCM using the procedure given in Example 18. The crude product was purified by pressurized silica gel column chromatography using a gradient elution of 1–4% MeOH-DCM. The title compound was obtained as a white foam by evaporation of a DCM solution under reduced pressure (84% yield).

Analysis calculated for ($C_{28}H_{33}N_3O_5$, 0.85 $CH_2Cl_2$, 0.15 $H_2O$) C, 61.16; H, 6.23; N, 7.42 Found C, 61.19; H, 6.04; N, 7.93 TLC: $R_f$=0.53 (90:10 DCM:MeOH) HPLC (method A): retention time 7.68 min FAB MS: m/z 494 ($M^+$+H)

EXAMPLE 34

1-(1-(4-(N-Acetyl-2-piperidinylethoxy)benzoyl)
piperidin-4-yl)-1,2-dihydro-4(H)-3,1-benzoxazin-2-
one

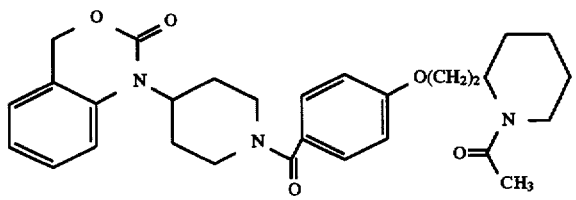

Step 1:

2-Hydroxyethyl-N-t-butyloxycarbonylpiperidine was etherified with ethyl 4-hydroxybenzoate using the DEAD/triphenylphosphine procedure given in Step 1 of Example 25. The crude product was purified by pressurized silica gel column chromatography using a gradient elution of 10–25% EtOAc-hexanes. 4-(N-t-Butyloxycarbonyl-2-piperidinylethoxy)benzoic acid ethyl ester was obtained as an oil (52% yield).

Step 2:

4-(N-t-Butyloxycarbonyl-2-piperidinylethoxy)benzoic acid ethyl ester was saponified with aqueous NaOH in MeOH using the procedure given in Step 3 of Example 11. 4-(N-t-Butyloxycarbonyl-2-piperidinylethoxy)benzoic acid was obtained as a foam by evaporation of a DCM solution (91% yield).

Step 3:

4-(N-t-Butyloxycarbonyl-2-piperidinylethoxy)benzoic acid was coupled to the hydrochloride salt of 1-(4-piperidinyl)-1,2-dihydro-4(H)-3,1-benzoxazin-2-one using the EDC/HOBT procedure described in Step 5 of Example 1. The crude product was purified by pressurized silica gel column chromatography using a gradient elution of 1–4% MeOH-DCM. 1-(1-(4-(N-t-Butyloxycarbonyl-2-piperidinylethoxy)benzoyl)piperidin-4-yl)-1,2-dihydro-4 (H)-3,1-benzoxazin-2-one was obtained as a white foam by evaporation of a DCM solution under reduced pressure (86% yield).

Step 4:

1-(1-(4-(N-t-Butyloxycarbonyl-2-piperidinylethoxy) benzoyl)piperidin-4-yl)-1,2-dihydro-4(H)-3,1-benzoxazin-2-one was deprotected with HCl gas in EtOAc using the procedure given in Step 4 of Example 1. The hydrochloride salt of 1-(1-(4-(2-piperidinylethoxy)benzoyl)piperidin-4-yl)-1,2-dihydro-4(H)-3,1-benzoxazin-2-one was obtained as a white solid (91% yield).

Step 5:

The hydrochloride salt of 1-(1-(4-(2-piperidinylethoxy) benzoyl)piperidin-4-yl)-1,2-dihydro-4(H)-3,1-benzoxazin-2-one was acetylated with acetic anhydride and DIEA in DCM using the procedure given in Example 18. The crude product was purified by pressurized silica gel column chromatography using a gradient elution of 1–4% MeOH-DCM. The title compound was obtained as a white foam by evaporation of a DCM solution under reduced pressure (88% yield).

Analysis calculated for ($C_{29}H_{35}N_3O_5$, 0.4 $CH_2Cl_2$) C, 65.43; H, 6.69; N, 7.79 Found C, 65.85; H, 5.82; N, 7.90 TLC: $R_f$=0.53 (90:10 DCM:MeOH) HPLC (method A): retention time 8.07 min FAB MS: m/z 506 ($M^+$+H)

EXAMPLE 35

1-(2,4-Dimethoxybenzoylpiperidin-4-yl)-3,4-
dihydroquinazolin-2(1H)-one

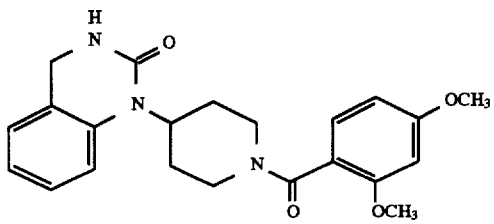

Step 1:

To a solution of 2-(aminomethyl)aniline (4.86 g, 39.8 mmol) in DMF (125 mL) was added a solution of di-t-butyldicarbonate (7.38 g, 0.339 mmol) in DMF (60 mL) dropwise over a period of 1 hour. After being stirred for 18 h at ambient temperature, the solvent was removed under reduced pressure. The residue was dissolved in EtOAc (100 mL) and washed with 5% aqueous citric acid (2×50 mL) and water (50 mL). The EtOAc layer was dried ($Na_2SO_4$), filtered, and the solvent was removed under reduced pressure to give 2-(t-butyloxycarbonylaminomethyl)aniline as an oil (75% yield).

Step 2:

To a stirred solution of 2-(t-butyloxycarbonylaminomethyl)aniline (2.18 g, 9.82 mmol) from Step 1 in dry toluene (100 mL) was added N-benzyl-4-piperidinone (2.04 g, 10.8 mmol) and crushed, activated 4 angstrom molecular sieves (5 g). The mixture was stirred at ambient temperature for 72 h. The sieves were removed by filtration and the solvent was removed under reduced pressure. The residue was dissolved in MeOH (100 mL) and acetic acid (1 mL) and NaCNBH$_3$ (2.25 g, 35.7 mmol) were added. After being stirred for 16 h at ambient temperature, 10 mL of saturated NaHCO$_3$ were added and the reaction was concentrated under reduced pressure. EtOAc (150 mL) was added, and the solution was washed with saturated aqueous NaHCO$_3$ (3×50 mL). The EtOAc layer was dried (MgSO$_4$), filtered, and the solvent was removed under reduced pressure to give 1-benzyl-4-((2-t-butyloxycarbonylaminomethyl)phenylamino)piperidine as an oil (90% yield).

Step 3:

To a solution of 1-benzyl-4-((2-t-butyloxycarbonylaminomethyl)phenylamino)piperidine (3.49 g, 8.83 mmol) from Step 2 in CHCl$_3$ (5 mL) was added TFA (5 mL). After 2 h, the solvents were removed under reduced pressure. The residue was dissolved in CHCl$_3$ (100 mL) and washed with saturated aqueous NaHCO$_3$ (75 mL). The CHCl$_3$ layer was concentrated under reduced pressure and the residue was purified by pressurized silica gel column chromatography using 96:4:0.4 CHCl$_3$:MeOH:NH$_4$OH as eluant. 1-Benzyl-4-((2-aminomethyl)phenylamino) piperidine was obtained as an oil (65% yield).

Step 4:

To a solution of 1-benzyl-4-((2-aminomethyl)phenylamino)piperidine (1.74 g, 5.90 mmol) from Step 3 in dry DMF (50 mL) was added 4-nitrophenyl chloroformate (1.25 g, 6.20 mmol) and DIEA (3.08 mL, 17.7 mmol). After the reaction had been stirred at ambient temperature for 24 h, the solvent was removed under reduced pressure. The residue was dissolved in DCM (100 mL) and washed with saturated aqueous NaHCO$_3$ (4×50 mL), dried (MgSO$_4$), and filtered. The solution was concetrated and the precipitate which formed was collected by filtration to give 1-(1-benzyl-4-piperidinyl)-3,4-dihydroquinazolin-2(1H)-one as a white solid (50% yield).

Step 5:

To a solution of 1-(1-benzyl-4-piperidinyl)-3,4-dihydroquinazolin-2(1H)-one (947 g, 295 mmol) from Step 4 in dry dichloroethane (20 mL) was added 1-chloroethyl chloroformate (0.35 mL, 3.2 mmol). The reaction was refluxed for 3 h. The solvent was rmoved under reduced pressure and the residue was dissolved in MeOH (50 mL) and the solution was refluxed for 1 h. The reaction was cooled to ambient temperature, conc. NH$_4$OH (1 mL) was added, and the solvent was removed under reduced pressure. The residue was purified by pressurized silica gel column chromatography using 90:10:1 CHCl$_3$:MeOH:NH$_4$OH as eluant. 1-(4-Piperidinyl)-3,4-dihydroquinazolin-2(1H)-one was obtained as an oil (48% yield).

Step 6:

To a solution of 1-(4-piperidinyl)-3,4-dihydroquinazolin-2(1H)-one (680 mg, 1.40 mmol) from Step 5 in DCM (15 mL) was added DIEA (0.366 mL, 2.1 mmol) followed by 2,4-dimethoxybenzoyl chloride (309 mg, 1.54 mmol). The reaction was stirred for 2 h and the solvent was removed under reduced pressure. The residue was dissolved in EtOAc (100 mL) and washed with 5% aqueous citric acid (50 mL) and saturated aqueous NaHCO$_3$ (2×50 mL). The EtOAc layer was dried (MgSO$_4$), filtered, and the solvent was removed under reduced pressure. The residue was purified by pressurized silica gel column chromatography eluting first with 95:5 EtOAc:CHCl$_3$ and then with 95:3:2 EtOAc:CHCl$_3$:MeOH. The title compound was obtained as a white solid (77% yield).

Analysis calculated for (C$_{22}$H$_{25}$N$_3$O$_4$, 0.7 CHCl$_3$, 0.15 EtOAc) C, 56.85; H, 5.51; N, 8.54 Found C, 56.92; H, 5.40; N, 8.54 TLC: R$_f$=0.53 (90:10 DCM:MeOH) HPLC (method A): retention time 7.67 min FAB MS: m/z 396 (M$^+$+H)

EXAMPLE 36

1-(2,4-Dimethoxybenzoylpiperidin-4-yl)-3,4-dihydro-3-methylquinazolin-2(1H)-one

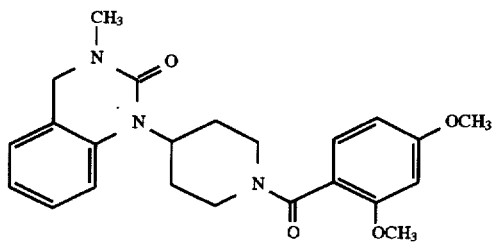

To a solution of 1-(2,4-dimethoxybenzoylpiperidin-4-yl)-3,4-dihydroquinazolin-2(1H)-one (100 mg, 2.53 mmol) from Example 35 in DMF (50 mL) was added NaiI (16 mg of a 60% suspension in mineral oil, 0.40 mmol) followed by iodomethane (0.031 mL, 0.50 mmol). The reaction was stirred for 18 h at ambient temperature. More NaH (10 mg, 0.25 mmol) and iodomethane (0.031 mL, 0.50 mmol) were added and the reaction was stirred at ambient temperature for 24 h. The reaction was quenched by the addition of HOAc (0.2 mL) and the solvents were removed under reduced pressure. The residue was purified by pressurized silica gel column chromatography using 90:10 EtOAc:hexanes as eluant. The title compound was obtained as an oil (45% yield). TLC: R$_f$=0.42 (97:3 CHCl$_3$:MeOH) HPLC (method A): retention time 8.53 min FAB MS: m/z 410 (M$^+$+H)

EXAMPLE 37

1-(1-(4-(t-Butyloxycarbonyl)-2-methoxybenzoyl) piperidin-4-yl)-1,2-dihydro-4(H)-3,1-benzoxazin-2-one

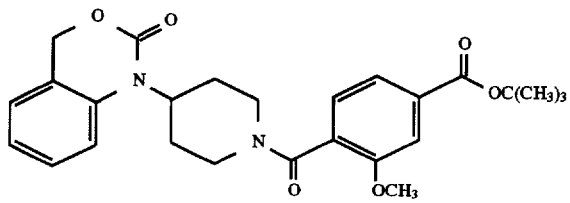

Step 1:

To a stirred 0° C. solution of 2-hydroxybenzene-1,4-dicarboxylic acid (2.5 g, 12.8 mmol) in DMF (50 mL) was added NaH (1.5 g of a 60% suspension in mineral oil, 38 mmol). After 10 min, iodomethane (2.36 mL, 38 mmol) was added and the reaction was warmed to ambient temperature and stirred for 24 h. The reaction was quenched by the addition of HOAc (2 mL) and the solvents were removed under reduced pressure. The residue was dissolved in EtOAc (150 mL) and washed with saturated aqueous NaHCO$_3$ (2×75 mL). The EtOAc layer was dried (MgSO$_4$), filtered, and the solvent was removed under reduced pressure. 2-Methoxy-1,4-bis(methoxycarbonyl)benzene was obtained by crystallization from ether (60% yield).

Step 2:

2-Methoxy-1,4-bis (methoxycarbonyl)benzene (1.61 g, 7.20 mmol) from Step 2 was dissolved in 20 mL of 1:1 THF:H$_2$O and to the stirred solution was added 1N NaOH (7.2 mL, 7.2 mmol). After 24 h, the reaction was acidified to pH 2 with 1N HCl. The reaction was concentrated under reduced pressure and then extracted with CHCl$_3$. The CHCl$_3$ layer was dried (MgSO$_4$), filtered and evaporated under reduced pressure. The residue was purified by pressurized silica gel column chromatography using 93:7 CHCl$_3$:A, where A=95:5 MeOH:HOAc. 1-Methoxycarbonyl-2-methoxybenzene 4-carboxylic acid was obtained as an oil (30% yield).

Step 3:

1-Methoxycarbonyl-2-methoxybenzene 4-carboxylic acid (810 mg, 3.86 mmol) from Step 2 was dissolved in dry toluene (50 mL) at 80° C. To the hot solution was added N,N-dimethylformamide di-t-butyl acetal (3.7 mL, 15 mmol). After 24 h, the solvent was removed under reduced pressure. The residue was dissolved in CHCl$_3$ (50 mL) and washed with saturated aqueous NaHCO$_3$ (2×50 mL). The CHCl$_3$ layer was dried (MgSO$_4$), filtered, and the solvent was removed under reduced pressure. The residue was purified by pressurized silica gel column chromatography using 92:8 hexanes:EtOAc as eluant. 4-(t-Butyloxycarbonyl)-1-methoxycarbonyl-2-methoxybenzene was obtained as an oil (77% yield).

Step 4:

4-(t-Butyloxycarbonyl)-1-methoxycarbonyl-2-methoxybenzene (770 mg, 2.9 mmol) from Step 3 was dissolved in 1:1 THF:H$_2$O (10 mL) and to the solution was added 1N NaOH (4 mL, 4 mmol). After being stirred at ambient temperature for 24 h, the solution was acidified to pH 2 with 1N HCl and the solvents were removed under reduced pressure. The residue was dissolved in CHCl$_3$ and washed with water. The CHCl$_3$ layer was dried (MgSO$_4$), filtered, and evaporated under reduced pressure to give 4-(t-butyloxycarbonyl)-2-methoxybenzene 1-carboxylic acid as a white solid (86% yield).

Step 5:

4-(t-butyloxycarbonyl)-2-methoxybenzene 1-carboxylic acid from Step 4 was coupled to the hydrochloride salt of 1-(4-piperidinyl)-1,2-dihydro-4(H)-3,1-benzoxazin-2-one using the EDC/HOBT procedure of Step 5 in Example 1.

The crude product was purified by pressurized silica gel column chromatography using 1:1 EtOAc:hexanes as eluant. The title compound was obtained as a foam by evaporation of an EtOAc solution under reduced pressure (81% yield).

Analysis calculated for (C$_{26}$H$_{30}$N$_2$O$_6$, 0.5 EtOAc) C, 65.86; H, 6.71; N, 5.49 Found C, 65.39; H, 6.46; N, 5.85 TLC: R$_f$=0.50 (65:35 EtOAc:hexanes) HPLC (method A): retention time 9.61 min FAB MS: m/z 467 (M$^+$+H)

EXAMPLE 38

1-(1-(4-Carboxy-2-methoxybenzoyl)piperidin-4-yl)-1,2-dihydro-4(H)-3,1 -benzoxazin-2-one

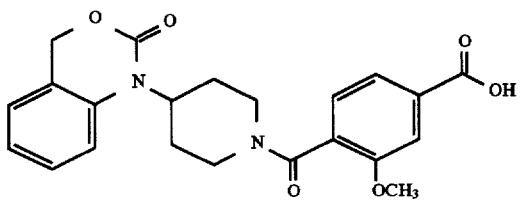

1-(1-(4-(t-Butyloxycarbonyl)-2-methoxybenzoyl) piperidin-4-yl)-1,2-dihydro-4(H)-3,1-benzoxazin-2-one from Example 36 (150 mg, 0.322 mmol) was dissolved in TFA (3 mL). After 1 h at ambient temperature, the solvent was removed under reduced pressure. The residue was dissolved in EtOAc (75 mL) and washed water (25 mL). The EtOAc layer was dried (MgSO$_4$), filtered, and the solvent was removed under reduced pressure to give the title compound as a foam (85% yield).

Analysis calculated for (C$_{22}$H$_{22}$N$_2$O$_6$, 0.7 TFA, 0.25 H$_2$O) C, 56.80; H, 4.73; N, 5.66 Found C, 56.77; H, 4.70; N, 5.81 TLC: R$_f$=0.26 (95:5 CHCl3:A, A=90:10 MeOH:HOAc) HPLC (method A): retention time 6.58 min FAB MS: m/z 411 (M$^+$+H)

EXAMPLE 39

1-(1-(4-(4-(t-Butyloxycarbonyl)piperazin-1-ylcarbonyl)-2-methoxybenzoyl)piperidin-4-yl)-1,2-dihydro-4(H)-3,1-benzoxazin-2-one

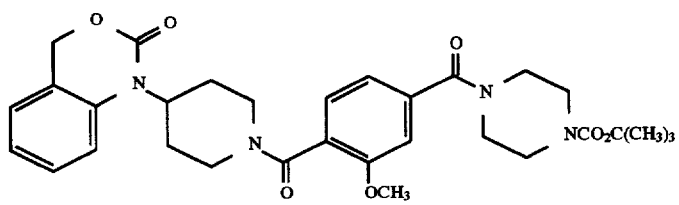

1-(1-(4-Carboxy-2-methoxybenzoyl)piperidin-4-yl)-1,2-dihydro-4(H)-3,1-benzoxazin-2-one from Example 38 was coupled to 1-(t-butyloxycarbonyl)piperazine using the EDC/HOBT procedure given in Step 5 of Example 1. The crude product was purified by pressurized column chromatography usin a gradient elution of 1–4% MeOH:DCM. The title compound was obtained as a solid by lyophilization from dioxane.

Analysis calculated for (C$_{31}$H$_{38}$N$_4$O$_7$, 0.55 dioxane, 0.4 DMF) C, 62.94; H, 6.94; N, 9.39 Found C, 62.90; H, 6.77;

N, 9.38 TLC: $R_f$=0.47 (96:4 DCM:MeOH) HPLC (method A): retention time 8.21 min FAB MS: m/z 579 (M$^+$+H)

EXAMPLE 40

1-(1-(4-(1-Piperazinyl)carbonyl)-2-methoxybenzoyl) piperidin-4-yl)-1,2-dihydro-4(H)-3,1-benzoxazin-2-one

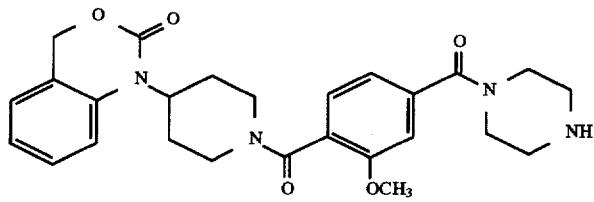

1-(1-(4-(4-(t-Butyloxycarbonyl)piperazin-1-yl)carbonyl)-2-methoxybenzoyl)piperidin-4-yl)-1,2-dihydro-4(H)-3,1-benzoxazin-2-one from Example 39 was N-deprotected with HCl in EtOAc as described in Step 4 of Example 1. The crude product was purified by preparative reverse phase HPLC. The TFA salt of the title compound was obtained as a powder by lyophilization from CH$_3$CN/H$_2$O/TFA.

Analysis calculated for (C$_{26}$H$_{30}$N$_4$O$_5$, 1.5 TFA, 0.5 H$_2$O) C, 52.88; H, 4.97; N, 8.51 Found C, 52.88; H, 4.96; N, 8.57 TLC: $R_f$=0.45 (95:5:0.5 DCM:MeOH:NH4OH) HPLC (method A): retention time 5.39 min FAB MS: m/z 479 (M$^+$+H)

EXAMPLE 41

4-(1-(4-(4-(1-t-Butyloxycarbonyl)piperidinyloxy)-2-methoxybenzoyl)piperidin-4-yl)-(2H)-1,4-benzoxazin-3(4H)-one

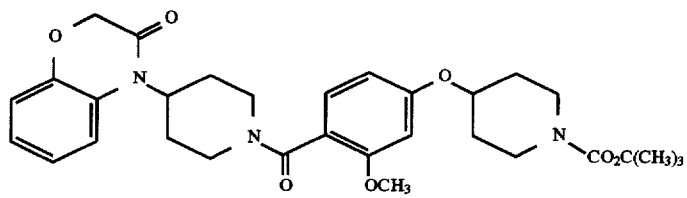

Step 1:

A solution of 2-hydroxyaniline (5.0 g, 46 mmol), N-t-butyloxycarbonyl-4-piperidinone (9.05 g, 46 mmol) and HOAc (5.7 mL, 100 mmol) in dry toluene (250 mL) was refluxed with azeotropic removal of water for 24 h. The solution was cooled to ambient temperature and to it was added NaCNBH$_3$ (5.8 g, 92 mmol). The resulting mixture was stirred at ambient temperature for 24 h. EtOAc (250 mL) was added and the solution was washed with saturated aqueous NaHCO$_3$ (4×100 mL). The organic phase was dried (MgSO$_4$), filtered, and the solvents were removed under reduced pressure. The residue was purified by pressurized silica gel column chromatography using a gradient elution of 15–25% EtOAc-hexanes. 1-t-Butyloxycarbonyl-4-(2-hydroxyphenylamino)piperidine was obtained as a solid (45% yield).

Step 2:

To a stirred 0° C. solution of 1-t-Butyloxycarbonyl-4-(2-hydroxyphenylamino)piperidine (5.2 g, 18 mmol) from Step 1 was added NaH (800 mg of a 60% suspension in mineral oil, 20 mmol). After 30 min, ethyl bromoacetate (2.2 mL, 20 mmol) was added and the reaction was warmed to ambient temperature and stirred for 2 h. The reaction was quenched by the addition of acetic acid (1 mL), and the solvents were removed under reduced pressure. The residue was purified by pressurized silica gel column chromatography using 20% EtOAc-hexanes as eluant. 1-t-Butyloxycarbonyl-4-((2-ethoxycarbonylmethoxyphenyl)amino)piperidine was obtained as an oil (90% yield).

Step 3:

To a solution of 1-t-butyloxycarbonyl-4-((2-ethoxycarbonylmethoxyphenyl)amino)piperidine (5.65 g, 15 mmol) from Step 2 in 4:1 MeOH:H$_2$O (60 mL) was added 1N NaOH (30 mL, 30 mmol). The reaction was stirred at ambient temperature for 3 h. 1N HCl was added to the reaction to obtain a pH 2 solution. The solvents were removed under reduced pressure to give 1-t-butyloxycarbonyl-4-((2-carboxymethoxyphenyl)amino) piperidine as a foam (99% yield).

Step 4:

1-t-Butyloxycarbonyl-4-((2-carboxymethoxyphenyl) amino)piperidine (5.2 g, 15 mmol) from Step 3 was cyclized using the EDC/HOBT coupling procedure given in Step 5 of Example 1. 4-(1-tert-butyloxycarbonyl-4-piperidinyl)-(2H)-1,4-benzoxazin-3(4H)-one was obtained as a foam (86% yield).

Step 5:

4-(1-tert-butyloxycarbonyl-4-piperidinyl)-(2H)-1,4-benzoxazin-3(4H)-one from Step 4 was N-deprotedcted with HCl in EtOAc using the procedure given in Step 4 of Example 1. The hydrochloride salt of 4-(4-piperidinyl)-(2H)-1,4-benzoxazin-3(4H)-one was obtained as a solid (95% yield).

Step 6:

4-(N-t-Butoxycarbonyl-4-piperidinyloxy)-2-methoxybenzoic acid from Step 4 of Example 25 was coupled to the hydrochloride salt of 4-(4-piperidinyl)-(2H)-1,4-benzoxazin-3 (4H)-one from Step 5 above using the EDC/HOBT procedure described in Step 5 of Example 1. The crude product was purified by pressurized silica gel column chromatography using a gradient elution of 1:1 to 5:1 EtOAc:hexanes. The title compound was obtained as a white foam by evaporation of an EtOAc solution under reduced pressure (85% yield).

Analysis calculated for (C$_{31}$H$_{39}$N$_3$O$_7$, 0.4 EtOAc) C, 65.15; H, 7.08; N, 6.99 Found C, 64.88; H, 6.69; N, 7.20 TLC: $R_f$=0.33 (4:1 EtOAc:hexanes) HPLC (method A): retention time 10.08 min FAB MS: m/z 566 (M$^+$+H)

EXAMPLE 42

3-(1-(4-(4-(1-t-Butyloxycarbonyl)piperidinyloxy)-2-methoxybenzoyl)piperidin-4-yl)-benzoxazolidin-2-one

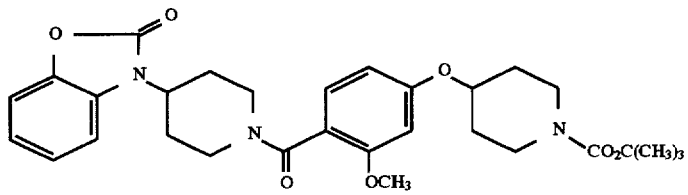

Step 1:

To a stirred 0° C. solution of 1-t-Butyloxycarbonyl-4-(2-hydroxyphenylamino)piperidine (3.0 g, 10 mmol) from Step 1 of Example 41 in dry THF (40 mL) was added DIEA (5.2 mL, 30 mmol), followed by triphosgene (1.08 g, 3.60 mmol). After 30 min, the reaction was warmed to ambient temperature and stirred for 24 h. The precipitated hydrochloride salt of DIEA was removed by filtration and the solvent was removed under reduced pressure. The residue was dissolved in EtOAc (200 mL) and washed with saturated aqueous $NaHCO_3$ (2×100 mL), water (100 mL), 5% aqueous citric acid (100 mL), and brine (100 mL). The EtOAc layer was dried ($MgSO_4$), filtered, and the solvent was removed under reduced pressure. 3-(1-t-Butyloxycarbonyl-4-piperidinyl)benzoxazolidin-2-one was obtained as a solid (82% yield).

Step 3:

3-(1-t-Butyloxycarbonyl-4-piperidinyl)benzoxazolidin-2-one from Step 1 was N-deprotected with HCl in EtOAc using the procedure given in Step 4 of Example 1. The hydrochloride salt of 3-( 4-piperidinyl)benzoxazolidin-2-one was obtained as a solid (96% yield).

Step 4:

4-(N-t-Butoxycarbonyl-4-piperidinyloxy)-2-methoxybenzoic acid from Step 4 of Example 25 was coupled to the hydrochloride salt of 3-(4-piperidinyl)benzoxazolidin-2-one from Step 3 above using the EDC/HOBT procedure described in Step 5 of Example 1. The crude product was purified by pressurized silica gel column chromatography using a gradient elution of 2:1 to 5:1 EtOAc:hexanes. The title compound was obtained as a white foam by evaporation of an EtOAc solution under reduced pressure (82% yield).

Analysis calculated for ($C_{30}H_{37}N_3O_7$, 0.4 EtOAc) C, 64.66; H, 6.90; N, 7.17 Found C, 64.62; H, 6.51; N, 7.51 TLC: $R_f$=0.40 (4:1 EtOAc:hexanes) HPLC (method A): retention time 10.03 min FAB MS: m/z 552 ($M^++H$)

EXAMPLE 43

1-(1-(4-(N-t-Butoxycarbonyl-4-piperidinyloxy)-2-methylbenzoyl)piperidin-4-yl)-1,2-dihydro-4(H)-3,1-benzoxazin-2-one

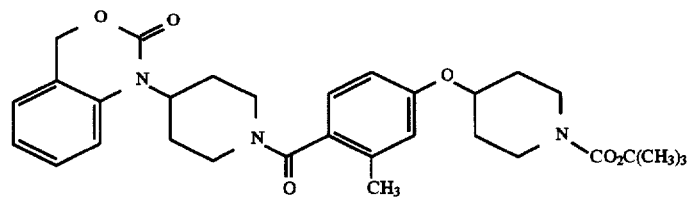

Step 1:

N-t-butyloxy-4-piperidinol was etherified with 4-hydroxy-2-methylacetophenone using the DEAD/triphenylphosphine procedure given in Step 1 of Example 25. The crude product was purified by pressurized silica gel column chromatography using 15:85 EtOAc:hexane as eluant. 4-(N-t-Butoxycarbonyl-4-piperidinyloxy)-2-methylacetophenone was obtained as an oil (60% yield).

Step 2:

4-(N-t-Butoxycarbonyl-4-piperidinyloxy)-2-methylacetophenone from Step 1 was convened to 4-(N-t-butoxycarbonyl-4-piperidinyloxy)-2-methylbenzoic acid (70% yield) using the haloform procedure described by Edwards, et al., *J. Am. Chem. Soc.* (1956), vol. 78, p.3821 except that refluxing was not neccessary.

Step 3:

4-(N-t-butoxycarbonyl-4-piperidinyloxy)-2-methylbenzoic is acid from Step 2 was coupled to the hydrochloride salt of 1-(4-piperidinyl)-1,2-dihydro-4(H)-3,1-benzoxazin-2-one using the EDC/HOBT procedure described in Step 5 of Example 1. The crude product was purified by pressurized silica gel column chromatography using 3:1 EtOAc:hexanes as eluant. The title compound was obtained as a white foam by evaporation of an EtOAc solution under reduced pressure (87% yield).

Analysis calculated for ($C_{31}H_{39}N_3O_6$, 0.45 EtOAc) C, 66.84; H, 7.29; N, 7.13 Found C, 66.54; H, 7.10; N, 7.48 TLC: $R_f$=0.39 (4:1 EtOAc:hexanes) HPLC (method A): retention time 9.95 min FAB MS: m/z 550 ($M^++H$)

EXAMPLE 44

1-(1-(4-Methoxy-2-nitrobenzoyl)piperidin-4-yl)-1,2-dihydro-4(H)-3,1-benzoxazin-2-one

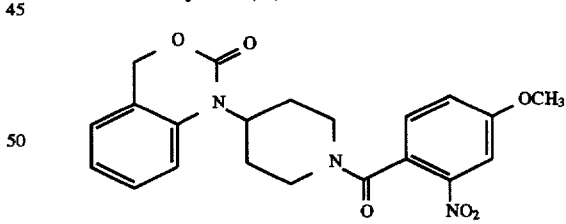

Step 1:

4-Methoxy-2-nitrotoluene (3.6 g, 18 mmol) and KMnO$_4$ (10 g, 63 mmol) in water (200 mL) were refluxed for 24 h. The reaction was cooled to ambient temperature and the solids were removed by filtration. The aqueous phase was made acidic (pH 2) by the addition of 1N HCl and was extracted with CHCl$_3$ (3×50 mL). The combined organic extracts were dried (MgSO$_4$) and filtered. The precipitate which formed upon concentration under reduced pressure was collected to give 4-methoxy-2-nitrobenzoic acid (80% yield).

Step 2:

4-Methoxy-2-nitrobenzoic acid from Step 1 was coupled to the hydrochloride salt of 1-(4-piperidinyl)-1,2-dihydro-4 (H)-3,1-benzoxazin-2-one using the EDC/HOBT procedure described in Step 5 of Example 1. The crude product was purified by pressurized silica gel column chromatography using 7:3 EtOAc:hexanes as eluant. The title compound was obtained as a white foam by evaporation of an EtOAc solution under reduced pressure (86% yield).

Analysis calculated for (C$_{21}$H$_{21}$N$_3$O$_6$, 0.35 EtOAc) C, 60.83; H, 5.42; N, 9.50 Found C, 66.45; H, 5.11; N, 9.60 TLC: R$_f$=0.31 (3:1 EtOAc:hexanes) HPLC (method A): retention time 7.72 min FAB MS: m/z 412 (M$^+$+H)

EXAMPLE 45

1-(1-(4-(1-(4(5)-Imidazolylacetyl)-4-piperidinyloxy)
-2-methoxybenzoyl)piperidin-4-yl)-1,2-dihydro-4(H)
-3,1-benzoxazin-2-one

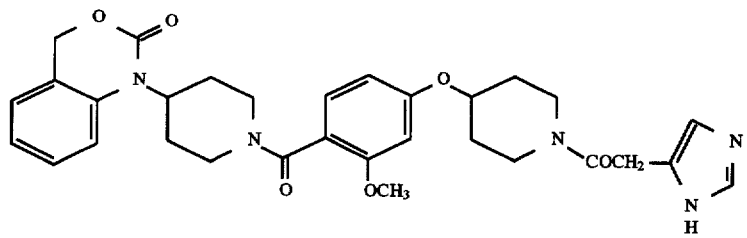

4(5)-Imidazole acetic acid was coupled to the hydrochloride salt of 1-(1-(4-(4-piperidinyloxy)-2-methoxybenzoyl) piperidin-4-yl)-1,2-dihydro-4(H)-3,1-benzoxazin-2-one using the EDC/HOBT procedure given in Step 5 of Example 1. The crude product was purified by pressurized silica gel column chromatography using a gradient elution of 5–10% A-DCM, where the A solvent is 5% NH$_4$OH-MeOH. The hydrochloride salt of the title compound was obtained as a foam by evaporation of a MeOH solution containing 1N HCl under reduced pressure (70% yield).

Analysis calculated for (C$_{31}$H$_{35}$N$_5$O$_6$, 2.0 HCl, 0.6 H$_2$O) C, 56.64; H, 5.86; N, 10.65 Found C, 56.79; H, 6.04; N, 10.63 TLC: R$_f$=0.35 (92:8:0.4 DCM:MeOH:NH$_4$OH) HPLC (method A): retention time 6.48 min FAB MS: m/z 574 (M$^+$+H)

EXAMPLE 46

1-(1-(4-(1-(Diethylaminoethylsulfonyl)-4-
piperidinyloxy)-2-methoxybenzoyl)piperidin-4-yl)-
1,2-dihydro-4(H)-3,1-benzoxazin-2-one

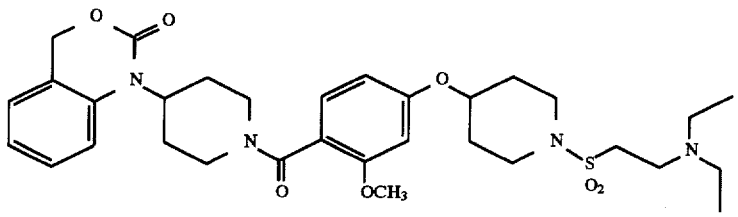

To a solution of the hydrochloride salt of 1-(1-(4-(4-piperidinyloxy)-2-methoxybenzoyl)piperidin-4-yl)-1,2-dihydro-4(H)-3,1-benzoxazin-2-one (150 mg, 0.30 mmol) and DIEA (0.16 mL, 0.90 mmol) in DCM (10 mL) was added 2-chloroethylsulfonyl chloride (54 mg, 0.33 mmol). The reaction was stirred at ambient temperature for 2 h, and the solvent was removed under reduced pressure. The residue was dissolved in EtOAc (50 mL) and washed with saturated aqueous NaHCO3 (2×25 mL). The organic phase was dried (MgSO$_4$), filtered, and the solvent was removed under reduced pressure. The product, 1-(1-(4-(1-vinyl sulfonyl-4-piperidinyloxy)-2-methoxybenzoyl)-piperidin-4-yl)-1,2-dihydro-4(H)-3,1-benzoxazin-2-one, was dissolved in MeOH (5 mL) and to the solution was added diethylamine (3 mL). After 48 h at ambient temperature, the solvents were removed under reduced pressure and the residue was purified by pressurized silica gel column chromatography using a gradient elution of 1–4% MeOH-DCM. The title compound was obtained as a foam by evaporation of a DCM solution under reduced pressure (42% yield).

Analysis calculated for (C$_{32}$H$_{44}$N$_4$O$_7$S, 0.25 CH$_2$Cl$_2$) C, 59.58; H, 6.90; N, 8.62 Found C, 59.59; H, 6.32; N, 8.59 TLC: R$_f$=0.18 (98:2 DCM:MeOH) HPLC (method A): retention time 6.93 min FAB MS: m/z 629 (M$^+$+H)

EXAMPLE 47

1-(1-(4-(1-(3 -Picolyl)-4-piperidinyloxy)-2-
methoxybenzoyl)piperidin-4-yl)-1,2-dihydro-4(H)-3,
1-benzoxazin-2-one

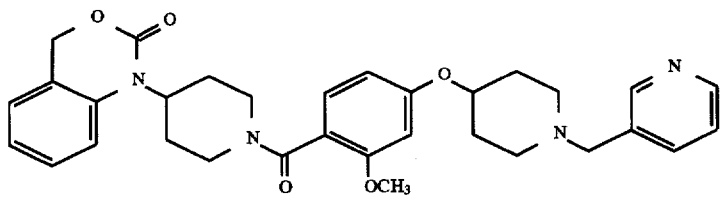

To a solution of the hydrochloride salt of 1-(1-(4-(4-piperidinyloxy)-2-methoxybenzoyl)piperidin-4-yl)-1,2-dihydro-4(H)-3,1-benzoxazin-2-one (150 g, 0.30 mmol) and DIEA (0.13 mL, 0.75 mmol) in DMF (5 mL) was added 3-picolyl chloride hydrochloride (54 g, 0.33 mmol). The reaction was stirred at ambient temperature for 48 h, and the solvent was removed under reduced pressure. The residue was purified by reverse phase HPLC. The TFA salt of the title compound was obtained as a powder by lyophilization from CH$_3$CN—H$_2$O—TFA (48% yield).

Analysis calculated for (C$_{32}$H$_{36}$N$_4$O$_5$, 2.4 TFA) C, 53.23; H, 4.66; N, 6.75 Found C, 53.20; H, 4.52; N, 6.87 TLC: R$_f$=0.30 (90:10:0.5 DCM:MeOH:NH4OH) HPLC (method A): retention time 6.93 min FAB MS: m/z 557 (M$^+$+H) $^1$H NMR (300 MHz, CDCl$_3$): δ

EXAMPLE 48

1-(1-(4-(1-(Ethoxycarbonylmethyl)-4-piperidinyloxy)-2-methoxybenzoyl)piperidin-4-yl)-1,2-dihydro-4(H)-3,1-benzoxazin-2-one Analysis calculated for (C$_{30}$H$_{37}$N$_3$O$_7$, 1.85 TFA, 0.1 H$_2$O) C, 52.95; H, 5.15; N, 5.50 Found C, 52.96; H, 4.85; N, 5.50 TLC: R$_f$=0.30 (95:5:0.25 DCM:MeOH:NH4OH) HPLC (method A): retention time 6.37 min FAB MS: m/z 552 (M$^+$+H)

EXAMPLE 49

1-(1-(4-(3-(N-t-Butyloxycarbonylpiperidin-4-ylcarbonylamino)propoxy)-2-hydroxybenzoyl)piperidin-4-yl)-1,2-dihydro-4(H)-3,1-benzoxazin-2-one

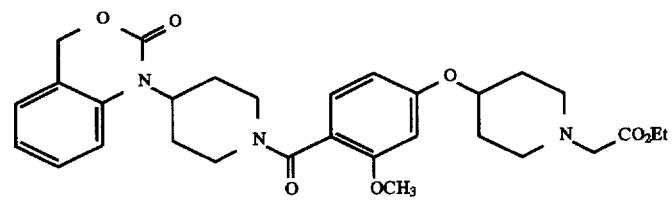

To a solution of the hydrochloride salt of 1-(1-(4-(4-piperidinyloxy)-2-methoxybenzoyl)piperidin-4-yl)-1,2-dihydro-4(H)-3,1-benzoxazin-2-one (150 mg, 0.mmol) and DIEA (mL, mmol) in DMF (mL) was added ethyl bromoacetate (55 mg, 0.33 mmol). The reaction was stirred at ambient temperature for 24 h, and the solvent was removed under reduced pressure. The residue was purified by reverse phase HPLC. The TFA salt of the title compound was obtained as a powder by lyophilization from CH$_3$CN—H$_2$O—TFA (55% yield).

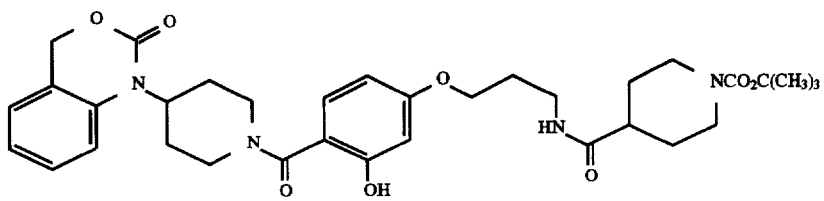

4-((1-t-Butoxycarbonyl-4-piperidinylcarbonyl)aminopropoxy)-2-hydroxybenzoic acid was coupled to 1-(piperidin-4-yl)-1,2-dihydro-4(H)-3,1-benzoxazin-2-one from Step 4 of Example 1 using the EDC/HOBT procedure of Step 5 in Example 1. The crude product was purified by pressurized silica gel column chromatography using a gradient elution of 2–5% MeOH-CHCl₃. The title compound was obtained as a white foam by evaporation of a CHCl₃ solution under reduced pressure (85% yield).

Analysis calculated for ($C_{34}H_{44}N_4O_8$ 0.5 DMF, 0.1 CHCl₃, 0.15 H₂O) C, 62.15; H, 7.02; N, 9.16 Found C, 62.17; H, 6.89; N, 9.00 TLC: $R_f$=0.34 (96:4 CHCl₃:MeOH) HPLC (method A): retention time 8.27 min FAB MS: m/z 637 (M⁺+H)

EXAMPLE 50

1-(1-(4-(3-(Piperidin-4-ylcarbonylamino)propoxy)-2-hydroxybenzoyl)piperidin-4-yl)-1,2-dihydro-4(H)-3,1-benzoxazin-2-one

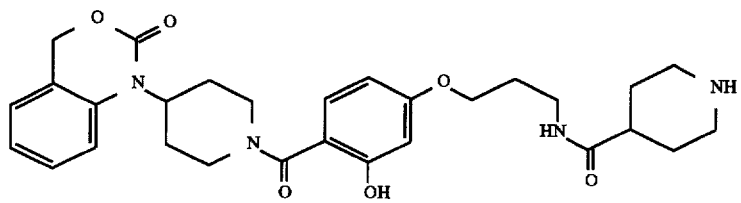

1-(1-(4-(3-((N-t-Butyloxycarbonyl-4-piperidinylcarbonyl)amino)propoxy)-2-hydroxybenzoyl)piperidin-4-yl)-1,2-dihydro-4(H)-3,1-benzoxazin-2-one from Example 49 was N-deprotected with HCl gas in EtOAc using the procedure given in Step 4 of Example 1. The hydrochloride salt of the title compound was obtained as a white solid (90% yield).

Analysis calculated for ($C_{29}H_{36}N_4O_6$, 2.0 HCl, 2.3 EtOAc, 0.85 ether, 0.38 CH₂Cl₂) C, 55.64; H, 7.29; N, 6.17 Found C, 55.65; H, 7.13; N, 6.18 TLC: $R_f$=0.23 (70:30:3 CH₂Cl₂:MeOH:NH₄OH) HPLC (method A): retention time 5.84 min FAB MS: m/z 537 (M⁺+H)

EXAMPLE 51

1-(1-(4-(N-t-Butoxycarbonyl-4-piperidinyloxy)-2-chlorobenzoyl)piperidin-4-yl)-1,2-dihydro-4(H)-3,1-benzoxazin-2-one

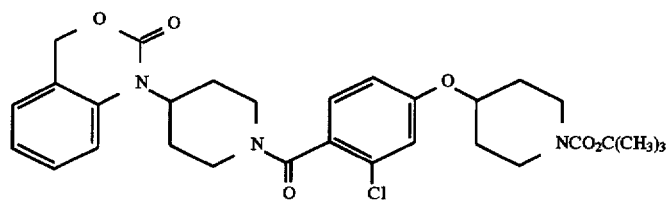

Step 1:

N-t-butyloxy-4-piperidinol was etherified with 2-chloro-4-hydroxybenzoic acid methyl ester usinf the DEAD/triphenylphosphine procedure given in Step 1 of Example 25. The crude product was purified by pressurized silica gel column chromatography using a gradient elution of 20–30% EtOAc-hexane. 4-(N-t-Butoxycarbonyl-4-piperidinyloxy)-2-chlorobenzoic acid methyl ester was obtained as a foam by evasporation of a DCM solution under reduced pressure (65% yield).

Step 2:

4-(N-t-Butoxycarbonyl-4-piperidinyloxy)-2-chlorobenzoic acid methyl ester was saponified to the carboxylic acid with aqueous NaOH in MeOH using the procedure of Step 3 in Example 11. 4-(N-t-Butoxycarbonyl-4-piperidinyloxy)-2-chlorobenzoic acid was obtained as a foam by evaporation of a DCM solution under reduced pressure (90% yield).

Step 3:

4-(N-t-Butoxycarbonyl-4-piperidinyloxy)-2-chlorobenzoic acid from Step 2 was coupled to the hydrochloride salt of 1-(4-piperidinyl)-1,2-dihydro-4(H)-3,1-benzoxazin-2-one using the EDC/HOBT procedure described in Step 5 of Example 1. The crude product was purified by pressurized silica gel column chromatography using a gradient elution of 2–6% MeOH-DCM. The title compound was obtained as a white foam by evaporation of an EtOAc-DCM solution under reduced pressure (82% yield).

Analysis calculated for ($C_{30}H_{36}ClN_3O_6$, 0.45 CH₂Cl₂, 0.25 EtOAc) C, 59.92; H, 6.22; N, 6.67 Found C, 59.87; H, 6.20; N, 6.69 TLC: $R_f$=0.28 (95:5 DCM:MeOH) HPLC (method A): retention time 10.47 min FAB MS: m/z 570 (M⁺+H)

EXAMPLE 52

1-(1-(4-(4-Piperidinyloxy)-2-chlorobenzoyl)
piperidin-4-yl)-1,2-dihydro-4(H)-3,1-benzoxazin-2-
one

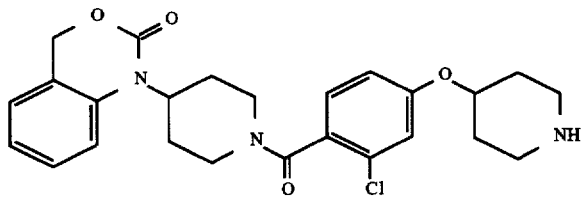

1-(1-(4-(N-t-Butoxycarbonyl-4-piperidinyloxy)-2-chlorobenzoyl)piperidin-4-yl)-1,2-dihydro-4(H)-3,1-benzoxazin-2-one (200 mg, 0.35 mmol) from Example 51 was treated with 4N HCl in dioxane (10 mL) at ambient temperature for 1 h. The dioxane was evaporated under reduced pressure and the residue was triturated in EtOAc-ether and filtered. The solid was dried in vacuo for 24 h to give the hydrochloride salt of the title compound (93 %).

Analysis calculated for ($C_{25}H_{28}ClN_3O_4$, 2.3 HCl, 0.35 EtOAc) C, 54.23; H, 5.71; N, 7.19 Found C, 54.31; H, 5.82; N, 7.19 TLC: $R_f$=0.30 (90:10:0.5 DCM:MeOH:NH$_4$OH) HPLC (method A): retention time 6.30 min FAB MS: m/z 470 (M$^+$+H) $^1$H NMR (300 MHz, CDCl$_3$): δ

EXAMPLE 53

1-(1-(4-(4-(N-Acetyl)piperidinyloxy)-2-chlorobenzoyl)piperidin-4-yl)-1,2-dihydro-4(H)-3,1-benzoxazin-2-one

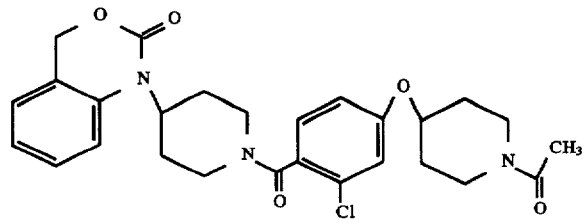

The hydrochloride salt of 1-(1-(4-(piperidinyloxy)-2-methoxybenzoyl)piperidin-4-yl)-1,2-dihydro-4(H)-3,1-benzoxazin-2-one from Example 51 was acetylated with acetic anhydride and DIEA in DCM using the procedure given in Example 18. The crude product was purified by pressurized silica gel column chromatography using a gradient elution of 2–5% MeOH-DCM. The title compound was obtained as a white solid by lyophilization from acetonitrile-H$_2$O (84% yield).

Analysis calculated for ($C_{27}H_{30}ClN_3O_5$, 1.0 H$_2$O) C, 61.18; H, 6.09; N, 7.93 Found C, 61.16; H, 5.77; N, 7.83 TLC: $R_f$=0.26 (95:5 DCM:MeOH) HPLC (method A): retention time 7.35 min FAB MS: m/z 513 (M$^+$+H)

EXAMPLE 54

1-(1-Benzyl-4-piperidyl)indol-2-one

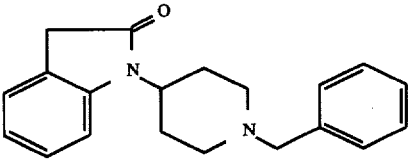

To a solution of 200 ml of methanol containing 2-aminophenylacetic acid (13.8 mmole), 1.82 ml (15.2 mmole) 1-benzyl-4-piperidone, and 4 ml acetic acid was added 20 g of 3 Angstrom molecular sieves and 1.91 g (30.4 mmole) of sodium triacetoxyborohydride at room temperature. The reaction mixture was protected from moisture and stirred overnight. After 12 hours, an additional 500 mg of sodium triacetoxyborohydride was added and stirring was continued for 4 hours more. Saturated sodium bicarbonate solution was added and most of the methanol was removed under reduced pressure. The aqueous solution was neutralized with acetic acid and extracted with ethyl acetate solution. The combined extracts were dried (sodium sulfate) and concentrated. Chromatography of the crude reaction product on silica gel (chloroform-methanol-concentrated ammonium hydroxide elution, 96:4:0.4, v/v) afforded 296 mg of a waxy solid. This material was dissolved in a solution of methanol and ether and treated with HCl gas. The resulting precipitate was collected, washed with ether and dried to give the title compound as a solid: m.p. 266°–270° C.

NMR: Consistent with structure; HPLC: >99% pure at 214 nM; TLC Rf=0.45 (CHCl$_3$—CH$_3$OH—NH$_4$OH; 95:5:0.5) FAB MS: 307 (M$^+$+H—HCl); Analysis calculated for $C_{20}H_{22}N_2O$.1.5HCl: C, 68.25; H, 6.66; N, 7.96. Found: C, 68.17; H, 6.42; N, 7.76.

EXAMPLE 55

1-(1-(2,4-dimethoxybenzoyl)-4-piperidyl)indol-2-one

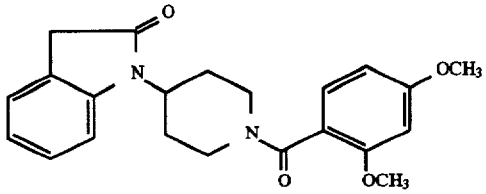

Step 1: Synthesis of 1-(4-piperidyl)indol-2-one

A solution of 10 ml of methanol containing 296 mg of 1-(1-benzyl-4-piperidyl)indol-2-one was treated with 300 mg of palladium hydroxide catalyst. The resulting suspension was hydrogenated at atmospheric pressure for 60 minutes at 23° C. More catalyst was added (100 mg) and the hydrogenation was continued for 30 minutes more. The reaction mixture was filtered through Celite, concentrated and azeotropically dried with toluene to yield 217 mg of 1-(4-piperidyl)indol-2-one.

Step 2: Synthesis of 1-(1-(2,4-dimethoxybenzoyl)-4-piperidyl)indol-2-one 1-(4-Piperidyl)indol-2-one (53 mg, 0.245 mmole), 2,4-dimethoxybenzoyl chloride (54 mg, 0.27 mmole), and 38 mL (0.27 mmole) triethylamine were mixed in 4 ml of chloroform at 0° C. The reaction mixture was stirred at 0° C.

for 5 minutes and then at 23° C. for 15 minutes during which time the pH was adjusted to 7.5 with triethylamine. The reaction mixture was concentrated under reduced pressure and the residue was purified by preparative thick layer chromatography (CHCl₃—CH₃OH—NH₄OH; 95:5:0.5) to yield 42 mg of the title compound: m.p. 88°–93° C.

NMR: Consistent with structure and confirms presence of solvate: HPLC: 97.7% pure at 214 nM; TLC R$_f$=0.56 (CHCl₃—CH₃OH—NH₄OH; 95:5:0.5) FAB MS: 381 (M⁺+H); Analysis calculated for C₂₂H₂₄N₂O₄.0.15CHCl₃: C, 66.79; H, 6.11; N, 7.03. Found: C, 66.96; H, 6.03; N, 6.75.

EXAMPLE 56

4-(1-(2,4-dimethoxybenzoyl)-4-piperidinyl)-(2H)-1,4-benzothiazin-3(4H)-one

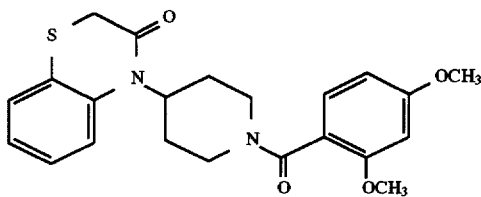

Step 1: Synthesis of Ethyl (2-aminophenyl)mercaptoacetate

Ethyl bromoacetate (1.47 g, 8.8 mmole) was added to a mixture of 2-aminothiophenol (1 g, 8 mmole) and triethylamine (1.4 ml, 10 mmole) in dry N,N,-dimethylformamide at 23° C. The reaction mixture was stirred for 12 hours diluted with 300 ml of ethyl acetate and washed with water and brine. The dried (sodium sulfate) extracts were concentrated in vacuo to afford the title compound.

Step 2: Synthesis of Ethyl 2-N-(1-benzyl-4-piperidyl) aminophenylmercapto acetate Ethyl (2-aminophenyl)mercaptoacetate (322 mg, 1.52 mmole), N-tert-butyloxycarbonylpiperidin-4-one (456 mg, 2.29 mmole), acetic acid (478 ml, 8.36 mmole), and sodium triacetoxyborohydride (966 mg, 4.56 mmole) were combined in 10 ml of dichloroethane at room temperature, protected from moisture and stirred overnight. Saturated sodium bicarbonate solution was added and the reaction mixture was extracted with ethyl acetate. The combined extracts were washed with sodium bicarbonate solution and brine, then dried and concentrated. The crude product was chromatographed on silica gel (ethyl acetate-hexane elution, 1:3 v/v) to give 210 mg of the title compound along with 99 mg of 2H-1,4-benzothiazin-3(4H)-one.

Steps 3 & 4: Synthesis of 4-(4-piperidyl)-(2H)-1,4-benzothiazin-3(4H)-one hydrochloride To an ice cold suspension of potassium hydride (46 mg, 0.398 mmole, 35% suspension) in 10 ml of dry tetrahydrofuran was added over 60 seconds a 1 ml solution of tetrahydrofuran containing 157 mg (0.398 mmole) of ethyl 2-N-(1-benzyl-4-piperidyl)aminophenylmercapto acetate. The reaction mixture was stirred at 0° C. for 30 minutes and diluted with ethyl acetate (200 ml). The organic phase was washed with water and brine, then dried and concentrated to give 149 mg of 4-(1-tert-butyloxycarbonyl-4-piperidyl)-(2H)-1,4-benzothiazin-3(4H)-one. This material was dissolved in 15 ml of dry ethyl acetate, cooled to 0° C., and treated with HCl gas for 10 minutes. The reaction flask was capped and the reaction mixture was stirred for 45 minutes more. All volatiles were removed under reduced pressure and the residue was azeotropically dried with toluene to give 123 mg of the title compound.

Step 5: Sythesis of 4-(1-(2,4-dimethoxybenzoyl)-4-piperidyl)-(2H)-1,4-benzothiazin-3(4H)-one 4-(4-Piperidyl)-(2H)-1,4-benzothiazin-3(4H)-one hydrochloride (75 mg, 0.264 mmole) was suspended in chloroform and treated with 41 ml of triethylamine. The reaction mixture was cooled to 0° C., 2,4-dimethoxybenzoyl chloride (58 mg, 0.29 mmole) and an additional 40 ml of triethyl amine were added. The reaction mixture was stirred for 15 minutes and then warmed to room temperature over a 10 minute period. An addional 6 mg of 2,4-dimethoxybenzoyl chloride was added to complete the reaction. After 10 minutes more, the reaction mixture was concentrated to half its volume and flash chromatographed on silica gel (ethyl acetate-hexane gradient elution, 1: to 2:1 to 3:1 v/v) to yield 59 mg of the title compound: m.p. 84°–87° C.

NMR: Consistent with structure and confirms presence of solvate: HPLC: 99.5% pure at 214 nM; TLC Rf=0.4 (ethyl acetate-hexane) FAB MS: 413 (M⁺+H); Analysis calculated for C₂₂H₂₄N₂O₄S.0.4C₄H₈O₂.0.1C₆H₁₂: C, 63.69; H, 6.32; N, 6.14. Found: C, 63.70; H, 6.26; N, 6.19.

EXAMPLE 57

1-(1-(2,4-Dimethoxybenzoyl)azetidin-3-yl)-1,2-dihydro-4(H)-3,1-benzoxazin-2-one

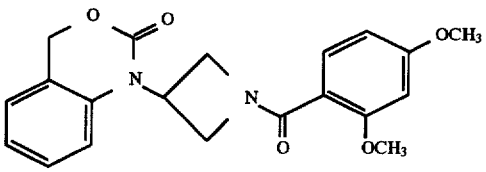

Step 1:

1-Diphenylmethylazetidin-3-one (1.92 g, 8.08 mmole), aminobenzylalcohol (496 mg, 4.03 mmole) and acetic acid (1.39 ml, 24.3 mmole) were combined with 20 ml of methanol at room temperature. Sodium cyanoborohydride (508 mg, 8.08 mmole) was added and the resulting mixture was stirred for 1.5 hours. Most of the solvent was removed under reduced pressure and the residue was partitioned between ethyl acetate (200 ml) and saturated sodium bicarbonate solution (20 ml). The organic phase was washed with brine, dried (sodium sulfate) and concentrated. Flash chromatography of the crude product on silica gel (hexane-ethyl acetate elution, 4:1 v/v) gave 960 mg (69%) of 1-diphenylmethyl-3-((2-hydroxymethyl)phenylamino) azetedine.

Step 2:

A suspension of 432 mg (1.25 mmole) 1-diphenylmethyl-3-((2-hydroxymethyl)phenylamino)azetidine and 412 mg of 20% palladium hydroxide catalyst in 12 ml of methanol was hydrogenated at atmospheric pressure and 23° C. for 2 hours. The reaction mixture was filtered through micropore filter paper, the filter cake was washed with methanol, and the filtrate was concentrated under reduced pressure. The resulting product was azeotropically dried with toluene to give 372 mg of 3-((2-hydroxymethyl)phenylamino) azetidine.

Step 3:

A 5:2 solvent mix of chloroform and tetrahydrofuran (14 ml) containing 3-((2-hydroxymethyl)phenylamino)azetidine (136 mg, 0.767 mmole) was cooled to 0° C. and treated with 2,4-dimethoxybenzoyl chloride (154 mg, 0.767 mmole). To this mixture was added triethylamine (107 ml, 0.767 mmole) with stirring. The reaction mixture was warmed to room temperature over 30 minutes and stirred for 30 minutes more. The solvent was removed in vacuo and the residue was dissolved in ethyl acetate (200 ml). The organic phase was washed in succession with brine (20 ml), 5% sodium bicarbonate solution (20 ml), and brine (20 ml). Concentration of the dried extracts afforded the product which was purified by flash chromatography on silica gel (ethyl acetate-hexane gradient elution, 50% to 85% ethyl acetate in hexane) yielding 125 mg of 1-(2,4-dimethoxybenzoyl)-3-((2-hydroxymethyl)phenylamino)azetidine.

Step 4:
1-(2,4-dimethoxybenzoyl)-3-((2-hydroxymethyl) phenylamino)azetidine (119 mg, 0.348 mmole) was dissolved in 10 ml of dry tetrahydrofuran and 0.048 ml of triethylamine was added. The resulting solution was cooled to 0° C. and treated with 34 mg of triphosgene and 0.048 ml of triethylamine. The pH of the reaction mixture was approximately 8. After 5 minutes the reaction mixture was warmed to room temperature and filtered. All volatiles were removed under reduced pressure and the residue was dissolved in ethyl acetate (200 ml). The organic phase was washed with brine, dried, and then concentrated to give 161 mg of crude product. Flash chromatography of the crude product on silica gel (ethyl acetate-hexane gradient elution, 50% to 80% ethyl acetate in hexane), followed by trituratation with ethyl ether-petroleum ether, afforded the analytical sample of the title compound.

m.p. 82°–85° C. NMR: Consistent with structure and confirms presence of solvate; HPLC: >94% pure at 214 nM; TLC Rf=0.12 (ethyl acetate-hexane, 4:1) FAB MS: 369 (M⁺+H); Analysis calculated for $C_{20}H_{20}N_2O_5 \cdot 0.25H_2O$: C, 64.41; H, 5.54; N, 7.51. Found: C, 64.48; H, 5.59; N, 7.38.

EXAMPLE 58

1-(1-Diphenylmethyl-3-azetidyl)-2,3,4,5-tetrahydro-1H-1-benzazepin-2-one

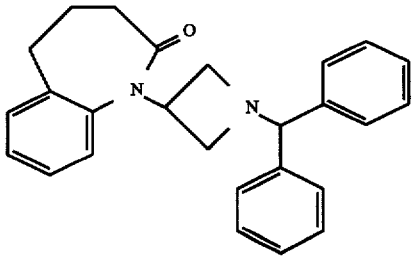

Step 1: Synthesis of methyl 4-(2-(1-diphenylmethyl-3-azetidyl)amino) phenylbutyrate 1-Diphenylmethylazetidin-3-one (2.0 g, 8.08 mmole), methyl 4-(2-aminophenyl)butyrate (0.815 g, 4.03 mmole) and acetic acid (1.45 ml, 25.3 mmole) were combined with 21 ml of methanol at room temperature. Sodium cyanoborohydride (530 mg, 8.43 mmole) was added and the resulting mixture was stirred for 3 hours. Most of the solvent was removed under reduced pressure and the residue was partitioned between ethyl acetate (250 ml) and saturated sodium bicarbonate solution (25 ml). The organic phase was washed with brine, dried (sodium sulfate) and concentrated. Flash chromatography of the crude product on silica gel (hexane-ethyl acetate elution, 4:1 v/v) gave 1.39 mg (79%) of the title compound.

Step 2: 1(1-Diphenylmethyl-3-azetidyl)-2,3,4,5-tetrahydro-1H-1-benzazepin-2-one

A solution of methyl 4-(2-(1-diphenylmethyl-3-azetidyl) amino) phenylbutyrate (316 mg, 0.762 mmole) in 23 ml of dry N,N-dimethylformamide was treated with a 35% mineral oil suspension of potassium hydride (96 mg, 0.838 mmole) at room temperature under nitrogen. The reaction mixture was stirred for 45 minutes and quenched with the addition of brine. The pH of the resulting solution was adjusted to approximately 7.5 with acetic acid and the volatiles were removed under reduced pressure to give 330 mg of a semi-solid. Flash chromatography of the crude product on silica gel (hexane-ethyl acetate elution, 3:2 v/v) gave 230 mg (79%) of the title compound as a solid:

m.p. 158°–161° C. NMR: Consistent with structure and confirms presence of solvate; HPLC: 97.8% pure at 214 nM; TLC Rf=0.39 (ethyl acetate-hexane, 1:1) FAB MS: 383 (M⁺+H); Analysis calculated for $C_{26}H_{26}N_2O \cdot 0.05CHCl_3$: C, 80.54; H, 6.76; N, 7.21. Found: C, 80.87; H, 6.70; N, 7.26.

EXAMPLE 59

1-(1-(2,4-dimethoxybenzoyl)-3-azetidyl)-2,3,4,5-tetrahydro-1H-1-benzazepin-2-one

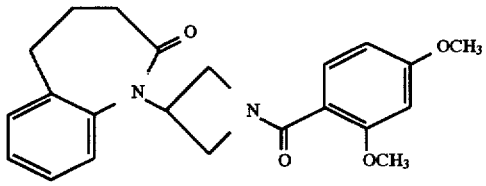

Step 1: Synthesis of methyl 4-(2-(3-azetidyl)amino) phenylbutyrate

Methyl 4-(2-(1-diphenylmethyl-3-azetidyl)amino) phenylbutyrate (630 mg, 1.52 mmole) and 630 mg of palladium hydroxide catalyst were mixed in 20 ml of methanol and hydrogenated at atmospheric pressure for 2 hours. The reaction mixture was filtered, the filter cake was washed with methanol, and the filtrated and combined washings were rotoevaporated under reduced pressure. The title compound was azeotropically dried with toluene and used in the next step without further purification.

Step 2: Synthesis of methyl 4-(2-(1-(2,4-dimethoxybenzoyl) -3-azetidyl)amino)phenylbutyrate A magnetically stirred solution of chloroform (5 ml) containing methyl 4-(2-(3-azetidyl)amino)phenylbutyrate (0.76 mmole) was cooled to 0° C. and treated with 2,4-dimethoxybenzoyl chloride (152 mg, 0.76 mmole). The pH of the resulting reaction mixture was adjusted with triethylamine (106 ml, 0.76 mmole). The reaction mixture was gradually warmed to ambient temperature and the solvent was removed under reduced pressure. The residual material was partitioned between ethyl acetate and brine. The organic phase was washed with a saturated sodium bicarbonate-brine mixture, dried, and concentrated in vacuo. The analytical material was obtained via preparative thick layer chromatography on silica gel (ethyl acetate-hexane elution, 4:1 v/v):

NMR: Consistent with structure; HPLC: 97.8% pure at 214 nM; TLC Rf=0.25 (ethyl acetate-hexane, 4:1) FAB MS: 413 (M⁺+H); Analysis calculated for $C_{23}H_{28}N_2O_5$: C, 66.97; H, 6.84; N, 6.79. Found: C, 67.12; H, 6.71; N, 6.42.

Step 3: 1(1-(2,4-dimethoxybenzoyl)-3-azetidyl)-2,3,4,5-tetrahydro-1H-1-benzazepin-2-one A solution of methyl 4-(2-(1-(2,4-dimethoxybenzoyl)-3-azetidyl)amino)phenylbutyrate (85 mg, 0.206 mmole) in 6.3 ml of dry N,N-dimethylformamide was treated with a 35% mineral oil suspension of potassium hydride (26 mg, 0.227 mmole) at room temperature under nitrogen. The reaction mixture was stirred for 30 minutes and quenched with the addition of brine. The pH of the resulting solution was adjusted to approximately 7.5 with acetic acid and the volatiles were removed under reduced pressure to give a semi-solid. Flash chromatography of the crude product on silica gel (chloroform-methanol gradient elution, 98:2 to 80:20) gave 51 mg of the title compound as a solid: m.p. 59°–62° C.

NMR: Consistent with structure and confirms presence of solvate; HPLC: 97.2% pure at 214 nM; TLC Rf=0.39 (ethyl acetate-hexane, 1:1) FAB MS: 381 (M$^+$+H); Analysis calculated for $C_{22}H_{24}N_2O_4$·0.05DMF·0.1CHCl$_3$: C, 67.47; H, 6.22; N, 7.25. Found: C, 67.21; H, 6.08; N, 6.92.

EXAMPLE 60

1-(1-(2,4-dimethoxybenzoyl)-2-cyanopiperidin-4-yl)-1,2-dihydro-4(H)-3,1-benzoxazin-2-one

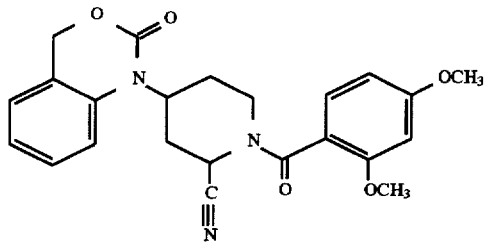

Step 1:

1-(4-piperidinyl)-1,2-dihydro-4(H)-3,1-benzoxazin-2-one (800 mg, 3.44 mmol) was treated with glacial acetic acid (0.197 mL, 3.44 mmol) and water (2 mL). To the solution was added a suspension of calcium hypochlorite (637 mg (85%), 3.78 mmol) in 1 mL of water. The resulting mixture was stirred at ambient temperature for 30 min and extracted with ether (100 mL). The ether layer was washed with water, brine, dried over Na$_2$SO$_4$, filtered, and concentrated under reduced pressure. Filtration of a precipitate gave 4-(1-chloropiperidinyl)-2-benzoxazinone (280 mg), and concentration of the filtrate gave an additional 628 mg, mp 122°–3° C. (decomposes). (NMR consistent with structure; TLC R$_f$=0.18, 1% ether in CH$_2$Cl$_2$).

Step 2:

To a solution of 1-(1-chloropiperidinyl)-1,2-dihydro-4(H)-3,1-benzoxazin-2-one from Step 1 (230 mg, 0.862 mmol) in warm ether (30 mL), and dried over MgSO$_4$ and CaCO$_3$ for 1 h and filtered. The filtrate was added dropwise to a suspension of potassium superoxide (135 mg, 1.90 mmol) and 10 mg of cis-dicyclohexano-18-crown-6 in ether (10 mL). The mixture was stirred at ambient temperature for 24 h. A second portion of of potassium superoxide (135 mg) and cis-dicyclohexano-18-crown-6 (10 mg) were added and stirring was continued for an additional 66 h. The mixture was filtered and the filtrate was added dropwise to a solution of cyanotrimethylsilane (0.172 mL, 1.29 mmol) in ether (10 mL). The reaction was stirrred at ambient temperature for 16 h, the solvent was removed under reduced pressure, and the residue was purified by pressurized silica gel coumn chromatography using 1% MeOH-DCM as eluant to give 1-(2-cyanopiperidin-4-yl)-1,2-dihydro-4(H)-3,1-benzoxazin-2-one as an oily foam (48% yield).

NMR: Consistent with structure; TLC Rf=0.36 (4% MeOH-DCM) FAB MS: 258 (M$^+$+H);

Step 3:

To a solution of 1-(2-cyanopiperidin-4-yl)-1,2-dihydro-4(H)-3,1-benzoxazin-2-one from Step 2 (198 mg, 0.768 mmol) in DCM (2 mL) was added 2,4-dimethoxybenzoyl chloride (197 mg, 0.845 mmol) follwed by triethylamine (0.118 mL, 0.845 mmol). After the reaction had been stirred at ambient temperature for 1 h, the solvent was removed under reduced pressure and the residue was purified by pressurized silica gel column chromatography usinf 10% ether-DCM as eluant. The title compound was obtained as a white solid, mp 176°–7° C. (63% yield).

NMR: Consistent with structure; HPLC: 93.2% pure at 214 nM; TLC Rf=0.33 (10% ether-DCM) FAB MS: 381 (M$^+$+H); Analysis calculated for $C_{23}H_{23}N_3O_5$: C, 65.54; H, 5.50; N, 9.97. Found: C, 65.51; H, 5.52; N, 9.89.

EXAMPLE 61

1-(1-(2,4-dimethoxybenzoyl)piperidin-4-yl)-4,4-dimethyl-1,2-dihydro-4(H)-3,1-benzoxazin-2-one

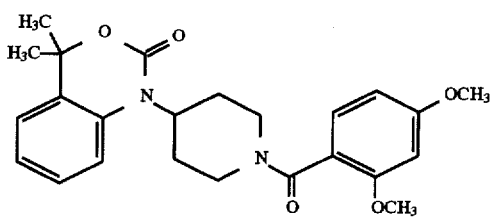

Step 1:

To a 0° C. solution of methylmagnesium bromide (45 mL of a 1.4M solution in toluene, 63 mmol) under nitrogen atmosphere was added a solution of ortho-aminoacetophenone (2.9 g, 21.5 mmol) in THF (20 mL). The mixture was warmed to ambient temperature for 45 min, cooled to 0° C., and poured into ice-water. The mixture was acidified with 6N HCl, adjusted to ca. pH 6 with saturated sodium bicarbonate solution, and then extracted with ether (2×100 mL). The combined ether fractions were dried (MgSO$_4$), filtered and the solvent was removed under reduced pressure to give the oily product, 2-aminophenyldimethyl carbinol.

Step 2:

2-Aminophenyldimethyl carbinol from Step 1 was reductively alkylated with 1-t-butyloxycarbonyl-4-piperidinone (2.6 g, 13.2 mmol) by the procedure given in Step 2 of Example 1 to give 4-(2-(1-methyl-1-hydroxyethyl)phenyl)amino-1-t-butyloxycarbonylpiperidine as an oil.

Steps 3 and 4:

4-(2-(1-Methyl-1-hydroxyethyl)phenyl)amino-1-t-butyloxycarbonylpiperidine from Step 2 was cyclized with triphosgene using the procedure given in Step 3 of Example 1. The product, 1-(1-t-butyloxycarbonylpiperidin-4-yl)-4,4-dimethyl-1,2-dihydro-4(H)-3,1-benzoxazin-2-one was N-deprotected using HCl in ethyl acetate using the procedure given in Step 4 of Example 1. The hydrochloride salt of 1-(piperidin-4-yl)-4,4-dimethyl-1,2-dihydro-4(H)-3,1-benzoxazin-2-one was obtained as a solid.

Step 5:

The hydrochloride salt of 1-(piperidin-4-yl)-4,4-dimethyl-1,2-dihydro-4(H)-3,1-benzoxazin-2-one was acylated with 2,4-dimethoxybenzoyl chloride using the procedure given in Step 6 of Example 35. The crude product was purified by pressurized silica gel column chromatography and then crystallization from ether-hexanes to give the title compound as a solid, mp 168.5°–171° C.

NMR: Consistent with structure; HPLC: 98.3% pure at 214 nM; TLC Rf=0.58 (160:10:1 CHCl$_3$:MeOH:NH$_4$OH) FAB MS: 381 (M$^+$+H); Analysis calculated for $C_{24}H_{28}N_2O_5$: C, 67.05; H, 6.71; N, 6.52. Found: C, 66.99; H, 6.67; N, 6.52.

EXAMPLE 62

1-(1-(2,4-dimethoxybenzoyl)piperidin-4-yl)-5-methyl-1,2-dihydro-4(H)-3,1-benzoxazin-2-one

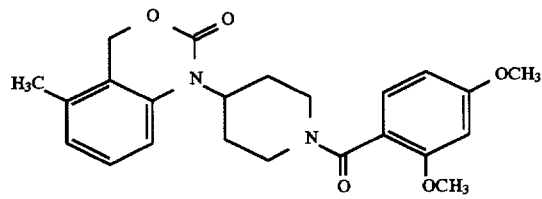

Step 1:

6-Methylanthranilic acid (5.0 g, 33 mmol) was combined with 80 mL of a 1N solution of borane in tetrahydrofuran. The resulting reaction mixture was heated to reflux for 4 h and then stirred at ambient temperature overnight. Sodium hydroxide solution (1N) was added and the biphasic mixture was concentrated under reduced pressure. The residue was dissolved in ethyl acetate and the organic phase was washed with water and brine, then dried (sodium sulfate) and concentrated to yield 4.5 g of 3-(2-hydroxymethyl)toluidine as a tan solid.

Step 2:

A mixture of 2.0 g (15 mmol) of 3-(2-hydroxymethyl) toluidine from Step 1, N-tert-butyloxycarbonylpiperidin-4-one (3.4 g, 17 mmol), and 1.7 mL (30 mmol) of glacial acetic acid in 72 mL of toluene was refluxed in a Dean-Stark apparatus for 4 h. The reaction mixture was cooled to ambient temperature, treated with 940 mg (15 mmol) of sodium cyanoborohydride, and stirred at ambient temperature overnight. More sodium cyanoborohydride (470 mg) was added and the pH of the reaction mixture was adjusted to 5 with the addition of acetic acid. After a total reaction time of 48 hours, the reaction mixture was partitioned between sodium bicarbonate solution and ethyl acetate. The layers were separated and the organic phase was washed with water and brine, then dried (sodium sulfate) and concentrated to give 3.6 g of 1-t-butyloxycarbonyl-4-(3-methyl-(2-hydroxymethyl)phenylamino)piperidine.

Steps 3, 4, and 5:

Cyclization of the product from Step 2 was accomplished with triphosgene, DIEA in THF as described in the procedure of Step 3 of Example 1. The product, 1-(1-(tert-butyloxycarbonyl)piperidin-4-yl)-5-methyl-1,2-dihydro-4(H)-3,1-benzoxazin-2-one, was N-deprotected with HCl in EtOAc using the procedure given in Step 4 of Example 1. The product, 1-(piperidin-4-yl)-5-methyl-1,2-dihydro-4(H)-3,1-benzoxazin-2-one hydrochloride, was acylated with 2,4-dimethoxybenzoyl chloride using a procedure analagous to that given in Step 6 of Example 35. The title compound was purified by pressurized silica gel chromatography using EtOAc-hexane as eluant.

NMR: Consistent with structure and confirms presence of solvate; HPLC: >99% pure at 214 nM; FAB MS: 522 (M$^+$+H); Elem. Anal. calc'd for $C_{23}H_{26}N_2O_5 \cdot 0.5$EtOAc: Calc'd: C, 66.06; H, 6.65; N, 6.16. Found: C, 65.83; H, 6.48; N, 6.51.

EXAMPLE 63

1-(1-(2,4-dimethoxybenzoyl)piperidin-4-yl)-1,2-dihydro-4 (H)-3,1-thienoxazin-2-one

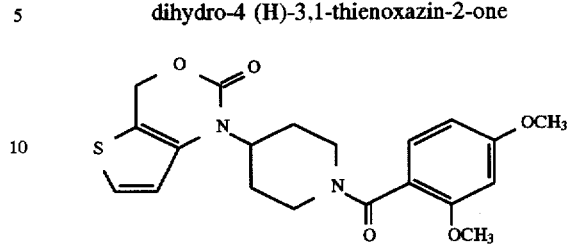

Step 1:

3-Amino-2-methoxycarbonylthiophene is reductively alkylated with 1-tert-butyloxycarbonylpiperidin-4-one and sodium cyanoborohydride to give 3-(1-tert-butyloxycarbonylpiperidin-4-ylamino)-2-methoxycarbonylthiophene.

Step 2:

The product from Step 1 is saponified with aqueous NaOH to give 3-(1-tert-butyloxycarbonylpiperidin-4-ylamino)thiophene-2-carboxylic acid.

Step 3:

The product from Step 2 is reduced with borane in THF to give 3-(1-tert-butyloxycarbonylpiperidin-4-ylamino)-2-hydroxymethylthiophene.

Step 4:

The product from Step 3 is cyclized with triphosgene and DIEA to give 1-(1-(tert-butyloxycarbonyl)piperidin-4-yl)-1,2-dihydro-4(H)-3,1-thienoxazin-2-one.

Step 5:

The product from Step 4 is N-deprotected using gaseous HCl in EtOAc to give the hydrochloride salt of 1-(piperidin-4-yl)-1,2-dihydro-4(H)-3,1-thienoxazin-2-one.

Step 6:

The product from Step 5 is acylated with 2,4-dimethoxybenzoyl chloride and DIEA to give the title compound.

EXAMPLE 64

1-(1-(4-(4-(1-(3-Chloropropylsulfonyl) piperidinyloxy)-2-methoxybenzoyl)piperidin-4-yl)-1,2-dihydro-4(H)-3,1-benzoxazin-2-one

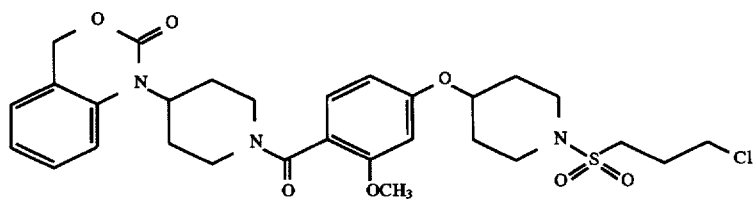

To a stirred 0° C. solution of 1-(1-(4-(4-piperidinyloxy)-2-methoxybenzoyl)piperidin-4-yl)-1,2-dihydro-4(H)-3,1-benzoxazin-2-one hydrochloride (2.0 g, 4.0 mmol) from Example 26 and DIEA (1.52 mL; 8.75 mmol) in CH$_2$Cl$_2$ (50 mL) was added 3-chloropropylsulfonyl chloride (0.770 g; 4.35 mmol) dropwise. The solution was stirred at 0° C. for 30 min and then at ambient temperature for 2 h. The solvent was removed under reduced pressure and the residue was dissolved in EtOAc (100 mL) and washed with saturated aqueous NaHCO$_3$ (2×50 mL) and brine (50 mL). The EtOAc layer was dried (MgSO$_4$), filtered, and the solvent was removed under reduced pressure. The residue was purified by pressurized silica gel column chromatography using a gradient elution of 1:99 to 3:97 MeOH:CH$_2$Cl$_2$. The title compound was obtained as an amorphous solid by evaporation of a CH$_2$Cl$_2$ solution under reduced pressure.

Analysis calculated for (C$_{29}$H$_{36}$ClN$_3$O$_7$S, 0.8 CH$_2$Cl$_2$) C, 53.09; H, 5.62; N, 6.23 Found C, 53.12; H, 5.50; N, 6.36 TLC: R$_f$=0.41 (96:4 CH$_2$Cl$_2$:MeOH) HPLC (method A): retention time 9.42 min FAB MS: m/z 605, 607 (M$^+$+H)

EXAMPLE 65

1-(1-(4-(4-(1-((3-Cyclopropylamino)propylsulfonyl)piperidinyloxy)-2-methoxybenzoyl)piperidin-4-yl)-1,2-dihydro-4(H)-3,1-benzoxazin-2-one

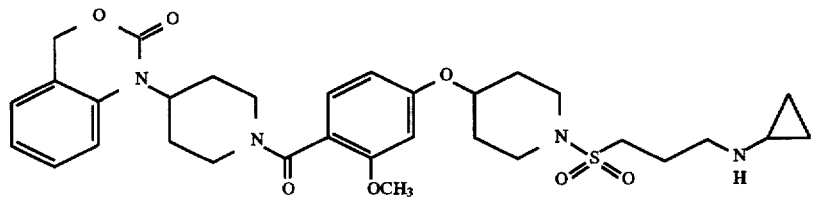

Step 1:
A solution of 1-(1-(4-(4-(1-(3-chloropropylsulfonyl)piperidinyloxy)-2-methoxybenzoyl)piperidin-4-yl)-1,2-dihydro-4(H)-3,1-benzoxazin-2-one (1.0 g, 1.65 mmol) from Example 64 and NaI (1.24 g; 8.25 mmol) in acetone (70 mL) was refluxed for 48 h. The solution was cooled to ambient temperature and the solvent was removed under reduced pressure. The residue was dissolved in EtOAc (100 mL) and washed with saturated aqueous NaHCO$_3$ (2×50 mL) and brine (50 mL). The EtOAc layer was dried (MgSO$_4$), filtered, and the solvent was removed under reduced pressure. The residue was purified by pressurized silica gel column chromatography using a gradient elution of 1:99 to 3:97 MeOH:CH$_2$Cl$_2$. 1-(1-(4-(4-(1-(3-iodopropylsulfonyl)piperidinyloxy)-2-methoxybenzoyl)piperidin-4-yl)-1,2-dihydro-4(H)-3,1-benzoxazin-2-one was obtained as an amorphous solid by evaporation of a CH$_2$Cl$_2$ solution under reduced pressure (TLC R$_f$=0.52 (98:2 CH$_2$Cl$_2$:MeOH); HPLC retention time=9.57 min (method A); FAB MS m/z=698 (M$^+$+H)).

Step 2:
1-(1-(4-(4-(1-(3-Iodopropylsulfonyl)piperidinyloxy)-2-methoxybenzoyl)piperidin-4-yl)-1,2-dihydro-4(H)-3,1-benzoxazin-2-one (0.50 g; 0.72 mmol) from Step 1 above was dissolved in 1:1 MeOH:DMF (20 mL) and cyclopropylamine (2 g; 35 mmol) was added. The solution was stirred at ambient temperature for 24 h. The solvents were removed under reduced pressure and the residue was dissolved in EtOAc (100 mL) and washed with saturated aqueous NaHCO$_3$ (2×50 mL) and brine (50 mL). The EtOAc layer was dried (MgSO$_4$), filtered, and the solvent was removed under reduced pressure. The residue was purified by pressurized silica gel column chromatography using a gradient elution of 1:99 to 4:96 A:B (A=95:5 MeOH:NH$_4$OH, B=CH$_2$Cl$_2$). The title compound was dissolved in MeOH and to the solution was added 2 equivalents of 1.0N aqueous HCl. The resulting solution was evaporated under reduced pressure and the residue was dissolved in 3:2 H$_2$O:CH$_3$CN and lyophilized. The HCl salt of the title compound was obtained as an amorphous powder.

Analysis calculated for (C$_{32}$H$_{42}$N$_4$O$_7$S, 1.45 HCl, 0.05 H$_2$O) C, 56.47; H, 6.45; N, 8.23 Found C, 56.46; H, 6.42; N, 8.38 TLC: R$_f$=0.27 (97:3:0.3 CH$_2$Cl$_2$:MeOH:NH$_4$OH) HPLC (method A): retention time 7.07 min FAB MS: m/z 627 (M$^+$+H)

EXAMPLE 66

1-(1-(4-(1-((3-N-Cyclopropyl-N-methylamino)propylsulfonyl)piperidin-4-yloxy)-2-methoxybenzoyl)piperidin-4-yl)-1,2-dihydro-4(H)-3,1-benzoxazin-2-one

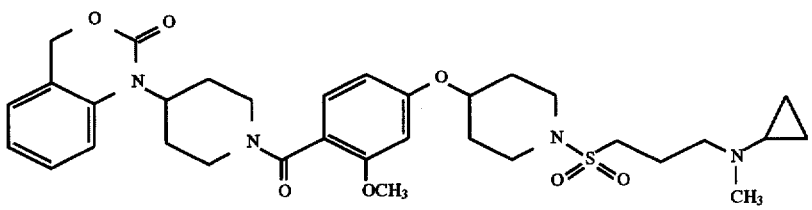

To a stirred solution of 1-(1-(4-(4-(1-(3-cyclopropylamino)propylsulfonyl)piperidinyloxy)-2-methoxybenzoyl)piperidin-4-yl)-1,2-dihydro-4(H)-3,1-benzoxazin-2-one (0.5 g, 0.80 mmol) from Example 65 in 100:1 MeOH:HOAc (10 mL) was added 37% aqueous formaldehyde (0.17 mL; 2.1 mmol) followed by the portionwise addition of NaBH$_3$CN (0.12 g; 1.9 mmol). After being stirred at ambient temperature for 18 h, the mixture was evaporated under reduced pressure and the residue was partitioned between EtOAc (150 mL) and saturated aqueous NaHCO₃ (100 mL). The organic phase was washed with brine (50 mL), dried (MgSO₄), filtered, and the solvent was removed under reduced pressure. The residue was purified by pressurized silica gel column chromatography using a gradient elution of 1:99 to 4:96 A:B (A=95:5 MeOH:NH₄OH, B=CH₂Cl₂). The title compound was dissolved in MeOH and to the solution was added 1.0 equivalent of tartaric acid. The resulting solution was evaporated under reduced pressure and the residue was dissolved in 3:2 H₂O:CH₃CN and lyophilized. The resulting amorphous powder was crystallized from water to give the hemi-tartrate salt of the title compound as a white crystalline solid.

Analysis calculated for (C₃₃H₄₄N₄O₇S, 0.5 tartaric acid, 3.16 H₂O) C, 54.39; H, 6.95; N, 7.25 Found C, 55.59; H, 6.35; N, 7.25 TLC: R_f=0.30 (97:3:0.3 CH₂Cl₂:MeOH:NH₄OH) HPLC (method A): retention time 7.10 min FAB MS: m/z 641 (M⁺+H)

EXAMPLE 67

1-(1-(4-(4-(1-(vinylsulfonyl)piperidinyloxy)-2-methoxybenzoyl)piperidin-4-yl)-1,2-dihydro-4(H)-3,1-benzoxazin-2-one

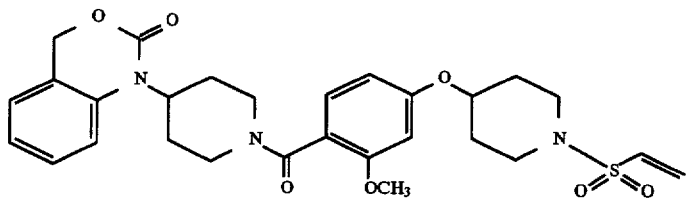

To a stirred 0° C. solution of 2-chloroethylsulfonyl chloride (1.92 g; 11.8 mmol) in CH₂Cl₂ (20 mL) was added a solution of (1-(1-(4-(4-piperidinyloxy)-2-methoxybenzoyl) piperidin-4-yl)-1,2-dihydro-4(H)-3,1-benzoxazin-2-one (5.0 g, 10.8 mmol) from Example 26 and DIEA (4.2 mL; 24 mmol) in CH₂Cl₂ (75 mL) dropwise. The reaction was stirred at 0° C. for 2 h and then at ambient temperature for 12 h. The reaction mixture was diluted with CH₂Cl₂ (100 mL) and washed with saturated aqueous NaHCO₃ (2×100 mL) and brine (50 mL). The CH₂Cl₂ layer was dried (MgSO₄), filtered, and the solvent was removed under reduced pressure. The residue was purified by pressurized silica gel column chromatography using a gradient elution of 1:99 to 3:97 MeOH:CH₂Cl₂. The title compound was obtained as an amorphous solid by evaporation of a CHCl₃ solution under reduced pressure.

Analysis calculated for (C₂₈H₃₃N₃O₇S, 0.5 CHCl₃) C, 55.62; H, 5.49; N, 6.83 Found C, 55.66; H, 5.62; N, 6.68 TLC: R_f=0.40 (96:4 CH₂Cl₂:MeOH) HPLC (method A): retention time 8.37 min FAB MS: m/z 556 (M⁺+H)

EXAMPLE 68

1-(1-(4-(4-(1-((3-amino-3-methyl)butylsulfonyl)-piperidinyloxy)-2-methoxybenzoyl)piperidin-4-yl)-1,2-dihydro-4(H)-3,1-benzoxazin-2-one

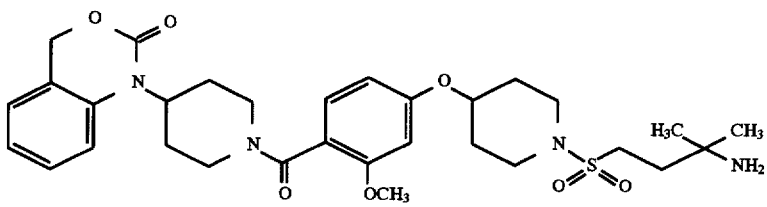

Step 1:

To a stirred solution of 1-(1-(4-(4-(1-(vinylsulfonyl)-piperidinyloxy)-2-methoxybenzoyl)piperidin-4-yl)-1,2-dihydro-4(H)-3,1-benzoxazin-2-one from Example 67 (0.30 g; 0.54 mmol) and 2-nitropropane (0.48 g; 5.4 mmol) in MeOH (10 mL) was added DBU (0.25 g; 2.8 mmol). The reaction ws stirred at ambient temperature for 18 h. HOAc (0.2 mL; 3 mmol) was added and the volatiles were removed under reduced pressure. The residue was dissolved in EtOAc (50 mL) and washed with 5% citric acid (25 mL), saturated aqueous NaHCO₃ (2×25 mL), and brine (25 mL). The organic phase was dried (MgSO₄), filtered, and the solvent was removed under reduced pressure. The residue was purified by pressurized silica gel column chromatography using a gradient elution of 1:99 to 3:97 MeOH:CH₂Cl₂ as eluant. 1-(1-(4-(4-(1-((3-methyl-3-nitro)butylsulfonyl) piperidinyloxy)-2-methoxybenzoyl)piperidin-4-yl)-1,2-dihydro-4(H)-3,1-benzoxazin-2-one was obtained as an amorphous solid (TLC R_f=0.25 (3:98 MeOH:CH₂Cl₂); HPLC retention time=9.38 min; FAB MS m/z 645 (M⁺+H).

Step 2:

1-(1-(4-(4-(1-((3-Methyl-3-nitro)butylsulfonyl) piperidinyloxy)-2-methoxybenzoyl)piperidin-4-yl)-1,2-dihydro-4(H)-3,1-benzoxazin-2-one (0.27 g; 0.42 mmol) from Step 1 above was dissolved in MeOH (15 mL). To the rapidly stirred solution was added NiCl₂ (0.17 g; 1.3 mmol) followed by NaBH₄ (0.51 g; 1.3 mmol) added in three portions over 15 min. Addition of the NaBH₄ was accompanied by the evolution of gas and a mild exotherm. The black suspension was rapidly stirred for 3 h at ambient temperature. An equal volume of EtOAc was added and the solids were removed by filtration through Celite. The filter-cake was washed with 1:1 MeOH:EtOAc and the filtrate solvents were removed under reduced pressure. The residue was suspended in CH₂Cl₂ (50 mL) and washed with saturated aqueous NaHCO₃ (50 mL). The organic phase was dried (MgSO₄), filtered, and the solvent was removed under reduced pressure. The residue was purified by preparative reverse phase HPLC using an H₂O:CH₃CN gradient containing 0.1% TFA. The fractions containing product were combined and lyophilized. The TFA salt of the title compound was obtained as an amorphous solid.

Analysis calculated for (C$_{31}$H$_{42}$N$_4$O$_7$S, 1.1 CF$_3$CO$_2$H) C, 53.87; H, 5.87; N, 7.57 Found C, 54.05; H, 5.64; N, 7.57

TLC: R$_f$=0.37 (95:5:0.25 CH$_2$Cl$_2$:MeOH:NH$_4$OH) HPLC (method A): retention time 7.33 min FAB MS: m/z 683 (M$^+$+H)

EXAMPLE 70

1-(1-(4-(4-(1-(2-(1-Amino-1-cyclopentyl)
ethylsulfonyl)-piperidinyloxy)-2-methoxybenzoyl)
piperidin-4-yl)-1,2-dihydro-4(H)-3,1-benzoxazin-2-
one

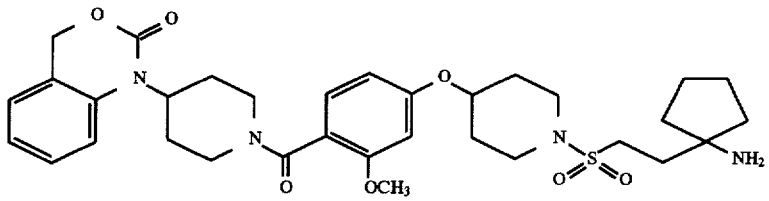

TLC: R$_f$=0.31 (92:8:0.4 CH$_2$Cl$_2$:MeOH:NH$_4$OH) HPLC (method A): retention time 6.95 min FAB MS: m/z 615 (M$^+$+H)

EXAMPLE 69

1-(1-(4-(4-(1-((3-(1-piperidinyl)-3-methyl)
butylsulfonyl)piperidinyloxy)-2-methoxybenzoyl)
piperidin-4-yl)-1,2-dihydro-4(H)-3,1-benzoxazin-2-
one

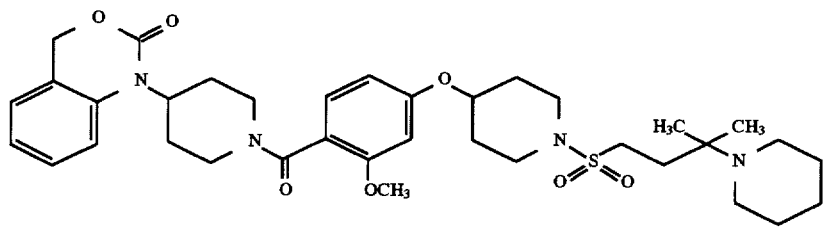

A solution of 1-(1-(4-(4-(1-(3-amino-3-methyl)butylsulfonyl)piperidinyloxy)-2-methoxybenzoyl)piperidin-4-yl)-1,2-dihydro-4(H)-3,1-benzoxazin-2-one trifluoroacetate from Example 68 (0.20 g; 0.27 mmol), sodium acetate (0.045 g; 0.54 mmol), and 25% aqueous glutaraldehyde (0.115 mL; 0.29 mmol) in 99:1 MeOH:HOAc (5 mL) was stirred at ambient temperature for 30 min. To the solution was added NaBH$_3$CN (0.035 g; 0.54 mmol). The reaction ws stirred at ambient temperature for 24 h. The solvents were removed under reduced pressure. The residue was dissolved in CH$_2$Cl$_2$ (50 mL) and washed with saturated aqueous NaHCO$_3$ (2×25 mL). The organic phase was dried (MgSO$_4$), filtered, and the solvent was removed under reduced pressure. The residue was purified by pressurized silica gel column chromatography using a gradient elution of 2:98 to 5:95 A:B (A=95:5 MeOH:NH$_4$OH, B=CH$_2$Cl$_2$). The title compound was dissolved in MeOH and 2 equivalents of 1N aqueous HCl was added. The solvent was removed under reduced pressure, the residue was dissolved in 3:1 H$_2$O:CH$_3$CN and lyophilized. The hydrochloride salt of the title compound was obtained as an amorphous solid.

Analysis calculated for (C$_{36}$H$_{50}$N$_4$O$_7$S, 1.9 HCl) C, 57.49; H, 6.96; N, 7.45 Found C, 57.42; H, 7.13; N, 7.69

Step 1:

To a stirred solution of 1-(1-(4-(4-(1-(vinylsulfonyl)-piperidinyloxy)-2-methoxybenzoyl)piperidin-4-yl)-1,2-dihydro-4(H)-3,1-benzoxazin-2-one from Example 67 (0.30 g; 0.54 mmol) and nitrocyclopentane (0.62; 0.54 mmol) in MeOH (10 mL) was added DBU (0.25 g; 2.8 mmol). The reaction ws stirred at ambient temperature for 18 h. HOAc (0.2 mL; 3 mmol) was added and the volatiles were removed under reduced pressure. The residue was dissolved in EtOAc (50 mL) and washed with 5% citric acid (25 mL), saturated aqueous NaHCO$_3$ (2×25 mL), and brine (25 mL). The organic phase was dried (MgSO$_4$), filtered, and the solvent was removed under reduced pressure. The residue was purified by pressurized silica gel column chromatography using a gradient elution of 1:99 to 3:97 MeOH:CH$_2$Cl$_2$ as eluant. 1-(1-(4-(4-(1-(2-(1-nitro-1-cyclopentyl) ethylsulfonyl)-piperidinyloxy)-2-methoxybenzoyl) piperidin-4-yl)-1,2-dihydro-4(H)-3,1-benzoxazin-2-one was obtained as an amorphous solid (TLC R$_f$=0.15 (2:98 MeOH:CH$_2$Cl$_2$); HPLC retention time=9.87 min (method A); FAB MS m/z 669 (M$^+$+H).

Step 2:

1-(1-(4-(4-(1-(2-(1-Nitro-1-cyclopentyl)ethylsulfonyl)-piperidinyloxy)-2-methoxybenzoyl)piperidin-4-yl)-1,2-dihydro-4(H)-3,1-benzoxazin-2-one (0.27 g; 0.40 mmol) from Step 1 above was dissolved in MeOH (15 mL). To the rapidly stirred solution was added NiCl$_2$ (0.156 g; 1.2 mmol) followed by NaBH$_4$ (0.046 g; 1.2 mmol) added in three portions oved 15 min. The black suspension was rapidly stirred for 18 h at ambient temperature. An equal volume of EtOAc was added and the solids were removed by filtration through Celite. The filtercake was washed with 1:1 MeOH:EtOAc and the filtrate solvents were removed under reduced pressure. The residue was suspended in CH$_2$Cl$_2$ (50 mL) and washed with saturated aqueous NaHCO₃ (50 mL). The organic phase was dried (MgSO4), filtered, and the solvent was removed under reduced pressure. The residue was purified by pressurized silica gel column chromatography using a gradient elution of 2:98 to 5:95 A:B (A=95:5 MeOH:NH₄OH, B=CH₂Cl₂). The title compound was dissolved in MeOH and 2 equivalents of 1N aqueous HCl was added. The solvent was removed under reduced pressure, the residue was dissolved in 3:1 H₂O:CH₃CN and lyophilized. The hydrochloride salt of the title compound was obtained as an amorphous solid.

Analysis calculated for (C₃₃H₄₄N₄O₇S, 1.5 HCl) C, 56.99; H, 6.59; N, 8.06 Found C, 56.90; H, 6.66; N, 8.20 TLC: R_f=0.26 (95:5:0.25 CH₂Cl₂:MeOH:NH₄OH) HPLC (method A): retention time 7.28 min FAB MS: m/z 641 (M⁺+H)

The hydrochloride salt of the title compound was obtained as an amorphous solid.

Analysis calculated for (C₃₅H₄₈N₄O₇S, 1.4 HCl, 0.5 H₂O) C, 57.67; H, 6.97; N, 7.87 Found C, 57.78; H, 7.09; N, 7.86 TLC: R_f=0.27 (95:5:0.25 CH₂Cl₂:MeOH:NH₄OH) HPLC (method A): retention time 7.27 min FAB MS: m/z 669 (M⁺+H)

EXAMPLE 72

1-(1-(4-(4-(1-((3-Azido)propylsulfonyl)-piperidinyloxy)-2-methoxybenzoyl)piperidin-4-yl)-1,2-dihydro-4(H)-3,1-benzoxazin-2-one

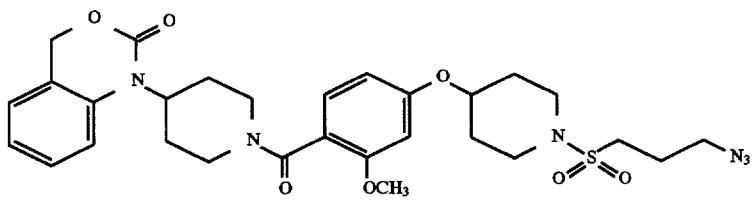

EXAMPLE 71

1-(1-(4-(4-(1-((2-(1-Dimethylamino-1-cyclopentyl)ethylsulfonyl)-piperidinyloxy)-2-methoxybenzoyl)piperidin-4-yl)-1,2-dihydro-4(H)-3,1-benzoxazin-2-one To a stirred solution of 1-(1-(4-(4-(1-(3-iodopropylsulfonyl)piperidinyloxy)-2-methoxybenzoyl) piperidin-4-yl)-1,2-dihydro-4(H)-3,1-benzoxazin-2-one from Step 1 of Example 65 (1.0 g; 1.4 mmol) in DMF (20 mL) was added NaN₃ (0.105 g; 1.6 mmol). The solution was warmed to 60° C. for 24 h. The solvent was removed under reduced pressure and the residue was dissolved in EtOAc

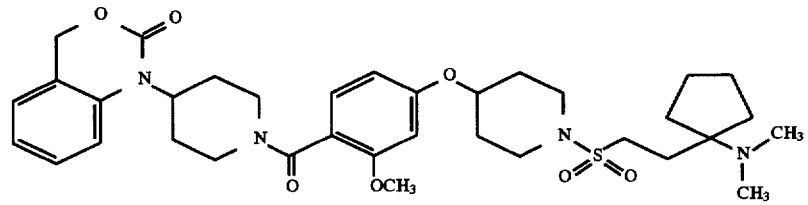

To a stirred solution of 1-(1-(4-(4-(2-(1-amino-1-cyclopentyl)ethylsulfonyl)piperidinyloxy)-2-methoxybenzoyl)piperidin-4-yl)-1,2-dihydro-4(H)-3,1-benzoxazin-2-one hydrochloride from Example 70 (0.20 g; 0.30 mmol), sodium acetate (0.036 g; 0.60 mmol), and 37% aqueous formaldehyde (0.075 mL; 0.93 mmol) in 99:1 MeOH:HOAc (5 mL) was added NaBH₃CN (0.057 g; 0.90 mmol). The reaction ws stirred at ambient temperature for 24 h. The solvents were removed under reduced pressure. The residue was dissolved in CH₂Cl₂ (50 mL) and washed with saturated aqueous NaHCO₃ (2×25 mL). The organic phase was dried (MgSO₄), filtered, and the solvent was removed under reduced pressure. The residue was purified by pressurized silica gel column chromatography using a gradient elution of 2:98 to 5:95 A:B (A=95:5 MeOH:NH₄OH, B=CH₂Cl₂). The title compound was dissolved in MeOH and 2 equivalents of 1N aqueous HCl was added. The solvent was removed under reduced pressure, the residue was dissolved in 3:1 H₂O:CH₃CN and lyophilized.

(100 mL) and washed with saturated aqueous NaHCO₃ (2×50 mL) and brine (50 mL). The EtOAc layer was dried (MgSO₄), filtered, and the solvent was removed under reduced pressure. The residue was purified by pressurized silica gel column chromatography using a gradient elution of 1:99 to 3:97 MeOH:CH₂Cl₂. The title compound was obtained as an amorphous solid.

Analysis calculated for (C₂₉H₃₆N₆O₇S, 0.4 CH₂Cl₂, 0.05 EtOAc) C, 54.60; H, 5.76; N, 12.91 Found C, 54.49; H, 5.78; N, 12.87 TLC: R_f=0.34 (98:2:0.2 CH₂Cl₂:MeOH:NH₄OH) HPLC (method A): retention time 9.10 min FAB MS: m/z 613 (M⁺+H)

EXAMPLE 73

1-(1-(4-(4-(1-((3-Amino)propylsulfonyl)-piperidinyloxy)-2-methoxybenzoyl)piperidin-4-yl)-1,2-dihydro-4(H)-3,1-benzoxazin-2-one

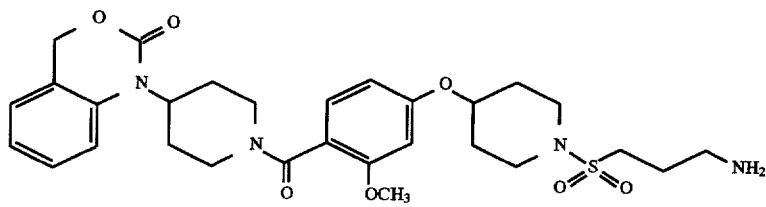

To a stirred solution of 1-(1-(4-(4-(1-((3-azido)propylsulfonyl)piperidinyl-oxy)-2-methoxybenzoyl)piperidin-4-yl)-1,2-dihydro-4(H)-3,1-benzoxazin-2-one from Example 72 (1.0 g; 1.6 mmol) in THF (20 mL) was added $H_2O$ (2 mL) and triphenylphosphine (0.47 g; 1.8 mmol). The solution was warmed to 40° C. for 24 h. The solvent was removed under reduced pressure and the residue was purified by pressurized silica gel column chromatography using a gradient elution of 2:98 to 6:94 A:B (A=95:5 MeOH:$NH_4OH$, B=$CH_2Cl_2$). The title compound was dissolved in MeOH containing 2 equivalents of 1N aqueous HCl. The MeOH was removed under reduced pressure and the residue was dissolved in 1:1 $H_2O:CH_3CN$ and lyophilized. The hydrochloride salt of the title compound was obtained as an amorphous solid.

Analysis calculated for ($C_{29}H_{38}N_4O_7S$, 1.1 HCl, 1.8 $H_2O$) C, 52.83; H, 6.53; N, 8.50 Found C, 52.80; H, 6.31; N, 7.51 TLC: $R_f$=0.27 (94:6:0.6 $CH_2Cl_2$:MeOH:$NH_4OH$) HPLC (method A): retention time 6.79 min FAB MS: m/z 587 ($M^+$+H)

EXAMPLE 74

1-(1-(4-(4-(1-((3-(N-Cyclopropyl-N-ethoxycarbonylmethylamino)propylsulfonyl)-piperidinyloxy)-2-methoxybenzoyl)piperidin-4-yl)-1,2-dihydro-4(H)-3,1-benzoxazin-2-one

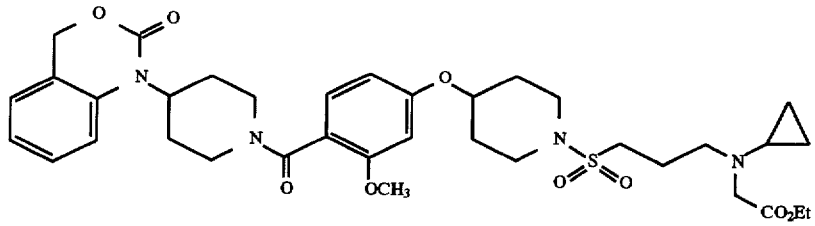

To a stirred solution of 1-(1-(4-(4-(1-((3-cyclopropylamino)propyl-sulfonyl)-piperidinyloxy)-2-methoxybenzoyl)piperidin-4-yl)-1,2-dihydro-4(H)-3,1-benzoxazin-2-one (0.25 g, 0.40 mmol) from Example 65 and DIEA (0.105 mL; 0.60 mmol) in DMF (5 mL) was added ethyl bromoacetate (0.075 g; 0.45 mmol). The solution was stirred at ambient temperature for 24 h. The solvent was removed under reduced pressure, the residue was dissolved in EtOAc (100 mL) and washed with saturated aqueous $NaHCO_3$ (2×50 mL) and brine (50 mL). The EtOAc layer was dried ($MgSO_4$), filtered, and the solvent was removed under reduced pressure. The residue was purified by pressurized silica gel column chromatography using a gradient elution of 1:99 to 3:97 MeOH:$CH_2Cl_2$. The title compound was obtained as an amorphous solid.

Analysis calculated for ($C_{36}H_{48}N_4O_9S$) C, 60.55; H, 6.79; N, 7.86 Found C, 60.31; H, 6.77; N, 7.70 TLC: $R_f$=0.26 (98:2:0.2 $CH_2Cl_2$:MeOH:$NH_4OH$) HPLC (method A): retention time 7.99 min FAB MS: m/z 713 ($M^+$+H)

EXAMPLE 75

1-(1-(4-(4-(1-((3-(N-Cyclopropyl-N-carboxymethylamino)propylsulfonyl)-piperidinyloxy)-2-methoxybenzoyl)piperidin-4-yl)-1,2-dihydro-4(H)-3,1-benzoxazin-2-one

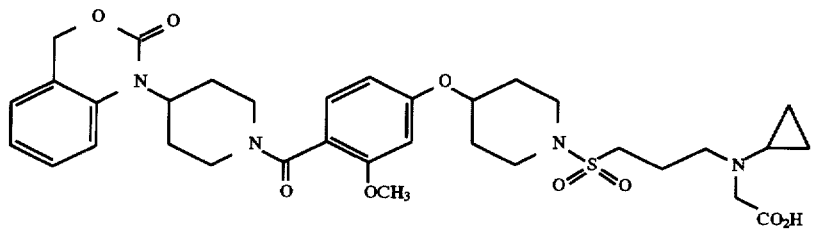

To a stirred solution of 1-(1-(4-(4-(1-((3-(N-cyclopropyl-N-ethoxycarbonylmethylamino)propyl-sulfonyl)-piperidinyloxy)-2-methoxybenzoyl)piperidin-4-yl)-1,2- dihydro-4(H)-3,1-benzoxazin-2-one (0.20 g, xx mmol) from Example 74 in MeOH (5 mL) was added 1N aqueous NaOH (0.40 mL; 0.40 mmol). The solution was stirred at ambient temperature for 24 h. TFA (0.10 mL) was added and the solvent was removed under reduced pressure. The residue was purified by preparative reverse phase HPLC using an $H_2O:CH_3CN$ gradient containing 0.1% TFA. The TFA salt of the title compound was obtained as an amorphous solid by lyophilization.

Analysis calculated for ($C_{34}H_{44}N_4O_9S$, 1.55 TFA, 0.35 $H_2O$) C, 51.34; H, 5.37; N, 6.46 Found C, 51.34; H, 5.36; N, 6.70 HPLC (method A): retention time 6.99 min FAB MS: m/z 685 (M$^+$+H)

EXAMPLE 76

1-(1-(4-(4-(1-((3-Acetamidinyl)propylsulfonyl)-piperidinyloxy)-2-methoxybenzoyl)piperidin-4-yl)-1,2-dihydro-4(H)-3,1-benzoxazin-2-one To a stirred solution of 1-(1-(4-(4-(1-((3-amino)propylsulfonyl)piperidinyl-oxy)-2-methoxybenzoyl)piperidin-4-yl)-1,2-dihydro-4(H)-3,1-benzoxazin-2-one from Example 73 (0.20 g; 0.34 mmol) in DMF (5 mL) was added 3,5-dimethylpyrazole-1-carboxamidine nitrate (0.10 g; 0.50 mmol) and DIEA (0.175 mL; 1.0 mmol). The solution was stirred at ambient temperature for 48 h. The solvent was removed under reduced pressure and the residue was purified by preparative reverse phase HPLC using an $H_2O:CH_3CN$ gradient containing 0.1% TFA. The TFA salt of the title compound was obtained as an amorphous solid by lyophilization.

Analysis calculated for ($C_{30}H_{40}N_6O_7S$, 1.45 TFA, 0.4 $H_2O$) C, 49.31; H, 5.31; N, 10.49 Found C, 49.29; H, 5.26; N, 10.88 HPLC (method A): retention time 6.98 min FAB MS: m/z 629 (M$^+$+H)

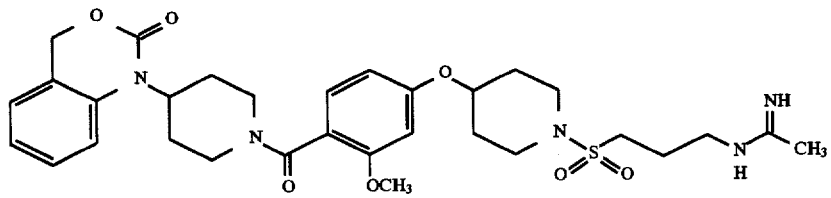

To a stirred solution of 1-(1-(4-(4-(1-((3-amino)propylsulfonyl)piperidinyl-oxy)-2-methoxybenzoyl)piperidin-4-yl)-1,2-dihydro-4(H)-3,1-benzoxazin-2-one from Example 73 (0.20 g; 0.34 mmol) in DMF (5 mL) was added ethyl acetimidate hydrochloride (0.093 g; 0.75 mmol) and DIEA (0.175 mL; 1.0 mmol). The solution was stirred at ambient temperature for 48 h. The solvent was removed under reduced pressure and the residue was purified by preparative reverse phase HPLC using an $H_2O:CH_3CN$ gradient containing 0.1% TFA. The TFA salt of the title compound was obtained as an amorphous solid by lyophilization.

Analysis calculated for ($C_{31}H_{41}N_5O_7S$, 1.6 TFA, 0.4 $H_2O$) C, 50.25; H, 5.35; N, 8.57 Found C, 50.25; H, 5.31; N, 8.79 HPLC (method A): retention time 6.90 min FAB MS: m/z 628 (M$^+$+H)

EXAMPLE 77

1-(1-(4-(4-(1-((3-Guanidinyl)propylsulfonyl)-piperidinyloxy)-2-methoxybenzoyl)piperidin-4-yl)-1,2-dihydro-4(H)-3,1-benzoxazin-2-one

EXAMPLE 78

1-(1-(4-(4-(1-((3-Ethylamino)propylsulfonyl)-piperidinyloxy)-2-methoxybenzoyl)piperidin-4-yl)-1,2-dihydro-4(H)-3,1-benzoxazin-2-one

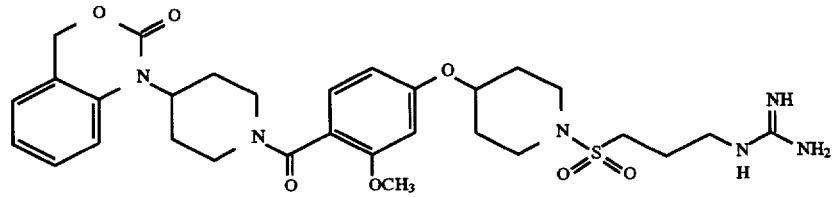

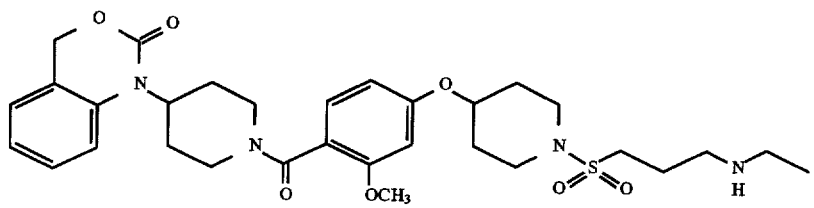

Into a 0° C. stirred solution of 1-(1-(4-(4-(1-(3-iodopropylsulfonyl)piperidinyloxy)-2-methoxybenzoyl)piperidin-4-yl)-1,2-dihydro-4(H)-3,1-benzoxazin-2-one from Step 1 of Example 65 (0.20 g; 0.29 mmol) in 1:1 MeOH:DMF (10 mL) was bubbled ethylamine. The reaction vessel was sealed and warmed to ambient temperature for 72 h. The solution was cooled to 0° C. and the reaction vessel was opened. The solvents were removed under reduced pressure and the residue was dissolved in EtOAc (100 mL) and washed with saturated aqueous $NaHCO_3$ (2×50 mL) and brine (50 mL). The EtOAc layer was dried ($MgSO_4$), filtered, and the solvent was removed under reduced pressure. The residue was purified by pressurized silica gel column chromatography using a gradient elution of 2:99 to 5:95 A:B (A=95:5 MeOH:$NH_4OH$, B=$CH_2Cl_2$). The title compound was dissolved in MeOH and to the solution was added 2 equivalents of 1.0N aqueous HCl. The resulting solution was evaporated under reduced pressure and the residue was dissolved in 3:2 $H_2O$:$CH_3CN$ and lyophilized. The HCl salt of the title compound was obtained as an amorphous powder.

Analysis calculated for ($C_{31}H_{42}N_4O_7S$, 1.4 HCl, 0.75 $H_2O$) C, 54.80; H, 6.66; N, 8.25 Found C, 54.84; H, 6.66; N, 7.73 TLC: $R_f$=0.17 (95:5:0.5 $CH_2Cl_2$:MeOH:$NH_4OH$) HPLC (method A): retention time 6.83 min FAB MS: m/z 615 ($M^++H$)

EXAMPLE 79

1-(1-(4-(4-(1-(3-(1-Pyrrolidinyl)propylsulfonyl)-piperidinyloxy)-2-methoxybenzoyl)piperidin-4-yl)-1,2-dihydro-4(H)-3,1-benzoxazin-2-one

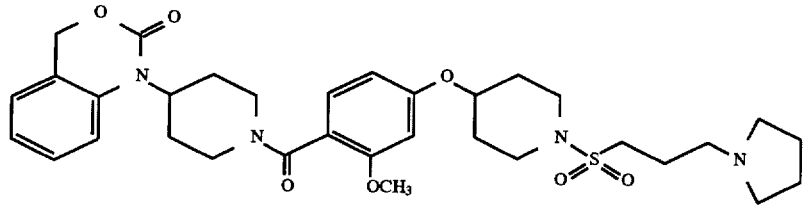

To stirred solution of 1-(1-(4-(4-(1-(3-iodopropylsulfonyl)piperidinyloxy)-2-methoxybenzoyl)piperidin-4-yl)-1,2-dihydro-4(H)-3,1-benzoxazin-2-one from Step 1 of Example 65 (0.20 g; 0.29 mmol) in MeOH (5 mL) was added pyrrolidine (0.50 mL; 5.6 mmol). The reaction was stirred at ambient temperature for 24 h. The solvents were removed under reduced pressure and the residue was dissolved in EtOAc (100 mL) and washed with saturated aqueous $NaHCO_3$ (2×50 mL) and brine (50 mL). The EtOAc layer was dried ($MgSO_4$), filtered, and the solvent was removed under reduced pressure. The residue was purified by pressurized silica gel column chromatography using a gradient elution of 2:98 to 5:95 A:B (A=95:5 MeOH:$NH_4OH$, B=$CH_2Cl_2$). The title compound was dissolved in MeOH and to the solution was added 2 equivalents of 1.0N aqueous HCl. The resulting solution was evaporated under reduced pressure and the residue was dissolved in 3:2 $H_2O$:$CH_3CN$ and lyophilized. The HCl salt of the title compound was obtained as an amorphous powder.

Analysis calculated for ($C_{33}H_{44}N_4O_7S$, 1.6 HCl, 0.6 $H_2O$) C, 55.82; H, 6.64; N, 7.89 Found C, 55.85; H, 6.64; N, 7.93 TLC: $R_f$=0.28 (95:5:0.5 $CH_2Cl_2$:MeOH:$NH_4OH$) HPLC (method A): retention time 7.02 min FAB MS: m/z 641 ($M^++H$)

EXAMPLE 80

1-(1-(4-(4-(1-(3-(Benzylamino)propylsulfonyl)-piperidinyloxy)-2-methoxybenzoyl)piperidin-4-yl)-1,2-dihydro-4(H)-3,1-benzoxazin-2-one

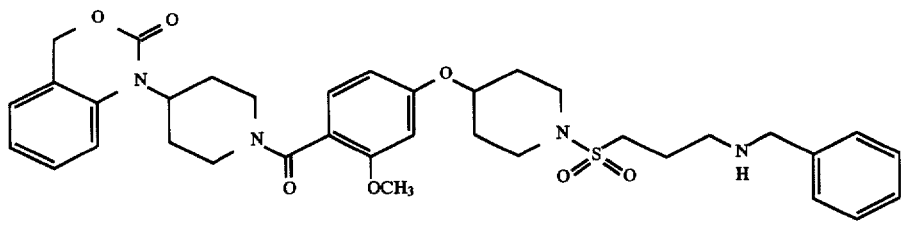

To stirred solution of 1-(1-(4-(4-(1-(3-iodopropylsulfonyl)piperidinyloxy)-2-methoxybenzoyl)piperidin-4-yl)-1,2-dihydro-4(H)-3,1-benzoxazin-2-one from Step 1 of Example 65 (0.20 g; 0.29 mmol) in MeOH (5 mL) was added benzylamine (0.5 mL; 3.7 mmol). The reaction was stirred at ambient temperature for 24 h. The solvents were removed under reduced pressure and the residue was dissolved in EtOAc (100 mL) and washed with saturated aqueous NaHCO$_3$ (2×50 mL) and brine (50 mL). The EtOAc layer was dried (MgSO$_4$), filtered, and the solvent was removed under reduced pressure. The residue was purified by pressurized silica gel column chromatography using a gradient elution of 2:98 to 5:95 A:B (A=95:5 MeOH:NH$_4$OH, B=CH$_2$Cl$_2$). The title compound was dissolved in MeOH and to the solution was added 2 equivalents of 1.0N aqueous HCl. The resulting solution was evaporated under reduced pressure and the residue was dissolved in 3:2 H$_2$O:CH$_3$CN and lyophilized. The HCl salt of the title compound was obtained as an amorphous powder.

Analysis calculated for (C$_{36}$H$_{44}$N$_4$O$_7$S, 1.3 HCl) C, 59.70; H, 6.30; N, 7.74 Found C, 59.69; H, X; 6.31, 7.64 TLC: R$_f$=0.45 (95:5:0.5 CH$_2$Cl$_2$:MeOH:NH$_4$OH) HPLC (method A): retention time 7.69 min FAB MS: m/z 677 (M$^+$+H)

EXAMPLE 81

1-(1-(4-(4-(1-(2-Aminoethylsulfonyl)-piperidinyloxy)-2-methoxybenzoyl)piperidin-4-yl)-1,2-dihydro-4(H)-3,1-benzoxazin-2-one

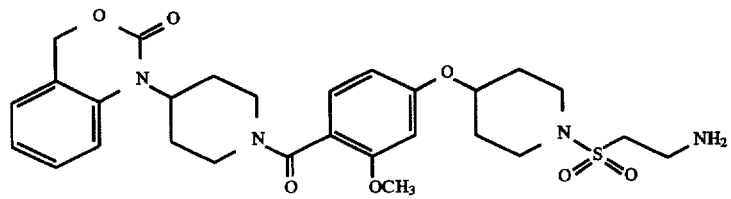

Into a 0° C. stirred solution of 1-(1-(4-(4-(1-(vinylsulfonyl)-piperidinyloxy)-2-methoxybenzoyl)piperidin-4-yl)-1,2-dihydro-4(H)-3,1-benzoxazin-2-one from Example 67 (0.50 g; 0.90 mmol) in 2:1 DMF:MeOH (10 mL) was bubbled gaseous ammonia for 15 min. The reaction vessel was sealed and the solution was warmed to 40° C. for 48 h. The reaction was cooled to 0° C. and the reaction vessel was opened. The solvents were removed under reduced pressure and the residue was purified by preparative reverse phase HPLC using an H$_2$O:CH$_3$CN gradient containing 0.1% TFA. The TFA salt of the title compound was obtained as an amorphous powder by lyophilization.

Analysis calculated for (C$_{28}$H$_{36}$N$_4$O$_7$S, 1.4 TFA, 2.45 H$_2$O) C, 47.64; H, 5.49; N, 7.22 Found C, 47.64; H, 5.49; N, 7.23 TLC: R$_f$=0.42 (93:7:0.7 CH$_2$Cl$_2$:MeOH:NH$_4$OH) HPLC (method A): retention time 6.61 min FAB MS: m/z 573 (M$^+$+H)

EXAMPLE 82

1-(1-(4-(4-(1-(2-(Ethylamino)ethylsulfonyl)-piperidinyloxy)-2-methoxybenzoyl)piperidin-4-yl)-1,2-dihydro-4(H)-3,1-benzoxazin-2-one

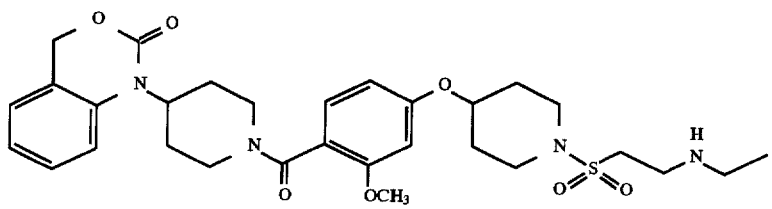

Into a 0° C. stirred solution of 1-(1-(4-(4-(1-(vinylsulfonyl)-piperidinyloxy)-2-methoxybenzoyl)piperidin-4-yl)-1,2-dihydro-4(H)-3,1-benzoxazin-2-one from Example 67 (0.20 g; 0.36 mmol) in 1:1 DMF:MeOH (10 mL) was bubbled gaseous ethylamine for 15 min. The reaction vessel was sealed and the solution was stirred at ambient temperature for 48 h. The reaction was cooled to 0° C. and the reaction vessel was opened. The solvents were removed under reduced pressure and the residue was purified by pressurized silica gel column chromatography using a gradient elution of 3:97 to 7:93 A:B (A=95:5 MeOH:NH$_4$OH, B=CH$_2$Cl$_2$). The title compound was dissolved in MeOH and to the solution was added 2 equivalents of 1.0N aqueous HCl. The resulting solution was evaporated under reduced pressure and the residue was dissolved in 3:2 H$_2$O:CH$_3$CN and lyophilized. The HCl salt of the title compound was obtained as an amorphous powder.

Analysis calculated for (C$_{30}$H$_{40}$N$_4$O$_7$S, 1.9 HCl, 0.6 H$_2$O) C, 52.92; H, 6.38; N, 8.23 Found C, 52.95; H, 6.39; N, 8.18 TLC: R$_f$=0.36 (96:4:0.4 CH$_2$Cl$_2$:MeOH:NH$_4$OH) HPLC (method A): retention time 7.21 min FAB MS: m/z 601 (M$^+$+H)

EXAMPLE 83

1-(1-(4-(4-(1-(2-(t-Butylamino)ethylsulfonyl)-piperidinyloxy)-2-methoxybenzoyl)piperidin-4-yl)-1,2-dihydro-4(H)-3,1-benzoxazin-2-one

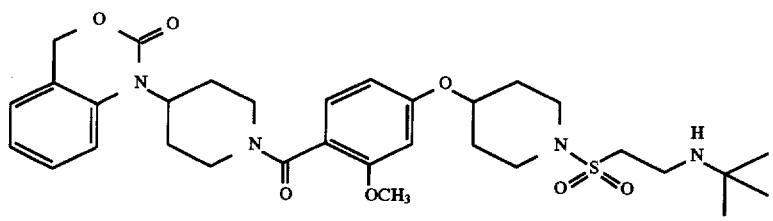

To stirred solution of 1-(1-(4-(4-(1-(vinylsulfonyl)-piperidinyloxy)-2-methoxybenzoyl)piperidin-4-yl)-1,2-dihydro-4(H)-3,1-benzoxazin-2-one from Example 67 (0.20 g; 0.36 mmol) in 1:1 DMF:MeOH (5 mL) was added t-butylamine (0.5 mL; 5.5 mmol). The solution was stirred at ambient temperature for 48 h. The solvents were removed under reduced pressure and the residue was purified by pressurized silica gel column chromatography using a gradient elution of 1:99 to 4:96 A:B (A=95:5 MeOH:NH$_4$OH, B=CH$_2$Cl$_2$). The title compound was dissolved in MeOH and to the solution was added 1.5 equivalents of 1.0N aqueous HCl. The resulting solution was evaporated under reduced pressure and the residue was dissolved in 3:2 H$_2$O:CH$_3$CN and lyophilized. The HCl salt of the title compound was obtained as an amorphous powder.

Analysis calculated for (C$_{32}$H$_{44}$N$_4$O$_7$S, 1.65 HCl, 0.05 H$_2$O) C, 55.71; H, 6.68; N, 8.12 Found C, 55.69; H, 6.68; N, 8.26 TLC: R$_f$=0.30 (97:3:0.3 CH$_2$Cl$_2$:MeOH:NH$_4$OH) HPLC (method A): retention time 7.26 min FAB MS: m/z 629 (M$^+$+H)

EXAMPLE 84

1-(1-(4-(4-(1-(2-(Cyclopropylamino)ethylsulfonyl)-piperidinyloxy)-2-methoxybenzoyl)piperidin-4-yl)-1,2-dihydro-4(H)-3,1-benzoxazin-2-one

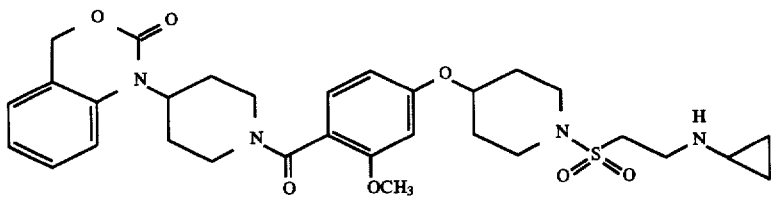

To stirred solution of 1-(1-(4-(4-(1-(vinylsulfonyl)-piperidinyloxy)-2-methoxybenzoyl)piperidin-4-yl)-1,2-dihydro-4(H)-3,1-benzoxazin-2-one from Example 67 (0.50 g; 0.90 mmol) in 1:1 DMF:MeOH (5 mL) was added cyclopropylamine (1 mL; 14 mmol). The solution was stirred at ambient temperature for 48 h. The solvents were removed under reduced pressure and the residue was purified by pressurized silica gel column chromatography using a gradient elution of 2:98 to 5:95 A:B (A=95:5 MeOH:NH$_4$OH, B=CH$_2$Cl$_2$). The title compound was dissolved in MeOH and to the solution was added 2 equivalents of 1.0N aqueous HCl. The resulting solution was evaporated under reduced pressure and the residue was dissolved in 3:2 H$_2$O:CH$_3$CN and lyophilized. The HCl salt of the title compound was obtained as an amorphous powder.

Analysis calculated for (C$_{31}$H$_{40}$N$_4$O$_7$S, 1.25 HCl, 0.4 H$_2$O) C, 55.94; H, 6.37; N, 8.42 Found C, 55.93; H, 6.38; N, 8.56 TLC: R$_f$=0.35 (95:5 CH$_2$Cl$_2$:MeOH) HPLC (method A): retention time 6.93 min FAB MS: m/z 613 (M$^+$+H)

EXAMPLE 85

1-(1-(4-(4-(1-(2-(N-Ethyl-2-Hydroxyethylamino)ethylsulfonyl)piperidinyloxy)-2-methoxybenzoyl)piperidin-4-yl)-1,2-dihydro-4(H)-3,1-benzoxazin-2-one

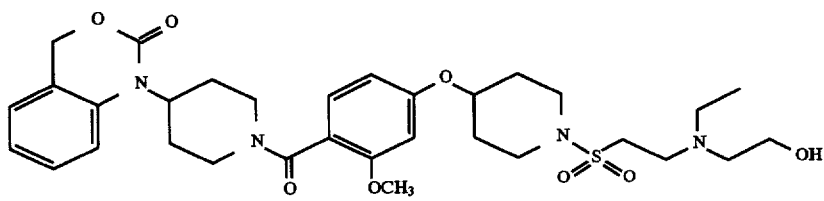

To stirred solution of 1-(1-(4-(4-(1-(vinylsulfonyl)-piperidinyloxy)-2-methoxybenzoyl)piperidin-4-yl)-1,2-dihydro-4(H)-3,1-benzoxazin-2-one from Example 67 (0.20 g; 0.36 mmol) in 1:1 DMF:MeOH (10 mL) was added N-ethyl ethanolamine (0.5 mL; 4.5 mmol). The solution was stirred at ambient temperature for 48 h. The solvents were removed under reduced pressure and the residue was purified by pressurized silica gel column chromatography using a gradient elution of 3:97 to 7:93 A:B (A=95:5 MeOH:NH$_4$OH, B=CH$_2$Cl$_2$). The title compound was dissolved in MeOH and to the solution was added 1.5 equivalents of 1.0N aqueous HCl. The resulting solution was evaporated under reduced pressure and the residue was dissolved in 3:2 H$_2$O:CH$_3$CN and lyophilized. The HCl salt of the title compound was obtained as an amorphous powder.

Analysis calculated for (C$_{32}$H$_{44}$N$_4$O$_8$S, 1.2 HCl, 2.5 H$_2$O) C, 52.39; H, 6.90; N, 7.64 Found C, 52.33; H, 6.91; N, 8.11 TLC: R$_f$=0.48 (90:10:1 CH$_2$Cl$_2$:MeOH:H$_2$O) HPLC (method B): retention time 15.01 min FAB MS: m/z 645 (M$^+$+H)

EXAMPLE 86

1-(1-(4-(4-(1-(2-(t-Butyloxycarbonylmethylamino)ethylsulfonyl)-piperidinyloxy)-2-methoxybenzoyl)piperidin-4-yl)-1,2-dihydro-4(H)-3,1-benzoxazin-2-one

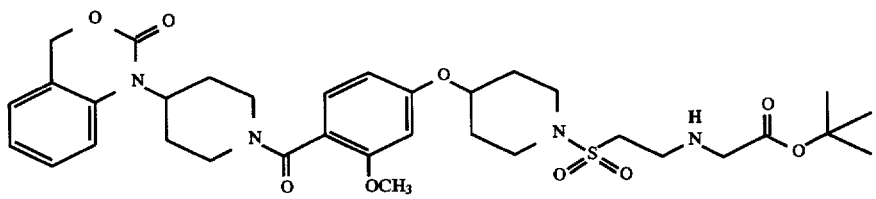

To stirred solution of 1-(1-(4-(4-(1-(vinylsulfonyl)piperidinyloxy)-2-methoxybenzoyl)piperidin-4-yl)-1,2-dihydro-4(H)-3,1-benzoxazin-2-one from Example 67 (0.20 g; 0.36 mmol) in 1:1 DMF:MeOH (5 mL) was added t-butyl glycine hydrochloride (0.4 g; 2.4 mmol) and DIEA (0.42 mL; 2.4 mmol). The solution was stirred at ambient temperature for 48 h. The solvents were removed under reduced pressure and the residue was partitioned between EtOAc (50 mL) and water (25 mL). The organic phase was washed with water (25 mL) and brine (25 mL). The organic phase was dried (MgSO$_4$), filtered, and the solvent was removed under reduced pressure. Evaporation of a CH$_2$Cl$_2$ solution under reduced pressure gave the title compound as an amorphous powder.

Analysis calculated for (C$_{34}$H$_{46}$N$_4$O$_9$S, 1.5 H$_2$O) C, 57.21; H, 6.92; N, 7.85 Found C, 57.24; H, 6.68; N, 7.83 TLC: R$_f$=0.67 (90:10:1 CH$_2$Cl$_2$:MeOH:H$_2$O) HPLC (method B): retention time 14.68 min FAB MS: m/z 687 (M$^+$+H)

EXAMPLE 87

1-(1-(4-(4-(1-(2-(Carboxymethylamino)ethylsulfonyl)-piperidinyloxy)-2-methoxybenzoyl)piperidin-4-yl)-1,2-dihydro-4(H)-3,1-benzoxazin-2-one

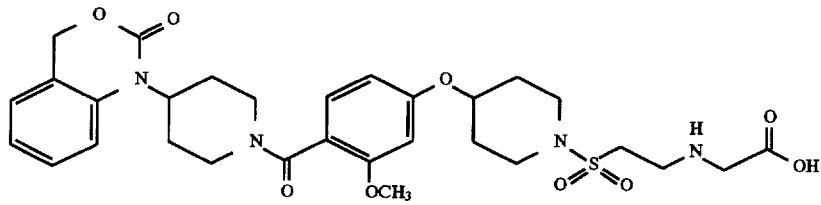

Into a 0° C. stirred solution of 1-(1-(4-(4-(1-(2-(t-butyloxycarbonylmethylamino)ethylsulfonyl)-piperidinyloxy)-2-methoxybenzoyl)piperidin-4-yl)-1,2-dihydro-4(H)-3,1-benzoxazin-2-one from Example 86 (0.15 g; 0.22 mmol) in EtOAc (5 mL) was bubbled gaseous HCl for 30 min. The solution was stirred at ambient temperature for 1 h and the solvent was removed under reduced pressure. The residue was purified by preparative reverse phase HPLC using an H$_2$O:CH$_3$CN gradient containing 0.1% TFA. The TFA salt of the title compound was obtained as an amorphous powder by lyophilization.

Analysis calculated for (C$_{30}$H$_{38}$N$_4$O$_9$S, 1.6 TFA) C, 49.04; H, 4.91; N, 6.89 Found C, 48.97; H, 4.89; N, 7.11 HPLC (method A): retention time 6.91 min FAB MS: m/z 645 (M$^+$+H)

EXAMPLE 88

1-(1-(4-(4-(1-(Methoxycarbonylmethylsulfonyl)-piperidinyloxy)-2-methoxybenzoyl)piperidin-4-yl)-1,2-dihydro-4(H)-3,1-benzoxazin-2-one

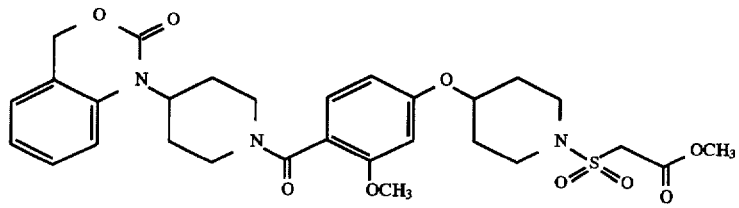

To a 0° C. stirred solution of 1-(1-(4-(4-piperidinyloxy)-2-methoxybenzoyl)piperidin-4-yl)-1,2-dihydro-4(H)-3,1-benzoxazin-2-one from Example 26 (0.50 g; 1.1 mmol) and DIEA (0.23 mL; 1.3 mmol) in CH$_2$Cl$_2$ (10 mL) was added methyl chlorosulfonylacetate (0.21 g; 1.2 mmol). The solution was stirred at 0° C. for 1 h and then at ambient temperature for 18 h. The solvent was removed under reduced pressure. The residue was dissolved in EtOAc (50 mL) and washed with saturated aqueous NaHCO$_3$ (2×25 mL) and brine (25 mL). The organic layer was dried (MgSO$_4$), filtered, and the solvent was removed under reduced pressure. The residue was purified by preparative reverse phase HPLC using an H$_2$O:CH$_3$CN gradient containing 0.1% TFA. The title compound was obtained as an amorphous powder by lyophilization.

Analysis calculated for (C$_{29}$H$_{35}$N$_3$O$_9$S, 1.4 TFA, 1.2 H$_2$O) C, 48.79; H, 5.00; N, 5.37 Found C, 48.79; H, 4.96; N, 5.54 TLC: R$_f$=0.33 (98:2 CH$_2$Cl$_2$:MeOH) HPLC (method A): retention time 8.86 min FAB MS: m/z 602 (M$^+$+H)

EXAMPLE 89

1-(1-(4-(4-(1-(Carboxymethylsulfonyl)-piperidinyloxy)-2-methoxybenzoyl)piperidin-4-yl)-1,2-dihydro-4(H)-3,1-benzoxazin-2-one

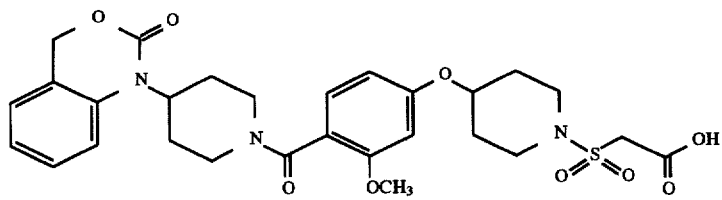

To a 0° C. stirred solution of 1-(1-(4-(4-(1-(methoxycarbonylmethylsulfonyl)-piperidinyloxy)-2-methoxybenzoyl)piperidin-4-yl)-1,2-dihydro-4(H)-3,1-benzoxazin-2-one from Example 91 (0.15 g; 0.25 mmol) in MeOH (5 mL) was added 1N aqueous NaOH (0.60 mL; 0.60 mmol). The solution was stirred at 0° C. for 1 h and then at ambient temperature for 24 h. The reaction was adjusted to pH 3 by the addition of 5% aqueous citric acid, and the solvents were removed under reduced pressure. The residue was purified by preparative reverse phase HPLC using an H$_2$O:CH$_3$CN gradient containing 0.1% TFA. The title compound was obtained as an amorphous powder by lyophilization.

Analysis calculated for (C$_{28}$H$_{33}$N$_3$O$_9$S, 0.8 H$_2$O) C, 55.86; H, 5.79; N, 6.98 Found C, 55.83; H, 5.64; N, 6.94 HPLC (method A): retention time 7.84 min FAB MS: m/z 588 (M$^+$+H)

EXAMPLE 90

1-(1-(4-(4-(1-(3-(Cyano)propylsulfonyl)-piperidinyloxy)-2-methoxybenzoyl)piperidin-4-yl)-1,2-dihydro-4(H)-3,1-benzoxazin-2-one

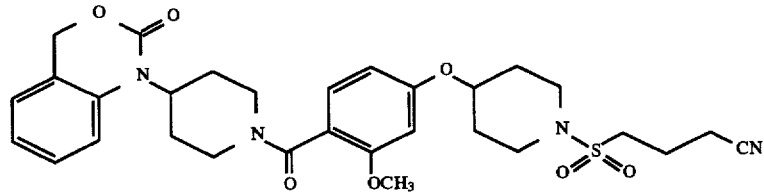

To a stirred solution of 1-(1-(4-(4-(1-(3-iodopropylsulfonyl)piperidinyloxy)-2-methoxybenzoyl)piperidin-4-yl)-1,2-dihydro-4(H)-3,1-benzoxazin-2-one from Step 1 of Example 65 (0.20 g; 0.29 mmol) in DMF (10 mL) was added NaCN (0.098 g; 2.0 mmol). The solution was warmed to 60° C. for 24 h. The solvent was removed under reduced pressure and the residue was dissolved in EtOAc (100 mL) and washed with saturated aqueous NaHCO$_3$ (2×50 mL) and brine (50 mL). The EtOAc layer was dried (MgSO$_4$), filtered, and the solvent was removed under reduced pressure. The residue was purified by pressurized silica gel column chromatography using a gradient elution of 1:99 to 3:97 MeOH:CH$_2$Cl$_2$. The title compound was obtained as an amorphous solid.

Analysis calculated for (C$_{30}$H$_{36}$N$_4$O$_7$S, 0.7 CH$_2$Cl$_2$) C, 56.19; H, 5.75; N, 8.54 Found C, 56.32; H, 5.69; N, 8.50 TLC: R$_f$=0.36 (97:3 CH$_2$Cl$_2$:MeOH) HPLC (method A): retention time 8.22 min FAB MS: m/z 597 (M$^+$+H)

EXAMPLE 91

1-(1-(4-(4-(1-(3-(N-Benzyl)pyrrolidinylsulfonyl)-piperidinyloxy)-2-methoxybenzoyl)piperidin-4-yl)-1,2-dihydro-4(H)-3,1-benzoxazin-2-one

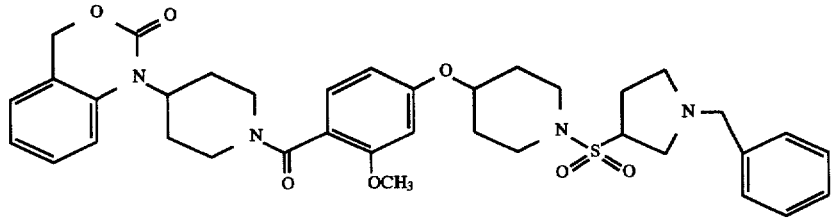

To stirred solution of 1-(1-(4-(4-(1-(vinylsulfonyl)-piperidinyloxy)-2-methoxybenzoyl)piperidin-4-yl)-1,2-dihydro-4(H)-3,1-benzoxazin-2-one from Example 67 (0.50 g; 0.73 mmol) in acetonitrile (10 mL) was added N-trimethylsilyl-N-cyanomethylbenzylamine (0.39 mL; 1.57 mmol) and AgF (0.20 g; 1.57 mmol). The solution was stirred at 75° C. for 4 h and then cooled to 23° C. and stirred for 14 h. The solvent was removed under reduced pressure and the crude mixture resuspended in $CH_2Cl_2$. The suspension was filtered through celite and the solvent removed under reduced pressure. The residue was purified by pressurized silica gel column chromatography using 9:1 $CHCl_3$:$^iPrOH$. Evaporation of a $CHCl_3$ solution of the title compound under reduced pressure gave an amorphous powder.

Analysis calculated for ($C_{37}H_{44}N_4O_7S$, 0.25 $CHCl_3$) C, 62.25; H, 6.21; N, 7.80 Found C, 62.25; H, 6.15; N, 8.04 TLC: $R_f$=0.50 (95:5 $CHCl_3$:iPrOH) HPLC (method A): retention time 9.56 min FAB MS: m/z 689 ($M^+$+H)

EXAMPLE 92

1-(1-(4-(4-(1-(3-Pyrrolidinylsulfonyl)-piperidinyloxy)-2-methoxybenzoyl)piperidin-4-yl)-1,2-dihydro-4(H)-3,1-benzoxazin-2-one

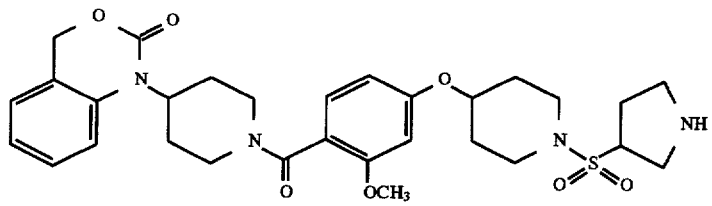

To stirred solution of 1-(1-(4-(4-(1-(3-(N-Benzyl) pyrrolidinylsulfonyl)piperidinyloxy)-2-methoxybenzoyl) piperidin-4-yl)-1,2-dihydro-4(H)-3,1-benzoxazin-2-one from Example 91 (0.20 g; 0.33 mmol) in dichloroethane (2 mL) was added 1-chloroethyl chloroformate (0.039 mL; 0.36 mmol). The mixture was heated at reflux for 3 h and then cooled to ambient temperature. The reaction mixture was concentrated in vacuo and redissolved in MeOH (5 mL). This solution was refluxed for 1 hour and cooled to ambient temperature. The reaction solvent was removed under reduced pressure and the residue purified by pressurized silica gel column chromatography using 95:5 $CH_2Cl_2$:MeOH. Evaporation of a $CH_2Cl_2$ solution of the title compound under reduced pressure gave an amorphous powder.

Analysis calculated for ($C_{30}H_{38}N_4O_7S$, 0.95 $CH_2Cl_2$) C, 54.79; H, 5.93; N, 8.26 Found C, 54.54; H, 5.76; N, 8.58 TLC: $R_f$=0.50 (85:15:0.75 $CH_2Cl_2$:MeOH:$NH_4OH$) HPLC (method A): retention time 7.77 min FAB MS: m/z 599 ($M^+$+H)

EXAMPLE 93

1-(1-(4-(4-(1-(3-(N-Ethyl)pyrrolidinylsulfonyl)-piperidinyloxy)-2-methoxybenzoyl)piperidin-4-yl)-1,2-dihydro-4(H)-3,1-benzoxazin-2-one

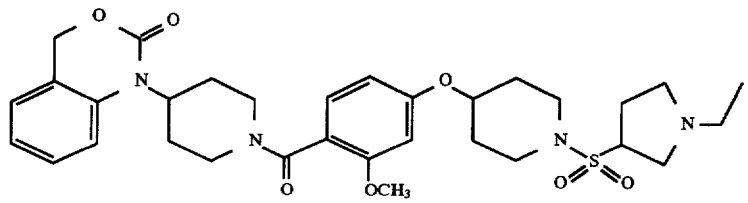

To stirred solution of 1-(1-(4-(4-(1-(3-pyrrolidinylsulfonyl)piperidinyloxy)-2-methoxybenzoyl) piperidin-4-yl)-1,2-dihydro-4(H)-3,1-benzoxazin-2-one from Example 92 (0.02 g; 0.039 mmol) in HOAc (1 mL) was added $NaBH_4$ (1.5 mg; 0.039 mmol). The reaction solution was stirred at ambient temperature for 18 h and then diluted with $H_2O$ (5 mL). The solution was made basic with saturated aqueous $NaHCO_3$ (5 mL) and 1M NaOH (5 mL). The solution was extracted with $CH_2Cl_2$ (5×5 mL). The organic phase was dried ($MgSO_4$), filtered, and the solvent was removed under reduced pressure. The residue was purified by pressurized silica gel column chromatography using 10:1 A:B (A=$CH_2Cl_2$, B=MeOH saturated with gaseous $NH_3$). The title compound was dissolved in MeOH and to the solution was added 2 equivalents of 1.0N aqueous HCl. The resulting solution was evaporated under reduced pressure and the residue was lyophilized from $H_2O$:$CH_3CN$. The HCl salt of the title compound was obtained as an amorphous powder.

Analysis calculated for ($C_{32}H_{42}N_4O_7S$, 1.6 HCl, 0.3 $H_2O$) C, 55.72; H, 6.46; N, 8.12 Found C, 55.74; H, 6.46; N, 7.94 TLC: $R_f$=0.90 [5:1 $CH_2Cl_2$:MeOH($NH_3$)] HPLC (method A): retention time 10.78 min FAB MS: m/z 627 ($M^+$+H).

EXAMPLE 94

1-(2-Cyano-1-(2,4-dimethoxybenzoyl)-4-piperidyl)-3,1-benzoxazin-2-one

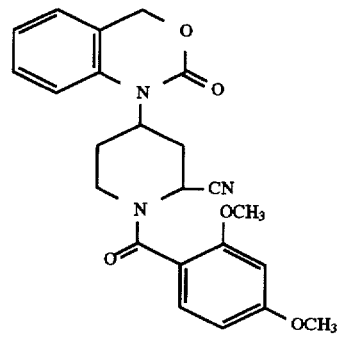

Step 1:

1-(4-Piperidyl)-3,1-benzoxazin-2-one (988 mg, 3.68 mmol) was treated with aqueous sodium carbonate and the resulting free base was extracted into ether. The dried (sodium sulfate) ether layer was evaporated in vacuo and the residue evaporated three times from methylene chloride/methanol. The residue was treated with methylene chloride and filtered to remove insoluble material. The methylene chloride solution was evaporated to dryness in vacuo and the residue treated with acetic acid (0.197 mL) and water (2 mL). To the resulting solution was added an aqueous suspension of pulverized calcium hypochlorite (637 mg). The mixture was stirred at ambient temperature for 30 min, then combined with water and extracted with ether. The ether layer was washed with water and with brine, dried over sodium sulfate, filtered, and evaporated to dryness in vacuo to give 1-(N-chloro-4-piperidyl)-3,1-benzoxazin-2-one.

Step 2:

1-(N-chloro-4-piperidyl)-3,1-benzoxazin-2-one from Step 1 above (230 mg, 0.86 mmol) was dissolved in warm ether (30 mL) and the solution was added dropwise to a suspension of potassium superoxide (135 mg, 1.9 mmol) and 18-crown-6 (10 mg, 0.04 mmol) in ether (10 mL). The mixture was stirred at ambient temperature for five days, with two additional lots of 135 mg each of potassium superoxide being added on the second and third days. The reaction was filtered and the filtrate was added dropwise to an ether solution of trimethylsilylcyanide (0.172 mL, 128 mg, 1.3 mmol). The mixture was stirred at ambient temperature for 18 hours, then evaporated to dryness in vacuo. The residue was chromatographed on silica gel eluted with 4:96 MeOH:CH$_2$Cl$_2$. The combined product fractions were evaporated to dryness in vacuo, and the residue was evaporated twice from ether to give 1-(2-cyano-4-piperidyl)-3,1-benzoxazin-2-one: MS (FAB): M+H @ m/e=258.

Step 3:

1-(2-Cyano-4-piperidyl)-3,1-benzoxazin-2-one from Step 2 above (198 mg, 0.77 mmol) was dissolved in methylene chloride (2 mL) and treated with 2,4-dimethoxybenzoyl chloride (170 mg, 0.84 mmol) followed by triethylamine (0.12 mL, 85 mg, 0.85 mmol). The mxiture was stirred at ambient temperature for one hour, then chromatographed on silica gel eluted with 1:9 ether:CH$_2$Cl$_2$. The product fractions were combined and evaporated to dryness in vacuo. The residue was crystallized from ether to give the title compound: mp 176°–177° C.

TLC: R$_f$=0.33 (1:9 ether:CH$_2$Cl$_2$) FAB MS: M+H @ m/e=422 HPLC: 93% Anal. cal'd for C$_{23}$H$_{23}$N$_3$O$_5$: C, 65.54; H, 5.50; N, 9.97. Found: C, 65.51; H, 5.52; N, 9.89.

EXAMPLE 95

1-(2-Carboxamido-1-(2,4-dimethoxybenzoyl)-4-piperidyl)-3,1-benzoxazin-2-one

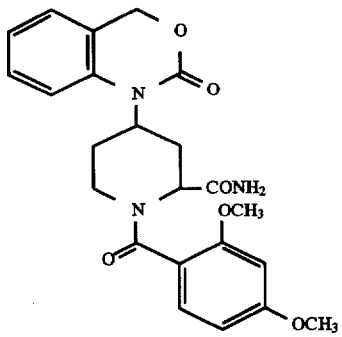

1-(2-Cyano-1-(2,4-dimethoxybenzoyl)-4-piperidyl)-3,1-benzoxazin-2-one (18.4 mg, 0.044 mmol) was dissolved in warm 95% ethanol (2 mL). The solution was cooled, and aqueous sodium hydroxide (0.005 mL of a 10% solution; 0.0125 mmol)) was added followed by 30% hydrogen peroxide (0.005 ml, 0.05 mmol). The mixture was stirred at 45°–50° C. for 6 h, then at ambient temperature for 66 hr. The mixture was concentrated in a stream of nitrogen, and the residue was treated with water, made basic with saturated sodium bicarbonate solution, and extracted with ethyl acetate. The organic layers were combined and washed with brine, dried over sodium sulfate, and filtered, and the filtrate was evaporated to dryness in vacuo. The residue was chromatographed on silica gel eluted with 3:97 MeOH:CH$_2$Cl$_2$. The product fractions were combined and evaporated to dryness in vacuo, and the residue was crystallized from ether to yield the title compound: mp 210°–212° C.

TLC: R$_f$=0.33 (3:97 MeOH:CH$_2$Cl$_2$) FAB MS: M+H @ m/e=440 HPLC: 94.3% Anal. cal'd for C$_{23}$H$_{25}$N$_3$O$_6$.0.05 C$_4$H$_{10}$O.0.45H$_2$O: C, 61.74; H, 5.90; N, 9.31. Found: C, 61.66; H, 5.61; N, 9.01.

EXAMPLE 96

1-(1-(2,4-Dimethoxybenzoyl)-4-piperidyl)-4-phenyl-3,1-benzoxazin-2-one

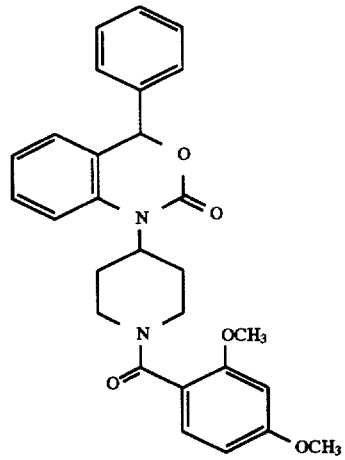

Step 1:

Acetic acid (2.28 mL, 2.4 g, 40.4 mmol) was added slowly to sodium borohydride (0.76 g, 20.2 mmol) in THF (20 mL) stirred in an ice bath. The mixture was stirred in the cold until hydrogen evolution had ceased. 2-Aminobenzophenone (2.0 g, 10.1 mmol) was added as the solid. The mixtuire was stirred under nitrogen at ambient temperature for 20 hours, after which time, TLC assay (silica gel, 1:9 EtOAc:hexane) indicated reaction was complete. The reaction mixture was treated with water (40 mL), then neutralized with saturated aqueous sodium bicarbonate and extracted with ethyl acetate. The organic layers were combined, dired over sodium sulfate, filtered, and evaporated to dryness in vacuo to give 2-aminobenzhydrol.

Step 2:

2-Aminobenzhydrol from Step 1 above (1.0 g, 5 mmol), N-Boc-4-piperidone (2.0 g, 10 mmol), and acetic acid (0.86 mL, 0.9 g, 15 mmol) were combined in methanol (10 mL). Sodium cyanoborohydride (0.79 g, 12.5 mmol) was added in portions, and the mixture was stirred at ambient temperature for 42 hours. The mixture was concentrated in vacuo. Ethyl acetate (100 mL) was added to the residue and the resulting mixture was washed with saturated aqueous sodium bicarbonate, dried over sodium sulfate, filtered, and evaporated in vacuo. The residue was chromatographed on silica gel eluted with 1:9 then 15:85 EtOAc:hexane. The combined product fractions were evaporated to dryness in vacuo to give phenyl-(2-(1-Boc-4-piperidinylamino)phenyl) carbinol.

Step 3:

Phenyl-(2-(1-Boc-4-piperidinylamino)phenyl) carbinol from Step 2 above (1.8 g, 4.7 mmol) was stirred in dry THF in an ice bath under nitrogen, and triphosgene (0.47 g, 1.57 mmol) was added followed by triethylamine (1.96 mL, 1.42 g, 14.1 mmol). The ice bath was removed and the mixture was stirred at ambient temperature for 18 hours. Water was added, and the mixture was extracted with ethyl acetate. The combined ethyl acetate fractions were washed with 1N HCl followed by saturated sodium bicarbonate, dried over sodium sulfate, filtered, and evaporated to dryness in vacuo to give 1-(1-Boc-4-piperidyl)-4-phenyl-3,1-benzoxazin-2-one.

Step 4:

1-(1-Boc-4-piperidyl)-4-phenyl-3,1-benzoxazin-2-one from Step 3 above (1.97 g, 4.67 mmol) was stirred in ethyl acetate in an ice bath, then saturated with HCl gas and stirred another 15 min in the cold. The mixture was evaporated in vacuo. Three portions of ethyl acetate were successively added and evaporated in vacuo to give 1-(4-piperidyl)-4-phenyl-3,1-benzoxazin-2-one hydrochloride.

Step 5:

1-(4-Piperidyl)-4-phenyl-3,1-benzoxazin-2-one hydrochloride from Step 4 above (0.185 g, 0.52 mmol) was stirred in methylene chloride (10 mL), and 2,4-dimethoxybenzoyl chloride (0.1 g, 0.52 mmol) was added followed by triethylamine (0.14 mL, 0.105 g, 1.04 mmol). The mixture was stirred at ambient temperature for 18 hours, then chromatographed on silica gel eluted with 500:10:1 CHCl$_3$:MeOH:NH$_4$OH. The combined product fractions were evaporated to dryness in vacuo. The residue was rechromatographed on silica gel eluted with ethyl acetate and the combined product fractions were evaporated to dryness in vacuo to give the title compound as an amorphous solid: mp 88°–120° C.

TLC: R$_f$=0.58 (EtOAc) FAB MS: M+H @ m/e=473 HPLC: 95% Anal. cal'd for C$_{28}$H$_{28}$N$_2$O$_5$.0.15EtOAc: C, 70.71; H, 6.06; N, 5.77. Found: C, 70.65; H, 6.00; N, 5.58.

EXAMPLE 97

1-(1-(2,4-Dimethoxybenzoyl)-4-piperidyl)-4-methyl-3,1-benzoxazin-2-one

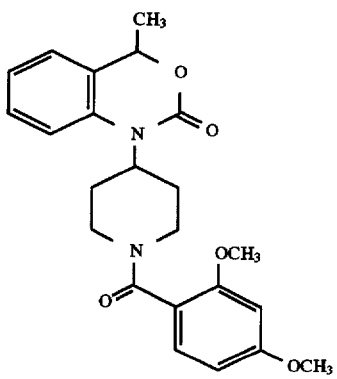

Step 1:

Sodium borohydride (1.12 g, 29.6 mmol) was stirred under nitrogen in THF (40 mL) in an ice bath. Acetic acid (3.38 mL, 3.55 g, 59.2 mmol) was added dropwise. The mixture was stirred until hydrogen evolution had ceased, then neat 2-aminoacetophenone (2.0 g, 14.8 mmol) was added dropwise. The mixture was stirred at ambient temperature for 5 days, then treated with water (40 mL) and neutralized with saturated aqueous sodium bicarbonate. The mixture was extracted with ether, and the combined ether layers were dried over sodium sulfate, filtered, and evaporated to dryness in vacuo to give methyl-2-aminophenyl carbinol.

Step 2:

Methyl-2-aminophenyl carbinol from Step 1 above (0.86 g, 6.3 mmol), N-Boc-4-piperidone (2.5 g, 12.6 mmol), and acetic acid (1.08 mL, 1.13 g, 18.9 mmol) were combined in methanol (10 mL). Sodium cyanoborohydride (0.79 g, 12.5 mmol) was added in portions, and the mixture was stirred at ambient temperature for 18 hours. The mixture was concentrated in vacuo. Ethyl acetate (100 mL) was added to the residue and the resulting mixture was washed with saturated aqueous sodium bicarbonate, dried over sodium sulfate, filtered, and evaporated in vacuo. The residue was chromatographed on silica gel eluted with 1:9 then 15:85 EtOAc:hexane. The combined product fractions were evaporated to dryness in vacuo to give methyl-(2-(1-Boc-4-piperidinylamino)phenyl) carbinol.

Step 3:

Methyl-(2-(1-Boc-4-piperidinylamino)phenyl) carbinol from Step 2 above (1.9 g, 5.9 mmol) was stirred in dry THF in an ice bath under nitrogen, and triphosgene (0.59 g, 1.98 mmol) was added followed by triethylamine (2.5 ml, 1.8 g, 17.8 mmol). The ice bath was removed and the mixture was stirred at ambient temperature for 18 hours. Water was added, and the mixture was extracted with ethyl acetate. The combined ethyl acetate fractions were washed with 1N HCl followed by saturated sodium bicarbonate, dried over sodium sulfate, filtered, and evaporated to dryness in vacuo to give 1-(1-Boc-4-piperidyl)-4-methyl-3,1-benzoxazin-2-one.

Step 4:

1-(1-Boc-4-piperidyl)-4-methyl-3,1-benzoxazin-2-one from Step 3 above (1.98 g, 5.72 mmol) was stirred in ethyl acetate in an ice bath, then saturated with HCl gas and stirred another 15 min in the cold. The mixture was evaporated in vacuo. Three portions of ethyl acetate were successively added and evaporated in vacuo to give 1-(4-piperidyl)-4-methyl-3,1-benzoxazin-2-one hydrochloride.

Step 5:

1-(4-Piperidyl)-4-methyl-3,1-benzoxazin-2-one hydrochloride from Step 4 above (0.24 g, 0.85 mmol) was stirred in methylene chloride (10 mL) and 2,4-dimethoxybenzoyl chloride (0.17 g, 0.85 mmol) was added followed by triethylamine (0.24 mL, 0.17 g, 1.7 mmol). The mixture was stirred at ambient temperature for 18 hours, then chromatographed on silica gel eluted with 500:10:1 CHCl$_3$:MeOH:NH$_4$OH. The combined product fractions were evaporated to dryness in vacuo. The residue was rechromatographed on silica gel eluted with ethyl acetate and the combined product fractions were evaporated to dryness in vacuo to give the title compound as an amorphous solid: mp 75°–95° C.

TLC: R$_f$=0.46 (EtOAc) FAB MS: M+H @ m/e=411 HPLC: 93% Anal. cal'd for C$_{23}$H$_{26}$N$_2$O$_5$.0.15 EtOAc.0.2 H$_2$O: C, 66.33; H, 6.51; N, 6.56 Found: C, 66.39; H, 6.15; N, 6.31

EXAMPLE 98

Methyl 1-(2,4-dimethoxybenzoyl)-4-(3,1-benzoxazin-2-one-1-yl)-3-piperidine carboxylate

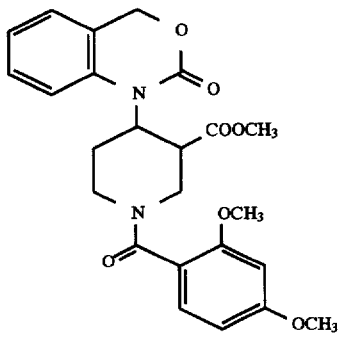

Step 1:

Methyl 4-oxo-3-piperidinecarboxylate hydrochloride (3.5 g, 18.1 mmol) was stirred in methylene chloride (30 mL) and treated is with di-t-butyl dicarbonate (3.6 g, 16.5 mmol) followed by triethylamine added dropwise to maintain the pH of the mixture (moistened E. Merck colorpHast sticks) in the range 7–8. The mixture was stirred at ambient temperature for 18 h, then washed with 1N HCl followed by saturated aqueous sodium bicarbonate. The organic layer was dried over sodium sulfate, filtered, and evaporated to dryness in vacuo to give methyl 1-Boc-4-oxo-3-piperidinecarboxylate.

Step 2:

Methyl 1-Boc-4-oxo-3-piperidinecarboxylate from Step 1 above (3.86 g, 15 mmol) was combined with 2-aminobenzyl alcohol (1.5 g, 12.2 mmol) and acetic acid (1.29 mL, 1.35 g, 22.5 mmol) in methanol (10 mL). Sodium cyanoborohydride (0.94 g, 15 mmol) was added and the mixture was stirred at ambient temperature for 3.5 h. The solvent was removed in vacuo and the residue treated with ethyl acetate (100 mL). The solution was washed with saturated aqueous sodium bicarbonate, dried over sodium sulfate, filtered, and evaporated to dryness in vacuo. The residue was chromatographed on silica gel eluted with 1:4, 1:2, and 3:5 EtOAc:hexane. The combined product fractions were evaporated to dryness in vacuo to give methyl 1-Boc-4-(2-hydroxymethylphenylamino)-3-piperidine carboxylate.

Step 3:

Methyl 1-Boc-4-(2-hydroxymethylphenylamino)-3-piperidine carboxylate from Step 2 above (4.1 g, 11.3 mmol) was stirred in THF (40 mL) in an ice bath and treated with triphosgene (1.11 g, 3.74 mmol) followed by triethylamine (4.7 mL, 3.41 g, 33.7 mmol). The mixture was stirred at ambient temperature for 18 h, then treated with an additional 0.47 g of triphosgene and 1.9 mL of triethylamine, and stirred an additional 4.5 h. Water was added and the mixture was extracted with ethyl acetate. The combined ethyl acetate layers were washed with 2N HCl then with saturated aqueous sodium bicarbonate, dried over sodium sulfate, filtered, and evaporated to dryness in vacuo. The residue was chromatographed on silica gel eluted with $CHCl_3$ followed by 1:99 $MeOH:CHCl_3$. The combined product fractions were evaporated to dryness in vacuo to give methyl 1-Boc-4-(3,1-benzoxazin-2-one-1-yl)-3-piperidine carboxylate.

Step 4:

Methyl 1-Boc-4-(3,1-benzoxazin-2-one-1-yl)-3-piperidine carboxylate from Step 3 above (0.6 g, 1.5 mmol) was stirred in ethyl acetate in an ice bath, then saturated with HCl gas and stirred another 15 min in the cold. The mixture was evaporated in vacuo. Three portions of ethyl acetate were successively added and evaporated in vacuo to give methyl 4-(3,1-benzoxazin-2-one-1-yl)-3-piperidine carboxylate hydrochloride.

Step 5:

Methyl 4-(3,1-benzoxazin-2-one-1-yl)-3-piperidine carboxylate hydrochloride from Step 3 above (0.26 g, 0.97 mmol) was stirred in methylene chloride (10 mL), and 2,4-dimethoxybenzoyl chloride (0.19 g, 0.95 mmol) was added followed by triethylamine (0.26 mL, 0.19 g, 1.9 mmol). The mixture was stirred at ambient temperature for 2.5 h, then chromatographed on silica gel eluted with 500:10:1 $CHCl_3:MeOH:NH_4OH$. The combined product fractions were evaporated to dryness in vacuo. The residue was rechromatographed on silica gel eluted with 4:1 EtOAc:hexane and the combined product fractions were evaporated to dryness in vacuo to give the title compound as a mixture of diastereomers (amorphous solid): mp 75°–100° C. (indistinct).

TLC: $R_f$=0.26, 0.39 (EtOAc) FAB MS: M+H @ m/e=455 HPLC: 38%+58% Anal. cal'd for $C_{24}H_{26}N_2O_7 \cdot 0.05$ EtOAc $\cdot 0.6$ $H_2O$: C, 61.88; H, 5.92; N, 5.96. Found: C, 61.75; H, 5.87; N, 6.29.

EXAMPLE 99

1-(1-(4-(1-(4-Carboxybutanoyl)-4-piperidinyloxy)-2-methoxybenzoyl)piperidin-4-yl)-1,2-dihydro-4(H)-3,1-benzoxazin-2-one

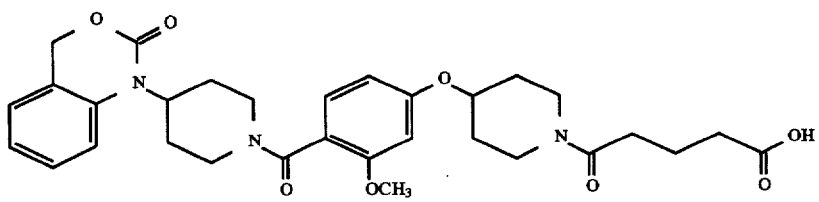

To stirred solution of 1-(1-(4-(4-piperidinyloxy)-2-methoxybenzoyl)piperidin-4-yl)-1,2-dihydro-4(H)-3,1-benzoxazin-2-one hydrochloride from Example 26 (0.15 g; 0.30 mmol) in $CH_2Cl_2$ (5 mL) was added glutaric anhydride (37 mg; 0.32 mmol) and DIEA (0.060 mL; 0.35 mmol). The solution was stirred at ambient temperature for 18 h and then diluted with $CH_2Cl_2$ (25 mL) and extracted with 5% aqueous citric acid (2×10 mL) and brine (10 mL). The organic phase was dried ($MgSO_4$), filtered, and the solvent was evaporated under reduced pressure to give the title compound as an amorphous powder.

HPLC (method A): retention time 7.05 min FAB MS: m/z 580 ($M^+$+H) Analysis calculated for ($C_{31}H_{37}N_3O_8$, 0.5 $CH_2Cl_2$, 0.05 $H_2O$) C, 60.72; H, 6.16; N, 6.74 Found C, 60.69; H, 5.83; N, 6.94

EXAMPLE 100

1-(1-(4-(1-(4-(4-Morpholino)butanoyl)-4-piperidinyloxy)-2-methoxybenzoyl)piperidin-4-yl)-1,2-dihydro-4(H)-3,1-benzoxazin-2-one

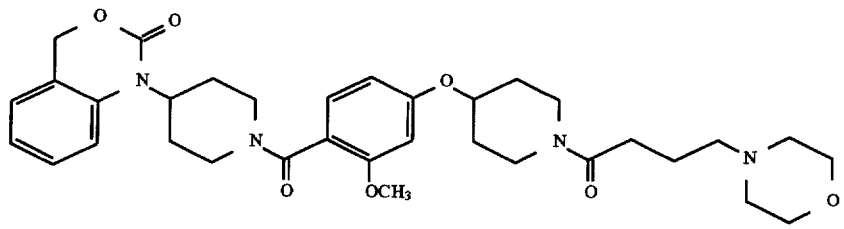

To stirred solution of 1-(1-(4-(4-piperidinyloxy)-2-methoxybenzoyl)piperidin-4-yl)-1,2-dihydro-4(H)-3,1-benzoxazin-2-one hydrochloride from Example 26 (0.15 g; 0.30 mmol) in DMF (5 mL) was added 4-(4-morpholino)butyric acid (57 mg, 0.33 mmol), BOP (145 mg, 0.33 mmol), and DIEA (0.16 mL, 0.92 mmol). The reaction solution was stirred at ambient temperature for 18 h, then evaporated under reduced pressure. The residue was dissolved in EtOAc (50 mL) and washed with saturated aqueous NaHCO₃ (2×25 mL) and brine (25 mL). The organic phase was dried (MgSO₄), filtered, and the solvent was removed under reduced pressure. The residue was purified by pressurized silica gel column chromatography using a gradient elution of 98:2 to 94:6 CH₂Cl₂:MeOH. The product-containing fractions were evaporated under reduced pressure and the residue was lyophilized from dioxane to give the title compound as an amorphous powder.

TLC: $R_f$=0.47 (93:7 CH₂Cl₂:MeOH) HPLC (method A): retention time 6.45 min FAB MS: m/z 621 (M⁺+H)

Analysis calculated for (C₃₄H₄₄N₄O₇, 0.1 dioxane, 1.85 H₂O) C, 62.32; H, 7.37; N, 8.45 Found C, 62.33; H, 7.03; N, 8.42

EXAMPLE 101

1-(1-(4-(1-(3-Amino-3,3-dimethylpropanoyl)-4-piperidinyloxy)-2-methoxybenzoyl)piperidin-4-yl)-1,2-dihydro-4(H)-3,1-benzoxazin-2-one

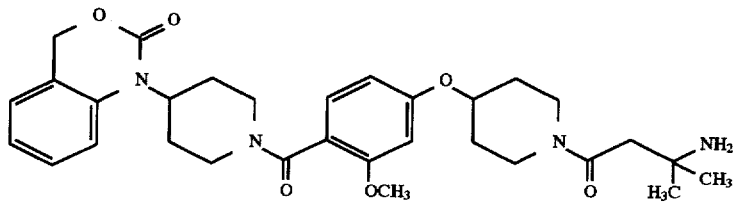

Step 1:
To stirred solution of 1-(1-(4-(4-piperidinyloxy)-2-methoxybenzoyl)piperidin-4-yl)-1,2-dihydro-4(H)-3,1-benzoxazin-2-one hydrochloride from Example 26 (0.15 g; 0.30 mmol) in DMF (5 mL) was added 3-(tert-butyloxycarbonylamino)-3,3-dimethylpropionic acid (72 g, 0.33 mmol), BOP (145 mg, 0.33 mmol), and DIEA (0.16 mL, 0.92 mmol). The reaction solution was stirred at ambient temperature for 18 h and the solvent was evaporated under reduced pressure. The residue was dissolved in EtOAc (50 mL) and washed with saturated aqueous NaHCO₃ (2×25 mL) and brine (25 mL). The organic phase was dried (MgSO₄), filtered, and the solvent was removed under reduced pressure. The residue was purified by pressurized silica gel column chromatography using a gradient elution of 99:1 to 98:2 CH₂Cl₂:MeOH. The product-containing fractions were evaporated under reduced pressure to give 1-(1-(4-(1-(3-(tert-butyloxycarbonylamino)-3,3-dimethylpropanoyl)-4-piperidinyloxy)-2-methoxybenzoyl)piperidin-4-yl)-1,2-dihydro-4(H)-3,1-benzoxazin-2-one as an amorphous powder (TLC $R_f$=0.43 (97:3 CH₂Cl₂:MeOH); HPLC retention time=9.35 min (method A); FAB MS m/z 665 (M⁺+H)).

Step 2:
To a solution of 1-(1-(4-(1-(3-(tert-butyloxycarbonylamino)-3,3-dimethylpropanoyl)-4-piperidinyloxy)-2-methoxybenzoyl)piperidin-4-yl)-1,2-dihydro-4(H)-3,1-benzoxazin-2-one from Step 1 above in CH₂Cl₂ (2 mL) was added TFA (1 mL). After 1 h, the solvents were removed under reduced pressure. The residue was dissolved in CH₂Cl₂ (xx mL) and washed with saturated aqueous NaHCO₃ (2xmL). The organic phase was dried (MgSO₄), filtered, and the solvent was removed under reduced pressure. The residue was purified by pressurized silica gel column chromatography using 97:3:0.3 CH₂Cl₂:MeOH:NH₄OH as eluant. The product-containing fractions were evaporated under reduced pressure and the residue was lyophilized from dioxane to give the title compound as an amorphous powder.

TLC: $R_f$=0.24 (98:2:0.2 CH₂Cl₂:MeOH:NH₄OH) HPLC (method A): retention time 6.51 min FAB MS: m/z 565 (M⁺+H) Analysis calculated for (C₃₁H₄₀N₄O₆, 0.6 dioxane, 2.5 H₂O) C, 62.32; H, 7.37; N, 8.45 Found C, 62.33; H, 7.03; N, 8.42

EXAMPLE 102

1-(1-(4-(1-(6-(t-Butyloxycarbonylamino)-2S-(t-Butyloxycarbonylamino)hexanoyl)-4-piperidinyloxy)-2-methoxybenzoyl)piperidin-4-yl)-1,2-dihydro-4(H)-3,1-benzoxazin-2-one

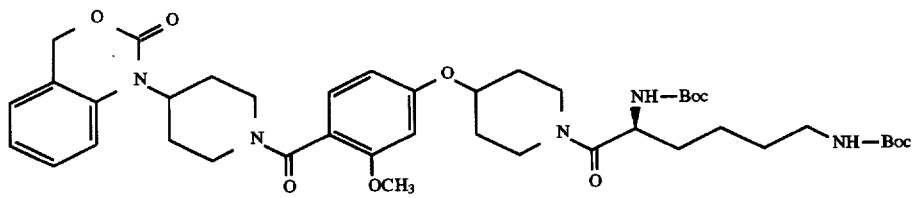

To stirred solution of 1-(1-(4-(4-piperidinyloxy)-2-methoxybenzoyl)piperidin-4-yl)-1,2-dihydro-4(H)-3,1-benzoxazin-2-one hydrochloride from Example 26 (0.15 g; 0.30 mmol) in DMF (5 mL) was added $N^{\alpha},N^{\epsilon}$-Boc-L-lysine (114 mg, 0.33 mmol), BOP (145 mg, 0.33 mmol), and DIEA (0.16 mL, 0.92 mmol). The reaction solution was stirred at ambient temperature for 18 h and the solvent was evaporated under reduced pressure. The residue was dissolved in EtOAc (50 mL) and washed with saturated aqueous $NaHCO_3$ (2×25 mL) and brine (25 mL). The organic phase was dried ($MgSO_4$), filtered, and the solvent was removed under reduced pressure. The residue was purified by pressurized silica gel column chromatography using a gradient elution of 99:1 to 97:3 $CH_2Cl_2$:MeOH. The product-containing fractions were evaporated under reduced pressure to give the title compound as an amorphous solid.

Analysis calculated for ($C_{42}H_{59}N_5O_{10}$, 1.1 $CH_2Cl_2$) C, 58.33; H, 6.95; N, 7.89 Found C, 62.33; H, 6.78; N, 7.86 TLC: $R_f$=0.49 (97:3 $CH_2Cl_2$:MeOH) HPLC (method A): retention time 9.89 min FAB MS: m/z 794 ($M^++H$)

EXAMPLE 103

1-(1-(4-(N-Acryloyl-4-piperidinyloxy)-2-methoxybenzoyl)piperidin-4-yl)-1,2-dihydro-4(H)-3,1-benzoxazin-2-one

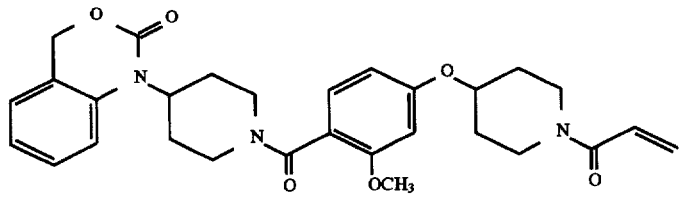

To a stirred 0° C. solution of 1-(1-(4-(4-piperidinyloxy)-2-methoxybenzoyl)piperidin-4-yl)-1,2-dihydro-4(H)-3,1-benzoxazin-2-one hydrochloride from Example 26 (1.5 g; 3.0 mmol) in $CH_2Cl_2$ (30 mL) was added acryloyl chloride (0.30 g, 3.3 mmol), and DIEA (0.61 mL, 3.5 mmol). The reaction solution was stirred at 0° C. for 1 h and then at ambient temperature for 18 h. The solvent was evaporated under reduced pressure, the residue was dissolved in EtOAc (150 mL) and washed with saturated aqueous $NaHCO_3$ (2×75 mL) and brine (75 mL). The organic phase was dried ($MgSO_4$), filtered, and the solvent was removed under reduced pressure. The residue was purified by pressurized silica gel column chromatography using a gradient elution of 99:1 to 97:3 $CH_2Cl_2$:MeOH. The product-containing fractions were evaporated under reduced pressure to give the title compound as an amorphous solid.

Analysis calculated for ($C_{29}H_{33}N_3O_6$, 0.25 $CH_2Cl_2$) C, 64.95; H, 6.24; N, 7.77 Found C, 64.88; H, 6.29; N, 7.75 TLC: $R_f$=0.32 (97:3 $CH_2Cl_2$:MeOH) HPLC (method A): retention time 7.55 min FAB MS: m/z 520 ($M^++H$)

EXAMPLE 104

1-(1-(4-(1-(6-Amino-2S-aminohexanoyl)-4-piperidinyloxy)-2-methoxybenzoyl)piperidin-4-yl)-1,2-dihydro-4(H)-3,1-benzoxazin-2-one

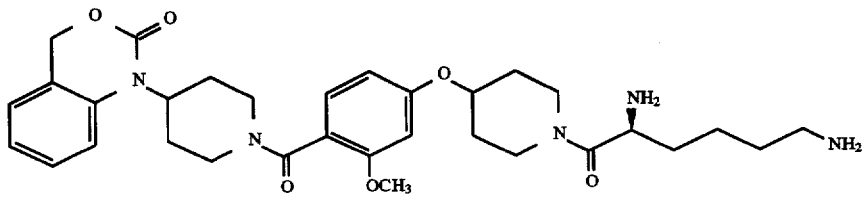

Into a stirred 0° C. solution of 1-(1-(4-(1-(6-(t-butyloxycarbonylamino)-2S-(t-Butyloxycarbonylamino) hexanoyl)-4-piperidinyloxy)-2-methoxybenzoyl)piperidin-4-yl)-1,2-dihydro-4(H)-3,1-benzoxazin-2-one (0.12 g; 0.15 mmol) from Example 97 in EtOAc (10 mL) was bubbled gaseous HCl for 20 min. The reaction was stirred at ambient temperature for 30 min, the solvent was removed under reduced pressure and the residue was dried in vacuo for 24 h. The HCl salt of the title compound was obtained as an amorphous solid.

Analysis calculated for ($C_{32}H_{43}N_5O_6$, 2.5 HCl, 0.5 EtOAc) C, 56.02; H, 6.84; N, 9.61 Found C, 56.01; H, 7.06; N, 9.63 TLC: $R_f$=0.28 (70:30:3 $CH_2Cl_2$:MeOH:$NH_4OH$) HPLC (method A): retention time 5.63 min FAB MS: m/z 594 ($M^+$+H)

EXAMPLE 105

1-(1-(4-(1-(4-Methylsulfonyl-2S -(t-butyloxycarbonylamino)butanoyl)-4-piperidinyloxy)-2-methoxybenzoyl)piperidin-4-yl)-1,2-dihydro-4(H)-3,1-benzoxazin-2-one To stirred solution of 1-(1-(4-(4-(N-acryloyl-4-piperidinyloxy)-2-methoxybenzoyl)piperidin-4-yl)-1,2-dihydro-4(H)-3,1-benzoxazin-2-one from Example 98 (0.10 g; 0.19 mmol) in MeOH (1 mL) was added 1-methylpiperazine (0.2 g; 2 mmol). The solution was stirred at ambient temperature for 18 h and then concentrated under reduced pressure. The residue was purified by pressurized silica gel column chromatography using a gradient elution of 98:2:0.1 to 94:6:0.3 $CH_2Cl_2$:MeOH:$NH_4OH$. The product containing fractions were evaporated under reduced pressure and the residue was lyophilized from 1:1 $H_2O$:$CH_3CN$ containing 0.1% TFA. The TFA salt of the title compound was obtained as an amorphous powder.

Analysis calculated for ($C_{34}H_{45}N_5O_6$, 0.65 TFA, 0.75 $H_2O$) C, 59.93; H, 6.72; N, 9.90 Found C, 59.97; H, 6.75; N,

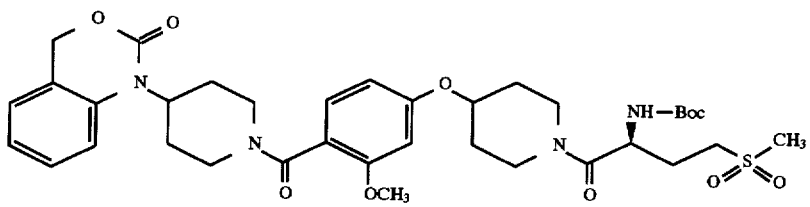

To stirred solution of 1-(1-(4-(4-piperidinyloxy)-2-methoxybenzoyl)piperidin-4-yl)-1,2-dihydro-4(H)-3,1-benzoxazin-2-one hydrochloride from Example 26 (0.15 g; 0.30 mmol) in DMF (5 mL) was added $N^\alpha$-Boc-L-methionine sulfone (93 mg, yy mmol), BOP (145 mg, 0.33 mmol), and DIEA (0.16 mL, 0.92 mmol). The reaction solution was stirred at ambient temperature for 18 h and the solvent was evaporated under reduced pressure. The residue was dissolved in EtOAc (75 mL) and washed with saturated aqueous $NaHCO_3$ (2×25 mL) and brine (25 mL). The organic phase was dried ($MgSO_4$), filtered, and the solvent was removed under reduced pressure. The residue was purified by pressurized silica gel column chromatography using a gradient elution of 99:1 to 97:3 $CHCl_3$:MeOH. The product-containing fractions were evaporated under reduced pressure to give the title compound as an amorphous solid.

Analysis calculated for ($C_{36}H_{48}N_4O_{10}S$, 1.45 $CHCl_3$) C, 49.86; H, 5.53; N, 6.21 Found C, 49.74; H, 5.67; N, 6.28 TLC: $R_f$=0.49 (95:5 $CHCl_3$:MeOH) HPLC (method A): retention time 8.22 min FAB MS: m/z 729 ($M^+$+H)

EXAMPLE 106

1-(1-(4-(1-(3-(4-Methyl-1-piperazinyl)propanoyl)-4-piperidinyloxy)-2-methoxybenzoyl)piperidin-4-yl)-1,2-dihydro-4(H)-3,1-benzoxazin-2-one 9.99 TLC: $R_f$=0.38 (93:7:0.7 $CH_2Cl_2$:MeOH:$NH_4OH$) HPLC (method A): retention time 6.24 min FAB MS: m/z 620 ($M^+$+H)

EXAMPLE 107

1-(1-(4-(1-(3-Dimethylaminopropanoyl)-4-piperidinyloxy)-2-methoxybenzoyl)piperidin-4-yl)-1,2-dihydro-4(H)-3,1-benzoxazin-2-one

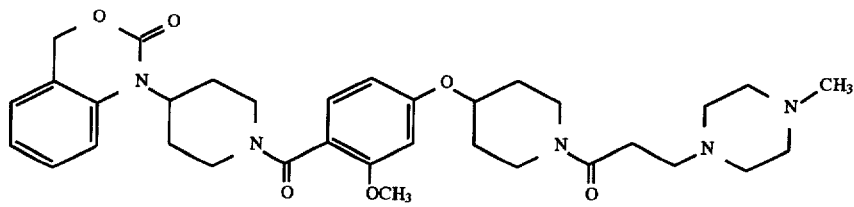

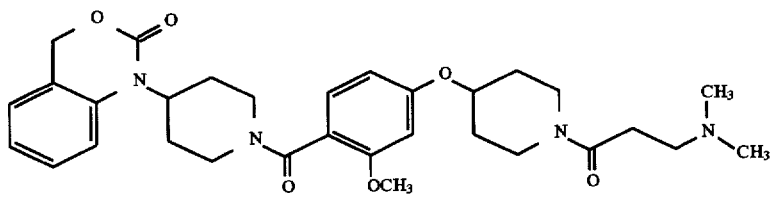

Into stirred 0° C. solution of 1-(1-(4-(N-acryloyl-4-piperidinyloxy)-2-methoxybenzoyl)piperidin-4-yl)-1,2-dihydro-4(H)-3,1-benzoxazin-2-one from Example 98 (0.15 g; 0.29 mmol) in MeOH (2 mL) was bubbled gaseous dimethylamine for 15 min. The solution was stirred at ambient temperature for 24 h and then concentrated under reduced pressure. The residue was purified by pressurized silica gel column chromatography using a gradient elution of 98:2:0.2 to 95:5:0.25 $CH_2Cl_2$:MeOH:$NH_4OH$. The product containing fractions were evaporated under reduced pressure and the residue was lyophilized from 1:1 $H_2O$:$CH_3CN$ containing 0.1% TFA. The TFA salt of the title compound was obtained as an amorphous powder.

Analysis calculated for ($C_{31}H_{40}N_4O_6$, 1.0 TFA, 2.5 $H_2O$, 0.95 $CH_3CN$) C, 54.95; H, 6.46; N, 9.09 Found C, 54.91; H, 6.28; N, 9.07 TLC: $R_f$=0.38 (93:7:0.7 $CH_2Cl_2$:MeOH:$NH_4OH$) HPLC (method A): retention time 5.85 min FAB MS: m/z 565 ($M^+$+H)

EXAMPLE 108

1-(1-(4-(1-(3,3-Dimethyl-4-carboxybutanoyl)-4-piperidinyloxy)-2-methoxybenzoyl)piperidin-4-yl)-1,2-dihydro-4(H)-3,1-benzoxazin-2-one

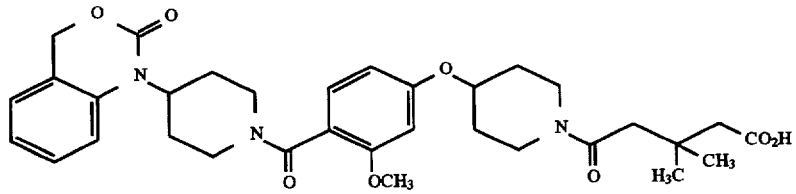

To stirred solution of 1-(1-(4-(4-piperidinyloxy)-2-methoxybenzoyl)piperidin-4-yl)-1,2-dihydro-4(H)-3,1-benzoxazin-2-one hydrochloride from Example 26 (0.15 g; 0.30 mmol) in $CH_2Cl_2$ (5 mL) was added 3,3-dimethylglutaric anhydride (47 mg; 0.33 mmol) and DIEA (0.057 mL; 0.33 mmol). The solution was stirred at ambient temperature for 18 h and then diluted with $CH_2Cl_2$ (25 mL) and extracted with 5% aqueous citric acid (2×10 mL) and brine (10 mL). The organic phase was dried (MgSO$_4$), filtered, and the solvent was evaporated under reduced pressure. The residue was lyophilized from 1:1 $H_2O$:$CH_3CN$ to give the title compound as an amorphous powder.

Analysis calculated for ($C_{33}H_{41}N_3O_8$, 1.05 $H_2O$, 0.1 $CH_3CN$) C, 63.22; H, 6.94; N, 6.88 Found C, 63.22; H, 6.68; N, 6.89 TLC: $R_f$=0.49 (95:5:0.5 $CH_2Cl_2$:MeOH:HOAc) HPLC (method A): retention time 7.94 min FAB MS: m/z 608 ($M^+$+H)

EXAMPLE 109

1-(1-(4-(1-(Carboxymethoxyacetyl)-4-piperidinyloxy)-2-methoxybenzoyl)piperidin-4-yl)-1,2-dihydro-4(H)-3,1-benzoxazin-2-one

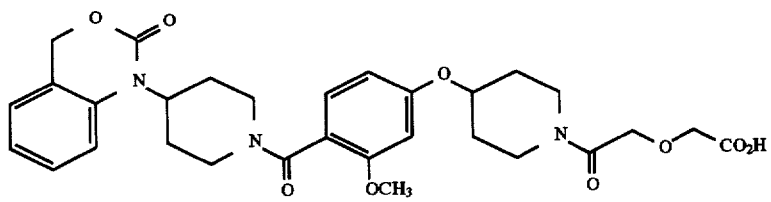

To stirred solution of 1-(1-(4-(4-piperidinyloxy)-2-methoxybenzoyl)piperidin-4-yl)-1,2-dihydro-4(H)-3,1-benzoxazin-2-one hydrochloride from Example 26 (0.15 g; 0.30 mmol) in $CH_2Cl_2$ (5 mL) was added diglycolic anhydride (38 g; 0.33 mmol) and DIEA (0.057 mL; 0.33 mmol). The solution was stirred at ambient temperature for 18 h and then diluted with $CH_2Cl_2$ (25 mL) and extracted with 5% aqueous citric acid (2×10 mL) and brine (10 mL). The organic phase was dried (MgSO$_4$), filtered, and the solvent was evaporated under reduced pressure. The residue was lyophilized from 1:1 H$_2$O:CH$_3$CN to give the title compound as an amorphous powder.

Analysis calculated for (C$_{30}$H$_{35}$N$_3$O$_9$, 0.95 H$_2$O) C, 60.17; H, 6.21; N, 7.02 Found C, 60.20; H, 6.15; N, 7.36 TLC: R$_f$=0.18 (85:15:1.5 CH$_2$Cl$_2$:MeOH:HOAc) HPLC (method A): retention time 6.90 min FAB MS: m/z 582 (M$^+$+H)

EXAMPLE 110

1-(1-(4-(1-(1-Carboxymethylcyclopent-1-ylacetyl)-4-piperidinyloxy)-2-methoxybenzoyl)piperidin-4-yl)-1,2-dihydro-4(H)-3,1-benzoxazin-2-one

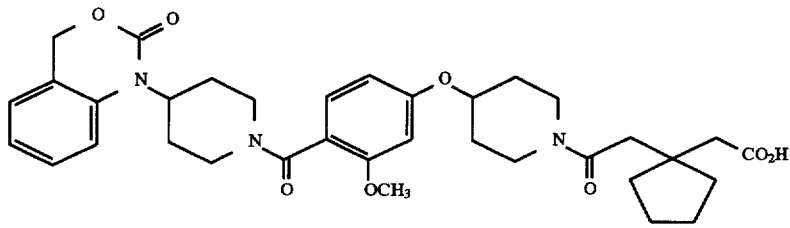

To stirred solution of 1-(1-(4-(4-piperidinyloxy)-2-methoxybenzoyl)piperidin-4-yl)-1,2-dihydro-4(H)-3,1-benzoxazin-2-one hydrochloride from Example 26 (0.15 g; 0.30 mmol) in CH$_2$Cl$_2$ (5 mL) was added 3,3-tetramethylene glutaric anhydride (55 mg; 0.33 mmol) and DIEA (0.057 mL; 0.33 mmol). The solution was stirred at ambient temperature for 18 h and then diluted with CH$_2$Cl$_2$ (25 mL) and extracted with 5% aqueous citric acid (2×10 mL) and brine (10 mL). The organic phase was dried (MgSO$_4$), filtered, and the solvent was evaporated under reduced pressure. The residue was lyophilized from 1:1 H$_2$O:CH$_3$CN to give the title compound as an amorphous powder.

Analysis calculated for (C$_{35}$H$_{43}$N$_3$O$_8$, 0.8 H$_2$O) C, 64.85; H, 6.94; N, 6.48 Found C, 64.89; H, 6.88; N, 6.43 TLC: R$_f$=0.51 (95:5:0.5 CH$_2$Cl$_2$:MeOH:HOAc) HPLC (method A): retention time 8.56 min FAB MS: m/z 634 (M$^+$+H)

EXAMPLE 111

1-(1-(4-(1-(4-(1-t-Butyloxycarbonyl-4-piperidinyloxy)benzoyl)-4-piperidinyloxy)-2-methoxybenzoyl)piperidin-4-yl)-1,2-dihydro-4(H)-3,1-benzoxazin-2-one

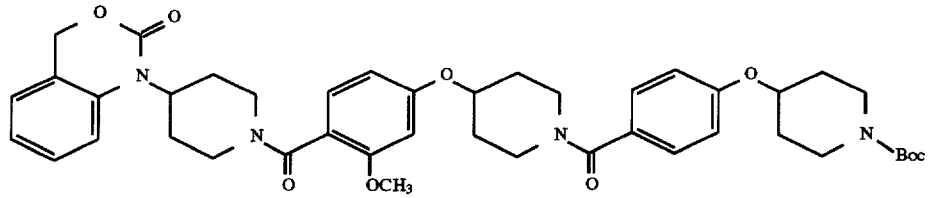

To stirred solution of 1-(1-(4-(4-piperidinyloxy)-2-methoxybenzoyl)piperidin-4-yl)-1,2-dihydro-4(H)-3,1-benzoxazin-2-one hydrochloride from Example 26 (0.15 g; 0.30 mmol) in DMF (5 mL) was added N-Boc-4-(4-piperidinyloxy)benzoic acid (106 mg, 0.33 mmol), BOP (145 mg, 0.33 mmol), and DIEA (0.16 mL, 0.92 mmol). The reaction solution was stirred at ambient temperature for 18 h and the solvent was evaporated under reduced pressure. The residue was dissolved in EtOAc (75 mL) and washed with saturated aqueous NaHCO$_3$ (2×25 mL) and brine (25 mL). The organic phase was dried (MgSO$_4$), filtered, and the solvent was removed under reduced pressure. The residue was purified by pressurized silica gel column chromatography using a gradient elution of 98:2 to 96:4 CH$_2$Cl$_2$:MeOH. The product-containing fractions were evaporated under reduced pressure to give the title compound as an amorphous solid.

Analysis calculated for (C$_{43}$H$_{52}$N$_4$O$_9$, 1.7 CH$_2$Cl$_2$) C, 58.78; H, 6.11; N, 6.13 Found C, 68.75; H, 5.94; N, 6.51 TLC: R$_f$=0.43 (95:5 CH$_2$Cl$_2$:MeOH) HPLC (method A): retention time 10.60 min FAB MS: m/z 769 (M$^+$+H)

EXAMPLE 112

1-(1-(4-(1-(4-(4-Piperidinyloxy)benzoyl)-4-piperidinyloxy)-2-methoxybenzoyl)piperidin-4-yl)-1,2-dihydro-4(H)-3,1-benzoxazin-2-one

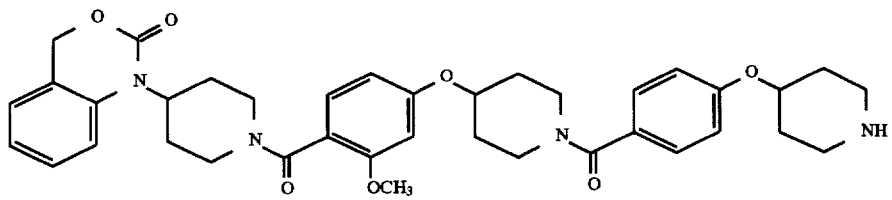

To a stirred 0° C. solution of 1-(1-(4-(1-(4-(1-t-Butyloxycarbonyl-4-piperidinyloxy)benzoyl)-4-piperidinyloxy)-2-methoxybenzoyl)piperidin-4-yl)-1,2-dihydro-4(H)-3,1-benzoxazin-2-one from Example 106 (0.10 g; 0.yy mmol) in $CH_2Cl_2$ (2 mL) was added TFA (1 mL). The reaction was stirred at ambient temperature for 1 h and then evaporated under reduced pressure. The residue was dissolved in $CH_2Cl_2$ and washed with saturated aqueous $NaHCO_3$. The $CH_2Cl_2$ was evaporated under reduced pressure and the residue was purified by pressurized silica gel column chromatography using a gradient elution of 95:5:0.25 to 90:10:0.5 $CH_2Cl_2$:MeOH:$NH_4OH$. The product-containing fractions were combined and lyophilized from 1:1 $H_2O$:$CH_3CN$ containing 0.1% TFA to give the TFA salt of the title compound as an amorphous powder.

Analysis calculated for ($C_{38}H_{44}N_4O_7$, 1.7 TFA, 1.15 $H_2O$) C, 56.29; H, 5.48; N, 6.34 Found C, 56.26; H, 5.48; N, 6.31 TLC: $R_f$=0.30 (91:9:0.9 $CH_2Cl_2$:MeOH:$NH_4OH$) HPLC (method A): retention time 6.94 min FAB MS: m/z 669 ($M^+$+H)

EXAMPLE 113

1-(1-(4-(1-(N-Phenylcarbamoyl)-4-piperidinyloxy)-2-methoxybenzoyl)piperidin-4-yl)-1,2-dihydro-4(H)-3,1-benzoxazin-2-one

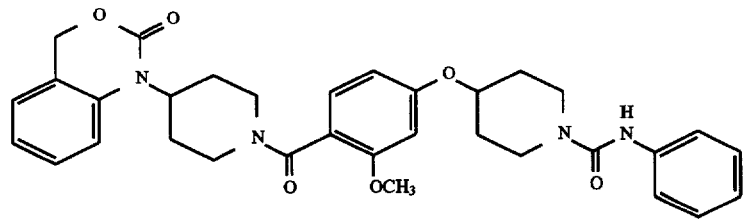

To stirred solution of 1-(1-(4-(4-piperidinyloxy)-2-methoxybenzoyl)piperidin-4-yl)-1,2-dihydro-4(H)-3,1-benzoxazin-2-one hydrochloride from Example 26 (0.15 g; 0.30 mmol) in $CH_2Cl_2$ (5 mL) was added phenyl isocyanate (39 mg; 0.33 mmol) and DIEA (0.057 mL; 0.33 mmol). The solution was stirred at ambient temperature for 18 h and then diluted with $CH_2Cl_2$ (25 mL) and extracted with 5% aqueous citric acid (2×10 mL) and brine (10 mL). The organic phase was dried ($MgSO_4$), filtered, and the solvent was evaporated under reduced pressure. The residue was purified by pressurized silica gel column chromatography using a gradient elution of 99:1 to 97:3 $CH_2Cl_2$:MeOH. The product-containing fractions were combined and evaporated under reduced pressure to give the title compound as an amorphous solid.

Analysis calculated for ($C_{33}H_{36}N_4O_6$, 0.2 $CH_2Cl_2$, 0.05 $H_2O$) C, 66.17; H, 6.11; N, 9.30 Found C, 66.20; H, 5.89; N, 9.25 TLC: $R_f$=0.37 (97:3 $CH_2Cl_2$:MeOH) HPLC (method A): retention time 8.54 min FAB MS: m/z 585 ($M^+$+H)

EXAMPLE 114

1-(1-(4-(1-(3-(N-Ethyl-N-cyclopropylmethylamino) propylsulfonyl)-piperidinyloxy)-2-methoxybenzoyl) piperidin-4-yl)-1,2-dihydro-4(H)-3,1-benzoxazin-2-one

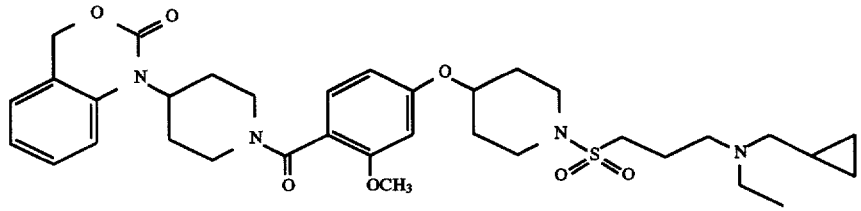

Into a stirred solution of 1-(1-(4-(1-(3-ethylaminosulfonyl)piperidinyloxy)-2-methoxybenzoyl) piperidin-4-yl)-1,2-dihydro-4(H)-3,1-benzoxazin-2-one hydrochloride Example 78 (0.10 g; 0.15 mmol) in 99:1

MeOH:HOAc (3 mL) was added NaOAc (25 mg, 0.30 mmol), cyclopropane carboxaldehyde (0.026 mL; 0.30 mmol) and NaBH$_3$CN (18 mg; 0.30 mmol). After 24 h at ambient temperature, the solvents were removed under reduced pressure and the residue was dissolved in EtOAc (100 mL) and washed with saturated aqueous NaHCO$_3$ (2×50 mL) and brine (50 mL). The EtOAc layer was dried (MgSO$_4$), filtered, and the solvent was removed under reduced pressure. The residue was purified by pressurized silica gel column chromatography using a gradient elution of 1:99 to 4:96 A:B (A=95:5 MeOH:NH$_4$OH, B=CH$_2$Cl$_2$). The title compound was dissolved in MeOH and to the solution was added 2.5 equivalents of 1.0N aqueous HCl. The resulting solution was evaporated under reduced pressure and the residue was dissolved in 3:2 H$_2$O:CH$_3$CN and lyophilized. The HCl salt of the title compound was obtained as an amorphous powder.

Analysis calculated for (C$_{35}$H$_{48}$N$_4$O$_7$S, 1.5 HCl, 0.55 H$_2$O) C, 57.31; H, 6.95; N, 7.64 Found C, 57.28; H, 6.95; N, 7.62 TLC: R$_f$=0.27 (96:4:0.4 CH$_2$Cl$_2$:MeOH:NH$_4$OH) HPLC (method A): retention time 7.36 min FAB MS: m/z 669 (M$^+$+H)

EXAMPLE 115

1-(1-(4-(1-(3-(N-Tetrahydroisoquinolinyl) propylsulfonyl)-piperidinyloxy)-2-methoxybenzoyl) piperidin-4-yl)-1,2-dihydro-4(H)-3,1-benzoxazin-2-one

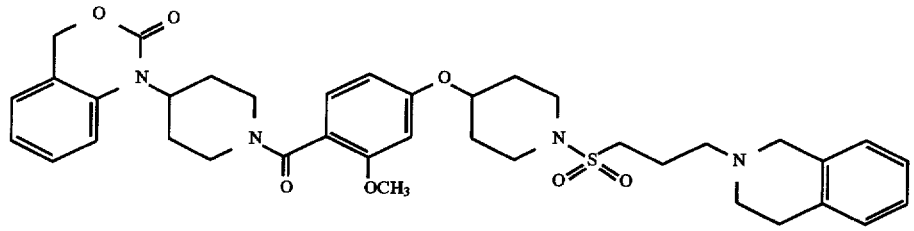

To stirred solution of 1-(1-(4-(1-(3-iodopropylsulfonyl)-piperidinyloxy)-2-methoxybenzoyl)piperidin-4-yl)-1,2-dihydro-4(H)-3,1-benzoxazin-2-one from Step 1 of Example 65 (0.15 g; 0.22 mmol) in DMF (2 mL) was added tetrahydroisoquinoline (36 mg; 0.26 mmol) and DIEA (0.046 mL, 0.26 mmol). The reaction was stirred at ambient temperature for 24 h. The solvent was removed under reduced pressure and the residue was dissolved in EtOAc (100 mL) and washed with saturated aqueous NaHCO$_3$ (2×50 mL) and brine (50 mL). The EtOAc layer was dried (MgSO$_4$), filtered, and the solvent was removed under reduced pressure. The residue was purified by pressurized silica gel column chromatography using a gradient elution of 2:98 to 4:96 A:B (A=95:5 MeOH:NH$_4$OH, B=CH$_2$Cl$_2$). The title compound was dissolved in MeOH and to the solution was added 2.5 equivalents of 1.0N aqueous HCl. The resulting solution was evaporated under reduced pressure and the residue was dissolved in 3:2 H$_2$O:CH$_3$CN and lyophilized. The HCl salt of the title compound was obtained as an amorphous powder.

Analysis calculated for (C$_{38}$H$_{46}$N$_4$O$_7$S, 1.45 HCl, 0.45 H$_2$O) C, 59.75; H, 6.38; N, 7.34 Found C, 59.74; H, 6.39; N, 7.57 TLC: R$_f$=0.42 (96:4:0.4 CH$_2$Cl$_2$:MeOH:NH$_4$OH) HPLC (method A): retention time 7.78 min FAB MS: m/z 703 (M$^+$+H)

EXAMPLE 116

1-(1-(4-(1-(3-(cis-2,6-Dimethyl-1-piperidinyl) propylsulfonyl)-piperidinyloxy)-2-methoxybenzoyl) piperidin-4-yl)-1,2-dihydro-4(H)-3,1-benzoxazin-2-one

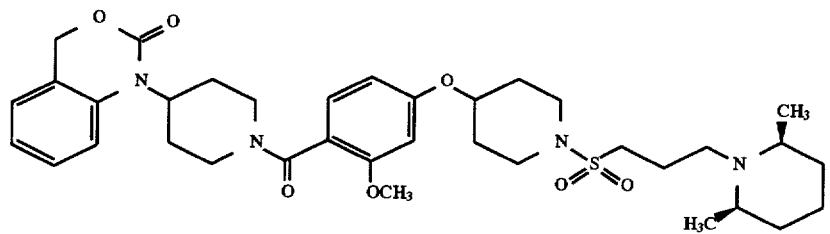

To stirred solution of 1-(1-(4-(1-(3-iodopropylsulfonyl)-piperidinyloxy)-2-methoxybenzoyl)piperidin-4-yl)-1,2-dihydro-4(H)-3,1-benzoxazin-2-one from Step 1 of Example 65 (0.15 g; 0.22 mmol) in MeOH (5 mL) was added cis-2,6-dimethylpiperidine (0.5 mL; 45 mmol). The reaction was stirred at ambient temperature for 24 h. The solvents were removed under reduced pressure and the residue was dissolved in EtOAc (100 mL) and washed with saturated aqueous NaHCO$_3$ (2×50 mL) and brine (50 mL). The EtOAc layer was dried (MgSO$_4$), filtered, and the solvent was removed under reduced pressure. The residue was purified by pressurized silica gel column chromatography using a gradient elution of 2:98 to 4:96 A:B (A=95:5 MeOH:NH₄OH, B=CH₂Cl₂). The title compound was dissolved in MeOH and to the solution was added 2.5 equivalents of 1.0N aqueous HCl. The resulting solution was evaporated under reduced pressure and the residue was dissolved in 3:2 H₂O:CH₃CN and lyophilized. The HCl salt of the title compound was obtained as an amorphous powder.

Analysis calculated for (C₃₆H₅₀N₄O₇S, 2.25 HCl, 0.60 H₂O) C, 55.73; H, 6.95; N, 7.22 Found C, 55.75; H, 6.94; N, 7.53 TLC: R$_f$=0.47 (95:5:0.5 CH₂Cl₂:MeOH:NH₄OH) HPLC (method A): retention time 7.46 min FAB MS: m/z 683 (M⁺+H)

EXAMPLE 117

1-(1-(4-(1-(3-(2S-methoxymethyl-1-pyrrolidinyl) propylsulfonyl)-piperidinyloxy)-2-methoxybenzoyl) piperidin-4-yl)-1,2-dihydro-4(H)-3,1-benzoxazin-2-one

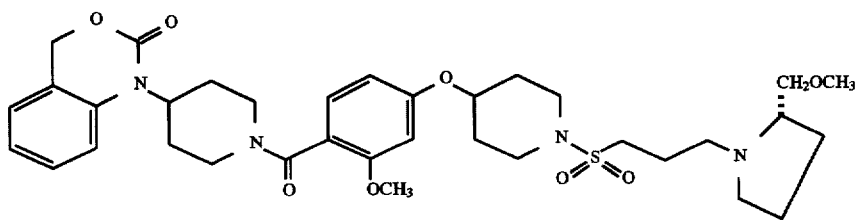

To stirred solution of 1-(1-(4-(1-(3-iodopropylsulfonyl)-piperidinyloxy)-2-methoxybenzoyl)piperidin-4-yl)-1,2-dihydro-4(H)-3,1-benzoxazin-2-one from Step 1 of Example 65 (0.15 g; 0.22 mmol) in DMF (2 mL) was added 2S-methyloxymethylpyrrolidine (0.030 mL; 0.25 mmol) and DIEA (0.045 mL, 0.26 mmol). The reaction was stirred at ambient temperature for 24 h. The solvent was removed under reduced pressure and the residue was dissolved in EtOAc (100 mL) and washed with saturated aqueous NaHCO₃ (2×50 mL) and brine (50 mL). The EtOAc layer was dried (MgSO₄), filtered, and the solvent was removed under reduced pressure. The residue was purified by pressurized silica gel column chromatography using a gradient elution of 2:98 to 5:95 A:B (A=95:5 MeOH:NH₄OH, B=CH₂Cl₂). The title compound was dissolved in MeOH and to the solution was added 2.5 equivalents of 1.0N aqueous HCl. The resulting solution was evaporated under reduced pressure and the residue was dissolved in 3:2 H₂O:CH₃CN and lyophilized. The HCl salt of the title compound was obtained as an amorphous powder.

Analysis calculated for (C₃₆H₅₀N₄O₇S, 1.75 HCl, 0.20 H₂O) C, 55.88; H, 6.72; N, 7.45 Found C, 55.86; H, 6.72; N, 7.67 TLC: R$_f$=0.30 (96:4:0.4 CH₂Cl₂:MeOH:NH₄OH) HPLC (method A): retention time 7.76 min FAB MS: m/z 685 (M⁺+H)

EXAMPLE 118

1-(1-(4-(1-(3-(3R-Hydroxy-1-pyrrolidinyl) propylsulfonyl)-piperidinyloxy)-2-methoxybenzoyl) piperidin-4-yl)-1,2-dihydro-4(H)-3,1-benzoxazin-2-one

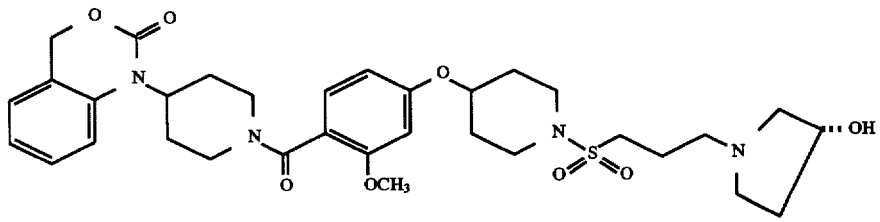

To stirred solution of 1-(1-(4-(1-(3-iodopropylsulfonyl)-piperidinyloxy)-2-methoxybenzoyl)piperidin-4-yl)-1,2-dihydro-4(H)-3,1-benzoxazin-2-one from Step 1 of Example 65 (0.15 g; 0.22 mmol) in DMF (2 mL) was added 2R-hydroxypyrrolidine (0.025 mL; 0.26 mmol) and DIEA (0.045 mL, 0.26 mmol). The reaction was stirred at ambient temperature for 24 h. The solvent was removed under reduced pressure and the residue was dissolved in EtOAc (100 mL) and washed with saturated aqueous NaHCO₃ (2×50 mL) and brine (50 mL). The EtOAc layer was dried (MgSO₄), filtered, and the solvent was removed under reduced pressure. The residue was purified by pressurized silica gel column chromatography using a gradient elution of 3:97 to 7:93 A:B (A=95:5 MeOH:NH₄OH, B=CH₂Cl₂). The title compound was dissolved in MeOH and to the solution was added 2.5 equivalents of 1.0N aqueous HCl. The resulting solution was evaporated under reduced pressure and the residue was dissolved in 3:2 H₂O:CH₃CN and lyophilized. The HCl salt of the title compound was obtained as an amorphous powder.

Analysis calculated for ($C_{36}H_{50}N_4O_7S$, 2.05 HCl, 0.55 $H_2O$) C, 53.45; H, 6.41; N, 7.56 Found C, 53.45; H, 6.41; N, 7.91 TLC: $R_f$=0.20 (94:6:0.6 $CH_2Cl_2$:MeOH:$NH_4OH$) HPLC (method A): retention time 7.19 min FAB MS: m/z 657 ($M^+$+H)

EXAMPLE 119

1-(1-(4-(1-(3-(3-Pyridylmethylamino)propylsulfonyl)-piperidinyloxy)-2-methoxybenzoyl)piperidin-4-yl)-1,2-dihydro-4(H)-3,1-benzoxazin-2-one

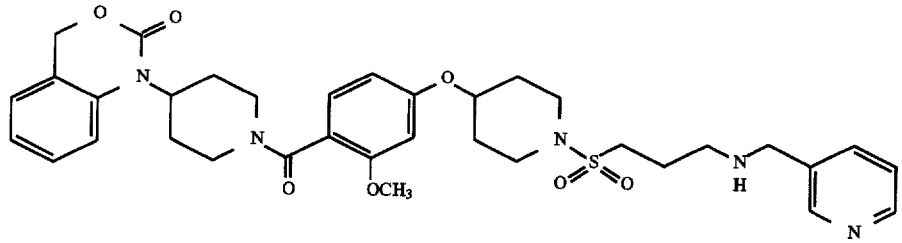

To stirred solution of 1-(1-(4-(1-(3-iodopropylsulfonyl)-piperidinyloxy)-2-methoxybenzoyl)piperidin-4-yl)-1,2-dihydro-4(H)-3,1-benzoxazin-2-one from Step 1 of Example 65 (0.15 g; 0.22 mmol) in DMF (2 mL) was added 3-aminomethylpyridine (0.030 mL; 0.26 mmol) and DIEA (0.045 mL, 0.26 mmol). The reaction was stirred at ambient temperature for 24 h. The solvent was removed under reduced pressure and the residue was dissolved in EtOAc (100 mL) and washed with saturated aqueous $NaHCO_3$ (2×50 mL) and brine (50 mL). The EtOAc layer was dried ($MgSO_4$), filtered, and the solvent was removed under reduced pressure. The residue was purified by pressurized silica gel column chromatography using a gradient elution of 2:98 to 5:95 A:B (A=95:5 MeOH:$NH_4OH$, B=$CH_2Cl_2$). The title compound was dissolved in MeOH and to the solution was added 2.5 equivalents of 1.0N aqueous HCl. The resulting solution was evaporated under reduced pressure and the residue was dissolved in 3:2 $H_2O$:$CH_3CN$ and lyophilized. The HCl salt of the title compound was obtained as an amorphous powder.

Analysis calculated for ($C_{36}H_{50}N_4O_7S$, 2.5 HCl, 2.05 $H_2O$) C, 52.16; H, 6.20; N, 8.69 Found C, 52.16; H, 5.91; N, 8.94 TLC: $R_f$=0.29 (95:5:0.5 $CH_2Cl_2$:MeOH:$NH_4OH$) HPLC (method A): retention time 6.50 min FAB MS: m/z 678 ($M^+$+H)

EXAMPLE 120

1-(1-(4-(1-(3-(4-Phenyl-1-piperidinyl)propylsulfonyl)-piperidinyloxy)-2-methoxybenzoyl)piperidin-4-yl)-1,2-dihydro-4(H)-3,1-benzoxazin-2-one

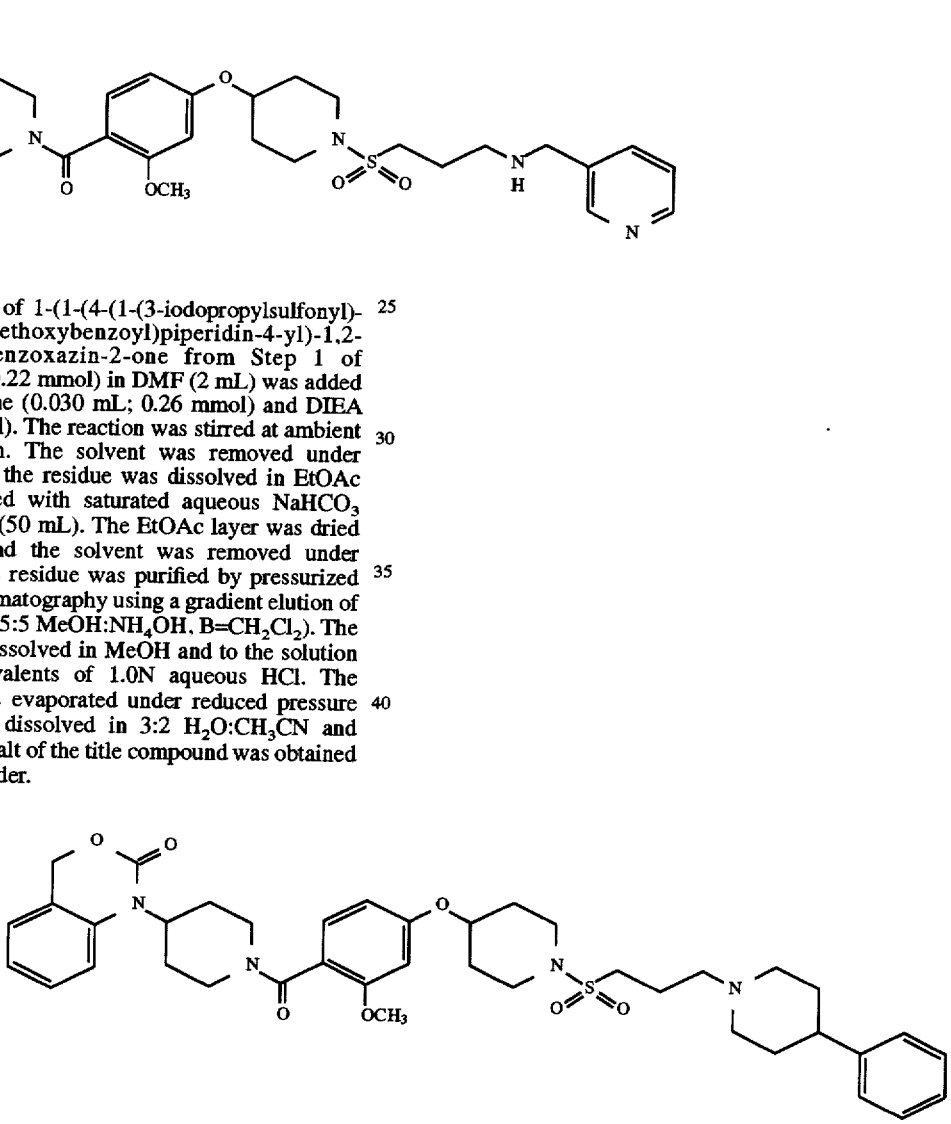

To stirred solution of 1-(1-(4-(1-(3-iodopropylsulfonyl)-piperidinyloxy)-2-methoxybenzoyl)piperidin-4-yl)-1,2-dihydro-4(H)-3,1-benzoxazin-2-one from Step 1 of Example 65 (0.15 g; 0.22 mmol) in DMF (2 mL) was added 4-phenylpiperidine (0.045 mL; 0.26 mmol) and DIEA (0.045 mL, 0.26 mmol). The reaction was stirred at ambient temperature for 24 h. The solvent was removed under reduced pressure and the residue was dissolved in EtOAc (100 mL) and washed with saturated aqueous $NaHCO_3$ (2×50 mL) and brine (50 mL). The EtOAc layer was dried (MgSO₄), filtered, and the solvent was removed under reduced pressure. The residue was purified by pressurized silica gel column chromatography using a gradient elution of 1:99 to 3:97 A:B (A=95:5 MeOH:NH₄OH, B=CH₂Cl₂). The title compound was dissolved in MeOH and to the solution was added 2.5 equivalents of 1.0N aqueous HCl. The resulting solution was evaporated under reduced pressure and the residue was dissolved in 3:2 H₂O:CH₃CN and lyophilized. The HCl salt of the title compound was obtained as an amorphous powder.

Analysis calculated for ($C_{36}H_{50}N_4O_7S$, 1.75 HCl, 0.10 H₂O) C, 60.31; H, 6.57; N, 7.03 Found C, 60.30; H, 6.58; N, 7.41 TLC: $R_f$=0.34 (97:3:0.3 CH₂Cl₂:MeOH:NH₄OH) HPLC (method A): retention time 8.63 min FAB MS: m/z 731 ($M^+$+H)

EXAMPLE 121

1-(1-(4-(1-(3-(4-(1-Piperidinyl)-1-piperidinyl)propylsulfonyl)-piperidinyloxy)-2-methoxybenzoyl)piperidin-4-yl)-1,2-dihydro-4(H)-3,1-benzoxazin-2-one

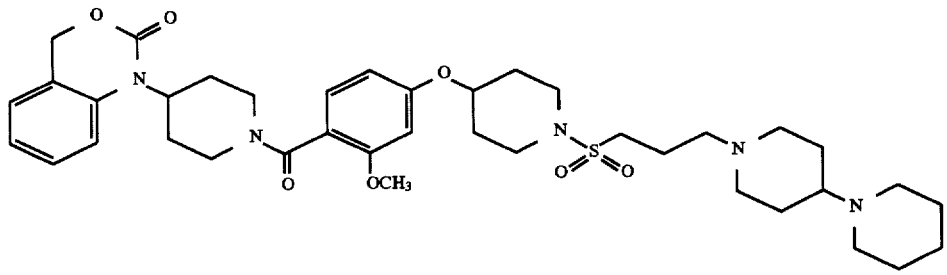

To stirred solution of 1-(1-(4-(1-(3-iodopropylsulfonyl)-piperidinyloxy)-2-methoxybenzoyl)piperidin-4-yl)-1,2-dihydro-4(H)-3,1-benzoxazin-2-one from Step 1 of Example 65 (0.15 g; 0.22 mmol) in DMF (2 mL) was added 4-(1-piperidinyl)piperidine (0.045 mL; 0.26 mmol) and DIEA (0.045 mL, 0.26 mmol). The reaction was stirred at ambient temperature for 24 h. The solvent was removed under reduced pressure and the residue was dissolved in EtOAc (100 mL) and washed with saturated aqueous NaHCO₃ (2×50 mL) and brine (50 mL). The EtOAc layer was dried (MgSO₄), filtered, and the solvent was removed under reduced pressure. The residue was purified by pressurized silica gel column chromatography using a gradient elution of 3:97 to 8:92 A:B (A=95:5 MeOH:NH₄OH, B=CH₂Cl₂). The title compound was dissolved in MeOH and to the solution was added 2.5 equivalents of 1.0N aqueous HCl. The resulting solution was evaporated under reduced pressure and the residue was dissolved in 3:2 H₂O:CH₃CN and lyophilized. The HCl salt of the title compound was obtained as an amorphous powder.

Analysis calculated for ($C_{36}H_{50}N_4O_7S$, 2.5 HCl, 2.2 H₂O) C, 53.91; 7.18, Y; N, 8.06 Found C, 53.91; H, 6.97; N, 8.35 TLC: $R_f$=0.28 (93:7:0.7 CH₂Cl₂:MeOH:NH₄OH) HPLC (method A): retention time 6.96 min FAB MS: m/z 738 ($M^+$+H)

EXAMPLE 122

1-(1-(4-(1-(3-(Azepin-1-yl)propylsulfonyl)-piperidinyloxy)-2-methoxybenzoyl)piperidin-4-yl)-1,2-dihydro-4(H)-3,1-benzoxazin-2-one

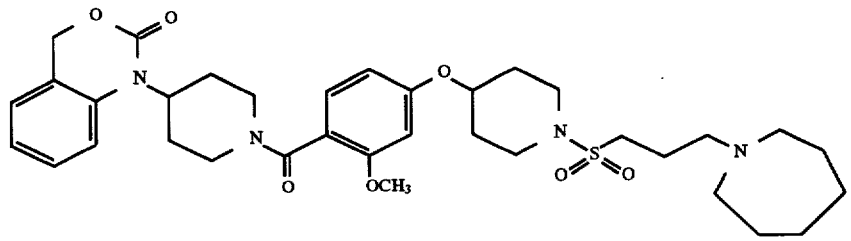

To stirred solution of 1-(1-(4-(1-(3-iodopropylsulfonyl)-piperidinyloxy)-2-methoxybenzoyl)piperidin-4-yl)-1,2-dihydro-4(H)-3,1-benzoxazin-2-one from Step 1 of Example 65 (0.15 g; 0.22 mmol) in MeOH (3 mL) was added azacycloheptane (0.25 mL; 2.3 mmol). The reaction was stirred at ambient temperature for 24 h. The solvent was removed under reduced pressure and the residue was dissolved in EtOAc (100 mL) and washed with saturated aqueous NaHCO₃ (2×50 mL) and brine (50 mL). The EtOAc layer was dried (MgSO₄), filtered, and the solvent was removed under reduced pressure. The residue was purified by pressurized silica gel column chromatography using a gradient elution of 2:98 to 6:94 A:B (A=95:5 MeOH:NH₄OH, B=CH₂Cl₂). The title compound was dissolved in MeOH and to the solution was added 2.5 equivalents of 1.0N aqueous HCl. The resulting solution was evaporated under reduced pressure and the residue was dissolved in 3:2 H$_2$O:CH$_3$CN and lyophilized. The HCl salt of the title compound was obtained as an amorphous powder.

Analysis calculated for (C$_{36}$H$_{50}$N$_4$O$_7$S, 1.65 HCl, 0.25 H$_2$O) C, 57.30; H, 6.89; N, 7.64 Found C, 57.33; H, 6.90; N, 7.72 TLC: R$_f$=0.16 (96:4:0.4 CH$_2$Cl$_2$:MeOH:NH$_4$OH) HPLC (method A): retention time 7.33 min FAB MS: m/z 669 (M$^+$+H)

EXAMPLE 123

1-(1-(4-(4-piperidinyloxy)-2-methoxyphenylacetyl) piperidin-4-yl)-1,2-dihydro-4(H)-3,1-benzoxazin-2-one

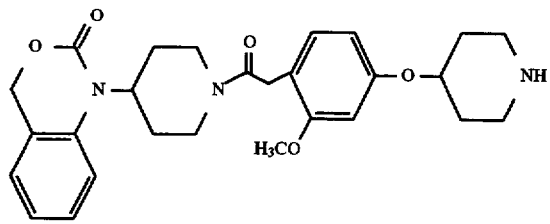

Step 1:

To a solution of 2-methoxy-(N-t-butyloxycarbonyl-4-piperidyloxy)benzoic acid (3.2 g; 9.1 mmol) from Step 3 of Example 25 in THF was added thionyl chloride (1 mL; 13.7 mmol) and pyridine (2 drops) while under a nitrogen atmosphere. The solution was stirred for 4 hours and then concentrated under reduced pressure to dryness. The residue was suspended in ether and filtered, and the filtrate was concentrated to dryness to yield 2-methoxy-(N-t-butyloxycarbonyl-4-piperidyloxy)benzoyl chloride.

Step 2:

A two phase mixture of ether (66 mL) and 40% aqueous potassium hydroxide (20 mL) was cooled to 0° C. and N-nitrosomethylurea (6.6 g) was added portionwise over 30 minutes. The resulting yellow diazomethane/ether solution was decanted and dried over potassium hydroxide. The diazomethane/ether solution was decanted and cooled to 0° C. At this point, a solution of 2-methoxy-(N-t-butyloxycarbonyl-4-piperidyloxy)benzoyl chloride from Step 1 above in THF was added dropwise to the diazomethane/ether solution. The resulting bronze solution was warmed to ambient temperature and stirred for 3 hours. Nitrogen was bubbled through the reaction mixture for 1 hour to remove excess diazomethane and the solution was concentrated under reduced pressure to dryness. The residue was purified by pressurized silica gel column chromatography (elute with 6:94 ether:methylene chloride) to yield 2-methoxy-(N-t-butyloxycarbonyl-4-piperidyloxy) phenyldiazomethyl ketone.

Step 3:

A solution of 2-methoxy-(N-t-butyloxycarbonyl-4-piperidyloxy)phenyldiazomethyl ketone (930 mg; 2.48 mmol) from Step 2 above in dry methanol (7 mL) was refluxed and a solution of freshly prepared silver benzoate (100 mg) in triethylamine (1 mL) was added portionwise over 45 minutes. The solution was refluxed for an additional 30 minutes, then cooled and filtered. The filtrate was concentrated to dryness and the crude oil was purified by pressurized silica gel column chromatography (elute with 5:95 methanol:methylene chloride) to yield methyl-2-methoxy-(N-t-butyloxycarbonyl-4-piperidyloxy)phenyl acetate.

Step 4:

To a solution of methyl-2-methoxy-(N-t-butyloxycarbonyl-4-piperidyloxy)phenyl acetate (1.37 g; 3.6 mmol) from Step 3 above in 27 mL of THF was added aqueous lithium hydroxide solution (4.5 mL; 1.01M) dropwise. The reaction mixture was stirred for 16 hours and concentrated to dryness under reduced pressure. The residue was partitioned between ethyl acetate and 0.5M aqueous hydrochloric acid. The organic phase was separated and the aqueous phase was extract with ethyl acetate (2×). The combined organic extracts were dried over sodium sulfate, filtered, and the solvent was removed under reduced pressure to yield 2-methoxy-(N-t-butyloxycarbonyl-4-piperidyloxy)phenylacetic acid.

Step 5:

To a solution of the hydrochloride salt of 1-(4-piperidinyl) -1,2-dihydro-4(H)-3,1-benzoxazin-2-one from Step 4 of Example 1 (250 mg; 0.93 mmol) in 8 mL of DMF was added 2-methoxy-(N-t-butyloxycarbonyl-4-piperidyloxy) phenylacetic acid (340 mg; 0.93 mmol), 1-ethyl-3-(3-dimethylaminopropyl)carbodiimide hydrochloride (213 mg; 1.11 mmol), and 1-hydroxybenzotriazole hydrate (147 mg; 1.09). Triethylamine (550 µL) was added to make the solution basic (pH 8–9). After stirring for 18 hours, the solvent was removed under reduced pressure. The residue was partitioned between ethyl acetate and sodium bicarbonate (sat., aqueous). The ethyl acetate layer was washed with saturated aqueous sodium bicarbonate and brine, dried, filtered, and concentrated under reduced pressure to an oil. The crude solid was purified by pressurized silica gel column chromatography (elute with 3:97 methanol:methylene chloride). 1-(1-(4-(1-tert-Butyloxycarbonyl-4-piperidinyloxy)-2-methoxyphenylacetyl)piperidin-4-yl)-1, 2-dihydro-4(H)-3,1-benzoxazin-2-one was obtained as a white solid from ether.

Step 6:

1-(1-(4-(1-tert-Butyloxycarbonyl-4-piperidinyloxy)-2-methoxyphenylacetyl)piperidin-4-yl)-1,2-dihydro-4(H)-3,1-benzoxazin-2-one from Step 5 above (0.20 g, 0.35 mmol) was dissolved in ethyl acetate and cooled in an ice bath. Once cool, the solution was saturated with gaseous HCl for 30 minutes. The mixture was evaporated to dryness. Ether was added and removed in vacuo three times, and the residue was triturated with ether and filtered to yield the hydrochloride salt of the title compound as a white solid.

HPLC: >96% pure FAB MS: M+H=480 CHN—Calc'd for C$_{27}$H$_{33}$N$_3$O$_5$, 1.45 HCl 0.95 H$_2$O Calc'd: C, 58.96; H, 6.66; N, 7.64. Found: C, 58.94; H, 6.66; N, 7.70.

EXAMPLE 124

1-(1-(4-(1-Diethylaminoethylsulfonyl-4-piperidinyloxy)-2-methoxyphenylacetyl)piperidin-4-yl)-1,2-dihydro-4(H)-3,1-benzoxazin-2-one

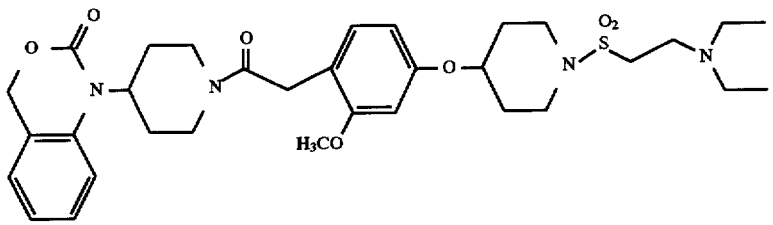

Step 1:

A stirred solution of 2-chloro-1-ethanesulfonyl chloride (0.036 mL, 0.35 mmol) in methylene chloride (3 mL) was cooled to 0° C. under nitrogen. A solution of 1-(1-(4-(4-piperidinyloxy)-2-methoxyphenylacetyl)piperidin-4-yl)-1, 2-dihydro-4(H)-3,1-benzoxazin-2-one (154 mg; 0.30 mmol) from Example 118 and diisopropylethylamine (0.26 mL) in methylene chloride (3 mL) was added dropwise. The resulting solution was allowed to slowly warm to ambient temperature and stirred for 18 hours. The solvent was removed under reduced pressure and the resulting residue was purified by flash chromatography (elute with 3:97 methanol:methylene chloride). 1-(1-(4-(1-Vinylsulfonyl-4-piperidinyloxy)-2-methoxyphenylacetyl)-piperidin-4-yl)-1, 2-dihydro-4(H)-3,1-benzoxazin-2-one was obtained as a white solid by precipitation from ether.

Step 2:

1-(1-(4-(1-Vinylsulfonyl-4-piperidinyloxy)-2-methoxyphenylacetyl)piperidin-4-yl)-1,2-dihydro-4(H)-3,1-benzoxazin-2-one (56 mg; 0.098 mmol) from Step 1 above was dissolved in methanol (2 mL) under nitrogen and diethylamine (0.1 mL) was added and the mixture was stirred for 18 hours. The solvent was removed under reduced pressure and the residue was purified by pressurized silica gel column chromatography (elute with 3:97 methanol:methylene chloride). The title compound was precipitated from ether to give a white solid.

HPLC: >96% pure FAB MS: M+H=643 CHN—Calc'd for $C_{33}H_{46}N_4O_7S$ 0.05 $Et_2O$ 0.35 $H_2O$ Calc'd: C, 61.08; H, 7.29; N, 8.58 Found: C, 60.98; H, 7.12; N, 8.58

EXAMPLE 125

1-(1-(4-Amino-2-methoxybenzoyl)piperidin-4-yl)-1, 2-dihydro-4(H)-3,1-benzoxazin-2-one

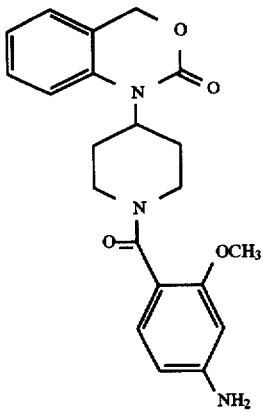

Step 1:

In an oven dried round bottom flask under an atmosphere of nitrogen was placed the hydrochloride salt of 1-(4-piperidinyl)-1,2-dihydro-4(H)-3,1-benzoxazin-2-one (0.537 g, 20 mmol) from Step 4 of Example 1, 2-methoxy-4-(tert-butoxycarbonyl)aminobenzoic acid (0.536 g, 20 mmol), HOBT (0.297 g, 22 mmol) and EDC (0.382 g, 22 mmol). The solids were dissolved in DMF (4 mL). After stirring for 2 minutes, triethylamine (0.65 mL) was added. The pH was adjusted to 9–10 by addition of additional triethylamine. The reaction was stirred for 18 h. The DMF was removeed under reduced pressure. The gum was dissolved in ether/$CH_2Cl_2$ and washed with saturated aqueous $NaHCO_3$, $H_2O$, 10% $KHSO_4$, and brine. The organic layer was dried over $Na_2SO_4$ and filtered. After concentrating, the gum was purified by pressurized silica gel column chromatography using 5:95 MeOH:$CH_2Cl_2$ as eluant. 1-(1-(4-tert-Butyloxycarbonylamino-2-methoxybenzoyl)piperidin-4-yl)-1,2-dihydro-4(H)-3,1-benzoxazin-2-one was collected and used in the next step.

Step 2:

In a round bottom flask under nitrogen was placed 1-(1-(4-tert-Butyloxycarbonylamino-2-methoxybenzoyl)piperidin-4-yl)-1,2-dihydro-4(H)-3,1-benzoxazin-2-one from Step 1 above (300 mg, 0.60 mmol). Ethyl acetate (15 mL) was added and the solution was cooled to 0° C. by an external ice/salt bath. Dry hydrogen chloride gas was bubbled into the solution for 15 minutes. The ethyl acetate was removed under reduced pressure and the white residue was twice slurried with ether and evaporated to dryness under reduced pressure to give the hydrochloride salt of the title compound.

HPLC: 98.9%. FAB MS: m/z=382 ($M^+$+H). C,H,N analysis cal'd for 1.05 $H_2O$ Cal'd C—57.74 Found C—57.76; Cal'd. H—6.02 Found H—6.00; Cal'd. N—9.62 Found N—9.68.

EXAMPLE 126

1-(1-(4-Acetylamino-2-methoxybenzoyl)piperidin-4-yl)-1,2-dihydro-4(H)-3,1-benzoxazin-2-one

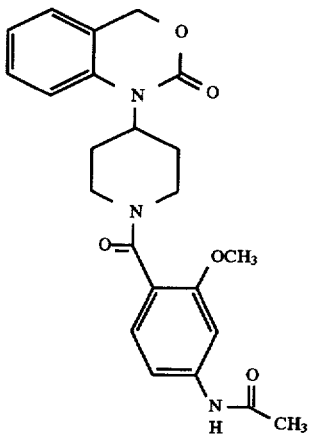

In an oven dried round bottom flask (50 mL) was placed 1-(1-(4-amino-2-methoxybenzoyl)piperidin-4-yl)-1,2-dihydro-4(H)-3,1-benzoxazin-2-one from Example 120 (42 mg, 0.10 mmol) and methylene chloride (3 mL). To the stirred slurry was added acetyl chloride (0.010 mL) followed by triethylamine (0.075 mL). The pH was maintained at 9–10 by adding more triethylamine and the reaction was stirred for 18 h. The solvent was removed under reduced pressure and the residue was purified by pressurized silica gel column chromatography using 3:97 MeOH:CH$_2$Cl$_2$ as eluant. The title compound was obtained as an amorphous solid by precipitation from ether.

HPLC: 93.77%. FAB MS: m/z=424 (M$^+$+H). C,H,N analysis cal'.d for 0.55 H$_2$O+0.25 ether: Cal'd C—63.78, Found C—63.73: Cal'd. H—6.38. Found H—6.38: Cal'd N—9.30. Found N—9.24.

EXAMPLE 127

1-(1-(4-Acetylamino-2-methoxybenzoyl)piperidin-4-yl)-1,2-dihydro-4(H)-3,1-benzoxazin-2-one

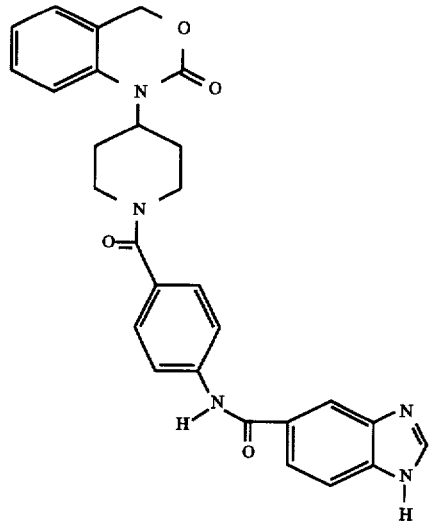

In an oven dried round bottom flask was placed 1-(1-(4-amino-2-methoxybenzoyl)piperidin-4-yl)-1,2-dihydro-4(H)-3,1-benzoxazin-2-one from Example 120 (116 mg, 0.30 mmol), EDC (63 mg, 0.33 mmol), HOBT (44 mg, 0.33 mmol) and 5-benzimidazolecarboxylic acid (48.6 mg, 0.30 mmol). The solids were dissolved in DMF (2 mL) and triethylamine was added until the pH of the reaction was 9–10. The mixture was stirred for 18 h and the solvent was removed under reduced pressure. The residue was purified by pressurized silica gel column chromatography using CH$_2$Cl$_2$:MeOHOH:NH$_4$OH (9:1:0.1) as eluant. The title compound was obtained as an amorphous solid.

HPLC: 93.73%. FAB MS: m/z=496 (M$^+$+H). Exact Mass determination Cal'd. for M+H 496.19862; Found 496.19848 C,H,N analysis: Cal'd C—67.68. Found C—62.41; Cal'd. H—5.09. Found H—5.05; Cal'd. N—14.14. Found N—14.07.

EXAMPLE 128

1-(1-(4-(1-(3-(Diethylamino)propanoyl)-4-piperidinyloxy)-2-methoxybenzoyl)piperidin-4-yl)-1,2-dihydro-4(H)-3,1-benzoxazin-2-one

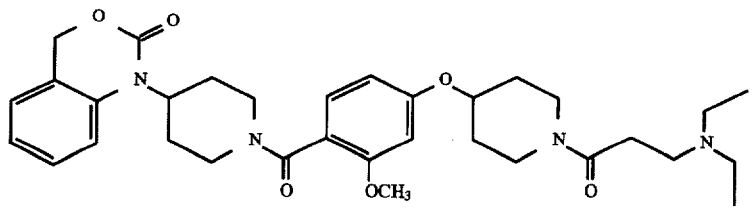

131

To stirred solution of 1-(1-(4-(4-piperidinyloxy)-2-methoxybenzoyl)piperidin-4-yl)-1,2-dihydro-4(H)-3,1-benzoxazin-2-one hydrochloride from Example 26 (0.15 g; 0.30 mmol) in DMF (5 mL) was added 3-diethylaminopropionic acid hydrochloride (70 mg, 0.33 mmol), HOBT (50 mg, 0.33 mmol), EDC (145 mg, 0.36 mmol), and DIEA (0.16 mL, 0.92 mmol). The reaction solution was stirred at ambient temperature for 18 h, then evaporated under reduced pressure. The residue was purified by preparative reverse phase HPLC using an $H_2O:CH_3CN$ gradient containing 0.1% TFA. The product-containing fractions were lyophilized to give the TFA salt of the title compound as an amorphous powder.

Analysis calculated for $(C_{33}H_{44}N_4O_6, 1.9 TFA)$ C, 53.36; H, 5.84; N, 6.76 Found C, 53.36; H, 5.83; N, 6.91 TLC: $R_f$=0.49 (60:30:4:6 $CH_2Cl_2$:MeOH:$H_2O$:$NH_4OH$) HPLC (method B): retention time 12.75 min FAB MS: m/z 593 ($M^+$+H)

EXAMPLE 129

1-(1-(4-(1-(N-(2-Diethylaminoethyl)carbamoyl)-4-piperidinyloxy)-2-methoxybenzoyl)piperidin-4-yl)-1,2-dihydro-4(H)-3,1-benzoxazin-2-one

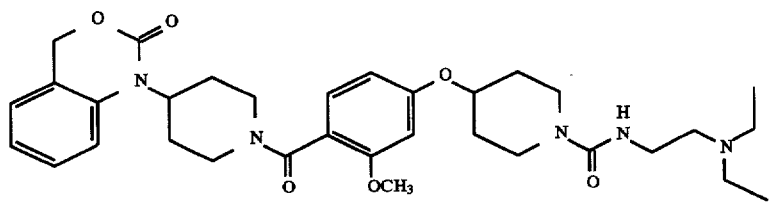

To stirred 0° C. solution of 1-(1-(4-(4-piperidinyloxy)-2-methoxybenzoyl)piperidin-4-yl)-1,2-dihydro-4(H)-3,1-benzoxazin-2-one hydrochloride from Example 26 (0.15 g; 0.30 mmol) in $CH_2Cl_2$ (5 mL) was added triphosgene (44 mg, 0.15 mmol) and DIEA (0.10 mL, 0.60 mmol). The reaction solution was stirred at 0° C. for 2 h and then at ambient temperature for 24 h. More DIEA was added (0.05 mL; 0.3 mmol), followed by diethylaminoethylamine (52 mg, 0.45 mmol) and the mixture was stirred at at ambient temperature for 72 h. The mixture was diluted with $CH_2Cl_2$ (20 mL) and extracted with saturated aqueous $NaHCO_3$ (20 mL) and brine (10 mL). The $CH_2Cl_2$ layer was dried ($MgSO_4$), filtered and concentrated under reduced pressure. The residue was purified by pressurized silica gel column chromatography using a gradient elution of 1:99 to 15:85 A:B (A=95:5 MeOH:$NH_4OH$, B=$CH_2Cl_2$). The product was dissolved in MeOH and to the solution was added 2.5 equivalents of 1.0M aqueous HCl. The MeOH was removed under reduced pressure, the residue was dissolved in $H_2O$ and lyophilized to give the HCl salt of the title compound as an amorphous powder.

Analysis calculated for $(C_{33}H_{45}N_5O_6, 2.0 HCl, 1.1 H_2O, 0.4 NH_4C_l)$ C, 54.91; H, 7.09; N, 10.48 Found C, 54.91; H, 7.44; N, 10.47 TLC: $R_f$=0.16 (90:10:1 $CH_2Cl_2$:MeOH:$NH_4OH$) HPLC (method B): retention time 12.87 min FAB MS: m/z 608 ($M^+$+H)

132

EXAMPLE 130

1-(1-(N-Methylpyrrole-2-carbonyl)piperidin-4-yl)-1,2-dihydro-4(H)-3,1-benzoxazin-2-one

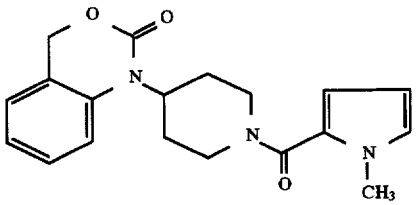

To a solution of the hydrochloride salt of 1-(4-piperidinyl)-1,2-dihydro-4(H)-3,1-benzoxazin-2-one (150 mg, 0.559 mmol) from Step 4 of Example 1 in DMF (10 mL) was added DIEA (0.19 mL, 1.1 mmol), BOP (297 mg, 0.67 mmol), and N-methylpyrrole-2-carboxylic acid (78 mg, 0.62 mmol). The reaction was stirred at ambient temperature for 18 h and the solvent was removed under reduced pressure. The residue was dissolved in EtOAc (50 mL) and washed with saturated aqueous $NaHCO_3$ (2×50 mL). The EtOAc layer was dried ($MgSO_4$), filtered, and the solvent was removed under reduced pressure. The residue was purified by pressurized silica gel column chromatography using 3:1 EtOAc:hexanes as eluant. The title compound was dissolved in $CH_2Cl_2$ and evaporated under reduced pressure to give an amorphous solid.

Analysis calculated for $(C_{19}H_{21}N_3O_3, 0.2 CH_2Cl_2)$ C, 64.71; H, 6.05; N, 11.79 Found C, 64.61; H, 6.03; N, 11.79 TLC: $R_f$=0.4 (3:1 EtOAc:hexanes) HPLC (method B): retention time 13.76 min FAB MS: m/z 340 ($M^+$+H)

EXAMPLE 131

1-(1-(Furyl-2-carbonyl)piperidin-4-yl)-1,2-dihydro-4(H)-3,1-benzoxazin-2-one

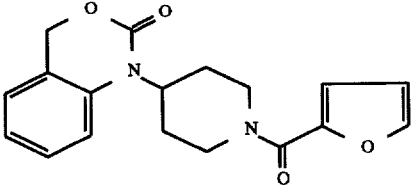

To a solution of the hydrochloride salt of 1-(4-piperidinyl)-1,2-dihydro-4(H)-3,1-benzoxazin-2-one (150 mg, 0.559 mmol) from Step 4 of Example 1 in DMF (10 mL) was added DIEA (0.19 mL, 1.1 mmol), BOP (297 mg, 0.67 mmol), and furan-2-carboxylic acid (69 mg, 0.62 mmol). The reaction was stirred at ambient temperature for 18 h and the solvent was removed under reduced pressure. The residue was dissolved in EtOAc (50 mL) and washed with saturated aqueous NaHCO₃ (2×50 mL). The EtOAc layer was dried (MgSO₄), filtered, and the solvent was removed under reduced pressure. The residue was purified by pressurized silica gel column chromatography using a gradient elution of 2:98 to 5:95 MeOH:CHCl₃. The title compound was dissolved in hexanes:CHCl₃ and evaporated under reduced pressure to give an amorphous solid.

Analysis calc'd for (C₁₈H₁₈N₂O₄, 0.25 CHCl₃, 0.05 hexanes) C, 61.80; H, 5.30; N, 7.77 Found C, 62.00; H, 5.34; N, 7.89 TLC: R_f=0.5 (2:98 MeOH:CHCl₃) HPLC (method B): retention time 11.80 min FAB MS: m/z 327 (M⁺+H)

EXAMPLE 132

1-(1-(Thienyl-2-carbonyl)piperidin-4-yl)-1,2-dihydro-4(H)-3,1-benzoxazin-2-one

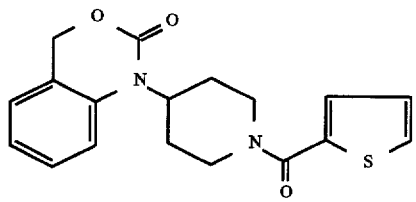

To a solution of the hydrochloride salt of 1-(4-piperidinyl)-1,2-dihydro-4(H)-3,1-benzoxazin-2-one (150 mg, 0.559 mmol) from Step 4 of Example 1 in DMF (10 mL) was added DIEA (0.19 mL, 1.1 mmol), BOP (297 mg, 0.67 mmol), and thiophene-2-carboxylic acid (79 mg, 0.62 mmol). The reaction was stirred at ambient temperature for 18 h and the solvent was removed under reduced pressure. The residue was dissolved in EtOAc (50 mL) and washed with saturated aqueous NaHCO₃ (2×50 mL). The EtOAc layer was dried (MgSO₄), filtered, and the solvent was removed under reduced pressure. The residue was purified by pressurized silica gel column chromatography using 3:1 EtOAc:hexanes as eluant. The title compound was dissolved in EtOAc and evaporated under reduced pressure to give an amorphous solid.

Analysis calc'd for (C₁₈H₁₈N₂O₃S, 0.25 EtOAc) C, 62.62; H, 5.53; N, 7.69 Found C, 62.30; H, 5.35; N, 7.81 TLC: R_f=0.45 (3:1 EtOAc:hexanes) HPLC (method B): retention time 13.68 min FAB MS: m/z 343 (M⁺+H)

EXAMPLE 133

1-(1-(4-(4-hydroxyphenyl)benzoyl)piperidin-4-yl)-1,2-dihydro-4(H)-3,1-benzoxazin-2-one

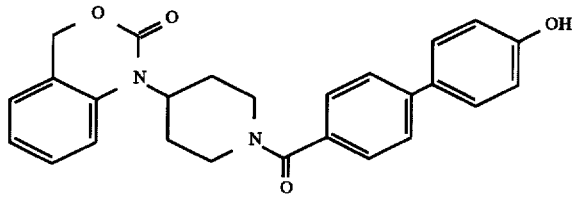

To a solution of the hydrochloride salt of 1-(4-piperidinyl)-1,2-dihydro-4(H)-3,1-benzoxazin-2-one (150 mg, 0.559 mmol) from Step 4 of Example 1 in DMF (10 mL) was added DIEA (0.19 mL, 1.1 mmol), BOP (297 mg, 0.67 mmol), and 4-(4-hydroxyphenyl)benzoic acid (133 mg, 0.62 mmol). The reaction was stirred at ambient temperature for 18 h and the solvent was removed under reduced pressure.

The residue was dissolved in EtOAc (50 mL) and washed with saturated aqueous NaHCO₃ (2×50 mL). The EtOAc layer was dried (MgSO₄), filtered, and the solvent was removed under reduced pressure. The residue was purified by pressurized silica gel column chromatography using 5:95 MeOH:CHCl₃ as eluant. The title compound was dissolved in CH₂Cl₂ and evaporated under reduced pressure to give an amorphous solid.

Analysis calc'd for (C₂₆H₂₄N₂O₄, 0.9 CH₂Cl₂) C, 63.99; H, 5.15; N, 5.55 Found C, 64.14; H, 5.16; N, 5.52 TLC: R_f=0.34 (5:95 MeOH:CHCl₃) HPLC (method B): retention time 15.61 min FAB MS: m/z 429 (M⁺+H)

EXAMPLE 134

1-(1-(4-(4-hydroxyphenoxy)benzoyl)piperidin-4-yl)-1,2-dihydro-4(H)-3,1-benzoxazin-2-one

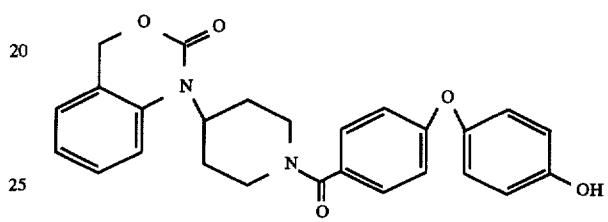

To a solution of the hydrochloride salt of 1-(4-piperidinyl)-1,2-dihydro-4(H)-3,1-benzoxazin-2-one (150 mg, 0.559 mmol) from Step 4 of Example 1 in DMF (10 mL) was added DIEA (0.19 mL, 1.1 mmol), BOP (297 mg, 0.67 mmol), and 4-(4-hydroxyphenoxy)benzoic acid (143 mg, 0.62 mmol). The reaction was stirred at ambient temperature for 18 h and the solvent was removed under reduced pressure. The residue was dissolved in EtOAc (100 mL) and washed with saturated aqueous NaHCO₃ (2×50 mL). The EtOAc layer was dried (MgSO₄), filtered, and the solvent was removed under reduced pressure. The residue was triturated in EtOAc to give the title compound as an amorphous solid.

Analysis calc'd for (C₂₆H₂₄N₂O₅, 0.25 EtOAc, 1.0 H₂O) C, 66.93; H, 5.82; N, 5.78 Found C, 66.88; H, 5.50; N, 6.02 TLC: R_f=0.28 (1:10:90 H₂O:MeOH:CHCl₃) HPLC (method B): retention time 15.84 min FAB MS: m/z 445 (M⁺+H)

EXAMPLE 135

1-(1-(4-(5-(2-Pyridyl)thienyl-2-carbonyl)piperidin-4-yl)-1,2-dihydro-4(H)-3,1-benzoxazin-2-one

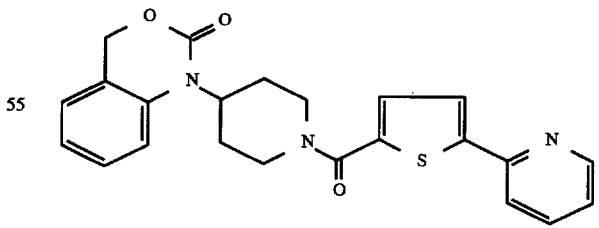

To a solution of the hydrochloride salt of 1-(4-piperidinyl)-1,2-dihydro-4(H)-3,1-benzoxazin-2-one (150 mg, 0.559 mmol) from Step 4 of Example 1 in DMF (10 mL) was added DIEA (0.19 mL, 1.1 mmol), BOP (297 mg, 0.67 mmol), and 5-(2-pyridyl)thiophene-2-carboxylic acid (127 mg, 0.62 mmol). The reaction was stirred at ambient temperature for 18 h and the solvent was removed under reduced pressure. The residue was dissolved in EtOAc (100 mL) and washed with saturated aqueous NaHCO₃ (2×50 mL). The EtOAc layer was dried (MgSO₄), filtered, and the solvent was removed under reduced pressure. The residue was purified by pressurized silica gel column chromatography using 0.25:5:95 NH₄OH:MeOH:CH₂Cl₂ as eluant. The title compound was dissolved in CH₂Cl₂ and evaporated under reduced pressure to give an amorphous solid.

Analysis calc'd for (C₂₃H₂₁N₃O₃S, 0.4 SiO₂) C, 62.28; H, 4.77; N, 9.47 Found C, 62.38; H, 4.67; N, 9.57 TLC: R$_f$=0.57 (95:5:0.5 CH₂Cl₂:MeOH:NH₄OH) HPLC (method B): retention time 13.54 min FAB MS: m/z 420 (M⁺+H)

EXAMPLE 136

1-(1-(4-(N-tert-Butyloxycarbonyl-4-hydroxyphenylglycyl)piperidin-4-yl)-1,2-dihydro-4(H)-3,1-benzoxazin-2-one

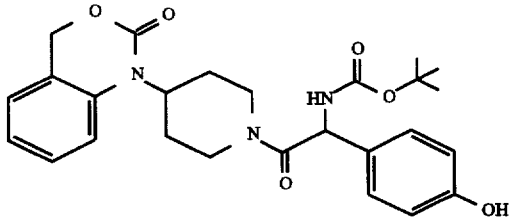

To a solution of the hydrochloride salt of 1-(4-piperidinyl)-1,2-dihydro-4(H)-3,1-benzoxazin-2-one (150 mg, 0.559 mmol) from Step 4 of Example 1 in DMF (10 mL) was added DIEA (0.19 mL, 1.1 mmol), BOP (297 mg, 0.67 mmol), and N-tert-butyloxycarbonyl-4-hydroxyphenylglycine (166 mg, 0.62 mmol). The reaction was stirred at ambient temperature for 18 h and the solvent was removed under reduced pressure. The residue was dissolved in EtOAc (50 mL) and washed with 5% aqueous citric acid (25 mL) and brine (25 mL). The EtOAc layer was dried (MgSO₄), filtered, and the solvent was removed under reduced pressure. The residue was purified by pressurized silica gel column chromatography using 3:1 EtOAc:hexanes as eluant. The title compound was dissolved in EtOAc and evaporated under reduced pressure to give an amorphous solid.

Analysis calc'd for (C₂₆H₃₁N₃O₆, 0.45 EtOAc, 0.8 H₂O) C, 62.34; H, 6.81; N, 7.85 Found C, 62.35; H, 6.54; N, 7.86 HPLC (method B): retention time 14.88 min FAB MS: m/z 482 (M⁺+H)

EXAMPLE 137

1-(1-(4-(N-tert-Butyloxycarbonylaminomethyl)-cyclohexylcarbonyl)piperidin-4-yl)-1,2-dihydro-4(H)-3,1-benzoxazin-2-one

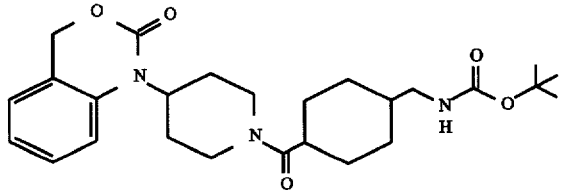

To a solution of the hydrochloride salt of 1-(4-piperidinyl)-1,2-dihydro-4(H)-3,1-benzoxazin-2-one (150 mg, 0.559 mmol) from Step 4 of Example 1 in DMF (10 mL) was added DIEA (0.19 mL, 1.1 mmol), BOP (297 mg, 0.67 mmol), and 4-(N-tert-butyloxycarbonylaminomethyl)-cyclohexane-1-carboxylic acid (159 mg, 0.62 mmol). The reaction was stirred at ambient temperature for 18 h and the solvent was removed under reduced pressure. The residue was dissolved in EtOAc (50 mL) and washed with 5% aqueous citric acid (25 mL) and brine (25 mL). The EtOAc layer was dried (MgSO₄), filtered, and the solvent was removed under reduced pressure. The residue was purified by pressurized silica gel column chromatography using a gradient elution of 20:80 to 65:35 EtOAc:hexanes. The title compound was dissolved in CH₂Cl₂ and evaporated under reduced pressure to give an amorphous solid.

Analysis calc'd for (C₂₆H₃₇N₃O₅, 0.2 EtOAc, 0.34 CH₂Cl₂) C, 62.92; H, 7.64; N, 8.11 Found C, 62.90; H, 7.73; N, 8.11 TLC: R$_f$=0.23 (65:35 EtOAc:hexanes) HPLC (method B): retention time 16.40 min FAB MS: m/z 472 (M⁺+H)

EXAMPLE 138

1-(1-(4-(Aminomethyl)cyclohexylcarbonyl)piperidin-4-yl)-1,2-dihydro-4(H)-3,1-benzoxazin-2-one

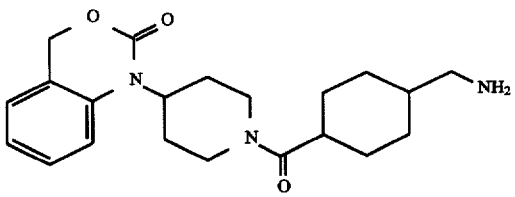

To a solution of 1-(1-(4-(N-tert-butyloxycarbonylaminomethyl)cyclohexylcarbonyl)piperidin-4-yl)-1,2-dihydro-4(H)-3,1-benzoxazin-2-one (100 mg, 0.21 mmol) from Example 137 in CH₂Cl₂ (2 mL) was added TFA (1 mL). The reaction was stirred at ambient temperature for 1 h and the solvent was removed under reduced pressure. The residue was suspended in Et₂O, the solid was collected by filtration and dried in vacuo to give the TFA salt of the title compound as an amorphous solid.

Analysis calc'd for (C₂₁H₂₉N₃O₃, 0.05 Et₂O, 1.45 TFA) C, 53.55; H, 5.77; N, 7.77 Found C, 53.55; H, 6.06; N, 8.01 HPLC (method B): retention time 9.63 min FAB MS: m/z 372 (M⁺+H)

EXAMPLE 139

1-(1-(4-Hydroxyphenylglycyl)piperidin-4-yl)-1,2-dihydro-4(H)-3,1-benzoxazin-2-one

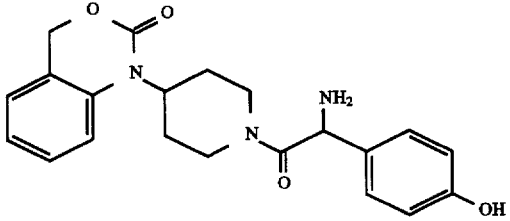

To a solution of 1-(1-(4-(N-tert-butyloxycarbonyl-4-hydroxyphenylglycyl)piperidin-4-yl)-1,2-dihydro-4(H)-3,1-benzoxazin-2-one (75 mg, 0.16 mmol) from Example 136 in CH₂Cl₂ (2 mL) was added TFA (1 mL). The reaction was stirred at ambient temperature for 1 h and the solvent was removed under reduced pressure. The residue was suspended in Et₂O, the solid was collected by filtration and dried in vacuo to give the TFA salt of the title compound as an amorphous solid.

Analysis calc'd for (C₂₁H₂₃N₃O₄, 1.2 TFA, 1.2 H₂O) C, 52.06; H, 4.97; N, 7.78 Found C, 52.04; H, 4.98; N, 7.48 HPLC (method B): retention time 9.13 min FAB MS: m/z 382 (M⁺+H)

EXAMPLE 140

1-tert-Butyloxycarbonyl-3-{3-Methoxy-4-[4-(2-oxo-4H-benzo[1,3]-oxazin-1-yl)-piperidine-1-carbonyl]-phenoxy}-pyrrolidine

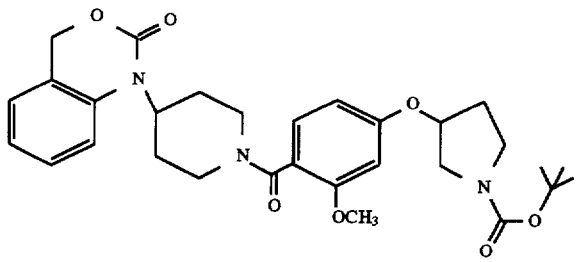

Step 1

A solution of methyl 2,4-dihydroxybenzoate (3.75 g, 21.7 mmol) and triphenylphosphine (7.01 g, 26.5 mmol) in THF (100 mL) was cooled to 0° C. under N₂. To the chilled solution was added 1-t-butoxycarbonyl-3-hydroxypyrrolidine (4.50 g, 24.1 mmol) and diethylazodicarboxylate (4.60 g, 4.16 mL, 26.5 mmol) in THF (50 mL) dropwise over a period of 20 minutes. The reaction was stirred for 18 hours, then the solvent was removed under reduced pressure. The residue was partitioned between ethyl acetate and aqueous saturated NaHCO₃. The organic layer was dried over MgSO₄, filtered, then the solvent was evaporated under reduced pressure. The residue was purified using pressurized silica gel column chromatography and eluted with a gradient of 15 to 20% ethyl acetate in hexanes. Methyl 2-hydroxy-4-(1-tert-butyloxycarbonyl-3-pyrrolidinyloxy)benzoate was recovered as a colorless oil.

TLC: $R_f$=0.52 in 25% ethyl acetate in hexanes HPLC (method A) retention time 10.48 min FAB MS m/z 338 (M⁺+H)

Step 2

To a stirred solution of methyl 2-hydroxy-4-(1-tert-butyloxycarbonyl-3-pyrrolidinyloxy)benzoate from Step 1 above (2.26 g, 6.70 mmol) in DMF (40 mL) under N₂, was added NaH (400 mg, 10.1 mmol). The reaction mixture was cooled, and CH₃I (0.83 mL, 13.4 mmol) was added via syringe. The reaction mixture was allowed to warm to ambient temperature, and stirred for an additional 2 hours. The solvent was removed under reduced pressure, and the residue was partitioned between ethyl acetate and aqueous NaHCO₃. The ethyl acetate layer was dried (MgSO₄), filtered, and evaporated under reduced pressure. The residue was purified using pressurized silica gel column chromatography, eluting with 20% ethyl acetate in hexanes. Methyl 2-methoxy-4-(1-tert-butyloxycarbonyl-3-pyrrolidinyloxy)-benzoate was obtained as a colorless oil which crystallized on standing overnight.

TLC: $R_f$=0.39 in 40% ethyl acetate in hexanes HPLC (method A) retention time 9.14 min FAB MS m/z 352 (M⁺+H)

Step 3

To a stirred solution of methyl 2-methoxy-4-(1-tert-butyloxycarbonyl-3-pyrrolidinyloxy)benzoate from Step 2 above (2.26 g, 6.43 mmol) in methanol (25 mL) was added 2N NaOH (16 mL, 32.2 mmol). The reaction mixture was refluxed for 30 minutes and cooled in a ice water bath. The solution was acidified with 5% citric acid, then the solvent was evaporated under reduced pressure. The residue was dissolved in ethyl acetate and washed with water (2×75 mL). The organic layer was dried (MgSO₄), filtered, then the solvent was evaporated to give 2-methoxy-4-(1-tert-butyloxycarbonyl-3-pyrrolidinyloxy)benzoic acid as a white solid which was used without further purification.

HPLC (method A) retention time 7.92 min FAB MS m/z 338 (M⁺+H)

Step 4

To a stirred solution of 2-methoxy-4-(1-tert-butyloxycarbonyl-3-pyrrolidinyloxy)benzoic acid from Step 3 above (100 g, 2.96 mmol) in DMF (50 mL) was added HOBT (453 mg, 2.96 mmol) and EDC (738 mg, 3.85 mmol), then DIEA was used to adjust the pH of the solution to 7.5. The reaction was allowed to stir for 30 minutes. 1-Piperidin-4-yl-1,4-dihydro-benzo[1,3]oxazine-2-one hydrochloride (796 mg, 2.96 mmol) from Step 4 of Example 1 was added to the reaction mixture and the pH was adjusted to 7.5 with DIEA. After 6 hours, the solvent was removed under reduced pressure, and the residue was dissolved in ethyl acetate (75 mL), washed with 5% citric acid (50 mL), water (50 mL), and saturated aqueous NaHCO₃ (50 mL), dried (MgSO₄), and filtered. The solvent was removed under reduced pressure, and the residue was purified using pressurized silica gel column chromatography, eluting with 2% methanol in methylene chloride. The title compound was obtained as an amorphous solid. 0.25 CH₂Cl₂, 0.8 H₂O Analysis calculated for C₃₀H₃₇N₃O₇, 0.25 CH₂Cl₂, 0.8 H₂O C, 61.86; H, 6.71; N, 7.16 Found C, 61.74; H, 6.37; N, 7.55 TLC: $R_f$=0.41 in 3% methanol in methylene chloride HPLC (method A) retention time 9.50 min FAB MS m/z 552 (M⁺+H)

EXAMPLE 141

1-tert-Butyloxycarbonyl-4-{3-methoxy-4-[4-(2-oxo-4H-benzo[1,3]-oxazin-1-yl)-piperidine-1-carbonyl]-phenoxymethyl}-piperidine

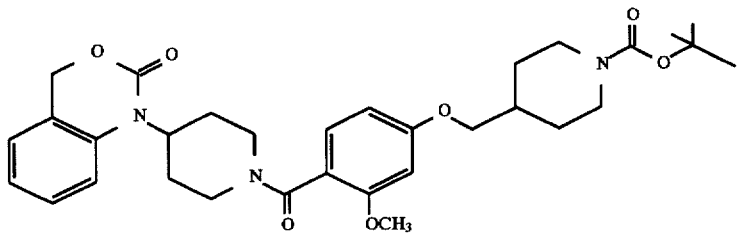

Step 1

A solution of methyl 2,4-dihydroxybenzoate (3.10 g, 18.0 mmol) and triphenylphosphine (5.80 g, 21.9 mmol) in THF (100 mL) was cooled to 0° C. under $N_2$. To the chilled solution was added 1-t-butoxycarbonyl-4-(hydroxymethyl) piperdine (4.00 g, 19.9 mmol) and diethylazodicarboxylate (3.80 g, 3.44 mL, 21.9 mmol) in THF (50 mL) dropwise over a period of 20 minutes. The reaction was stirred for 18 hours, and the solvent removed under reduced pressure. The residue was partitioned between ethyl acetate and aqueous saturated $NaHCO_3$. The organic layer was dried ($MgSO_4$) and filtered, then the solvent was evaporated under reduced pressure. The residue was purified using pressurized silica gel column chromatography with a gradient elution of 15–20% ethyl acetate in hexanes. Methyl 2-hydroxy-4-(1-tert-butyloxycarbonyl-4-piperidinylmethoxy)benzoate was recovered as a colorless oil which crystallized on standing.

TLC: $R_f$=0.42 in 25% ethyl acetate in hexaness HPLC (method A) retention time 11.97 min FAB MS m/z 366 ($M^+$+H)

Step 2

To a stirred solution of methyl 2-hydroxy-4-(1-tert-butyloxycarbonyl-4-piperidinylmethoxy)benzoate from Step 1 above (820 mg, 2.24 mmol) in DMF (25 mL) under $N_2$ was added NaH (134 mg, 3.36 mmol). The reaction mixture was cooled, and $CH_3I$ (0.28 mL, 4.48 mmol) was added via syringe. The reaction mixture was allowed to warm to room temperature, then stirred for an additional 2 hours. The solvent was removed under reduced pressure, then the residue was partitioned between ethyl acetate and aqueous $NaHCO_3$. The ethyl acetate layer was dried ($MgSO_4$), filtered, then evaporated under reduced pressure. The residue was purified using pressurized silica gel column chromatography, eluting with 30% ethyl acetate in hexanes. Methyl 2-methoxy-4-(1-tert-butyloxycarbonyl-4-piperidinylmethoxy)-benzoate was a white solid.

TLC: $R_f$=0.45 in 30% ethyl acetate in hexaness HPLC (method A) retention time 10.41 min FAB MS m/z 380 ($M^+$+H)

Step 3

To a stirred solution of methyl 2-methoxy-4-(1-tert-butyloxycarbonyl-4-piperidinylmethoxy)benzoate from Step 2 above (750 mg, 1.98 mmol) in methanol (10 mL) was added 2N NaOH (4.95 mL, 9.90 mmol). The reaction mixture was refluxed for 30 minutes then cooled in a ice water bath. The solution was acidified with 5% citric acid and the solvent evaporated under reduced pressure. The residue was dissolved in ethyl acetate and washed with water (2×25 mL). The organic layer was dried ($MgSO_4$), filtered, then the solvent was evaporated to give 2-methoxy-4-(1-tert-butyloxycarbonyl-4-piperidinylmethoxy)benzoic acid as a white solid which was used without further purification.

HPLC (method A) retention time 9.18 min FAB MS m/z 365 ($M^+$+H)

Step 4

To a stirred solution of 2-methoxy-4-(1-tert-butyloxycarbonyl-4-piperidinylmethoxy)benzoic acid from Step 3 above (700 mg, 1.91 mmol) in 30 mL of DMF was added HOBT (292 mg, 1.91 mmol) and EDC (475 mg, 2.48 mmol), then DIEA was used to adjust the pH of the solution to 7.5. The reaction was stirred for 30 minutes. 1-Piperidin-4-yl-1,4-dihydro-benzo[1,3]oxazine-2-one hydrochloride from Step 4 of Example 1 (515 mg, 1.91 mmol) was added to the reaction mixture and the pH was adjusted to 7.5 with DIEA. After 6 hours, the solvent was removed under reduced pressure, and the residue was dissolved in ethyl acetate (50 mL), washed sequentially with 5% citric acid (50 mL), water (50 mL), saturated aqueous $NaHCO_3$ (50 mL), then dried ($MgSO_4$) and filtered. The solvent was removed under reduced pressure, and the residue was purified using pressurized silica gel column chromatography, eluting with 1% methanol in methylene chloride. The title compound was obtained as a white solid.

Analysis calculated for $C_{32}H_{41}N_3O_7$, 0.05 MeOH, 1.25 $H_2O$ C, 63.75; H, 7.29; N, 6.96 Found C, 63.75; H, 6.71; N, 6.84 TLC: $R_f$=0.38 in 3% methanol in methylene chloride HPLC (method A) retention time 10.46 min FAB MS m/z 579 ($M^+$+H)

EXAMPLE 142

1-{1-[4-(1-acetyl-azetidin-3-yloxy-2-methoxy-benzoyl]-piperidin-4-yl}-1,4-dihydro-benzo[1,3]oxazin-2-one

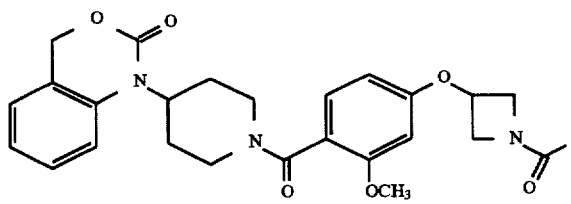

Step 1

A solution of methyl 2,4-dihydroxybenzoate (3.40 g, 19.6 mmol) and triphenylphosphine (6.29 g, 24.0 mmol) in THF (75 mL) was cooled to 0° C. under $N_2$. To the chilled solution was added 1-diphenylmethyl-3-hydroxyazetidine (5.22 g, 21.8 mmol) and diethylazodicarboxylate (4.18 g, 3.78 mL, 24.0 mmol) in THF (50 mL) dropwise over a period of 20 minutes. The reaction was stirred for 18 hours, and the solvent removed under reduced pressure. The residue was partitioned between ethyl acetate and aqueous saturated $NaHCO_3$. The organic layer was dried ($MgSO_4$), filtered, and the solvent evaporated under reduced pressure. The residue was purified using pressurized silica gel column chromatography and eluting using a gradient elution of 15–20% of ethyl acetate in hexanes. Methyl 2-hydroxy-4-(1-diphenylmethyl-3-azetidinyloxy)benzoate was recovered as a white solid.

TLC: $R_f$=0.33 in 10% ethyl acetate in hexanes HPLC (method A) retention time 7.82 min FAB MS m/z 390 ($M^+$+H)

Step 2

A solution of methyl 2-hydroxy-4-(1-diphenylmethyl-3-azetidinyloxy)benzoate from Step 1 above (750 mg) and $Pd(OH)_2$ (750 mg) in 250 mL of ethanol under an atmosphere of $H_2$ (balloon) at ambient temperature was stirred for 16 hours. The mixture was cautiously filtered through Celite, and the filtercake was washed with ethanol. The solvent was removed under reduced pressure, and the crude product purified using pressurized silica gel column chromatography and eluting with 10% methanol in methylene chloride. Methyl 2-hydroxy-4-(3-azetidinyloxy)benzoate was recovered as a white solid.

TLC: $R_f$ 0.23 in 90:10:0.5/methylene chloride:methanol:$NH_4OH$ HPLC (method A) retention time 4.66 min FAB MS m/z 224 ($M^+$+H)

Step 3

To a stirred, ice-cold solution of methyl 2-hydroxy-4-(3-azetidinyloxy)benzoate from step 2 above (1.42 g, 6.50 mmol) in DMF (30 mL) was added di-tertbutyldicarbonate (1.28 g, 5.85 mmol). The reaction was stirred for 6 hours, then allowed to warm to ambient temperature. The solvent was removed under reduced pressure and the residue was partitioned between ethyl acetate and 5% citric acid solution (50 mL). The organic layer was then washed with water (50 mL), dried ($MgSO_4$), filtered, and the solvent was removed under reduced pressure. The product was purified using pressurized silica gel column chromatography, eluting with 10% ethyl acetate in hexanes. Methyl 2-hydroxy-4-(1-tert-butyloxycarbonyl-3-azetidinyloxy)benzoate was recovered as a white solid.

TLC: $R_f$=0.24 in 20% ethyl acetate in hexanes HPLC (method A) retention time 10.38 min FAB MS m/z 324 ($M^+$+H)

Step 4

To a stirred solution of methyl 2-hydroxy-4-(1-tert-butyloxycarbonyl-3-azetidinyloxy)benzoate from Step 3 above (1.30 g, 4.02 mmol) in DMF (40 mL) under $N_2$ was added NaH (241 mg, 6.03 mmol). The reaction mixture was cooled, and $CH_3I$ (0.50 mL, 8.04 mmol) was added via syringe. The reaction mixture was allowed to warm to ambient temperature, then stirred for an additional 2 hours. The solvent was removed under reduced pressure and the residue was partitioned between ethyl acetate and aqueous $NaHCO_3$. The ethyl acetate layer was dried ($MgSO_4$), filtered, and evaporated under reduced pressure. The residue was purified using pressurized silica gel column chromatography, eluting with 20% ethyl acetate in hexanes. Methyl 2-methoxy-4-(1-tert-butyloxycarbonyl-3-azetidinyloxy)benzoate was obtained as a colorless oil which crystallized on standing overnight.

TLC: $R_f$=0.55 in 40% ethyl acetate in hexanes HPLC (method A) retention time 11.24 min FAB MS m/z 310 ($M^+$+H)

Step 5

To a stirred solution of methyl 2-methoxy-4-(1-tert-butyloxycarbonyl-3-azetidinyloxy)benzoate from Step 4 above (200 mg, 0.647 mmol) in methanol (10 mL) was added 2N NaOH (5 mL, 10 mmol). The reaction mixture was refluxed for 30 minutes, then cooled in a ice water bath. The solution was acidified with 5% citric acid then the solvent was evaporated under reduced pressure. The residue was dissolved in ethyl acetate and washed with water (2×25 mL). The aqueous layer was made alkaline (pH=9) with DIEA, cooled, then di-tertbutyldicarbonate (275 mg, 1.26 mmol) was added to the stirring solution. After 4 hours, the aqueous solution was extracted with diethyl ether (50 mL), and then made acidic by addition of 1N HCl (25 mL). The aqueous layer was extracted with methylene chloride (3×25 mL) and the organic layers were collected, dried ($MgSO_4$), filtered, and the solvent was evaporated under reduced pressure. 2-Methoxy-4-(1-tert-butyloxycarbonyl-3-azetidinyloxy)benzoic acid was obtained as a white solid which was used without further purification.

HPLC (method A) retention time 7.74 min FAB MS m/z 324 ($M^+$+H)

Step 6

A solution of 2-methoxy-4-(1-tert-butyloxycarbonyl-3-azetidinyloxy)benzoic acid from Step 5 above (250 mg, 0.773 mmol) and BOP reagent (342 mg, 0.850 mmol) in DMF (20 mL) were stirred for 30 minutes. 1-Piperidin-4-yl-1,4-dihydro-benzo[1,3]oxazine-2-one hydrochloride from Step 4 of Example 1 (189 mg, 0.703 mmol) was added to the reaction mixture, and DIEA was used to adjust the pH of the solution to 7.5. After 6 hours, the solvent was removed under reduced pressure. The residue was dissolved in ethyl acetate (75 mL) and sequentially washed with 5% citric acid (50 mL), water (50 mL), saturated aqueous $NaHCO_3$ (50 mL), then dried ($MgSO_4$) and filtered. The solvent was removed under reduced pressure and the residue was purified using pressurized silica gel column chromatography, eluting with 3% methanol in methylene chloride. 1-{1-[4-(1-tert-Butyloxycarbonyl-azetidin-3-yloxy-2-methoxybenzoyl]-piperidin-4-yl}-1,4-dihydro-benzo[1,3]oxazin-2-one was obtained as an amorphous solid. To a solution of 1-{1-[4-(1-tert-butyloxycarbonyl-azetidin-3-yloxy-2-methoxy-benzoyl]-piperidin-4-yl}-1,4-dihydro-benzo[1,3]oxazin-2-one (300 mg) in methylene chloride (10 mL) was added TFA (0.430 mL). The reaction mixture was allowed to stir for 3 hours at ambient temperature. The solvent was evaporated under reduced pressure, and the residue was lyophilized from water-acetonitrile to yield the TFA salt of 1-{1-[4-(3-azetidinyloxy-2-methoxy-benzoyl]-piperidin-4-yl}-1,4-dihydro-benzo[1,3]oxazin-2-one as a white solid. 1.55 TFA, 1.35 $H_2O$ Analysis calculated for $C_{24}H_{27}N_3O_5$, 1.55 TFA, 1.35 $H_2O$ C, 50.97; H, 4.93; N, 6.58 Found C, 50.98; H, 4.95; N, 6.56 TLC: $R_f$=0.17 in 90:10:1/methylene chloride:methanol:$NH_4OH$ HPLC (method) retention time 5.79 min FAB MS m/z 438 ($M^+$+H)

Step 7

To a stirred solution of the free base of 1-{1-[4-(3-azetidinyloxy-2-methoxy-benzoyl]-piperidin-4-yl}-1,4-dihydro-benzo[1,3]oxazin-2-one from Step 6 above (125 mg, 0.249 mmol) in methylene chloride (5 mL) was added acetic anhydride (0.054 mL, 0.571 mmol). The solution was stirred at ambient temperature for 4 hours. Aqueous saturated $NaHCO_3$ (10 mL) was added, and the reaction mixture was allowed to stir for 30 minutes. The organic phase was washed with aqueous saturated $NaHCO_3$ (2×10 mL), dried ($MgSO_4$), filtered, and the solvent was removed under reduced pressure. The residue was purified by pressurized silica gel column chromatography using 2% methanol in methylene chloride. The title compound was obtained as a white amorphous solid.

Analysis calculated for $C_{26}H_{29}N_3O_6$, 0.15 EtOAc, 0.8 $H_2O$ C, 62.99; H, 6.32; N, 8.29 Found C, 63.00; H, 5.71; N, 8.28 TLC: $R_f$=0.29 in 4% methanol in methylene chloride HPLC (Method) retention time 6.72 min FAB MS m/z 480 (M⁺+H)

EXAMPLE 143

1-tert-Butyloxycarbonyl-3-{3-methoxy-4-[4-(2-oxo-4H-benzo[1,3]-oxazin-1-yl)-piperidine-1-carbonyl]-phenoxy}-piperidine

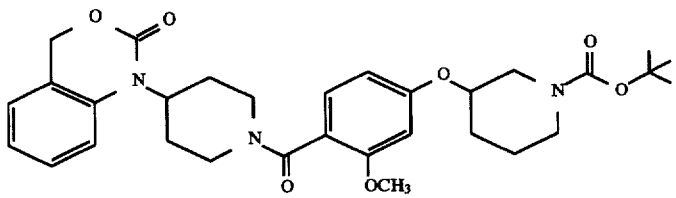

Step 1

To a stirred solution of 3-hydroxypiperidine hydrochloride (5.0 g, 36.3 mmol) in DMF (100 mL) was added DIEA (7.0 mL, 40.0 mmol). The solution was cooled to 0° C., and di-tertbutyldicarbonate (7.14 g, 32.7 mmol) was added to the reaction mixture. The reaction was stirred for 6 hours and then warmed to ambient temperature. The solvent was removed under reduced pressure. The residue was dissolved in ethyl acetate, washed with 5% citric acid (75 mL), and water (75 mL). The organic layer was dried (MgSO₄), filtered, and the solvent was evaporated under reduced pressure. 1-tert-Butyloxyhydroxypiperidine was obtained as a white solid and used without further purification.

TLC: Rf=0.53 in 3% methanol in methylene chloride FAB MS m/z 202 (M++H)

Step 2

A solution of methyl 2,4-dihydroxybenzoate (3.49 g, 20.2 mmol) and triphenylphosphine (6.52 g, 24.6 mmol) in THF (100 mL) was cooled to 0° C. under N₂. To the chilled solution was added 1-t-butoxycarbonyl-3-hydroxypiperdine (4.50 g, 22.4 mmol) and diethylazodicarboxylate (4.28 g, 3.87 mL, 24.6 mmol) in THF (50 mL) dropwise over a period of 20 minutes. The reaction was stirred for 18 hours and the solvent was removed under reduced pressure. The residue was partitioned between ethyl acetate and aqueous saturated NaHCO₃. The organic layer was dried (MgSO₄), filtered, and the solvent was evaporated under reduced pressure. The residue was purified using pressurized silica gel column chromatography with a gradient elution of 15-8% ethyl acetate in hexanes. Methyl 2-hydroxy-4-(1-tert-butyloxycarbonyl-3-piperidinyloxy)benzoate was recovered as a colorless oil.

TLC: Rf=0.33 in 15% ethyl acetate in hexanes HPLC (method A) retention time 11.02 min FAB MS m/z 352 (M++H)

Step 3

To a stirred solution of methyl 2-hydroxy-4-(1-tert-butyloxycarbonyl-3-piperidinyloxy)benzoate from Step 2 above (1.50 g, 4.27 mmol) in DMF (40 mL) under N₂ was added NaH (246 mg, 6.41 mmol). The reaction mixture was cooled, then CH₃I (0.53 mL, 8.54 mmol) was added via syringe. The reaction mixture was warmed to ambient temperature and stirred for 2 hours. The solvent was removed under reduced pressure and the residue was partitioned between ethyl acetate and aqueous NaHCO₃. The ethyl acetate layer was dried (MgSO₄), filtered, and evaporated under reduced pressure. The residue was purified using pressurized silica gel column chromatography, eluting with 20% ethyl acetate in hexanes. Methyl 2-methoxy-4-(1-tert-butyloxycarbonyl-3-piperidinyloxy)benzoate was obtained as a colorless oil which crystallized on standing overnight.

TLC: Rf=0.23 in 25% ethyl acetate in hexanes HPLC (method A) retention time 9.54 min FAB MS m/z 366 (M++H)

Step 4

To a stirred solution of methyl 2-methoxy-4-(1-tert-butyloxycarbonyl-3-piperidinyloxy)benzoate from Step 3 above (1.35 g, 3.69 mmol) in methanol (25 mL) was added 2N NaOH (9.2 mL, 18.5 mmol). The reaction mixture was heated to reflux for 30 minutes and then cooled in an ice water bath. The solution was acidified with 5% citric acid and the solvent was evaporated under reduced pressure. The residue was dissolved in ethyl acetate and washed with water (2×75 mL). The organic layer was dried (MgSO₄), filtered, and the solvent was evaporated to give 2-methoxy-4-(1-tert-butyloxycarbonyl-3-piperidinyloxy)benzoic acid as a white solid which was used without further purification.

HPLC (method A) retention time 8.25 min. FAB MS m/z 352 (M++H)

Step 5

To a stirred solution of 2-methoxy-4-(1-tert-butyloxycarbonyl-3-piperidinyloxy)benzoic acid from Step 4 above (1.10 g, 3.13 mmol) was added HOBT (527 mg, 3.44 mmol) and EDC (780 mg, 4.07 mmol). DIEA was used to adjust the pH of the solution to 7.5. The reaction was stirred for 30 minutes. 1-Piperidin-4-yl-1,4-dihydro-benzo [1,3]oxazine-2-one hydrochloride (841 mg, 3.13 mmol) from Step 4 of Example 1 was added to the reaction mixture and the pH was adjusted to 7.5 with DIEA. After 6 hours, the solvent was removed under reduced pressure and the residue was dissolved in EtOAc (75 mL) and washed sequentially with 5% citric acid (50 mL), water (50 mL), saturated aqueous NaHCO₃ (50mL), then dried (MgSO₄) and filtered. The solvent was removed under reduced pressure, then the residue was purified using pressurized silica gel column chromatography, eluting with 2% methanol in methylene chloride.

Analysis calculated for $C_{31}H_{39}N_3O_7$, 0.55 EtOAc, 0.25 $CH_2Cl_2$ C, 63.23; H, 6.96; N, 6.61 Found C, 63.25; H, 6.82; N, 6.52 TLC: $R_f$=0.38 in 2% methanol in methylene chloride. HPLC (Method A) retention time 9.31 min FAB MS m/z 566 (M⁺+H)

EXAMPLE 144

1-(1-{4-[1-(2-chloro-6-methyl-pyridin-4-ylmethyl)-piperidin-4-yloxy]-2-methoxy-benzoyl}-piperidin-4-yl)-1,4-dihydro-benzo[1,3]oxazin-2-one

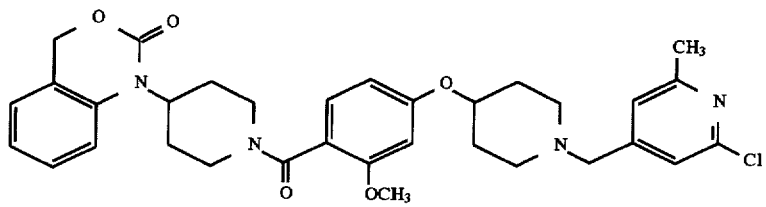

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in DMF (5 mL) was added 4-chloromethyl-2-chloro-4-methylpyridine (52.6 mg, 0.299 mmol) and DIEA (96.5 mg, 0.13 mL, 0.747 mmol). The solution was stirred at 50° C. for 18 hours. The solvent was removed under reduced pressure and the residue was partitioned between aqueous saturated NaHCO₃ (10 mL) and methylene chloride. The organic phase was dried (MgSO₄), filtered, and the solvent was removed under reduced pressure. The residue was purified by pressurized silica gel column chromatography using 4% methanol in methylene chloride as eluant. The title compound was obtained as a white amorphous solid.

Analysis calculated for C₃₃H₃₇ClN₄O₅, 0.30 CH₂Cl₂ C, 63.42; H, 6.01; N, 8.88 Found C, 63.39; H, 6.16; N, 9.17 TLC: R_f=0.38 in 4% methanol in methylene chloride HPLC (Method A) retention time 7.08 min FAB MS m/z 605 (M⁺+H)

EXAMPLE 145

1-(1-{4-[1-(2,6-dimethyl-pyridin-4-ylmethyl)-piperidin-4-yloxy]-2-methoxy-benzoyl}-piperidin-4-yl)-1,4-dihydro-benzo[1,3]oxazin-2-one

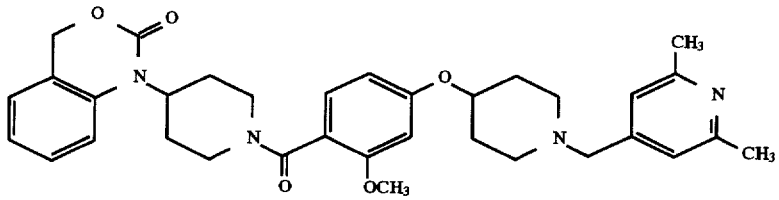

To a stirred solution of 1-(1-{4-[piperidin-4-yloxy]-2-methoxy-benzoyl}-piperidin-4-yl)-1,4-dihydro-benzo[1,3] oxazin-2-one hydrochloride from Example 26 (125 mg, 0.249 mmol) in DMF (5 mL) was added 4-chloromethyl-2, 6-dimethylpyridine (47.1 mg, 0.299 mmol) and DIEA (96.5 mg, 0.13 mL, 0.747 mmol). The solution was stirred at 50° C. for 18 hours. The solvent was removed under reduced pressure. The residue was partitioned between aqueous saturated NaHCO₃ (10 mL) and methylene chloride. The organic phase was dried (MgSO₄), filtered, and the solvent was removed under reduced pressure. The residue was purified by pressurized silica gel column chromatography using 5% methanol in methylene chloride as eluant. The product was further purified by preparative reverse phase HPLC using an acetonitrile:water gradient containing TFA. The TFA salt of the title compound was obtained as a white amorphous solid by lyophilization.

Analysis calculated for C₃₂H₃₅ClN₄O₅, 2.5 TFA, 0.4 H₂O C, 52.30; H, 4.94; N, 6.19 Found C, 52.28; H, 4.84; N, 6.33 TLC: R_f=0.28 in 5% methanol in methylene chloride HPLC (Method A) retention time 5.79 min FAB MS m/z 585 (M⁺+H)

EXAMPLE 146

1-(1-{4-[1-(2-chloro-pyridin-3-ylmethyl)-piperidin-4-yloxy]-2-methoxy-benzoyl}-piperidin-4-yl)-1,4-dihydro-benzo[1,3]oxazin-2-one

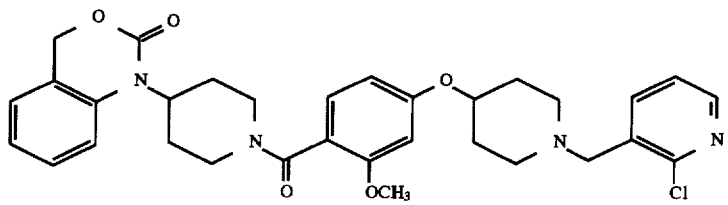

To a stirred solution of 1-(1-{4-[piperidin-4-yloxy]-2-methoxy-benzoyl}-piperidin-4-yl)-1,4-dihydro-benzo[1,3] oxazin-2-one hydrochloride from Example 26 (125 mg, 0.249 mmol) in DMF (5 mL) was added 3-chloromethyl-2-chloropyridine (48.4 mg, 0.299 mmol) and DIEA (96.5 mg, 0.13 mL, 0.747 mmol). The solution was stirred at 50° C. for 18 hours. The solvent was removed under reduced pressure.

The residue was partitioned between aqueous saturated NaHCO₃ (10 mL) and methylene chloride. The organic phase was dried (MgSO₄), filtered, and the solvent was removed under reduced pressure. The residue was purified by pressurized silica gel column chromatography using 3% methanol in methylene chloride as eluant. The product was further purified by preparative reverse phase HPLC using an acetonitrile:water gradient containing TFA. The TFA salt of the title compound was obtained as a white amorphous solid by lyophilization.

chloride:methanol:NH₄OH HPLC (Method A) retention time 5.79 min FAB MS m/z 571 (M⁺+H)

EXAMPLE 148

1-(1-{2-methoxy-4-[1-(6-methyl-pyridin-3-ylmethyl)piperidin-4-yloxy]-benzoyl}-piperidin-4-yl)-1,4-dihydro-benzo[1,3]oxazin-2-one

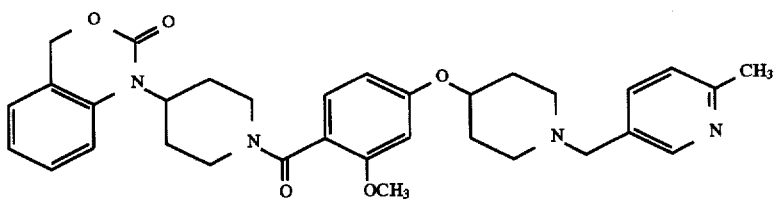

Analysis calculated for $C_{32}H_{35}C_iN_4O_5$, 1.65 TFA C, 54.40; H, 4.74; N, 7.19 Found C, 54.34; H, 4.81; N, 7.26 TLC: $R_f$=0.24 in 3% methanol in methylene chloride HPLC (Method A) retention time 6.69 min FAB MS m/z 591 (M⁺+H)

EXAMPLE 147

1-(1-{2-methoxy-4-[1-(2-methyl-pyridin-3-ylmethyl)piperidin-4-yloxy]-benzoyl}-piperidin-4-yl)-1,4-dihydro-benzo[1,3]oxazin-2-one

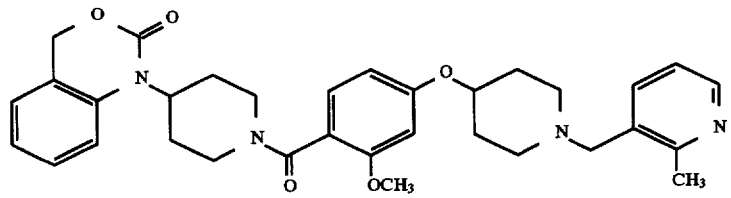

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in DMF (5 mL) was added 3-chloromethyl-2-methylpyridine (36.9 mg, 0.260 mmol) and DIEA (96.5 mg, 0.13 mL, 0.747 mmol). The solution was stirred at 50° C. for 18 hours. The solvent was removed under reduced pressure. The residue was partitioned between aqueous saturated NaHCO₃ (10 mL) and methylene chloride. The organic phase was dried (MgSO₄), filtered, and the solvent was removed under reduced pressure. The residue was purified by pressurized silica gel column chromatography using 95:5:0.5 methylene chloride:methanol:NH₄OH as eluant. The title compound was dissolved in methanol and 1.0 equivalent of 1N aqueous HCl was added. The solution was evaporated to dryness under reduced pressure. The residue was crystallized from a mixture of ethyl acetate and methanol to give the monohydrochloride salt of the title compound as a white crystalline solid.

Analysis calculated for $C_{33}H_{38}N_4O_5$, 1.0 HCl, 1.6 H₂O C, 62.32; H, 6.69; N, 8.81 Found C, 62.44; H, 6.29; N, 8.80 TLC: $R_f$=0.28 in 95:5:0.5/methylene To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in DMF (5 mL) was added 3-chloromethyl-6-methylpyridine (36.9 mg, 0.260 mmol) and DIEA (96.5 mg, 0.13 mL, 0.747 mmol). The solution was stirred at 50° C. for 18 hours. The solvent was removed under reduced pressure. The residue was partitioned between aqueous saturated NaHCO₃ (10 mL) and methylene chloride. The organic phase was dried (MgSO₄), filtered, and the solvent was removed under reduced pressure. The residue was purified by pressurized silica gel column chromatography using 95:5:0.5 methylene chloride:methanol:NH₄OH as eluant. The title compound was obtained as a white amorphous solid.

Analysis calculated for $C_{33}H_{38}N_5O_4$, 0.25 CH₂Cl₂ C, 67.46; H, 6.56; N, 9.47 Found C, 67.46; H, 6.43; N, 9.08 TLC: $R_f$=0.19 in 95:5:0.5/methylene chloride:methanol:NH₄OH HPLC (Method A) retention time 5.75 min FAB MS m/z 571 (M⁺+H)

EXAMPLE 149

1-(1-{2-methoxy-4-[1-(5-methoxycarbonyl-2-pyrididyl)piperidin-4-yloxy]-benzoyl}-piperidin-4-yl)-1,4-dihydro-benzo[1,3]oxazin-2-one

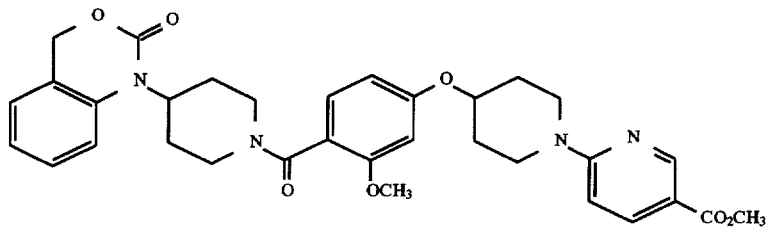

To a stirred solution of 1-(1-{4-[piperidin-4-yloxy]-2-methoxy-benzoyl}-piperidin-4-yl)-1,4-dihydro-benzo[1,3]oxazin-2-one hydrochloride-from Example 26 (125 mg, 0.249 mmol) in DMF (5 mL) was added methyl 6-chloronicotinate (51.3 mg, 0.299 mmol) and DIEA (96.5 mg, 0.13 mL, 0.747 mmol). The solution was stirred at 130° C. for 24 hours and the solvent removed under reduced pressure. The residue was partitioned between aqueous saturated NaHCO₃ (10 mL) and methylene chloride. The organic phase was dried (MgSO₄), filtered, and the solvent was removed under reduced pressure. The residue was purified by pressurized silica gel column chromatography using 4% methanol in methylene chloride as eluant. The product was dissolved in MeOH and 2.5 equivalents of 1M aqueous HCl were added. The solution was evaporated under reduced pressure. The residue was dissolved in 1:1 CH₃CN:H₂O and lyophilized. The title compound was obtained as a tan amorphous solid.

Analysis calculated for $C_{33}H_{36}N_4O_7$, 2.2 HCl, 0.8 H₂O C, 57.00; H, 5.77; N, 8.06 Found C, 57.00; H, 5.76; N, 8.10 TLC: $R_f$=0.40 in 6% methanol in methylene chloride HPLC (Method A) retention time 7.45 min FAB MS m/z 601 (M⁺+H)

EXAMPLE 150

1-(1-{2-methoxy-4-[1-(5-nitro-2-pyridyl)piperidin-4-yloxy]-benzoyl}-piperidin-4-yl)-1,4-dihydro-benzo[1,3]oxazin-2-one

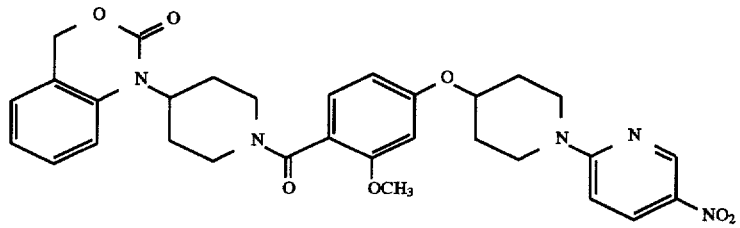

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in DMF (4 mL) was added 2-chloro-3-nitropyridine (48.8 mg, 0.299 mmol) and DIEA (96.5 mg, 0.13 mL, 0.747 mmol). The solution was stirred at ambient temperature for 18 hours. The solvent was removed under reduced pressure. The residue was partitioned between aqueous saturated NaHCO₃ (10 mL) and methylene chloride. The organic phase was dried (MgSO₄), filtered, and the solvent was removed under reduced pressure. The residue was purified by pressurized silica gel column chromatography using 98:2:0.2 methylene chloride:methanol:NH₄OH as eluant. The product was dissolved in MeOH and 2.5 equivalents of 1M aqueous HCl were added. The solution was evaporated under reduced pressure. The residue was dissolved in 1:1 CH₃CN:H₂O and lyophilized. The title compound was obtained as a yellow amorphous solid, 2.5 HCl Analysis calculated for $C_{31}H_{33}N_5O_7$, 2.5 HCl C, 54.85; H, 5.27; N, 10.32 Found C, 54.49; H, 5.59; N, 10.34 TLC: $R_f$=0.50 in 4% methanol in methylene chloride HPLC (Method A) retention time 10.14 min FAB MS m/z 588 (M⁺+H)

EXAMPLE 151

1-(1-{2-methoxy-4-[1-(5-amino-2-pyridyl)piperidin-4-yloxy]-benzoyl}-piperidin-4-yl)-1,4-dihydro-benzo[1,3]oxazin-2-one

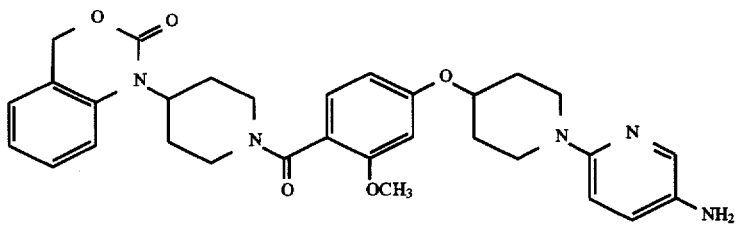

To a stirred solution of 1-(1-{2-methoxy-4-[1-(5-nitro-2-pyridyl)piperidin-4-yloxy]-benzoyl}-piperidin-4-yl)-1,4-dihydro-benzo[1,3]oxazin-2-one from Example 150 (400 mg, 0.681 mmol) in methanol (5 mL) was added 4 mL of 1N HCl and 50 mg of tin metal. The solution was stirred on a steam bath for 30 minutes. The reaction mixture was cooled, and the solvent was evaporated under reduced pressure. The residue was partitioned between aqueous saturated NaHCO$_3$ (10 mL) and EtOAc. The aqueous layer was extracted twice more with EtOAc (50 mL). The organic layers were combined, dried (MgSO$_4$), filtered, and the solvent was removed under reduced pressure. The residue was purified by pressurized silica gel column chromatography using 92:8:0.5 methylene chloride:methanol:NH$_4$OH as eluant. The title compound was obtained as an off-white amorphous solid by evaporation of an EtOAc solution under reduced pressure.

Analysis calculated for C$_{31}$H$_{35}$N$_5$O$_5$, 0.25 EtOAc, 0.8 H$_2$O C, 64.69; H, 6.55; N, 11.79 Found C, 64.71; H, 6.53; N, 11.82 TLC: R$_f$=0.18 in 92:8:0.5 methylene chloride:methanol:NH$_4$OH HPLC (Method A) retention time 6.58 min FAB MS m/z 558 (M$^+$+H)

EXAMPLE 152

1-(1-{2-methoxy-4-[1-(4-chloropyrimidin-2-yl)piperidin-4-yloxy]-benzoyl}-piperidin-4-yl)-1,4-dihydro-benzo[1,3]oxazin-2-one

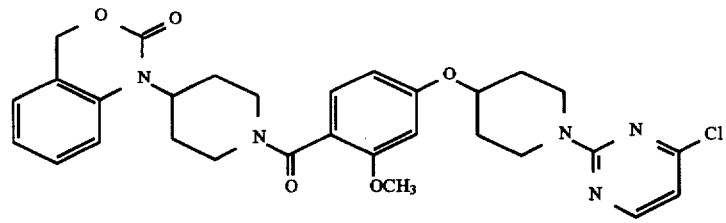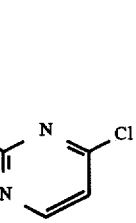

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in DMF (4 mL) was added 2,4-dichloropyrimidine (44.5 mg, 0.299 mmol) and DIEA (96.5 mg, 0.13 mL, 0.747 mmol). The solution was stirred at ambient temperature for 18 hours. The solvent was removed under reduced pressure. The residue was partitioned between aqueous saturated NaHCO$_3$ (10 mL) and methylene chloride. The organic phase was dried (MgSO$_4$), filtered, and the solvent was removed under reduced pressure. The residue was purified by pressurized silica gel column chromatography using 3% methanol in methylene chloride as eluant. The title compound was obtained as an off-white amorphous solid.

Analysis calculated for C$_{30}$H$_{32}$ClN$_5$O$_5$, 0.7 CH$_2$Cl$_2$ C, 57.83; H, 5.28; N, 10.99 Found C, 57.93; H, 5.25; N, 11.13 TLC: R$_f$=0.28 in 3% methanol in methylene chloride HPLC (Method A) retention time 8.03 min FAB MS m/z 578 (M$^+$+H)

EXAMPLE 153

1-(1-{4-[1-(2,3-dichloro-thieno[3,2-c]pyridin-6-ylmethyl)-piperidin-4-yloxy]-2-methoxy-benzoyl}-piperidin-4-yl)-1,4-dihydro-benzo[1,3]-oxazin-2-one

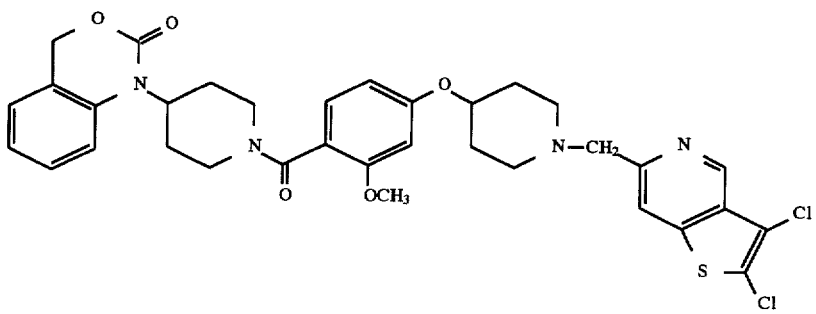

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (100 mg, 0.215 mmol) in DMF (5 mL) was added 2-(chloromethyl)-2,3-dichlorothienopyridine (59.9 mg, 0.237 mmol) and DIEA (96.5 mg, 0.13 mL, 0.747 mmol). The solution is was stirred at 50° C. for 18 hours. The solvent was removed under reduced pressure. The residue was partitioned between aqueous saturated NaHCO$_3$ (10 mL) and methylene chloride. The organic phase was dried (MgSO$_4$), filtered, and the solvent was removed under reduced pressure. The residue was purified by pressurized silica gel column chromatography using 3% methanol in methylene chloride as eluant. The title compound was obtained as a tan amorphous solid by evaporation of an EtOAc solution under reduced pressure.

Analysis calculated for C$_{34}$H$_{34}$C$_{12}$N$_4$O$_5$, 0.7 EtOAc C, 59.46; H, 5.37; N, 7.54 Found C, 59.07; H, 5.28; N, 7.62 TLC: R$_f$=0.29 in 5% methanol in methylene chloride HPLC (Method A) retention time 8.39 min FAB MS m/z 681 (M$^+$+H)

EXAMPLE 154

1-(1-{2-methoxy-4-[1-(5-phenyl-[1,2,4]oxadiazol-3-ylmethyl)-piperidin-4-yloxy]-benzoyl}-piperidin-4-yl)-1,4-dihydro-benzo[1,3]-oxazin-2-one methylene chloride. The organic phase was dried (MgSO$_4$), filtered, then the solvent was removed under reduced pressure. The residue was purified by pressurized silica gel column chromatography using 3% methanol in methylene chloride as eluant. The title compound was obtained as a white amorphous solid.

Analysis calculated for C$_{35}$H$_{37}$N$_5$O$_6$, 0.75 H$_2$O C, 65.96; H, 6.09; N, 10.99 Found C, 66.00; H, 5.77; N, 10.91 TLC: R$_f$=0.19 in 3% methanol in methylene chloride HPLC (Method A) retention time 7.66 min FAB MS m/z 624 (M$^+$+H)

EXAMPLE 155

1-[1-(4-{1-[2-(4-chlorophenyl)-thiazol-4-ylmethyl]-piperidin-4-yloxy}-2-methoxy-benzoyl)-piperidin-4-yl]-1,4-dihydro-benzo[1,3]oxazin-2-one

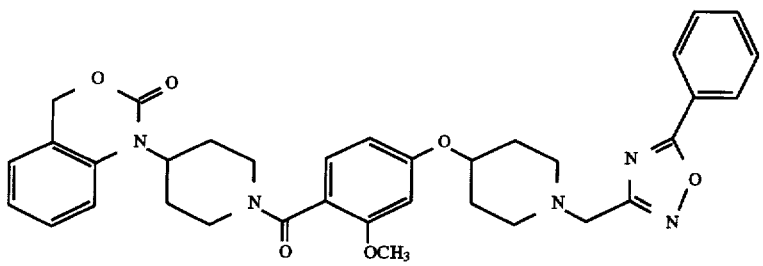

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in DMF (5 mL) was added 3-(chloromethyl)-5-phenyl-1,2,4-oxadiazole (53.3 mg, 0.274 mmol) and DIEA (96.5 mg, 0.13 mL, 0.747 mmol). The solution was stirred at 50° C. for 18 hours, and then the solvent was removed under reduced pressure. The residue was partitioned between aqueous saturated NaHCO$_3$ (10 mL) and

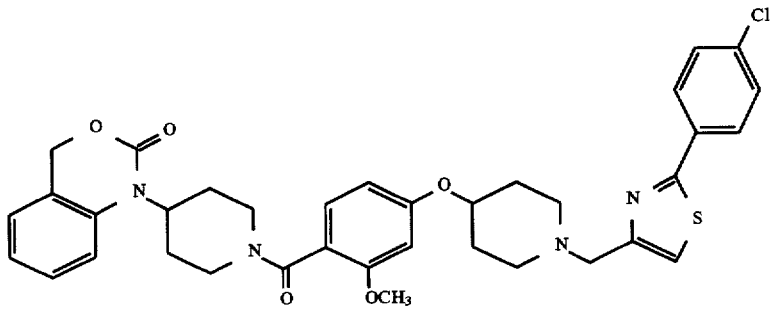

To a stirred solution of 1-(1-{4-[piperidin-4-yloxy]-2-methoxy-benzoyl}-piperidin-4-yl)-1,4-dihydro-benzo[1,3] oxazin-2-one hydrochloride from Example 26 (125 mg, 0.249 mmol) in DMF (5 mL) was added 4-(chloromethyl)-2-(4-chlorophenyl)thiazole (66.9 mg, 0.274 mmol) and DIEA (96.5 mg, 0.13 mL, 0.747 mmol). The solution was stirred at 50° C. for 18 hours and then the solvent was removed under reduced pressure. The residue was partitioned between aqueous saturated NaHCO$_3$ (10 mL) and methylene chloride. The organic phase was dried (MgSO$_4$), filtered, then the solvent was removed under reduced pressure. The residue was purified by pressurized silica gel column chromatography using 3% methanol in methylene chloride as eluant. The title compound was obtained as a white amorphous solid by lyophilization from water-acetonitrile.

Analysis calculated for C$_{36}$H$_{37}$ClN$_4$O$_5$S, 1.1 H$_2$O C, 62.38; H, 5.70; N, 8.08 Found C, 62.41; H, 5.72; N, 8.11 TLC: R$_f$=0.26 in 3% methanol in methylene chloride HPLC (Method) retention time 8.72 min FAB MS m/z 673 (M$^+$+H)

EXAMPLE 156

6-(4-{3-methoxy-4-[4-(2-oxo-4H-benzo[1,3]oxazin-1-yl)-piperidine-1-carbonyl]-phenoxy}-piperidin-1-ylmethyl)-1H-pyrimidine-2,4-dione

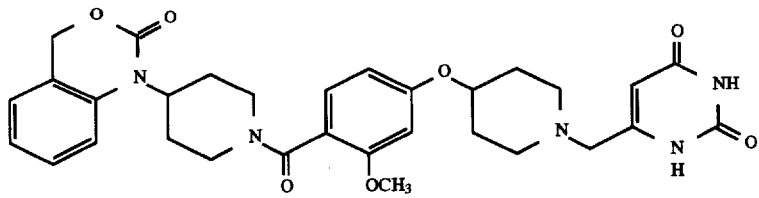

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in DMF (5 mL) was added 6-(chloromethyl)uracil (44.9 mg, 0.274 mmol) and DIEA (96.5 mg, 0.13 mL, 0.747 mmol). The solution was stirred at 50° C. for 18 hours and then the solvent was removed under reduced pressure. The residue was partitioned between aqueous saturated NaHCO$_3$ (10 mL) and methylene chloride. The organic phase was dried (MgSO$_4$), filtered, then the solvent was removed under reduced pressure. The residue was purified by preparative HPLC using a water-acetonitrile gradient containing 0.1% TFA. The TFA salt of the title compound was obtained as a white amorphous powder by lyophilization from water-acetonitrile.

Analysis calculated for C$_{31}$H$_{35}$N$_5$O$_7$, 2.0 TFA C, 51.41; H, 4.56; N, 8.57 Found C, 51.08; H, 4.95; N, 8.72 TLC: R$_f$=0.32 in 5% methanol in methylene chloride HPLC (Method A) retention time 5.85 min FAB MS m/z 590 (M$^+$+H)

EXAMPLE 157

1-(1-{2-methoxy-4-[1-(2-methyl-thiazol-4-ylmethyl)-piperidin-4-yloxy]-benzoyl}-piperidin-4-yl)-1,4,dihydro-benzo[1,3]oxazin-2-one

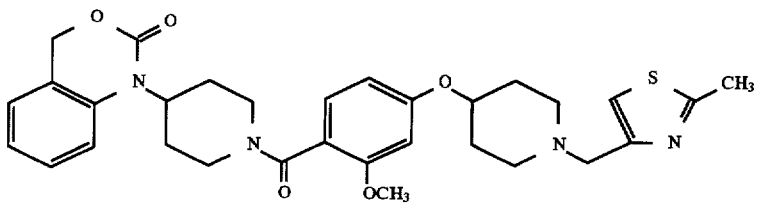

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in DMF (5 mL) was added 4-(chloromethyl)-2-methylthiazole HCl (50.4 mg, 0.274 mmol) and DIEA (96.5 mg, 0.13 mL, 0.747 mmol). The solution was stirred at 50° C. for 18 hours and then the solvent was removed under reduced pressure. The residue was partitioned between aqueous saturated NaHCO₃ (10 mL) and methylene chloride. The organic phase was dried (MgSO₄), filtered, and the solvent was removed under reduced pressure. The residue was purified by pressurized silica gel column chromatography using 3% methanol in methylene chloride as eluant. The title compound was obtained as a white amorphous solid.

Analysis calculated for C₃₁H₃₆N₄O₅S, 0.25 CH₂Cl₂, 0.10 H₂O C, 62.58; H, 6.17; N, 9.34 Found C, 62.56; H, 6.14; N, 9.39 TLC: R$_f$=0.33 in 5% methanol in methylene chloride HPLC (Method A) retention time 6.61 min FAB MS m/z 577 (M⁺+H)

EXAMPLE 158

1-(1-{4-[1-(1H-benzoimidazol-2-ylmethyl)-piperidin-4-yloxy]-2-methoxy-benzoyl}-piperidin-4-yl)-1,4,dihydro-benzo[1,3]oxazin-2-one

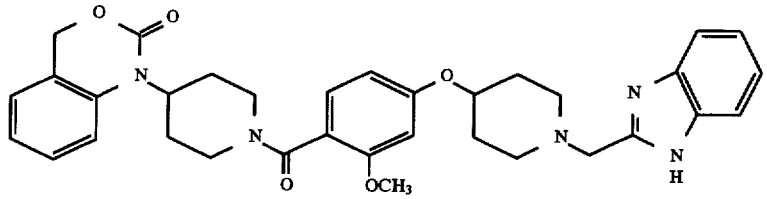

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in DMF (5 mL) was added 2-(chloromethyl) benzimidazole (45.6 mg, 0.274 mmol) and DIEA (96.5 mg, 0.13 mL, 0.747 mmol). The solution was stirred at 50° C. for 18 hours and then the solvent was removed under reduced pressure. The residue was partitioned between aqueous saturated NaHCO₃ (10 mL) and methylene chloride. The organic phase was dried (MgSO₄), filtered, and the solvent was removed under reduced pressure. The residue was purified by pressurized silica gel column chromatography using 3% methanol in methylene chloride as eluant. The title compound was obtained as a white amorphous solid.

Analysis calculated for C₃₄H₃₇N₅O₅, 0.6 CH₂Cl₂ C, 64.26; H, 5.95; N, 10.83 Found C, 64.38; H, 6.16; N, 10.77 TLC: R$_f$=0.35 in 5% methanol in methylene chloride HPLC (Method A) retention time 6.77 min FAB MS m/z 596 (M⁺+H)

EXAMPLE 159

1-{1-[2-methoxy-4-(1-[quinolin-3-ylmethyl] piperidin-4-yloxy)benzoyl]-piperidin-4-yl}-1,4,dihydro-benzo[1,3]oxazin-2-one

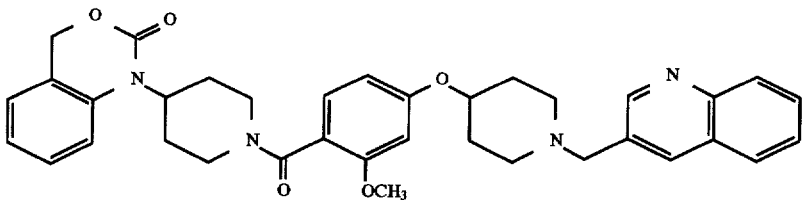

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in methylene chloride (2 mL) was added 3-quinolinecarboxaldehyde (78.3 mg, 0.498 mmol), NaOAc (41 mg, 0.502 mmol) and Na(OAc)₃BH (105.5 mg, 0.498 mmol). The solution was stirred at ambient temperature for 18 hours. Aqueous saturated NaHCO₃ (5 mL) was added, and the solvents were removed under reduced pressure. The residue was suspended in ethyl acetate (50 mL) and washed with water (2×25 mL). The organic phase was dried (MgSO₄) and filtered, and the solvent was removed under reduced pressure. The residue was purified by prepative reverse phase HPLC using a water-acetonitrile gradient containing 0.1% TFA. The TFA salt of the title compound was obtained as a white amorphous powder by lyophilization from water-acetonitrile.

Analysis calculated for C₃₆H₃₈N₄O₅. 2.25 TFA C. 56.34; H, 4.70; N, 6.49 Found C, 56.35; H, 4.82; N, 6.54 TLC: R$_f$=0.20 in 3% methanol in methylene chloride HPLC (Method A) retention time 6.48 min FAB MS m/z 607 (M⁺+H)

EXAMPLE 160

1-{1-[4-(1-[furan-3-ylmethyl]piperidin-4-yloxy)-2-methoxy-benzoyl]-piperidin-4-yl}-1,4,dihydro-benzo[1,3]oxazin-2-one

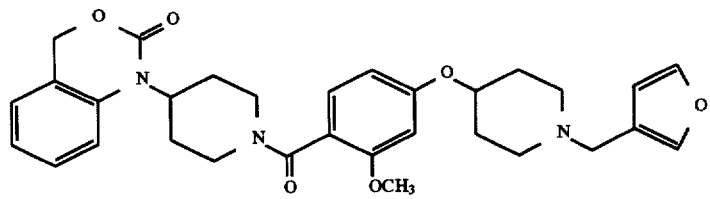

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in methanol (4 mL) was added 3-furaldehyde (29.9 mg, 0.027 mL, 0.311 mmol), NaOAc (102 mg, 1.25 mmol) and NaBH₃CN (36.8 mg, 0.31 mmol). The solution was stirred at ambient temperature for 18 hours. Aqueous saturated NaHCO₃ (5 mL) was added, and the solvents were removed under reduced pressure. The residue was suspended in ethyl acetate (50 mL) and washed with water (2×25 mL). The organic phase was dried (MgSO₄) and filtered, and the solvent was removed under reduced pressure. The residue was purified by pressurized silica gel column chromatography using 3% methanol in methylene chloride as eluant. The title compound was obtained as a white amorphous solid.

Analysis calculated for C₃₁H₃₅N₃O₆. 0.55 CH₂Cl₂. 0.4 H₂O C, 63.20; H, 6.20; N, 7.01 Found C, 63.15; H, 6.20; N, 7.21 TLC: R$_f$=0.37 in 3% methanol in methylene chloride HPLC (Method A) retention time 6.79 min FAB MS m/z 546 (M⁺+H)

EXAMPLE 161

1-{1-[2-methoxy-4-(1-[thiophen-3-ylmethyl]piperidin-4-yloxy)benzoyl]-piperidin-4-yl}-1,4,dihydro-benzo[1,3]oxazin-2-one

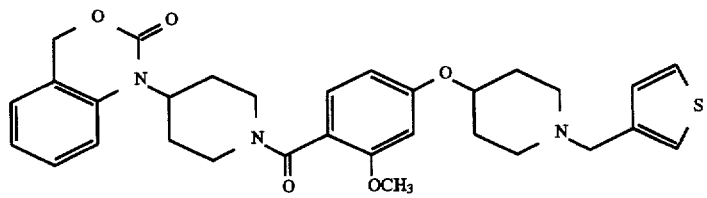

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in methanol (4 mL) was added 3-thiophenecarboxaldehyde (36.8 mg, 0.029 mL, 0.311 mmol), NaOAc (102 mg, 1.25 mmol) and NaBH₃CN (36.8 mg, 0.31 mmol). The solution was stirred at ambient temperature for 18 hours. Aqueous saturated NaHCO₃ (5 mL) was added, and the solvents were removed under reduced pressure. The residue was suspended in ethyl acetate (50 mL) and washed with water (2×25 mL). The organic phase was dried (MgSO₄) and filtered, and the solvent was removed under reduced pressure. The residue was purified by pressurized silica gel column chromatography using 3% methanol in methylene chloride as eluant. The title compound was obtained as a white amorphous solid.

Analysis calculated for C₃₁H₃₅N₃O₅S, 0.45 CH₂Cl₂ C, 62.96; H, 6.03; N, 7.00 Found C, 62.85; H, 6.02; N, 7.24 TLC: R$_f$=0.36 in 5% methanol in methylene chloride HPLC (Method A) retention time 7.06 min FAB MS m/z 562 (M⁺+H)

EXAMPLE 162

1-[1-(2-trifluoromethoxybenzoyl)-piperidin-4-yl]-1,4-dihydro-benzo-[1,3]oxazin-2-one

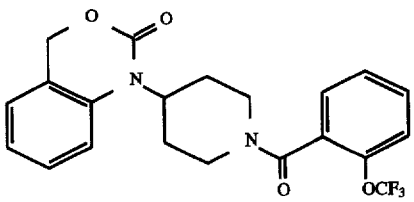

161

To a stirred solution of 1-(piperidin-4-yl)-1,4-dihydro-benzo[1,3]oxazine-2-one hydrochloride from Step 4 of Example 1 (100 mg, 0.372 mmol) and DIEA (0.065 mL, 0.37 mmol) in methylene chloride (2 mL) was added 2-(trifluoromethoxy)benzoyl chloride (83.5 mg, 0.372 mmol). The reaction mixture was stirred at ambient temperature for 1.5 hours. The organic layer was washed with 5% citric acid (2×10 mL), dried with $MgSO_4$, filtered, and evaporated under reduced pressure. The residue was purified by pressurized silica gel column chromatography using 3% methanol in methylene chloride as eluant. The title compound was obtained as a white amorphous solid.

Analysis calculated for $C_{21}H_{19}F_3N_2O_4$, 0.15 $CH_2Cl_2$ C, 58.64; H, 4.49; N, 6.47 Found C, 58.85; H, 4.31; N, 6.40 TLC: $R_f$=0.41 in 3% methanol in methylene chloride HPLC (method A) retention time 8.60 min FAB MS m/z 421 ($M^+$+H)

EXAMPLE 163

1-(1-{2-methoxy-4-[1-(2-methoxypyridin-3-ylmethyl)-piperidin-4-yloxy]-benzoyl}-piperidin-4-yl)-1,4-dihydro-benzo[1,2]oxazin-2-one

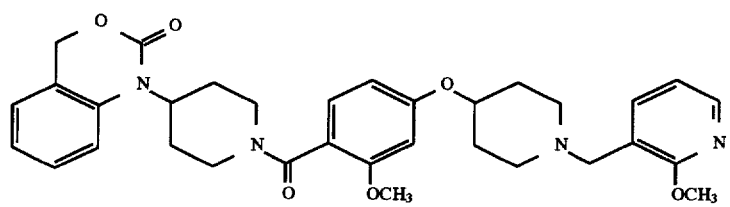

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in DMF (5 mL) was added 3-chloromethyl-3-methoxymethylpyridine (47.1 mg, 0.299 mmol) and DIEA (96.5 mg, 0.13 mL, 0.747 mmol). The solution was stirred at 50° C. for 18 hours and the solvent was removed under reduced pressure. The residue was partitioned between aqueous saturated $NaHCO_3$ (10 mL) and methylene chloride. The organic phase was dried ($MgSO_4$), filtered, and the solvent was removed under reduced pressure. The residue was purified by pressurized silica gel column chromatography using 4% methanol in methylene chloride as eluant. The product was further purified by preparative reverse phase HPLC using a water-acetonitrile gradient containing 0.1% TFA. The TFA salt of the title compound was obtained as a white amorphous solid by lyophilization.

Analysis calculated for $C_{33}H_{38}N_4O_6$, 1.55 TFA C, 56.79; H, 5.22; N, 7.34 Found C, 56.72; H, 5.27; N, 7.48 TLC:

162

$R_f$=0.18 in 4% methanol in methylene chloride HPLC (Method A) retention time 6.48 min FAB MS m/z 587 ($M^+$+H)

EXAMPLE 164

1-(1-{4-[1-(2-hydroxypiperidin-3-ylmethyl)-piperidin-4-yloxy]-2-methoxy-benzoyl}-piperidin-4-yl)-1,4-dihydro-benzo[1,2]oxazin-2-one

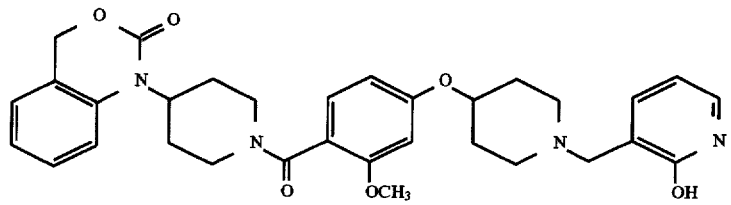

To a stirred solution of 1-(1-{2-methoxy-4-[1-(2-methoxy-pyridin-3-ylmethyl)-piperidin-4-yloxy]-benzoyl}-piperidin-4-yl)-1,4-dihydro-benzo[1,2]oxazin-2-one from Example 163 (30 mg, 0.051 mmol) in THF (5 mL) was added 1N HCl (5 mL). The solution was stirred at reflux for 85 hours and the solvent removed under reduced pressure. The residue was purified by preparative reverse phase HPLC using a water-acetonitrile gradient containing 0.1% TFA. The title compound was obtained as a white amorphous powder by lyophilization.

Analysis calculated for $C_{32}H_{36}N_4O_6$, 1.85 TFA, 0.75 $H_2O$ C, 54.70; H, 5.20; N, 6.59 Found C, 54.75; H, 5.56; N, 6.60

TLC: $R_f$=0.26 in 94:6:0.5 methylene chloride:methanol:$NH_4OH$ HPLC (Method A) retention time 6.03 min FAB MS m/z 573 ($M^+$+H)

EXAMPLE 165

1-(1-{2-methoxy-4-[1-(2-methoxymethylpyridin-4-ylmethyl)-piperidin-4-yloxy]-benzoyl}-piperidin-4-yl)-1,4-dihydro-benzo[1,2[oxazin-2-one

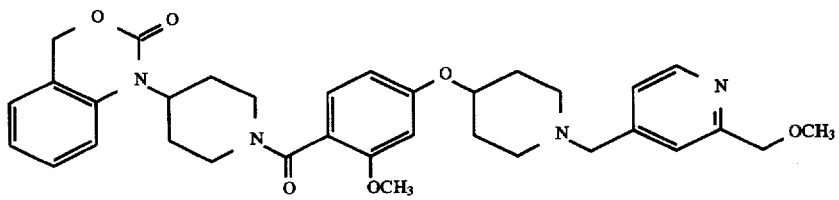

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in methylene chloride (3 mL) was added 2-methylmethoxy-4-pyridinecarboxaldehyde (45.2 mg, 0.299 mmol), HOAc (0.025 mL, 0.498 mmol) and Na(OAc)$_3$BH (91.1 mg, 0.498 mmol). The solution was stirred at ambient temperature for 18 hours. Aqueous saturated NaHCO$_3$ (5 mL) was added, and the solvents were removed under reduced pressure. The residue was suspended in ethyl acetate (50 mL) and washed with water (2×25 mL). The organic phase was dried (MgSO$_4$) and filtered, and the solvent was removed under reduced pressure. The residue was purified by prepative reverse phase HPLC using a water-acetonitrile gradient containing 0.1% TFA. The TFA salt of the title compound was obtained as a white amorphous powder by lyophilization from H$_2$O-CH$_3$CN.

Analysis calculated for C$_{34}$H$_{40}$N$_4$O$_6$, 2.5 TFA, 0.9 H$_2$O C, 51.93; H, 4.95; N, 6.21 Found C, 51.91; H, 4.82; N, 6.24 TLC: R$_f$=0.36 in 97:3:0.3 methylene chloride:methanol:NH$_4$OH HPLC (Method A) retention time 5.97 min FAB MS m/z 601 (M$^+$+H)

EXAMPLE 166

1-(1-{2-methoxy-4-[1-(1-oxy-pyridin-3-ylmethyl)-piperidin-4-yloxy]-benzoyl}-piperidin-4-yl)-1,4-dihydro-benzo[1,2]oxazin-2-one

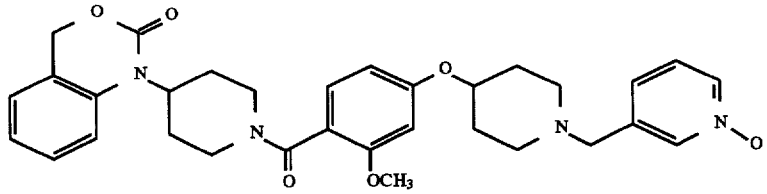

To a stirred solution of 1-(1-{4-[piperidin-4-yloxy]-2-methoxy-benzoyl}-piperidin-4-yl)-1,4-dihydro-benzo[1,3] oxazin-2-one hydrochloride from Example 26 (125 mg, 0.249 mmol) in DMF (5 mL) was added 3-chloromethylpyridine-N-oxide (34.9 mg, 0.274 mmol) and DIEA (96.5 mg, 0.13 mL, 0.747 mmol). The solution was stirred at 50° C. for 18 hours and the solvent was removed under reduced pressure. The residue was partitioned between aqueous saturated NaHCO$_3$ (10 mL) and methylene chloride. The organic phase was dried (MgSO$_4$), filtered, and the solvent was removed under reduced pressure. The residue was purified by pressurized silica gel column chromatography using 90:10:0.1 methylene chloride:methanol:NH$_4$OH. The product was dissolved in 1:1 water:acetonitrile containing 2.5 equivalents of 1N aqueous HCl and lyophilized. The HCl salt of the title compound was obtained as a white amorphous solid.

Analysis calculated for C$_{32}$H$_{36}$N$_4$O$_6$, 0.05 H$_2$O, 1.3 HCl C, 61.89; H, 6.07; N, 9.02 Found C, 61.87; H, 6.07; N, 9.33 TLC: R$_f$=0.29 in 90:10:0.1 methylene chloride:methanol:NH$_4$OH HPLC (Method A) retention time 5.74 min FAB MS m/z 573 (M$^+$+H)

EXAMPLE 167

4-{3-allyloxy-4-(2-oxo-4H-benzo[1,3]oxazin-1-yl)-piperidin-1-carbonyl]-phenoxy}-piperidine-1-t-butyl carbamate

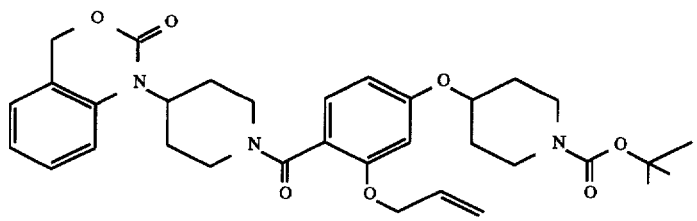

Step 1

To a stirred solution of methyl 2-hydroxy-4-(1-tertbutyloxycarbonyl-4-piperidinyloxy)benzoate from Step XX of Example XX (2.50 g, 7.11 mmol) in DMF (50 mL) under $N_2$ was added NaH (427 mg, 10.7 mmol). The reaction mixture was cooled, and allyl bromide (1.23 mL, 14.2 mmol) was added via syringe. The reaction mixture was allowed to warm to ambient temperature and stirred for 2 hours. The solvent was removed under reduced pressure and the residue partitioned between ethyl acetate and aqueous $NaHCO_3$. The ethyl acetate layer was dried $(MgSO_4)$, filtered, and evaporated under reduced pressure. The residue was purified using pressurized silica gel column chromatography using a gradient elution of 10–15% ethyl acetate in hexanes. Methyl 2-allyloxy-4-(1-tertbutyloxycarbonyl-4-piperidinyloxy)benzoate was obtained as a thick colorless oil.

TLC: $R_f$=0.28 in 20% ethyl acetate in hexanes HPLC (method A) retention time 10.95 min FAB MS m/z 392 $(M^++H)$

Step 2

To a stirred solution of methyl 2-allyloxy-4-(1-tertbutyloxycarbonyl-4-piperidinyloxy)benzoate (2.50 g, 6.39 mmol) from Step 1 above in methanol (40 mL) was added 2N NaOH (15.9 mL, 31.9 mmol). The reaction mixture was refluxed for 30 minutes and cooled in a ice water bath. The solution was acidified with 5% citric acid and the solvent was evaporated under reduced pressure. The residue was dissolved in EtOAC and washed with water (2×75 mL). The organic layer was dried $(MgSO_4)$, filtered, and the solvent was evaporated under reduced pressure to give 2-allyloxy-4-(1-tertbutyloxycarbonyl-4-piperidinyloxy)benzoic acid as a white solid, which was used without further purification.

TLC: $R_f$=0.41 in 80:20:0.2 methylene chloride:methanol:$NH_4OH$ HPLC (method A) retention time 9.58 min FAB MS m/z 378 $(M^++H)$

Step 3

To a stirred solution of 2-allyloxy-4-(1-tertbutyloxycarbonyl-4-piperidinyloxy)benzoic acid (1.00 g, 2.65 mmol) from Step 2 above was added HOBT (453 mg, 2.96 mmol) and EDC (738 mg, 3.85 mmol) and DIEA was used to adjust the pH of the solution to 7.5. The reaction was allowed to stir for 30 minutes. 1-(Piperidin-4-yl)-1,4-dihydro-benzo[1,3]oxazine-2-one hydrochloride from Step 4 of Example 1 (796 mg, 2.96 mmol) was added to the reaction mixture and the pH was adjusted to 7.5 with DIEA. After 6 hours, the solvent was removed under reduced pressure, and the residue was dissolved in ethyl acetate (75 mL), washed with 5% citric acid (50 mL), water (50 mL), and saturated aqueous $NaHCO_3$ (50 mL), dried $(MgSO_4)$, and filtered. The solvent was removed under reduced pressure, and the residue was purified using pressurized silica gel column chromatography, eluting with 1% methanol in methylene chloride. The title compound was obtained as a white amorphous solid by evaporation of an EtOAc solution under reduced pressure.

Analysis calculated for $C_{33}H_{41}N_3O_7$, 1.25 $H_2O$, 0.1 EtOAc C, 64.38; H, 7.17; N, 6.74 Found C, 64.40; H, 7.01; N, 6.73 TLC: $R_f$=0.27 in 2% methanol in methylene chloride HPLC (method A) retention time 10.53 min FAB MS m/z 592 $(M^++H)$

EXAMPLE 168

4-{4-[4-(2-oxo-4H-benzo[1,3]-oxazin-1-yl)-piperidine-1-carbonyl]-3-propoxy-phenoxy}-piperidine-1-t-butyl carbamate

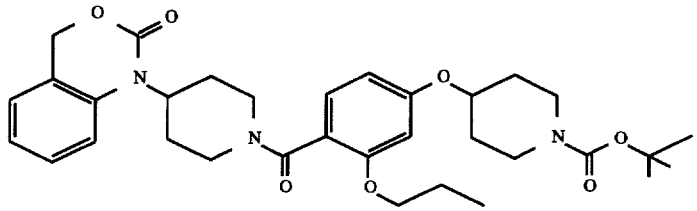

To a stirred solution of 2-propoxy-4-(1-tertbutyloxycarbonyl-4-piperidinyloxy)benzoic acid (300 mg; 0.791 mmol) in DMF (30 mL) was added HOBT hydrate (143 mg; 0.94 mmol) and EDC (212 mg, 1.11 mmol). The pH of the solution was adjusted to 7.5 using DIEA. The mixture was stirred at ambient temperature for 30 minutes, and 1-(piperidin-4-yl)-1,4-dihydro-benzo[1,3] oxazine-2-one hydrochloride from Step 4 of Example 1 (193 mg; 0.718 mmol) was added. The pH was adjusted to 7.5 using DIEA. The reaction was completed in 16 hours. The solvent was removed under reduced pressure. The residue was suspended in ethyl acetate (20 mL) and washed with 5% aqueous citric acid (2×15 mL), water (2×15 mL), and saturated aqueous $NaHCO_3$ (2×15 mL). The organic phase was dried $(MgSO_4)$ and filtered, and the solvent was removed under reduced pressure. The residue was purified by pressurized silica gel column chromatography using 1% methanol in methylene chloride as eluant. The title compound was obtained as a white amorphous solid by evaporation of an EtOAc solution under reduced pressure.

Analysis calculated for $C_{33}H_{43}N_3O_7$, 0.8 $H_2O$.0.05 EtOAc C, 65.09; H, 7.40; N, 6.86 Found C, 65.12; H, 7.17;

N, 6.86 TLC: $R_f$=0.29 in 1:1 ethyl acetate:hexanes HPLC (method A) retention time 10.84 min FAB MS m/z 594 (M$^+$+H)

EXAMPLE 169

1-(1-(4-(1-(N-t-butylmethyl-3-pyrrolidinylsulfonyl)-4-piperidinyloxy)-2-methoxybenzoyl)piperidin-4-yl)-1,2-dihydro-4(H)-3,1-benzoxazin-2-one

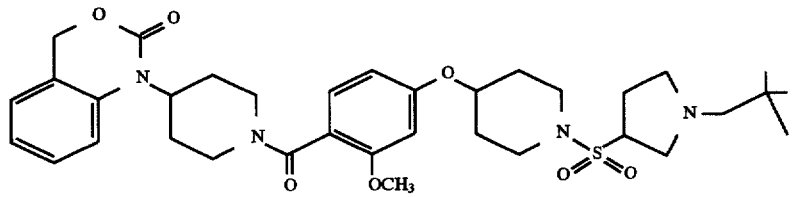

To stirred solution of 1-(1-(4-(1-(3-pyrrolidinylsulfonyl) piperidinyloxy)-2-methoxybenzoyl)piperidin-4-yl)-1,2-dihydro-4(H)-3,1-benzoxazin-2-one from Example 92 (0.045 g; 0.08 mmol) in MeOH (1 mL) was added pivaldehyde (0.12 mmol; 13.3 µL) and then NaCNBH$_3$ (12.6 mg; 0.20 mmol). The reaction solution was stirred at ambient temperature for 18 h and then diluted with H$_2$O (5 mL). The solution was made basic with saturated aqueous NaHCO$_3$ (5 mL), and then extracted with CH$_2$Cl$_2$ (5×5 mL). The organic phase was dried (MgSO$_4$), filtered, and the solvent was removed under reduced pressure. The residue was purified by pressurized silica gel column chromatography using 10:1 CH$_2$Cl$_2$:MeOH(NH$_3$). The title compound was dissolved in MeOH and to the solution was added 2 equivalents of 1.0N aqueous HCl. The resulting solution was evaporated under reduced pressure and the residue was lyophilized from H$_2$O:CH$_3$CN. The HCl salt of the title compound was obtained as an amorphous powder.

Analysis calculated for (C$_{35}$H$_{48}$N$_4$O$_7$S, 1.95 HCl, 0.5 H$_2$O) C, 56.19; H, 6.87; N, 7.49 Found C, 56.20; H, 6.71; N, 7.59 TLC: $R_f$=0.80 [9:1 CHCl$_3$:$^i$PrOH] HPLC (method A): retention time 11.53 min FAB MS: m/z 669 (M$^+$+H)

EXAMPLE 170

1-(1-(4-(1-(3-(N-methyl)pyrrolidinylsulfonyl)-piperidinyloxy)-2-methoxybenzoyl)piperidin-4-yl)-1,2-dihydro-4(H)-3,1-benzoxazin-2-one

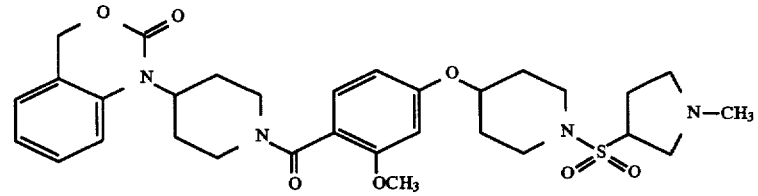

To stirred solution of 1-(1-(4-(1-(3-pyrrolidinylsulfonyl)-piperidinyloxy)-2-methoxybenzoyl)piperidin-4-yl)-1,2-dihydro-4(H)-3,1-benzoxazin-2-one from Example 92 (0.10 g; 0.17 mmol) in MeOH (2 mL) was added 37% aqueous formaldehyde(0.05 mL), HOAc (10 µL) and then NaCNBH$_3$ (22.0 mg; 0.34 mmol). The reaction solution was stirred at ambient temperature for 18 h and then diluted with H$_2$O (5 mL). The solution was made basic with sat. NaHCO$_3$ (5 mL) and extracted with CH$_2$Cl$_2$ (5×5 mL). The organic phase was dried (MgSO$_4$), filtered, and the solvent was removed under reduced pressure. The residue was purified by pressurized silica gel column chromatography using 10:1 CH$_2$Cl$_2$:MeOH(NH$_3$). The title compound was dissolved in MeOH and to the solution was added 2 equivalents of 1.0N aqueous HCl. The resulting solution was evaporated under reduced pressure and the residue was lyophilized from H$_2$O:CH$_3$CN. The HCl salt of the title compound was obtained as an amorphous powder.

Analysis calculated for (C$_{31}$H$_{40}$N$_4$O$_7$S, 1.65 HCl) C, 55.39; H, 6.25; N, 8.34 Found C, 55.38; H, 6.21; N, 8.42 TLC: $R_f$=0.30 [9:1 CH$_2$Cl$_2$:MeOH(NH$_3$)] HPLC (method A): retention time 10.38 min FAB MS: m/z 613 (M$^+$+H)

EXAMPLE 171

1-(1-(4-(1-(3-(N-(2-methylpyridin-3-ylmethyl) pyrrolidinylsulfonyl)piperidinyloxy)-2-methoxybenzoyl)piperidin-4-yl)-1,2-dihydro-4(H)-3,1-benzoxazin-2-one

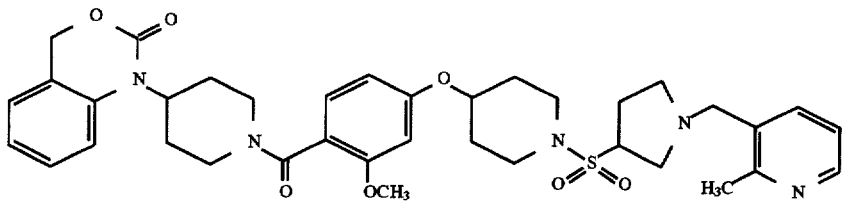

To stirred solution of 1-(1-(4—(1-(3-pyrrolidinylsulfonyl)piperidinyloxy)-2-methoxybenzoyl)piperidin-4-yl)-1,2-dihydro-4(H)-3,1-benzoxazin-2-one from Example 92 (0.04 g; 0.08 mmol) in DMF (2 mL) was added diisopropylethylamine (69.7 μL; 0.40 mmol) and 3-chloromethylpyridine (21.2 mg; 0.12 mmol). The reaction solution was heated to 60° C. for 16 h and then cooled to ambient temperature. The reaction mixture was concentrated under reduced pressure. The residue was purified by pressurized silica gel column chromatography using 10:1 $CH_2Cl_2$:MeOH($NH_3$). The title compound was dissolved in MeOH and to the solution was added 2 equivalents of 1.0N aqueous HCl. The resulting solution was evaporated under reduced pressure and the residue was lyophilized from $H_2O$:$CH_3CN$. The HCl salt of the title compound was obtained as an amorphous powder.

Analysis calculated for ($C_{37}H_{45}N_5O_7S$, 2.0 HCl, 0.75 $CH_2Cl_2$) C, 54.00; H, 5.82; N, 8.34 Found C, 53.99; H, 5.97; N, 8.33 TLC: $R_f$=0.85 [9:1 $CHCl_3$:MeOH($NH_3$)] HPLC (method A): retention time 9.99 min FAB MS: m/z 704 ($M^+$+H)

EXAMPLE 172

1-(1-(4-(1-(N-Benzyl-3-pyrrolidinylcarbonyl)-4-piperidinyloxy)-2-methoxybenzoyl)piperidin-4-yl)-1,2-dihydro-4(H)-3,1-benzoxazin-2-one

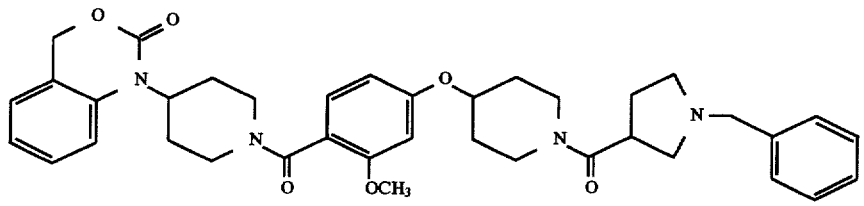

To stirred solution of 1-(1-(4-(N-acryloyl-4-piperidinyloxy)-2-methoxybenzoyl)piperidin-4-yl)-1,2-dihydro-4(H)-3,1-benzoxazin-2-one from Example 103 (0.50 g; 0.96 mmol) in acetonitrile (20 mL) was added N-trimethylsilyl-N-cyanomethylbenzylamine (0.47 mL; 1.92 mmol) and AgF (0.24 g; 1.92 mmol). The solution was stirred at 75° C. for 24 h and then cooled to ambient temperature. The reaction solvent was removed under reduced pressure and the crude mixture resuspended in $CH_2Cl_2$. The suspension was filtered through Celite and the solvent was removed under reduced pressure. The residue was purified by pressurized silica gel column chromatography using 19:1 $CHCl_3$:MeOH($NH_3$). Evaporation of a $CHCl_3$ solution of the title compound under reduced pressure gave an amorphous powder.

Analysis calculated for ($C_{38}H_{44}N_4O_6$, 0.30 $CH_2Cl_2$) C, 67.82; H, 6.63; N, 8.26 Found C, 67.85; H, 6.61; N, 8.42 TLC: $R_f$=0.70 [9:1 $CHCl_3$:MeOH($NH_3$)] HPLC (method A): retention time 10.94 min FAB MS: m/z 653 ($M^+$+H)

EXAMPLE 173

1-(1-(4-(1-(3-Pyrrolidinylcarbonyl)-4-piperidinyloxy)-2-methoxybenzoyl)piperidin-4-yl )-1,2-dihydro-4(H)-3,1-benzoxazin-2-one

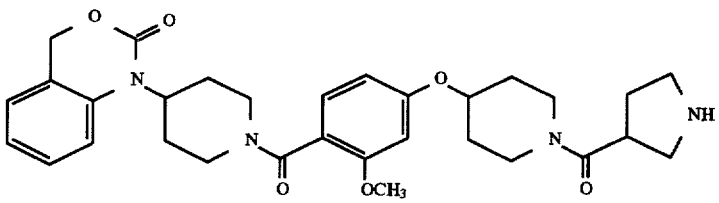

To stirred solution of 1-(1-(4-(1-(N-benzyl-3-pyrrolidinylcarbonyl)-4-piperidinyloxy)-2-methoxybenzoyl)piperidin-4-yl)-1,2-dihydro-4(H)-3,1-benzoxazin-2-one from Example 172 (0.34 g; 0.52 mmol) in dichloroethane (10 mL) was added freshly distilled 1-chloroethyl chloroformate (0.084 mL; 0.78 mmol) and 1,8-bis(dimethylamino)-naphthalene (10.7 mg; 0.05 mmol). The mixture was heated at reflux for 3 h and then cooled to ambient temperature. The reaction mixture was concentrated in vacuo and redissolved in MeOH (5 mL). This solution was refluxed for 1 hour and cooled to ambient temperature. The solvent was removed under reduced pressure and the residue was purified by pressurized silica gel column chromatography using 95:5 CH₂Cl₂:MeOH. The title compound was dissolved in MeOH and to the solution was added 2 equivalents of 1.0N aqueous HCl. The resulting solution was evaporated under reduced pressure and the residue was lyophilized from H₂O:CH₃CN. The HCl salt of the title compound was obtained as an amorphous powder.

Analysis calculated for (C₃₁H₃₈N₄O₆, 2.15 H₂O, 1.75 HCl) C, 56.04; H, 6.68; N, 8.43 Found C, 56.05; H, 6.69; N, 8.34 TLC: R$_f$=0.20 [85:15:0.75 CH₂Cl₂:MeOH(NH₃)] HPLC (method A): retention time 9.74 min FAB MS: m/z 563 (M⁺+H)

EXAMPLE 174

1-(1-(4-(1-(N-2-methylpyridin-3-ylmethyl-3-pyrrolidinylcarbonyl)-4-piperidinyloxy)-2-methoxybenzoyl)piperidin-4-yl)-1,2-dihydro-4(H)-3,1-benzoxazin-2-one TLC: R$_f$=0.80 [9:1 CHCl₃:MeOH(NH₃)] HPLC (method A): retention time 8.92 min FAB MS: m/z 668 (M⁺+H)

EXAMPLE 175

1-(1-(4-(1-(1-(t-Butoxycarbonyl)piperazin-4-ylsulfonyl)-4-piperidinyloxy)-2-methoxybenzoyl)piperidin-4-yl)-1,2-dihydro-4(H)-3,1-benzoxazin-2-one

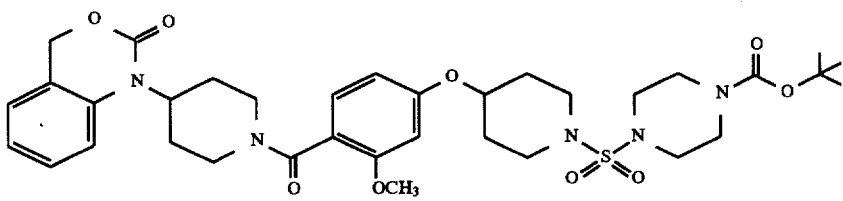

To stirred solution of 1-(1-(4-(4-piperidinyloxy)-2-methoxybenzoyl)piperidin-4-yl)-1,2-dihydro-4(H)-3,1-benzoxazin-2-one from Example 26 (0.100 g; 0.21 mmol) in CH₂Cl₂ (5 mL) was added triethylamine (0.200 mL; 1.44 mmol) and 4-(t-butoxycarbonyl)piperazine-1-sulfonyl chloride (304 mg; 1.07 mmol). The reaction solution was stirred at ambient temperature for 22 h and then diluted with CH₂Cl₂ (10 mL) and extracted with 10% NaOH (3×10 mL). The organic phase was dried (MgSO₄), filtered and concentrated under reduced pressure. The residue was purified by pressurized silica gel column chromatography using 10:1 CH₂Cl₂:MeOH(NH₃). The title compound obtained as an amorphous powder.

Analysis calculated for (C₃₅H₄₇N₅O₉S, 0.25 CH₂Cl₂) C, 57.59; H, 6.51; N, 9.53 Found C, 57.65; H, 6.74; N, 9.66

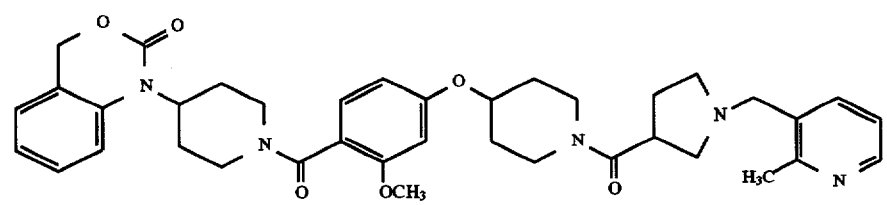

To stirred solution of 1-(1-(4-(1-(3-pyrrolidinylcarbonyl)-4-piperidinyloxy)-2-methoxybenzoyl)piperidin-4-yl)-1,2-dihydro-4(H)-3,1-benzoxazin-2-one from Example 173 (0.075 g; 0.13 mmol) in DMF (2 mL) was added DIEA (0.113 mL; 0.65 mmol) and 3-chloromethylpyridine (35.4 mg; 0.20 mmol). The reaction solution was heated to 60° C. for 16 h and then cooled to ambient temperature. The reaction mixture was concentrated under reduced pressure. The residue was purified by pressurized silica gel column chromatography using 10:1 CH₂Cl₂:MeOH(NH₃). The title compound was dissolved in MeOH and to the solution was added 2 equivalents of 1.0N aqueous HCl. The resulting solution was evaporated under reduced pressure and the residue was lyophilized from H₂O:CH₃CN. The HCl salt of the title compound was obtained as an amorphous powder.

Analysis calculated for (C₃₈H₄₅N₅O₆, 1.85 HCl, 1.9 H₂O) C, 59.37; H, 6.64; N, 9.11 Found C, 59.36; H, 6.65; N, 9.03

TLC: R$_f$=0.5 [9:1 CHCl₃:MeOH(NH₃)] HPLC (method A): retention time 10.03 min FAB MS: m/z 714 (M⁺+H)

EXAMPLE 176

1-(1-(4-(1-(Piperazin-4-ylsulfonyl)-4-piperidinyloxy)-2-methoxybenzoyl)piperidin-4-yl)-1,2-dihydro-4(H)-3,1-benzoxazin-2-one

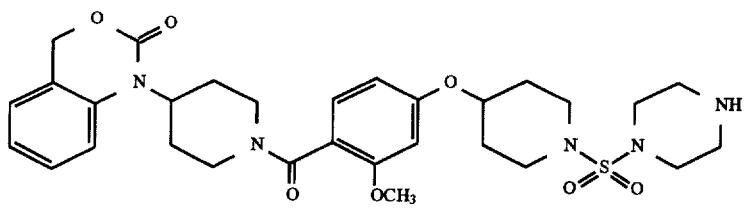

To stirred solution of 1-(1-(4-(1-(1-(t-Butoxycarbonyl)piperazin-4-ylsulfonyl)-4-piperidinyloxy)-2-methoxybenzoyl)piperidin-4-yl)-1,2-dihydro-4(H)-3,1-benzoxazin-2-one from Example 175 (0.03 g; 0.043 mmol) in MeOH (2 mL) at 0° C. was added a stream of anhydrous HCl gas. The reaction solution was stirred at ambient temperature for 22 h and then concentrated under reduced pressure. The residue was purified by pressurized silica gel column chromatography using 10:1 CH$_2$Cl$_2$:MeOH(NH$_3$). The title compound was obtained as an amorphous powder.

Analysis calculated for (C$_{30}$H$_{39}$N$_5$O$_7$S, 0.80 CH$_2$Cl$_2$) C, 54.26; H, 6.00; N, 10.27 Found C, 54.30; H, 6.08; N, 10.09 TLC: R$_f$=0.45 [9:1 CHCl$_3$:MeOH(NH$_3$)] HPLC (method A): retention time 6.93 min FAB MS: m/z 614 (M$^+$+H)

EXAMPLE 177

1-(1-(4-(1-(1-(2-methylpyridin-3-ylmethyl)piperazin-4-ylsulfonyl)-4-piperidinyloxy)-2-methoxybenzoyl)piperidin-4-yl)-1,2-dihydro-4(H)-3,1-benzoxazin-2-one

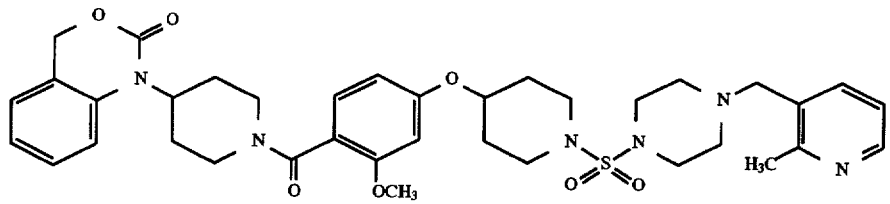

To stirred solution of 1-(1-(4-(1-(piperazin-4-ylsulfonyl)-4-piperidinyloxy)-2-methoxybenzoyl)piperidin-4-yl)-1,2-dihydro-4(H)-3,1-benzoxazin-2-one from Example 176 (0.10 g; 0.16 mmol) in DMF (5 mL) was added diisopropylethylamine (0.140 mL; 0.80 mmol) and 3-chloromethylpyridine (39.7 mg; 0.22 mmol). The reaction solution was heated to 60° C. for 16 h and then cooled to ambient temperature. The reaction mixture was concentrated under reduced pressure. The residue was purified by pressurized silica gel column chromatography using 10:1 CH$_2$Cl$_2$:MeOH(NH$_3$). The title compound was dissolved in MeOH and to the solution was added 3 equivalents of 1.0N aqueous HCl. The resulting solution was evaporated under reduced pressure and the residue was lyophilized from H$_2$O:CH$_3$CN. The HCl salt of the title compound was obtained as an amorphous powder.

Analysis calculated for (C$_{37}$H$_{46}$N$_6$O$_7$S, 2.5 HCl, 0.9 CH$_2$Cl$_2$) C, 51.41; H, 5.73; N, 9.49 Found C, 51.42; H, 5.93; N, 9.72 TLC: R$_f$=0.60 [9:1 CHCl$_3$:MeOH(NH$_3$)] HPLC (method A): retention time 10.29 min FAB MS: m/z 719 (M$^+$+H)

EXAMPLE 178

1-(1-(4-(1-(1-methylpiperazin-4-ylsulfonyl)-4-piperidinyloxy)-2-methoxybenzoyl)piperidin-4-yl)-1,2-dihydro-4(H)-3,1-benzoxazin-2-one

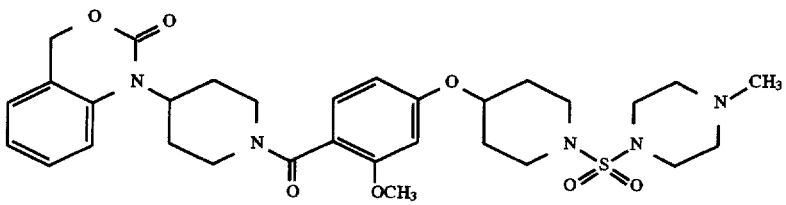

To stirred solution of 1-(1-(4-(1-(piperazin-4-ylsulfonyl)-4-piperidinyloxy)-2-methoxybenzoyl)piperidin-4-yl)-1,2-dihydro-4(H)-3,1-benzoxazin-2-one from Example 176 (0.10 g; 0.17 mmol) in 37% formaldehyde in H$_2$O (5 mL) was added NaCNBH$_3$ (11 mg; 0.17 mmol). The reaction solution was stirred at ambient temperature for 18 h and then diluted with CH$_2$Cl$_2$ (5 mL). The solution was made basic with sat. NaHCO$_3$ (5 mL) and 1M NaOH (5 mL) and then extracted with CH$_2$Cl$_2$ (5×5 mL). The organic phase was dried (MgSO$_4$), filtered, and the solvent was removed under reduced pressure. The residue was purified by pressurized silica gel column chromatography using 10:1 $CH_2Cl_2$:MeOH($NH_3$). The title compound was dissolved in MeOH and to the solution was added 3 equivalents of 1.0N aqueous HCl. The resulting solution was evaporated under reduced pressure and the residue was lyophilized from $H_2O$:$CH_3CN$. The HCl salt of the title compound was obtained as an amorphous powder.

Analysis calculated for ($C_{31}H_{41}N_5O_7S$, 2.5 HCl, 0.8 $H_2O$) C, 50.77; H, 6.20; N, 9.55 Found C, 50.74; H, 6.05; N, 9.55 TLC: $R_f$=0.85 [5:1 $CH_2Cl_2$:MeOH($NH_3$)] HPLC (method A): retention time 10.57 min FAB MS: m/z 628 ($M^+$+H)

EXAMPLE 179

1-(1-(4-(1-(1-ethylpiperazin-4-ylsulfonyl)-4-piperidinyloxy)-2-methoxybenzoyl)piperidin-4-yl)-1,2-dihydro-4(H)-3,1-benzoxazin-2-one

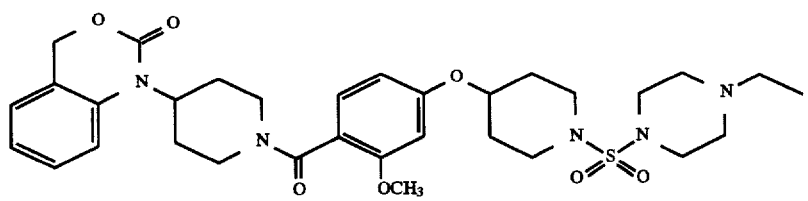

To stirred solution of 1-(1-(4-(1-(piperazin-4-ylsulfonyl)-4-piperidinyloxy)-2-methoxybenzoyl)piperidin-4-yl)-1,2-dihydro-4(H)-3,1-benzoxazin-2-one from Example 176 (0.10 g; 0.17 mmol) in HOAc (2 mL) was added $NaBH_4$ (11.0 mg; 0.17 mmol). The reaction solution was stirred at ambient temperature for 18 h and then concentrated under reduced pressure. The residue was redissolved in $CH_2Cl_2$ (5mL) and extracted with sat. $NaHCO_3$ (5 mL) and 10% NaOH (5 mL). The organic phase was dried ($MgSO_4$), filtered, and the solvent was removed under reduced pressure. The residue was purified by pressurized silica gel column chromatography using 10:1 $CH_2Cl_2$:MeOH($NH_3$). The title compound was dissolved in MeOH and to the solution was added 2.5 equivalents of 1.0N aqueous HCl. The resulting solution was evaporated under reduced pressure and the residue was lyophilized from $H_2O$:$CH_3CN$. The HCl salt of the title compound was obtained as an amorphous powder.

Analysis calculated for ($C_{32}H_{43}N_5O_7S$, 2.05 HCl) C, 53.62; H, 6.34; N, 9.77 Found C, 53.59; H, 6.27; N, 9.54 TLC: $R_f$=0.90 [9:1 $CH_2Cl_2$:MeOH($NH_3$)] HPLC (method A): retention time 10.60 min FAB MS: m/z 642 m ($M^+$+H)

EXAMPLE 180

1-(1-(4-(1-((3-N-Cyclopropyl-N-methylamino)propylsulfonyl)piperidin-4-yloxy)-2-methoxyphenylacetyl)piperidin-4-yl)-1,2-dihydro-4(H)-3,1-benzoxazin-2-one

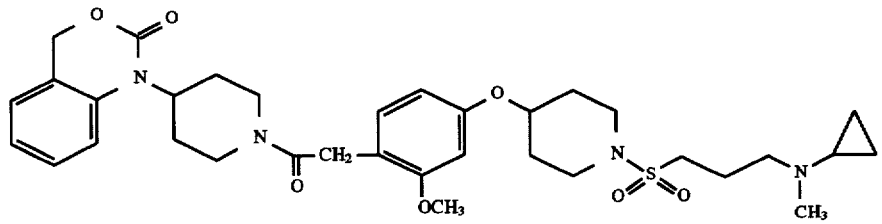

Step 1

To a stirred 0° C. solution of 1-(1-(4-(4-piperidinyloxy)-2-methoxyphenylacetyl)piperidin-4-yl)-1,2-dihydro-4(H)-3,1-benzoxazin-2-one hydrochloride (1.0 g, 1.9 mmol) from Example 123 and DIEA (0.83 mL; 4.8 mmol) in $CH_2Cl_2$ (50 mL) was added 3-chloropropylsulfonyl chloride (0.34 g; 1.9 mmol) dropwise. The reaction mixture was diluted with $CH_2Cl_2$ (100 mL) and washed with 5% aqueous citric acid (50 mL), saturated aqueous $NaHCO_3$ (2×50 mL) and brine (50 mL). The EtOAc layer was dried ($MgSO_4$), filtered, and the solvent was removed under reduced pressure. 1-(1-(4-(1-(3-Chloropropylsulfonyl)piperidin-4-yloxy)-2-methoxyphenylacetyl)piperidin-4-yl)-1,2-dihydro-4(H)-3,1-benzoxazin-2-one was obtained as an amorphous solid (TLC: $R_f$=0.40 (98:2 $CH_2Cl_2$:MeOH); HPLC (method A): retention time 9.50 min).

Step 2

A solution of 1-(1-(4-(1-(3-chloropropylsulfonyl)piperidin-4-yloxy)-2-methoxyphenylacetyl)piperidin-4-yl)-

1,2-dihydro-4(H)-3,1-benzoxazin-2-one (1.2 g, 1.8 mmol) from Step 1 above and NaI (2.5 g; 17 mmol) in acetone (70 mL) was heated at reflux for 48 h. The solution was cooled to ambient temperature and the solvent was removed under reduced pressure. The residue was dissolved in $CH_2Cl_2$ (100 mL) and washed with saturated aqueous $NaHCO_3$ (2×50 mL), 5% aqueous sodium sulfite (2×50 mL), and brine (50 mL). The $CH_2Cl_2$ layer was dried ($MgSO_4$), filtered, and the solvent was removed under reduced pressure to give 1-(1-(4-(1-(3-iodopropylsulfonyl)piperidin-4-yloxy)-2-methoxyphenylacetyl)piperidin-4-yl)-1,2-dihydro-4(H)-3,1-benzoxazin-2-one as an amorphous solid (TLC $R_f$=0.40 (98:2 $CH_2Cl_2$:MeOH); HPLC (method A) retention time= 9.80 min).

Step 3

1-(1-(4-(1-(3-Iodopropylsulfonyl)piperidin-4-yloxy)-2-methoxyphenylacetyl)piperidin-4-yl)-1,2-dihydro-4(H)-3,1-benzoxazin-2-one (0.50 g; 0.72 mmol) from Step 2 above was dissolved in 1:1 MeOH:DMF (10 mL) and cyclopropylamine (2 g; 35 mmol) was added. The solution was stirred at ambient temperature for 24 h. The solvents were removed under reduced pressure and the residue was dissolved in $CH_2Cl_2$ (100 mL) and washed with saturated aqueous $NaHCO_3$ (2×50 mL) and brine (50 mL). The $CH_2Cl_2$ layer was dried ($MgSO_4$), filtered, and the solvent was removed under reduced pressure to give 1-(1-(4-(1-((3-cyclopropylamino)-propylsulfonyl)piperidin-4-yloxy)-2-methoxyphenylacetyl)piperidin-4-yl)-1,2-dihydro-4(H)-3,1-benzoxazin-2-one as an amorphous solid (TLC: $R_f$=0.28 (97:3:0.3 $CH_2Cl_2$:MeOH:$NH_4OH$); HPLC (method A): retention time 7.10 min; FAB MS: m/z 641 ($M^++H$)).

Step 4

To a stirred solution of 1-(1-(4-(1-(3-cyclopropylamino)propylsulfonyl)piperidin-4-yloxy)-2-methoxyphenylacetyl)-piperidin-4-yl)-1,2-dihydro-4(H)-3,1-benzoxazin-2-one (0.5 g, 0.78 mmol) from Step 3 above in 100:1 MeOH:HOAc (10 mL) was added 37% aqueous formaldehyde (0.17 mL; 2.1 mmol) followed by the portionwise addition of $NaBH_3CN$ (0.12 g; 1.9 mmol). After being stirred at ambient temperature for 18 h, the mixture was evaporated under reduced pressure and the residue was partitioned between $CH_2Cl_2$ (150 mL) and saturated aqueous $NaHCO_3$ (100 mL). The organic phase was washed with brine (50 mL), dried ($MgSO_4$), filtered, and the solvent was removed under reduced pressure. The residue was purified by pressurized silica gel column chromatography using a gradient elution of 1:99 to 4:96 A:B (A=95:5 MeOH:$NH_4OH$, B=$CH_2Cl_2$). The title compound was dissolved in MeOH and to the solution was added 2 equivalents of 1.0N aqueous HCl. The resulting solution was evaporated under reduced pressure and the residue was dissolved in 3:2 $H_2O$:$CH_3CN$ and lyophilized. The HCl salt of the title compound was obtained as an amorphous powder.

Analysis calculated for ($C_{34}H_{46}N_4O_7S$, 1.0 HCl, 0.55 $H_2O$) C, 58.24; H, 6.91; N, 7.99 Found C, 58.19; H, 6.85; N, 8.25 TLC: $R_f$=0.27 (95:5:0.25 $CH_2Cl_2$:MeOH:$NH_4OH$) HPLC (method A): retention time 7.10 min FAB MS: m/z 655 ($M^++H$)

EXAMPLE 181

1-(1-(4-(1-((3-(3-Pyridylmethylamino)-3-methyl)butylsulfonyl)piperidin-4-yloxy)-2-methoxybenzoyl)piperidin-4-yl)-1,2-dihydro-4(H)-3,1-benzoxazin-2-one

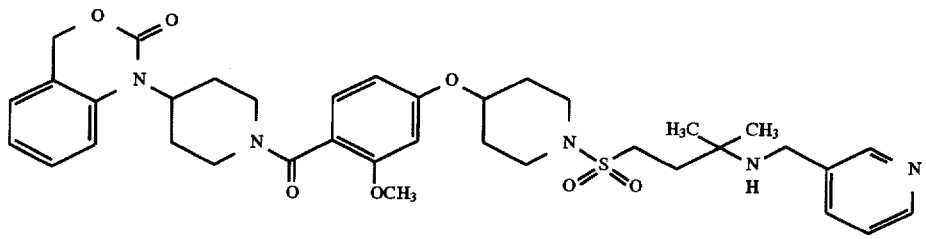

A solution of 1-(1-(4-(1-(3-amino-3-methyl)butylsulfonyl)piperidin-4-yloxy)-2-methoxybenzoyl)piperidin-4-yl)-1,2-dihydro-4(H)-3,1-benzoxazin-2-one trifluoroacetate from Example 68 (0.20 g; 0.33 mmol), sodium acetate (0.045 g; 0.54 mmol), and pyridine-3-carboxaldehyde (0.071 g; 0.66 mmol) in $CH_2Cl_2$ (10 mL) was stirred at ambient temperature for 30 min. To the solution was added $NaBH(OAc)_3$ (0.xx g; 0.xx mmol). The reaction was stirred at ambient temperature for 24 h. The reaction mixture was diluted with $CH_2Cl_2$ (50 mL) and washed with saturated aqueous $NaHCO_3$ (2×25 mL). The organic phase was dried ($MgSO_4$), filtered, and the solvent was removed under reduced pressure. The residue was purified by pressurized silica gel column chromatography using a gradient elution of 2:98 to 5:95 A:B (A=95:5 MeOH:$NH_4OH$, B=$CH_2Cl_2$). The title compound was dissolved in MeOH and 3 equivalents of 1N aqueous HCl was added. The solvent was removed under reduced pressure, the residue was dissolved in 3:1 $H_2O$:$CH_3CN$ and lyophilized. The hydrochloride salt of the title compound was obtained as an amorphous solid.

Analysis calculated for ($C_{37}H_{47}N_5O_7S$, 2.9 HCl, 1.55 $H_2O$) C, 52.94; H, 6.36; N, 8.34 Found C, 52.93; H, 6.37; N, 8.44 TLC: $R_f$=0.53 (98:2:0.5 $CH_2Cl_2$:MeOH:$NH_4OH$) HPLC (method B): retention time 12.4 min FAB MS: m/z 706 ($M^++H$)

EXAMPLE 182

1-(1-(4-(1-(3-Fluorobenzyl)piperidin-4-yloxy)-2-methoxybenzoyl)piperidin-4-yl)-1,2-dihydro-4(H)-3,1-benzoxazin-2-one

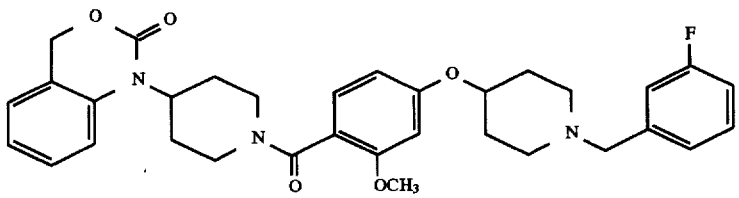

To a stirred solution of 3-fluoro-1-bromomethylbenzene (0.060 g; 0.32 mmol) in CH$_2$Cl$_2$ (10 mL) was added a solution of (1-(1-(4-(4-piperidinyloxy)-2-methoxybenzoyl)piperidin-4-yl)-1,2-dihydro-4(H)-3,1-benzoxazin-2-one (0.15 g, 0.32 mmol) from Example 26 and DIEA (0.11 mL; 0.64 mmol). The reaction was stirred at ambient temperature for 2 h. The reaction mixture was diluted with CH$_2$Cl$_2$ (100 mL) and washed with saturated aqueous NaHCO$_3$ (2×100 mL) and brine (50 mL). The CH$_2$Cl$_2$ layer was dried (MgSO$_4$), filtered, and the solvent was removed under reduced pressure. The residue was purified by pressurized silica gel column chromatography using a gradient elution of 97.5:2.5:0.25 to 95:5:0.5 CH$_2$Cl$_2$:MeOH:NH$_4$OH. The title compound was dissolved in MeOH and 3 equivalents of 1N aqueous HCl were added. The solvent was removed under reduced pressure, the residue was dissolved in 3:1 H$_2$O:CH$_3$CN and lyophilized. The hydrochloride salt of the title compound was obtained as an amorphous solid.

Analysis calculated for (C$_{33}$H$_{36}$N$_3$O$_5$, 2.0 HCl, 0.35 H$_2$O) C, 60.71; H, 5.97; N, 6.44 Found C, 60.74; H, 5.88; N, 6.43 TLC: R$_f$=0.40 (92:8:0.4 CH$_2$Cl$_2$:MeOH:NH$_4$OH) HPLC (method B): retention time 13.6 min FAB MS: m/z 574 (M$^+$+H)

EXAMPLE 183

1-(1-(4-(1-(3-Methoxybenzyl)piperidin-4-yloxy)-2-methoxybenzoyl)piperidin-4-yl)-1,2-dihydro-4(H)-3,1-benzoxazin-2-one

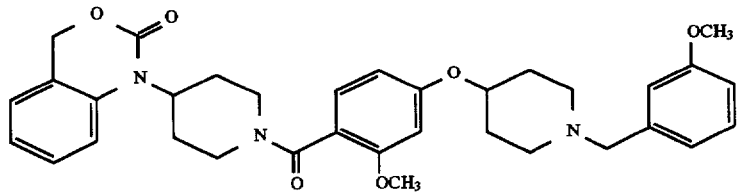

To a stirred solution of 3-methoxy-1-chloromethylbenzene (0.050 g; 0.32 mmol) in CH$_2$Cl$_2$ (10 mL) was added a solution of (1-(1-(4-(4-piperidinyloxy)-2-methoxybenzoyl)piperidin-4-yl)-1,2-dihydro-4(H)-3,1-benzoxazin-2-one (0.15 g, 0.032 mmol) from Example 26 and DIEA (0.11 mL; 0.64 mmol). The reaction was stirred at ambient temperature for 18 h. The reaction mixture was diluted with CH$_2$Cl$_2$ (100 mL) and washed with saturated aqueous NaHCO$_3$ (2×100 mL) and brine (50 mL). The CH$_2$Cl$_2$ layer was dried (MgSO$_4$), filtered, and the solvent was removed under reduced pressure. The residue was purified by preparative reverse phase HPLC using a water-acetonitrile gradient containing 0.1% TFA. Lyophilization of the product-containing fractions gave the TFA salt of the title compound as an amorphous solid.

Analysis calculated for (C$_{34}$H$_{39}$N$_3$O$_6$, 1.65 TFA, 0.40 H$_2$O) C, 57.36; H, 5.35; N, 5.38 Found C, 57.33; H, 5.35; N, 5.51 TLC: R$_f$=0.41 (92:8:0.4 CH$_2$Cl$_2$:MeOH:NH$_4$OH) HPLC (method B): retention time 13.8 min FAB MS: m/z 586 (M$^+$+H)

EXAMPLE 184

1-(1-(4-(1-(3-Cyanobenzyl)piperidin-4-yloxy)-2-methoxybenzoyl)piperidin-4-yl)-1,2-dihydro-4(H)-3,1-benzoxazin-2-one

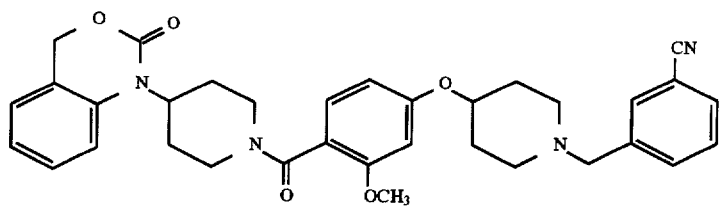

To a stirred solution of 3-cyano-1-bromomethylbenzene (0.063 g; 0.32 mmol) in $CH_2Cl_2$ (10 mL) was added a solution of (1-(1-(4-(4-piperidinyloxy)-2-methoxybenzoyl)piperidin-4-yl)-1,2-dihydro-4(H)-3,1-benzoxazin-2-one (0.15 g, 0.32 mmol) from Example 26 and DIEA (0.11 mL; 0.64 mmol). The reaction was stirred at ambient temperature for 18 h. The reaction mixture was diluted with $CH_2Cl_2$ (100 mL) and washed with saturated aqueous $NaHCO_3$ (2×100 mL) and brine (50 mL). The $CH_2Cl_2$ layer was dried ($MgSO_4$), filtered, and the solvent was removed under reduced pressure. The residue was purified by pressurized silica gel column chromatography using 95.5:5:0.5 $CH_2Cl_2$:MeOH:$NH_4OH$ as eluant. The title compound was obtained as an amorphous solid by evaporation of a methylene chloride solution under reduced pressure.

Analysis calculated for ($C_{34}H_{36}N_4O_5$, 0.15 $NH_4OH$, 0.8 $H_2O$) C, 68.02; H, 6.44; N, 9.68 Found C, 67.99; H, 6.64; N, 9.65 TLC: $R_f$=0.49 (92:8:0.4 $CH_2Cl_2$:MeOH:$NH_4OH$) HPLC (method B): retention time 13.1 min FAB MS: m/z 581 ($M^+$+H)

EXAMPLE 185

1-(1-(4-(1-(5-Chloro-2-thiophenylmethyl)piperidin-4-yloxy)-2-methoxybenzoyl)piperidin-4-yl)-1,2-dihydro-4(H)-3,1-benzoxazin-2-one

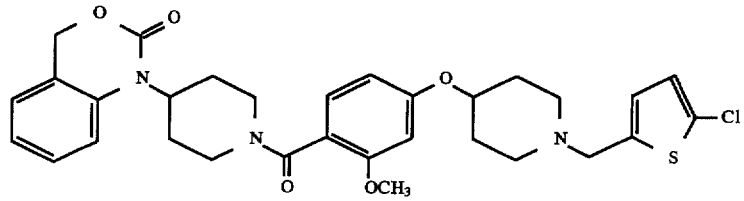

To a stirred solution of 5-chloro-1-chloromethylthiophene (0.053 g; 0.32 mmol) in $CH_2Cl_2$ (10 mL) was added a solution of (1-(1-(4-(4-piperidinyloxy)-2-methoxybenzoyl) piperidin-4-yl)-1,2-dihydro-4(H)-3,1-benzoxazin-2-one (0.15 g, 0.32 mmol) from Example 26 and DIEA (0.11 mL; 0.64 mmol). The reaction was stirred at ambient temperature for 18 h. The reaction mixture was diluted with $CH_2Cl_2$ (100 mL) and washed with saturated aqueous $NaHCO_3$ (2×100 mL) and brine (50 mL). The $CH_2Cl_2$ layer was dried ($MgSO_4$), filtered, and the solvent was removed under reduced pressure. The residue was purified by preparative reverse phase HPLC using a water-acetonitrile gradient containing 0.1% TFA. Lyophilization of the product-containing fractions gave the TFA salt of the title compound as an amorphous solid.

Analysis calculated for ($C_{31}H_{34}ClN_3O_5S$, 1.85 TFA, 0.25 $H_2O$) C, 51.35; H, 4.51; N, 5.18 Found C, 51.37; H, 4.50; N, 5.39 HPLC (method B): retention time 14.1 min FAB MS: m/z 597 ($M^+$+H)

EXAMPLE 186

1-(1-(4-(1-(2-Pyrazinylmethyl)piperidin-4-yloxy)-2-methoxybenzoyl)piperidin-4-yl)-1,2-dihydro-4(H)-3,1-benzoxazin-2-one

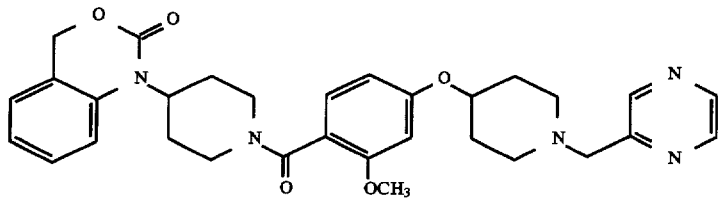

To a stirred solution of 2-chloromethylpyrazine (0.041 g; 0.32 mmol; ref: *J. Org. Chem.*, 1973, vol. 38, p. 2049) in $CH_2Cl_2$ (10 mL) was added a solution of (1-(1-(4-(4-piperidinyloxy)-2-methoxybenzoyl)piperidin-4-yl)-1,2-dihydro-4(H)-3,1-benzoxazin-2-one (0.15 g, 0.32 mmol) from Example 26 and DIEA (0.11 mL; 0.32 mmol). The reaction was stirred at ambient temperature for 18 h. The reaction mixture was diluted with $CH_2Cl_2$ (100 mL) and washed with saturated aqueous $NaHCO_3$ (2×100 mL) and brine (50 mL). The $CH_2Cl_2$ layer was dried ($MgSO_4$), filtered, and the solvent was removed under reduced pressure. The residue was purified by pressurized silica gel column chromatography using a gradient elution of 97.5:2.5:0.25 to 95:5:0.5 $CH_2Cl_2$:MeOH:$NH_4OH$. The title compound was dissolved in MeOH and 10 equivalents of TFA were added. The solvent was removed under reduced pressure, the residue was dissolved in 3:1 $H_2O$:$CH_3CN$ and lyophilized. The TFA salt of the title compound was obtained as an amorphous solid.

Analysis calculated for ($C_{31}H_{35}N_5O_5$, 2 TFA, 1.35 $H_2O$, 0.4 $CH_3CN$) C, 52.03; H, 4.99; N, 9.15 Found C, 52.00; H, 4.93; N, 9.15 TLC: $R_f$=0.44 (92:8:0.4 $CH_2Cl_2$:MeOH:$NH_4OH$) HPLC (method B): retention time 11.4 min FAB MS: m/z 558 ($M^++H$)

The hydrochloride salt of the title compound was obtained as an amorphous solid.

Analysis calculated for ($C_{33}H_{37}N_3O_6$, 0.65 HCl, 0.2 $H_2O$) C, 62.38; H, 6.19; N, 6.61 Found C, 62.39; H, 6.19; N, 6.77 TLC: $R_f$=0.45 (98:2:0.5 $CH_2Cl_2$:MeOH:$NH_4OH$) HPLC (method B): retention time 12.6 min FAB MS: m/z 572 ($M^++H$)

EXAMPLE 188

1-(1-(4-(1-(3,5-Dihydroxybenzyl)-piperidin-4-yloxy)-2-methoxybenzoyl)piperidin-4-yl)-1,2-dihydro-4(H)-3,1-benzoxazin-2-one

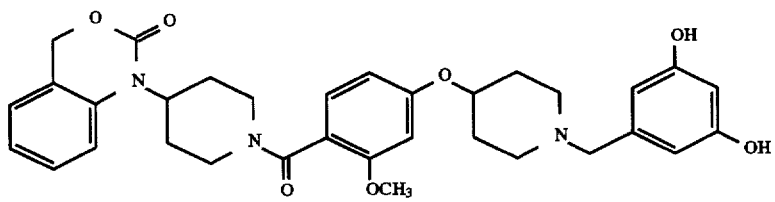

A solution of (1-(1-(4-(4-piperidinyloxy)-2-methoxybenzoyl)piperidin-4-yl)-1,2-dihydro-4(H)-3,1-benzoxazin-2-one (0.15 g, 0.32 mmol) from Example 26 and 3,5-dihydroxybenzaldehyde (0.088 g; 0.64 mmol) in dichloroethane (10 mL) was stirred at ambient temperature for 30 min. To the solution was added $NaBH(OAc)_3$ (0.20 g; 0.96 mmol). The reaction ws stirred at ambient temperature for 24 h. The solvents were removed under reduced pressure.

EXAMPLE 187

1-(1-(4-(1-(3-Hydroxybenzyl)-piperidin-4-yloxy)-2-methoxybenzoyl)piperidin-4-yl)-1,2-dihydro-4(H)-3,1-benzoxazin-2-one

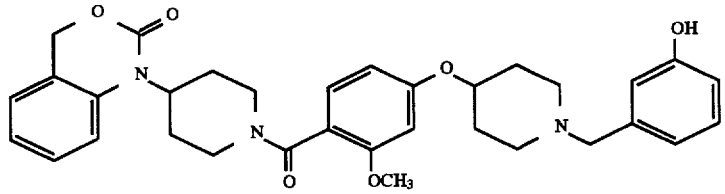

A solution of (1-(1-(4-(4-piperidinyloxy)-2-methoxybenzoyl)piperidin-4-yl)-1,2-dihydro-4(H)-3,1-benzoxazin-2-one (0.15 g, 0.32 mmol) from Example 26 and 3-hydroxybenzaldehyde (0.078 g; 0.64 mmol) in dichloroethane (10 mL) was stirred at ambient temperature for 30 min. To the solution was added $NaBH(OAc)_3$ (0.20 g; 0.0.96 mmol). The reaction ws stirred at ambient temperature for 24 h. The solvents were removed under reduced pressure. The residue was diluted with $CH_2Cl_2$ (50 mL) and washed with saturated aqueous $NaHCO_3$ (2×25 mL). The organic phase was dried ($MgSO_4$), filtered, and the solvent was removed under reduced pressure. The residue was purified by pressurized silica gel column chromatography using a gradient elution of 2.5:97.5 to 5:95 A:B (A=95:5 MeOH:$NH_4OH$, B=$CH_2Cl_2$). The title compound was dissolved in MeOH and 1 equivalent of 1N aqueous HCl was added. The solvent was removed under reduced pressure, the residue was dissolved in 3:1 $H_2O$:$CH_3CN$ and lyophilized.

The residue was diluted with $CH_2Cl_2$ (50 mL) and washed with saturated aqueous $NaHCO_3$ (2×25 mL). The organic phase was dried ($MgSO_4$), filtered, and the solvent was removed under reduced pressure. The residue was purified by preparative reverse phase HPLC using a water-acetonitrile gradient containing 0.1% TFA. Lyophilization of the product-containing fractions gave the TFA salt of the title compound as an amorphous solid.

Analysis calculated for ($C_{33}H_{37}N_3O_7$, 1.95 TFA1, 1.0 $H_2O$) C, 53.53; H, 4.98; N, 5.07 Found C, 53.50; H, 4.97; N, 5.29 HPLC (method B): retention time 11.9 min FAB MS: m/z 588 ($M^++H$)

EXAMPLE 189

1-(1-(4-(N-t-Butoxycarbonyl-4-piperidinyloxy)-2-methoxybenzoyl)piperidin-4-yl)-3,4-dihydro-2(1H)-qninolinone

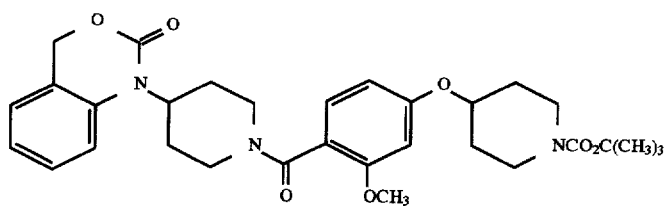

To 100 mL of dry degassed DMF was added 1-(piperidin-4-yl)-3,4-dihydro-2(1H)-quinolinone (1.0 gm, 4.34 mmol; prepared by the method of Ogawa et al. *J. Med. Chem.* 1993, vol. 36, pages 2011–2017). To the stirred solution was added 4-(1-tert-butyloxycarbonyl-4-piperidinyl)-2-methoxybenzoic acid (1.5 gm, 4.3 mmol) from Step 3 of Example 25, followed by HOBT (730 mg, 4.8 mmol), EDC (911 mg, 4.8 mmol) and DIEA (1.0 mL, 5.7 mmol). After stirring at ambient temperature overnight the solvent was removed under reduced pressure and the residue was partitioned between ethyl acetate and saturated aqueous sodium bicarbonate. The organic layer was washed with water (2×), brine and was dried over anhydrous MgSO$_4$. The solution was filtered and the solvent was removed under reduced pressure to give an oil which was purified by pressurized silica gel column chromatography using 1:1 EtOAc:hexanes as eluant. The product-containing fractions were combined and the solvent was removed under reduced pressure and the residue was precipitated from EtOAc-hexanes, filtered, and dried in vacuo for 16 hrs to give the title compound in as an amorphous solid.

Analysis: C$_{32}$H$_{41}$N$_3$O$_6$, 0.4 EtOAc 0.15 H$_2$O Calc. C, 67.07; H, 7.46; N, 6.98 Found C, 67.12; H, 0.75; N, 6.99 TLC: Rf=0.5 (90:10 CHCl$_3$:MeOH) HPLC (method A): retention time=10.10 min, purity=99% FAB MS: m/z=564 (M+H$^+$)

EXAMPLE 190

1-(1-(4-(4-Piperidinyloxy)-2-methoxybenzoyl)piperidin-4-yl)-3,4-dihydro-2(1H)-quinolinone

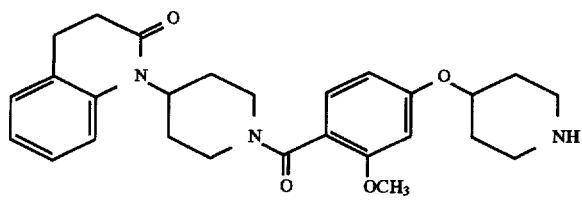

To 250 mL of dry ethyl acetate under N$_2$ was added 1-(1-(4-(N-t-Butoxycarbonyl-4-piperidinyloxy)-2-methoxybenzoyl)piperidin-4-yl)-3,4-dihydro-2(1H)-quinolinone (1.5 gm, 2.65 mmol) from Example 189 and the solution was cooled to 0° C. in an ice-water bath. Anhydrous HCl gas was bubbled into the solution at 0° C. until for 30 min. The saturated solution was stirred for an additional 30 min at 0° C. then the ice bath was removed and N$_2$ was bubbled through the mixture to remove excess HCl. Addition of hexane caused precipitation of the HCl salt. The solid was dried in vacuo to remove solvent and then was partitioned between ethyl acetate and saturated aqueous sodium bicarbonate. The organic layer was washed with water (2×) and brine, and was dried over anhydrous MgSO$_4$. The solvent was removed under reduced pressure to give the title compound as an amorphous solid.

Analysis: C$_{27}$H$_{31}$N$_3$O$_4$, 0.2 EtOAc 1.95 H$_2$O Calc. C, 64.91; H, 7.15; N, 8.17 found C, 64.93; H, 7.09, N, 8.15

TLC: Rf=0.15 (80:20 CHCl$_3$:MeOH) HPLC (method A): retention time=6.16 min, purity=99% FAB MS: m/z=462 (M+H$^+$)

EXAMPLE 191

1-(1-(4-(N-Acetyl-4-piperidinyloxy)-2-methoxybenzoyl)piperidin-4-yl)-3,4-dihydro-2(1H)-quinolinone

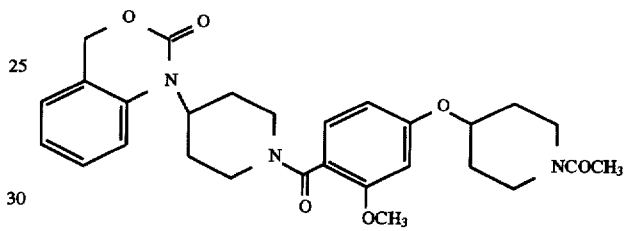

To a solution of 1-(1-(4-(4-piperidinyloxy)-2-methoxybenzoyl)piperidin-4-yl)-3,4-dihydro-2(1H)-quinolinone (150 mg, 0.27 mmol) from Example 190 in methylene chloride (10 mL) was added acetic anhydride (0.050 mL, 0.54 mmol) and DIEA (0.050 mL, 0.27 mmol) and the reaction was stirred at ambient temperature for 2 hours. The solvent was removed under reduced pressure and the residue was partitioned between ethyl acetate and saturated aqueous sodium bicarbonate. The organic layer was washed with water (2×) and brine, and was dried over anhydrous MgSO$_4$. The solvent was removed under reduced pressure to give the title compound as an amorphous solid.

Analysis: C$_{29}$H$_{33}$N$_3$O$_5$, 0.35 EtOAc 1.05 H$_2$O C, 65.98; H, 6.90; N, 7.59 Found C, 65.94; H, 7.16; N, 7.59 TLC: Rf=0.4 (90:10 CHCl$_3$:MeOH) HPLC (method A): retention time=7.52 min, purity=99% FAB MS: m/z=504 (M+H$^+$)

EXAMPLE 192

1-(1-(4-(N-Vinylsulfonyl-4-piperidinyloxy)-2-methoxybenzoyl)piperidin-4-yl)-3,4-dihydro-2(1H)-quinolinone

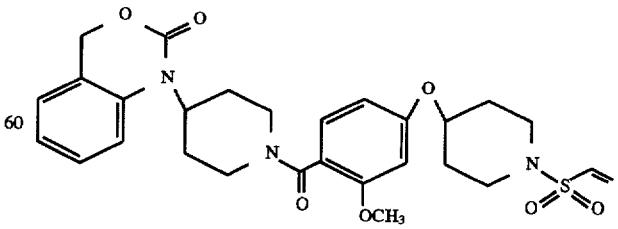

To a 25 mL flask containing 3 mL of methylene chloride was added 2-chloro-1-ethanesulfonyl chloride (0.046 mL, 0.44 mmol) and the solution was cooled to 0° C. under $N_2$. To a 10 mL addition funnel containing 8 mL of methylene chloride was added 1-(1-(4-(4-piperidinyloxy)-2-methoxybenzoyl)piperidin-4-yl)-3,4-dihydro-2(1H)-quinolinone (200 mg, 0.4 mmol) from Example 190 and DIEA (0.35 mL, 2.0 mmol). This solution was added slowly over 15 min to the cold, stirred solution of sulfonyl chloride. The reaction mixture was stirred at 0° C. for 30 min and then at ambient temperature for 16 hrs. The solvent was removed under reduced pressure and the residue was partitioned between ethyl acetate and water. The layers were separated and aqueous phase was extracted with ethyl acetate (3×). The combined organic phases were dried over $MgSO_4$ and filtered. The solvent was removed under reduced pressure and the residue purified by pressurized silica gel column chromatography using 95:5 $CH_2Cl_2$:MeOH as eluant. The product-containing fractions were combined and the solvent was removed under reduced pressure to give the title compound as an amorphous solid.

Analysis: $C_{29}H_{35}N_3O_6S$, 0.55 $H_2O$ C, 61.80; H, 6.46; N, 7.46 Found C, 61.82; H, 6.37; N, 7.43 TLC: Rf=0.2 (95:5 $CHCl_3$:MeOH) HPLC (method A): retention time=8.62 min, purity=99% FAB MS: m/z=554 (M+H$^+$)

EXAMPLE 193

1-(1-(4-(2-Diethylaminoethylsulfonyl-4-piperidinyloxy)-2-methoxybenzoyl)piperidin-4-yl)-3,4-dihydro-2(1H)-quinolinone

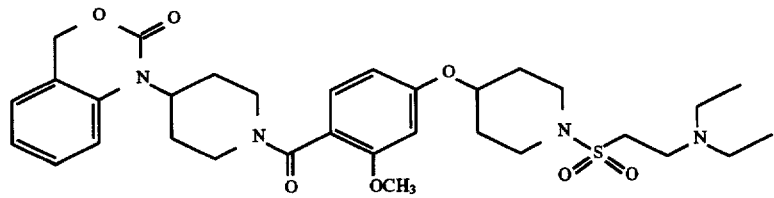

To a solution of 1-(1-(4-(N-vinylsulfonyl-4-piperidinyloxy)-2-methoxybenzoyl)piperidin-4-yl)-3,4-dihydro-2(1H)-quinolinone (80 mg, 0.14 mmol) from Example 192 in 5 mL of dry MeOH was added diethylamine (0.14 mL, 1.4 mmol) and the reaction stirred at ambient temperature for 16 hours. The solvent was removed under reduced pressure and the residue was purified by pressurized silica gel column chromatography using 98:2 $CH_2Cl_2$:MeOH as eluant. The product-containing fractions were combined and the solvent was removed under reduced pressure. The residue was dissolved in EtOAc and the solvent was removed under reduced pressure to give the title compound as an amorphous solid.

Analysis: $C_{33}H_{46}N_4O_6S$, 0.05 EtOAc 1.25 $H_2O$ C, 60.99; H, 7.54; N, 8.57 Found C, 60.96; H, 0.15; N, 8.34 TLC: Rf=0.6 (95:5 $CHCl_3$:MeOH) HPLC (method A): retention time=7.48 min, purity=97% FAB MS: m/z=627(M+H$^+$)

EXAMPLE 194

1-(1-(4-(N-tert-Butyloxycarbonyl-4-piperidinyloxy)-2-methoxyphenylacetyl)piperidin-4-yl)-3,4-dihydro-2(1H)-quinolinone

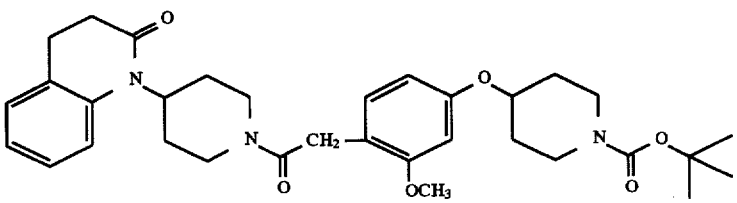

To 100 mL of dry degassed DMF was added 1-(piperidin-4-yl)-3,4-dihydro-2(1H)-quinolinone (1.0 gm, 4.34 mmol; prepared by the method of Ogawa et al. *J. Med. Chem.* 1993, vol. 36, pages 2011–2017). To the stirred solution was added 4-(N-tert-butyloxycarbonyl-4-piperidinyloxy)-2-methoxyphenylacetic acid (1.59 gm, 4.34 mmol) from Step 4 of Example 123, followed by HOBT (730 mg, 4.8 mmol), EDC (911 mg, 4.8 mmol) and DIEA (1.0 mL, 5.7). After stirring at ambient temperature overnight the solvent was removed under reduced pressure and the residue was partitioned between ethyl acetate and saturated aqueous sodium bicarbonate. The organic layer was washed with water (2×) and brine, and was dried over anhydrous $MgSO_4$. The solution was filtered and the solvent was removed under reduced pressure to give an oil which was purified by pressurized silica gel column chromatography using 98:2 $CH_2Cl_2$:MeOH as eluant. The product-containing fractions were evaporated under reduced pressure to give the title compound as an amorphous solid.

Analysis: $C_{33}H_{43}N_3O_6$ 0.2 $H_2O$ C, 68.17; H, 7.53; N, 7.23 Found C, 68.60; H, 7.50; N, 7.27 TLC: Rf=0.45 (95:5 $CHCl_3$:MeOH) HPLC (method A): retention time=10.34 min, purity=99% FAB MS: m/z=578 (M+H$^+$)

EXAMPLE 195

1-(1-(4-(4-Piperidinyloxy)-2-methoxyphenylacetyl) piperidin-4-yl)-3,4-dihydro-2(1H)-quinolinone

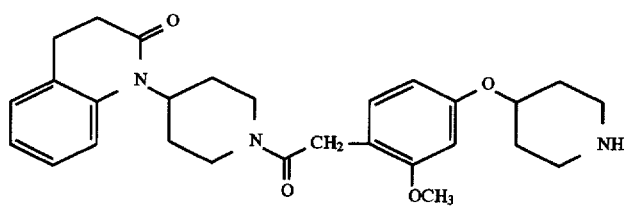

To 250 mL of dry ethyl acetate under N₂ was added 1-(1-(4-(N-tert-Butyloxycarbonyl-4-piperidinyloxy)-2-methoxyphenylacetyl)-piperidin-4-yl)-3,4-dihydro-2(1H)-quinolinone (1.2 g, 2 mmol) from Example 194, and the solution was cooled to 0° C. in an ice-water bath. Anhydrous HCl gas was bubbled into the solution at 0° C. for 30 min. The solution was stirred for an additional 30 min at 0° C. then the ice bath was removed and N₂ was bubbled through the solution to remove the excess HCl. Addition of hexane caused precipitation of the HCl salt. The solid was dried in vacuo to remove solvent and then was partitioned between ethyl acetate and saturated aqueous sodium bicarbonate. The organic layer was washed with water and brine and was dried over anhydrous MgSO₄. The solvent was removed under reduced pressure. The residue was dissolved in methylene chloride and the solvent was removed under reduced pressure to give the title compound as an amorphous solid.

Analysis: C₂₈H₃₅N₃O₄, 1.3 CH₂Cl₂, 0.15 H₂O C, 59.57; H, 6.47; N, 7.11 Found C, 59.59; H, 6.28; N, 7.23 TLC: Rf=0.15 (90:10 CHCl₃:MeOH) HPLC (method A): retention time=7.1 min, purity=97% FAB MS: m/z=478 (M+H⁺)

EXAMPLE 196

1-(1-(4-(1-(3-Methyl-2-pyridylmethyl)-4-piperidinyloxy)-2-methoxyphenylacetyl)piperidin-4-yl)-3,4-dihydro-2(1H)-quinolinone

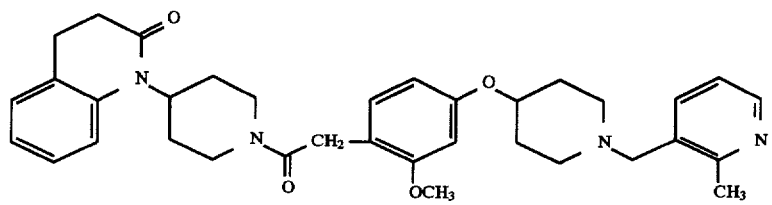

To a solution of 1-(1-(4-(4-piperidinyloxy)-2-methoxyphenylacetyl)piperidin-4-yl)-3,4-dihydro-2(1H)-quinolinone (200 mg, 0.34 mmol) from Example 195 in dry degassed DMF (5 mL) was added 2-methyl-3-chloromethylpyridine (100 mg, 0.68 mmol) and DIEA (0.10 mL, 0.66 mmol) and the reaction was warmed to 50° C. for 72 hours. The solvent was removed under reduced pressure and the residue was purified by pressurized silica gel column chromatography using 98:2 CH₂Cl₂:MeOH as eluant. The product-containing fractions were combined and the solvent was removed under reduced pressure. The residue was lyophilized from acetonitrile-water to give the title compound as an amorphous solid.

Analysis: C₃₅H₄₂N₄O₄, 0.75 H₂O C, 70.50; H, 7.35; N, 9.40 Found C, 70.46; H, 7.13; N, 9.48 TLC: Rf=0.4 (95:5 CHCl₃:MeOH) HPLC (method A): retention time=6.92 min, purity=95% FAB MS: m/z=583 (M+H⁺)

EXAMPLE 197

1-[1-(3-iodo-benzoyl)-piperidin-4-yl]-1,4-dihydro-benzo[1,3]oxazin-2-one

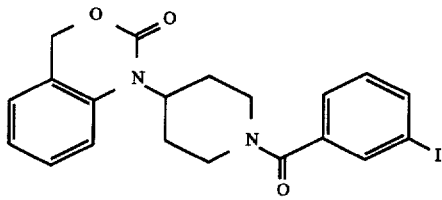

To a solution of 1-piperidin-4-yl-1,4-dihydro-benzo[1,3]oxazine-2-one hydrochloride (2 g, 7.44 mmol) from Step 4 of Example 1 in methylene chloride (200 mL) was added 3-iodo benzoic acid (2.03 g, 8.18 mmol) followed by HOBT (1.21 g, 8.92 mmol), DIEA (1.3 mL, 7.44 mmol), and EDC (1.71 g, 8.92 mmol). After 18 h, the mixture was concentrated, then partitioned between ethyl acetate and 1M sodium hydroxide (250 mL of each). The ethyl acetate layer was washed with 1M HCl and brine, then dried over sodium sulfate and concentrated. Flash chromatography (3% methanol in methylene chloride as eluant) afforded the title compound as a white foam.

HPLC: method C, Retention time=14.07 min; FAB MS: M+1 at 463

Analysis calculated for C20H19N2O3I1 C 51.96; H 4.14; N 6.06 Found: C 52.03; H 4.27; N 6.13

EXAMPLE 198

3-{3-[4-(2-oxo-4H-benzo1,3]oxazin-1-yl)-piperidine-1-carbonyl]-phenyl}-acrylic acid methyl ester

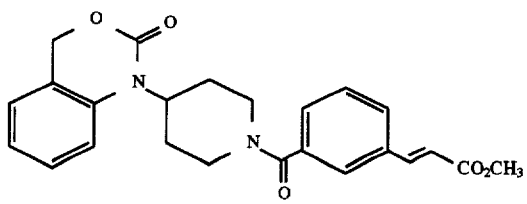

To a solution of 1-[1-(3-iodo-benzoyl)-piperidin-4-yl]-1,4-dihydro-benzo[1,3]oxazin-2-one from Example 197 (500 mg, 1.08 mmol) in DMF (50 mL) was added methyl acrylate (0.117 mL, 1.3 mmol), followed by sodium acetate (176 mg, 2.16 mmol), sodium bicarbonate (182 mg, 2.16 mmol), and palladium acetate (24 mg, 0.11 mmol). The temperature was increased to approximately 100° C. After 4 h, the mixture was cooled then concentrated. Flash chromatography (70% ethyl acetate in hexanes as eluant) afforded the title compound as a white foam.

HPLC: method A, retention time=9.33 min; 98% FABMS: M+1 at 421

Analysis calculated for C24H24N2O5+0.35 water C 67.54; H 5.83; N 6.56 Found: C 67.50; H 5.73; N 6.35

EXAMPLE 199

3-{3-[4-(2-oxo-4H-benzo1,3]oxazin-1-yl)-piperidine-1-carbonyl]-phenyl}-propionic acid methyl ester

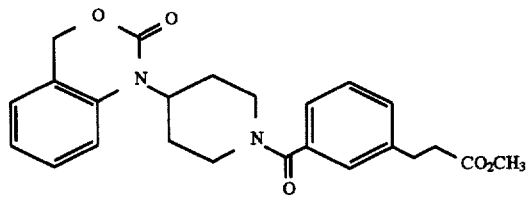

To a solution of 3-{3-[4-(2-oxo-4H-benzo1,3]oxazin-1-yl)-piperidine-1-carbonyl]-phenyl}-acrylic acid methyl ester from Example 198 (150 mg, 0.357 mmol) in methanol (15 mL) was added palladium black (15 mg). The mixture was placed under a hydrogen atmosphere at room pressure. After 4 h, the mixture was concentrated. Flash chromatography (70% ethyl acetate in hexanes as eluant) afforded the title compound as a white foam.

HPLC: method A, retention time=9.48 min; 98% FABMS: M+1 at 423

Analysis calculated for C24H26N2O5 C 67.85; H 6.52; N 6.70 Found: C 68.23; H 6.20; N 6.63

EXAMPLE 200

4-[4-(2-oxo-4H-benzo[1,3]oxazin-1-yl)-piperidine-1-carbonyl]-benzaldehyde

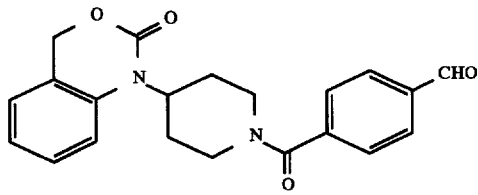

To a solution of 1-piperidin-4-yl-1,4-dihydro-benzo[1,3] oxazine-2-one hydrochloride (2 g, 7.44 mmol) from Step 4 of Example 1 in methylene chloride (200 mL) was added 4-carboxy benzaldehyde (1.23 g, 8.18 mmol) followed by HOBT (1.21 g, 8.92 mmol), DIEA (1.3 mL, 7.44 mmol), and EDC (1.71 g, 8.92 mmol). After 18 h, the mixture was concentrated, then partitioned between ethyl acetate and 1M sodium hydroxide (250 mL of each). The ethyl acetate layer was then washed with 1M HCl and brine, then dried over sodium sulfate and concentrated. Flash chromatography (70% ethyl acetate in hexanes as eluant) afforded the title compound as a whim foam.

HPLC: method C, retention time=13.90 min; FABMS: M+1 at 365

Analysis calculated for C21H20N2O4+0.35 methylene chloride+0.1 hexanes C 65.46; H 5.53; N 6.96 Found: C 65.50; H 5.63; N 7.12

EXAMPLE 201

1-[1-(4-hydroxymethyl-benzoyl)-piperidin-4-yl]-1,4,dihydro-benzo[1,3]oxazin-2-one

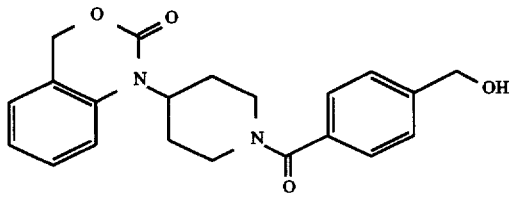

To a solution of 4-[4-(2-oxo-4H-benzo[1,3]oxazin-1-yl) piperidine-1-carbonyl]-benzaldehyde from Example 200 (200 mg, 0.549 mmol) in methanol (15 mL) was added sodium borohydride in several portions while monitoring the course of the reaction by TLC. After 4 h, the mixture was concentrated, then partitioned between ethyl acetate and 1M sodium hydroxide (50 mL of each). The ethyl acetate layer was washed with brine, dried over sodium sulfate, then concentrated. Flash chromatography (80% ethyl acetate in hexanes as eluant) afforded the title compound as a white foam.

HPLC: method A, retention time=7.48 min; 98% FABMS: M+1 at 367

Analysis calculated for C21H22N2O4+0.70 water C 66.54; H 6.22; N 7.39 Found: C 66.57; H 6.12; N 7.18

EXAMPLE 202

1-[1-(4-methoxymethyl-benzoyl)-piperidin-4-yl]-1,4,dihydro-benzo[1,3]oxazin-2-one

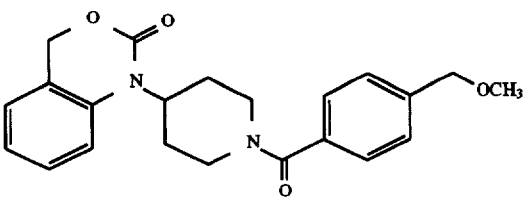

To a solution of 1-[1-(4-hydroxymethyl-benzoyl) piperidin-4-yl]-1,4,dihydro-benzo[1,3]oxazin-2-one from Example 201 (100 mg, 0.273 mmol) in THF (15 mL) was added methyl iodide (1 mL), followed by sodium hydride (60% dispersion in oil, 22 mg, 0.546 mmol). After 18 h, the mixture was concentrated, then partitioned between ethyl acetate and 1M HCl (50 mL of each). The ethyl acetate layer was washed with brine, dried over sodium sulfate, then concentrated. Flash chromatography (5% methanol in methylene chloride as eluant) afforded the title compound as a white foam.

HPLC: method A, retention time=8.59 min; 98% FABMS: M+1 at 381

Analysis calculated for C22H24N2O4+0.30 water C 68.47; H 6.43; N 6.91 Found: C 68.46; H 6.47; N 6.91

EXAMPLE 203

1-[1-(3-hydroxy-2-phenyl-propionyl)-piperidin-4-yl]
-1,4-dihydro-benzo[1,3]oxazin-2-one

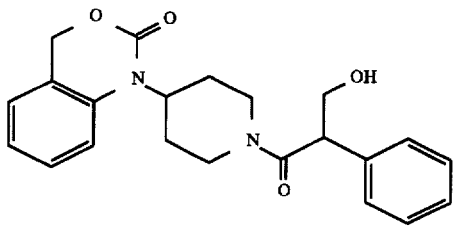

To a solution of 1-piperidin-4-yl-1,4-dihydro-benzo[1,3]oxazine-2-one hydrochloride (200 mg, 0.744 mmol) from Step 4 of Example 1 in DMF (50 mL) was added tropic acid (136 mg, 0.818 mmol), followed by BOP (395 mg, 0.893 mmol). After stirring for 18 h at room temperature, the mixture was concentrated, then partitioned between water and ethyl acetate (50 mL each). The ethyl acetate layer was dried over sodium sulfate then concentrated. Purification by flash chromatography using a gradient from 60 to 80% ethyl acetate in hexanes as eluant afforded the title compound as a white foam.

HPLC: method A, retention time=8.28 min; 98% FABMS: M+1 at 381

Analysis calculated for C22H24N2O4+0.90 water C 66.61; H 6.56; N 7.06 Found: C 66.65; H 6.37; N 6.90

EXAMPLE 204

1-[1-(2-methoxy-2-phenyl-acetyl)-piperidin-4-yl]-1,4-dihydro-benzo[1,3]oxazin-2-one

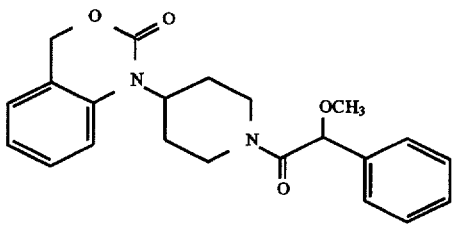

To a solution of 1-piperidin-4-yl-1,4-dihydro-benzo[1,3]oxazine-2-one hydrochloride (100 mg, 0.372 mmol) from Step 4 of Example 1 in DMF (25 mL) was added alpha methoxy phenylacetic acid (68 mg, 0.409 mmol), followed by BOP (197 mg, 0.446 mmol). After stirring for 18 h at room temperature, the mixture was concentrated, then partitioned between water and ethyl acetate (50 mL each). The ethyl acetate layer was dried over sodium sulfate then concentrated. Purification by flash chromatography using a gradient from 60 to 70% ethyl acetate in hexanes as eluant afforded the title compound as a white foam.

HPLC: method A, retention time=8.43 min; 95% FABMS: M+1 at 381

Analysis calculated for C22H24N2O4+0.30 water C 68.47; H 6.43; N 7.26 Found: C 68.46; H 6.37; N 7.63

EXAMPLE 205

1-{1-[2-hydroxy-2-(4-methoxy-phenyl)-acetyl]-piperidin-4-yl}-1,4-dihydro-benzo[1,3]oxazin-2-one

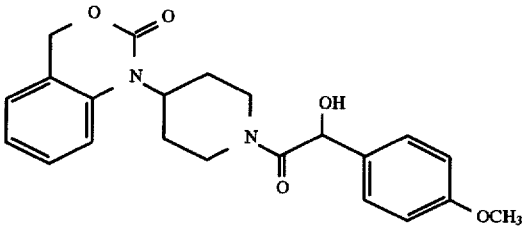

To a solution of 1-piperidin-4-yl-1,4-dihydro-benzo[1,3]oxazine-2-one hydrochloride (150 mg, 0.558 mmol) from Step 4 of Example 1 in DMF (50 mL) was added 4-methoxy mandelic acid (112 mg, 0.613 mmol), followed by BOP (296 mg, 0.670 mmol). After stirring for 18 h at room temperature, the mixture was concentrated, then partitioned between water and ethyl acetate (50 mL each). The ethyl acetate layer was dried over sodium sulfate then concentrated. Purification by flash chromatography using 5% methanol in methylene chloride as eluant afforded the title compound as a whim foam.

HPLC: method A, retention time=8.86 min; 95% FABMS: M+1 at 397

Analysis calculated for C22H24N2O5+0.40 water C 65.46; H 6.19; N 6.94 Found: C 65.51; H 6.19; N 7.20

EXAMPLE 206

1-{1-[2-methoxy-2-(4-methoxy-phenyl)-acetyl]-piperidin-4-yl}-1,4-dihydro-benzo[1,3]oxazin-2-one

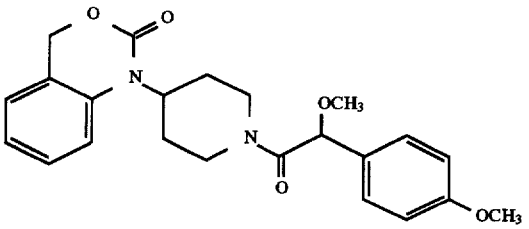

To a solution of 1-{1-[2-hydroxy-2-(4-methoxy-phenyl)acetyl]-piperidin-4-yl}-1,4-dihydro-benzo[1,3]oxazin-2-one from Example 205 (100 mg, 0.252 mmol) in THF (25 mL) was added methyl iodide (0.50 mL). Sodium hydride (0.28 mmol) was added and the reaction progress was monitored by TLC. After 5 h, the mixture was concentrated. Purification by flash chromatography using 5% methanol in methylene chloride as eluant afforded the desired product as a white foam.

HPLC: method A, retention time=10.02 min; 98% FABMS: M+1 at 411

Analysis calculated for C23H26N2O5+1.05 water C 64.33; H 6.60; N 6.52 Found: C 64.31; H 6.20; N 7.39

EXAMPLE 207

1-(1-(4-(N-t-Butoxycarbonyl-4-piperidinyloxy)-2-propargyloxybenzoyl)piperidin -4-yl)-1,2-dihydro-4(H)-3,1-benzoxazin-2-one

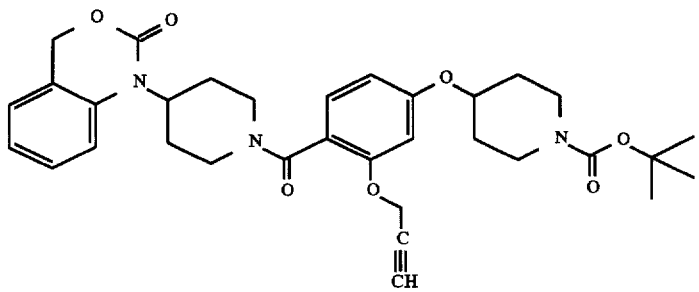

Step 1

Methyl 2-hydroxy-4-(N-t-butyloxycarbonyl-4-piperidinyloxy)benzoate (0.5 gm, 1.42 mmol) from Step 1 of Example 25 was dissolved in DMF (5 mL) and propargyl bromide (186 mg, 1.56 mmol) was added followed by cesium carbonate (925 mg, 2 eq.) and the mixture was stirred 16 hrs. The solids were removed by filtration and the filtrate solvents were removed under reduced pressure. The residue was purified by pressurized silica gel column chromatography using 1:1 ethyl acetate:hexanes as eluant. Methyl 2-propargyloxy-4-(N-t-butyloxycarbonyl-4-piperidinyloxy)benzoate was obtained as a gum.

Step 2

Methyl 2-propargyloxy-4-(N-t-butyloxycarbonyl-4-piperidinyloxy)benzoate (467 mg, 1.2 mmol) from Step 1 above was dissolved in methanol (10 mL) and to the stirred solution was added 1N NaOH (2.4 mL). The reaction was stirred for 4 h at 50° C. The cooled reaction was acidified with 5% aqueous citric acid (25 mL). The methanol was removed under reduced pressure and the remaining aqueous was extracted with methylene chloride (4×50 mL). The combined organic extracts were washed with water and brine, dried over magnesium sulfate and filtered. The solvent was removed under reduced pressure to give 2-propargyloxy-4-(N-t-butyloxycarbonyl-4-piperidinyloxy) benzoic acid.

Step 3

2-Propargyloxy-4-(N-t-butyloxycarbonyl-4-piperidinyloxy)benzoic acid (100 mg, 0.27 mmol) from Step 2 above was dissolved in DMF (10 mL) and 1-(4-piperidinyl)-1,2-dihydro-4(H)-3,1-benzoxazin-2-one hydrochloride from Step 4 of Example 1 (70 mg, 0.29 mmol) was added followed by HOBT (44.4 mg, 0.29 mmol), EDC (55.6 mg, 0.29 mmol) and DIEA (0.05 mL). The reaction was stirred for 16 hrs. The solvent was removed under reduced pressure and the residue was purified by pressurized silica gel column chromatography using 95:5 methylene chloride:methanol as eluant. The title compound was obtained as an amorphous solid by precipitiation from ethyl acetate and hexane.

Analysis: $C_{33}H_{39}N_3O_7$, 0.95 $H_2O$ calc. C 65.31 H 6.79 N 6.93 found 65.31 6.60 7.24

TLC: Rf=0.45 (95:5:0.5 $CH_2Cl_2$:MeOH:$H_2O$) HPLC (method A): retention time=9.91 min, purity=99% FAB MS: m/z=590 (M+H$^+$)

EXAMPLE 208

1-(1-(4-(N-t-Butoxycarbonyl-4-piperidinyloxy)-2-hydroxybenzoyl)piperidin-4-yl)-1,2-dihydro-4(H)-3,1-benzoxazin-2-one

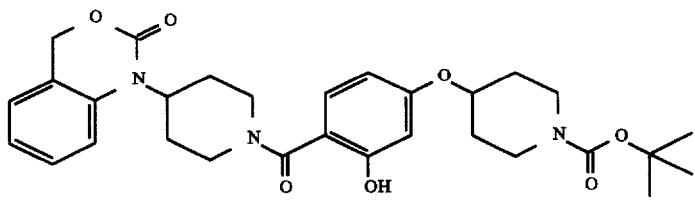

Step 1

Methyl 2-hydroxy-4-(N-t-Butyloxycarbonyl-4-piperidinyloxy)benzoate from Step 1 of Example 25 (0.5 gm, 1.42 mmol) was dissolved in methanol (10 mL) and 1N NaOH (2.4 mL) was added with stirring. The reaction was stirred for 4 hours at ambient temperature. The reaction was neutralized to pH 3 with 4N HCl, the methanol was removed under reduced pressure, and the remaining aqueous phase was extracted with methylene chloride (4×50 mL). The combined organic extracts were washed with water and brine, dried over magnesium sulfate and filtered. The solvent was removed under reduced pressure to give 2-hydroxy-4-piperidinyloxybenzoic acid.

Step 2

2-Hydroxy-4-piperidinyloxybenzoic acid from Step 1 above (100 mg, 0.30 mmol) was dissolved in DMF (10 mL) and 1-(4-piperidinyl)-1,2-dihydro-4(H)-3,1-benzoxazin-2-one hydrochloride from Step 4 of Example 1 (79 mg, 0.33 mmol) was added followed by HOBT (50.5 mg, 0.33 mmol), EDC (63 mg, 0.33 mmol) and DIEA (0.055 mL). The reaction stirred for 16 hrs. The solvent was removed under reduced pressure and the residue was purified by pressurized silica gel column chromatography using 95:5 methylene chloride:methanol as eluant. The product-containing fractions were combined and the solvent was removed under reduced pressure. The residue was further purified by preparative reverse phase HPLC using a H2O:CH3CN gradient containing 0.1% TFA. The title compound was obtained as an amorphous solid by lyophilization of the product-containing fractions.

Analysis: $C_{30}H_{37}N_3O_7$, 0.95 $CF_3CO_2H$ and 1.95 $H_2O$ calc. C 55.12 H 6.07 N 6.05 found 55.13 6.05 6.02

TLC: Rf=0.35 (95:5:0.5 CHCl₃:MeOH:NH₄OH) HPLC (method A): retention time=9.34 min, purity=99% FAB MS: m/z=552 (M+H⁺)

EXAMPLE 209

1-(1-(4-(N-t-Butoxycarbonyl-4-piperidinyloxy)-2-cyclopropylmethoxybenzoyl)piperidin-4-yl)-1,2-dihydro-4(H)-3,1-benzoxazin-2-one

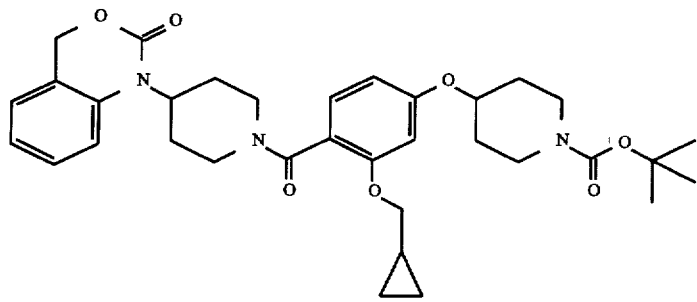

Step 1

Methyl 2-hydroxy-4-(N-t-butyloxycarbonyl-4-piperidinyloxy)benzoate (1.0 gm, 2.84 mmol) from Step 1 of Example 25 was dissolved in DMF (5 mL) and bromomethylcyclopropane (0.30 mL, 3.12 mmol) was added followed by cesium carbonate (1.8 g, 2 eq.) and the mixture was stirred 16 hrs. The mixture was filtered and the filtrate solvent was removed under reduced pressure. The residue was purified by pressurized silica gel column chromatography using 1:1 ethyl acetate:hexanes as eluant to give methyl 2-hydroxy-4-(N-t-butyloxycarbonyl-4-piperidinyloxy)-benzoate (1 g, 2.5 mmol).

Step 2

Methyl 2-hydroxy-4-(N-t-butyloxycarbonyl-4-piperidinyloxy)-benzoate (1 g, 2.5 mmol) from Step 1 above was dissolved in methanol (20 ml) and to the stirred solution was added 1N NaOH (5 mL). The reaction was stirred for 4 hrs. The reaction was neutralized with to pH 3 with 4N HCl, the methanol was removed under reduced pressure, and the remaining aqueous phase was extracted methylene chloride (4×100 mL). The combined organic extracts were washed with water and brine, dried over magnesium sulfate and filtered. The solvent was removed under reduced pressure to give 2-cyclopropylmethoxy-4-(N-t-butyloxycarbonyl-4-piperidinyloxy)benzoic acid (820 mg, 2.0 mmol).

Step 3

2-Cyclopropylmethoxy-4-(N-t-butyloxycarbonyl-4-piperidinyloxy)benzoic acid (820 mg, 2.0 mmol) from Step 2 above was dissolved in DMF (10 mL) and 1-(4-piperidinyl)-1,2-dihydro-4(H)-3,1-benzoxazin-2-one hydrochloride from Step 4 of Example 1 (515 mg, 2.2 mmol) was added followed by HOBT (300 mg, 2.2 mmol), EDC (420 mg, 2.2 mmol) and DIEA (0.75 mL). The reaction stirred for 16 hrs. The solvent was removed under reduced pressure and the residue was purified by pressurized silica gel column chromatography using 95:5 methylene chloride:methanol as eluant. The title compound was obtained as an amorphous solid by precipitation from ethyl acetate and hexanes.

Analysis: C₃₄H₄₃N₃O₇, 1.9 H₂O calc. C 63.80 H 7.37 N 6.57 found 63.83 7.25 7.02

TLC: Rf=0.45 (95:5:0.5 CH₂Cl₂:MeOH:NH₄OH) HPLC (method A): retention time=10.86 min, purity=98% FAB MS: m/z=606 (M+H⁺)

EXAMPLE 210

1-(1-(4-(N-Acetyl-4-piperidinyloxy)-2-hydroxybenzoyl)piperidin-4-yl)-1,2-dihydro-4(H)-3,1-benzoxazin-2-one

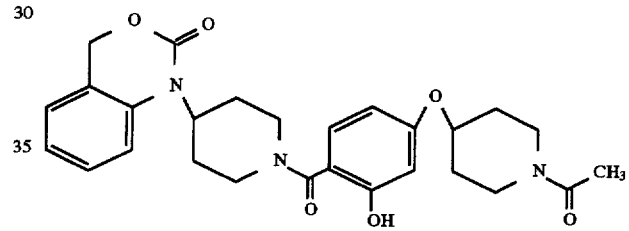

Step 1

To 200 mL of dry ethyl acetate under N₂ was added 1-(1-(4-(N-tert-butyloxycarbonyl-4-piperidinyloxy)-2-hydroxybenzoyl)piperidin-4-yl)-1,2-dihydro-4(H)-3,1-benzoxazin-2-one (900 mg) from Example 208 and the solution was cooled to 0° C. in an ice-water bath. Anhydrous HCl gas was bubbled into the solution at 0° C. for 30 min. The saturated solution was stirred for an additional 30 min at 0° C., then the ice bath was removed and N₂ was bubbled through the solution to remove excess HCl. Addition of hexane precipitated the HCl salt. The solid was dried in vacuo to remove solvent and then was partitioned between ethyl acetate and saturated aqueous sodium bicarbonate. The organic layer was washed with water and brine, dried over anhydrous MgSO₄ and filtered. The solvent was removed under reduced pressure to give 1-(1-(4-(4-piperidinyloxy)-2-hydroxybenzoyl)piperidin-4-yl)-1,2-dihydro-4(H)-3,1-benzoxazin-2-one as an amorphous solid.

Step 2

To a solution of 1-(1-(4-(4-piperidinyloxy)-2-hydroxybenzoyl)piperidin-4-yl)-1,2-dihydro-4(H)-3,1-benzoxazin-2-one (100 mg, 2.2 mmol) from Step 1 above in CH₂Cl₂ (50 mL) was added pyridine (0.25 mL, 1.25 eq) and acetic anhydride (0.23 mL, 1.1 eq.) and the reaction was stirred at ambient temperature for 16 hours. The solvent was removed under reduced pressure and the resulting mixture was purified by preparative reverse phase HPLC using an H2O:CH3CN gradient containing 0.1% TFA. The fractions containing product were combined and lyophilized to give the title compound as an amorphous solid.

Analysis: $C_{27}H_{31}N_3O_6$ 0.6 TFA 1.05 $H_2O$ calc. C 58.30 H 5.85 N 7.23 found 58.28 5.56 7.63

TLC: Rf=0.3 (95:5 $CHCl_3$:MeOH) HPLC (method A): retention time=8.03 min. purity=99% FAB MS: m/z=494 (M+H$^+$)

EXAMPLE 211

1-(1-(4-(N-(3-Methoxylcarbonylbenzyl)-4-piperidinyloxy)-2-hydroxybenzoyl)piperidin-4-yl)-1,2-dihydro-4(H)-3,1-benzoxazin-2-one

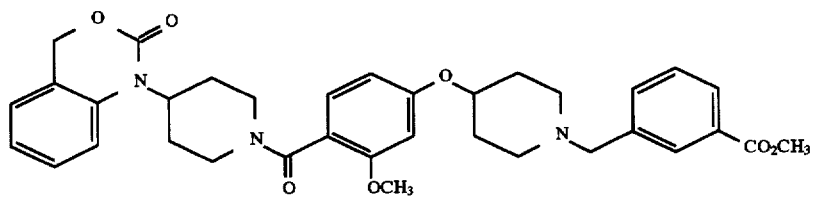

To a stirred solution of 1-(1-(4-(4-piperidinyloxy)-2-methoxybenzoyl)piperidin-4-yl)-1,2-dihydro-4(H)-3,1-benzoxazin-2-one from Example 26 (200 mg, 0.43 mmol) in dry DMF (10 mL) was added methyl 3-chloromethylbenzoate (400 mg, 5 eq) followed by DIEA (0.15 mL, 2 eq) and the solution was warmed to 50° C. for 72 hours. The solvent was removed under reduced pressure and the residue was purified by preparative reverse phase HPLC using a $CH_3CN$:$H_2O$ gradient containing 0.1% TFA. The product-containing fractions were combined and lyophilized to give the TFA salt of title compound as an amorphous solid.

Analysis: $C_{35}H_{39}N_3O_7$ 1.65 TFA 0.15 $H_2O$ calc. C 57.17 H 5.13 N 5.22 found 57.19 5.13 5.39

TLC: Rf=0.4 (95:5 $CHCl_3$:MeOH) HPLC (method A): retention time=8.39 min. purity=99% FAB MS: m/z=614 (M+H$^+$)

EXAMPLE 212

1-(1-(4-(N-(4-Carboxamidopyrimidin-2-yl)-4-piperidinyloxy)-2-hydroxybenzoyl)piperidin-4-yl)-1,2-dihydro-4(H)-3,1-benzoxazin-2-one

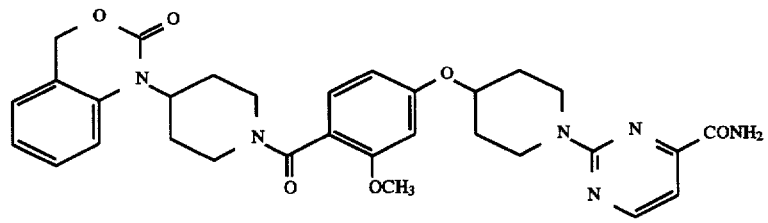

To a stirred solution of 1-(1-(4-(4-piperidinyloxy)-2-methoxybenzoyl)piperidin-4-yl)-1,2-dihydro-4(H)-3,1-benzoxazin-2-one from Example 26 (200 mg, 0.43 mmol) in dry DMF (5 mL) was added 2-chloropyrimidine 4-carboxamide (0.074 g, 0.47 mmol) followed by DIEA (0.16 mL, 0.86 mmol) and the solution was warmed to 50° C. for 16 hours. The solvent was removed under reduced pressure and the residue was dissolved in CH2Cl2 (100 mL) and washed with saturated aqueous NaHCO3 (2×50 mL). The organic phase was dried (MgSO4), filtered, and the solvent was removed under reduced pressure. The residue was triturated in EtOAc to give the title compound as an amorphous solid.

Analysis: $C_{31}H_{34}N_6O_6$ 0.95 $H_2O$ calc. C 61.67 H 5.99 N 13.92 found 61.50 5.73 13.97

TLC: Rf=0.19 (97:3 $CH_2Cl_2$:MeOH) HPLC (method A): retention time=8.15 min. purity=99% FAB MS: m/z=587 (M+H$^+$)

EXAMPLE 213

1-(1-(4-(N-(4-Cyanopyrimidin-2-yl)-4-piperidinyloxy)-2-hydroxybenzoyl)piperidin-4-yl)-1,2-dihydro-4(H)-3,1-benzoxazin-2-one

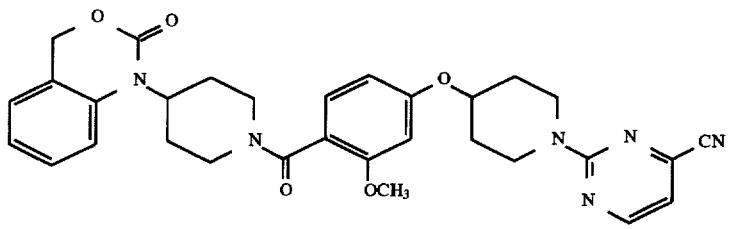

To a solution of 1-(1-(4-(N-(4-carboxamidopyrimidin-2-yl)-4-piperidinyloxy)-2-hydroxybenzoyl)piperidin-4-yl)-1,2-dihydro-4(H)-3,1-benzoxazin-2-one from Example 212 (500 mg.0.85 mmol) in dry CH2Cl2 (20 mL) stirring at ambient temperature under argon was added methyl (carboxysulfamoyl)triethylammonium hydroxide inner salt (Burgess reagent) (600 mg, 3 eq.) in 5 portions over 2 hours. The reaction was stirred for 16 hours. The solvent was removed under reduced pressure and the residue was purified by pressurized silica gel column chromatography using 3:7 EtOAc:hexanes. The fractions containing product were combined and the solvent was removed under reduced pressure. The product was further purified by preparative reverse phase HPLC using an H2O:CH3CN gradient containing 0.1% TFA. The fractions containing product were combined and lyophilized to give the title compound as an amorphous solid.

Analysis: $C_{31}H_{32}N_6O_5$ 1.05 TFA 0.15 $H_2O$ calc. C 57.52 H 4.86 N 12.16 found 57.54 4.77 12.38

TLC: Rf=0.5 (95:5 $CHCl_3$:MeOH) HPLC (method A): retention time=10.81 min, purity=99% FAB MS: m/z=692 (M+H$^+$)

EXAMPLE 214

1-(1-(4-Hydroxy-2-methoxybenzoyl)piperidin-4-yl)-1,2-dihydro-4(H)-3,1-benzoxazin-2-one

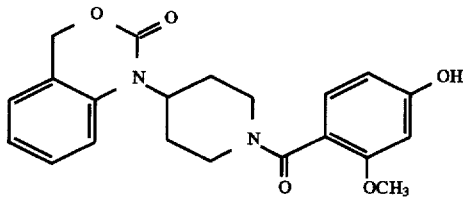

Step 1

To a solution of methyl 2,4-dihydroxybenzoate (50 gm, 300 mmol) in acetone (1 L) was added potassium carbonate (150 gm) and benzyl bromide (37 mL, 1.1 eq). The mixture was refluxed for 6 hours and cooled to ambient temperature. The reaction was poured into ice cold aqueous 1M HCl (1 L) and the aqueous mixture was extracted with ether (3×500 mL). The combined organic extracts were dried over MgSO4 and filtered and the solvent was removed under reduced pressure. Methyl 2-hydroxy-4-benzyloxybenzoate was obtained by crystallization from EtOH in 60% yield.

Step 2

To a solution of methyl 2-hydroxy-4-benzyloxybenzoate (50 g, 194 mmol) in dry DMF (500 mL) was added methyl iodide (30 mL, 2.5 eq) and the solution was cooled to 0° C. under argon. The solution was stirred at 0° C. and sodium hydride (60% dispersion in mineral oil, 12 g, 1.5 eq) was added in several portions over 15 minutes. The reaction was allowed to warm to ambient temperature with stirring over 18 hours. The reacton was quenched with 12 mL of acetic acid and the solvent was removed under reduced pressure. The residue was partitioned between methylene chloride (700 mL) and saturated sodium bicarbonate (700 mL) and the organic layer was washed with water (2×700 mL), brine, dried over MgSO4, and filtered. The solvent was removed under reduced pressure to give methyl 2-methoxy-4-benzyloxybenzoate as a crystalline solid in 90% yield.

Step 3

To a solution of methyl 2-methoxy-4-benzyloxybenzoate (40 g, 147 mmol) from Step 2 above in EtOAc (200 mL) in a Parr shaker flask was added 2 gm of 10% Pd/C catalyst. The reaction was shaken under on a Parr hydrogenation apparatus under 55 psi of $H_2$ for 24 hours. The catalyst was filtered off under a blanket of argon and the solvent was removed under reduced pressure. The resulting solid washed with a small volume of EtOAc and filtered and dried in vacuo for 24 hours to give methyl 2-methoxy-4-hydroxybenzoate in 99% yield.

Step 4

To a solution of the methyl 2-methoxy-4-hydroxybenzoate (27 g, 147 mmol) from Step 3 above in MeOH (250 mL) was added 2N sodium hydroxide (147 mL, 2 eq) and the reaction was stirred for 5 hours at 40° C. The reaction was brought to pH 4 with the addition of 6N HCl and the solvent was reduced to one-third volume under reduced pressure. The aqueous mixture was extracted with methylene chloride (5×300 mL) and the combined organic phases were washed with water, brine, and dried over $MgSO_4$. The solution was filtered and the solvent removed under reduced pressure to give a solid which was suspended in ether and filtered. 2-Methoxy-4-hydroxybenzoic acid was obtained in 80% yield.

Step 5

To a solution of 1-(4-piperidinyl)-1,2-dihydro-4(H)-3,1-benzoxazin-2-one hydrochloride from Step 4 of Example 1 (5 g, 19 mmol) in dry DMF (200 mL) under argon at ambient temperature was added 2-methoxy-4-hydroxybenzoic acid from Step 4 above (3.13 g, 1 eq) followed by HOBT (3 g, 1.1 eq) and EDC (4 g, 1.1 eq) and DIEA (6.5 mL, 2 eq). The reaction stirred for 18 hours. The solvent was removed under reduced pressure and the residue was partitioned between methylene chloride (700 mL) and saturated sodium bicarbonate (700 mL) and the organic layer was washed with water (2×700 mL), brine, dried over MgSO4 and filtered. The solvent was removed under reduced pressure to give an oil which was purified by pressurized silica gel column chromatography using 98:2 CH2Cl2:MeOH as eluant. The title compound was obtained as an amorphous solid.

Analysis: $C_{21}H_{22}N_2O_5$ 0.2 MeOH calc. C 65.48 H 5.91 N 7.21 found 65.44 5.77 7.39

TLC: Rf=0.4 (95:5 $CHCl_3$:MeOH) HPLC (method A): retention time=7.21 min, purity=98% FAB MS: m/z=383 (M+H$^+$)

EXAMPLE 216

1-(1-(4-(3-Methoxycarbonylbenzyloxy)-2-methoxybenzoyl)piperidin-4-yl)-1,2-dihydro-4(H)-3,1-benzoxazin-2-one

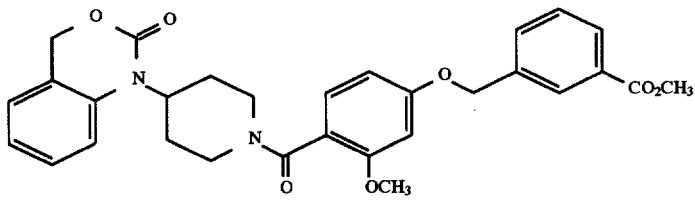

EXAMPLE 215

1-(1-(4-Benzyloxy-2-methoxybenzoyl)piperidin-4-yl)-1,2-dihydro-4(H)-3,1-benzoxazin-2-one

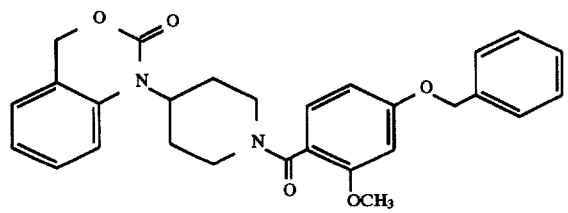

To a solution of 1-(4-piperidinyl)-1,2-dihydro-4(H)-3,1-benzoxazin-2-one hydrochloride from Step 4 of Example 1 (228 mg, 0.78 mmol) in dry DMF under argon at ambient temperature was added 2-methoxy-4-benzoxybenzoic acid (200 mg, 0.78 mmol) followed by HOBT (131 mg, 1.1 eq) and EDC (163 mg, 1.1 eq) and DIEA (0.25 mL, 2 eq). The reaction stirred for 18 hours and the solvent was removed under reduced pressure. The residue was partitioned between methylene chloride (100 mL) and saturated sodium bicarbonate (100 mL) and the organic layer was washed 2xs with 100 mL volumes of water, brine, and dried over MgSO4. The organics were filtered and the solvent was removed under reduced pressure to give an oil which was purified by pressurized silica gel column chromatography using 98:2 CH2Cl2:MeOH as eluant. The fractions containing product were combined and the solvent was removed under reduced pressure to give a foam which was dried in vacuo for 24 hours. The title compound was obtained in 80% yield.

Analysis: $C_{28}H_{28}N_2O_5$ 0.95 H2O calc. C 68.67 H 6.15 N 5.72 found 68.61 6.06 5.91

TLC: Rf=0.5 (95:5 CHCl3:MeOH) HPLC (method A): retention time=10.5 min, purity=98% FAB MS: m/z=473 (M+H+)

To a stirred solution of 1-(1-(4-hydroxy-2-methoxybenzoyl)piperidin-4-yl)-1,2-dihydro-4(H)-3,1-benzoxazin-2-one from Example 214 (250 mg, 0.65 mmol) in dry DMF (10 mL) was added cesium carbonate (423 mg, 2 eq) followed by methyl 3-chloromethyl benzoate (240 mg, 2 eq) and the reaction was warmed to 50° C. and stirred for 18 hours. The reaction was filtered and the solvent was removed under reduced pressure. The residue was purified by preparative reverse phase HPLC using a CH3CN:H2O gradient containing 0.1% TFA. The fractions containing product were combined and the solvent removed under reduced pressure. The residue was partitioned between EtOAc (100 mL) and saturated sodium bicarbonate solution (100 mL). The organic layer was washed with water (100 mL), and brine, dried over MgSO4, and filtered. The solvent was removed under reduced pressure to give a foam which was dried in vacuo for 24 hours giving the title compound in 60% yield.

Analysis: $C_{30}H_{30}N_2O_7$ 0.6 H2O calc. C 66.55 H 5.81 N 5.17 found 66.49 5.63 5.17

TLC: Rf=0.4 (90:10 CHCl3:MeOH) HPLC (method A): retention time=10.29 min, purity=98% FAB MS: m/z=531 (M+H+)

EXAMPLE 217

1-(1-(4-(3-Nitrobenzyloxy)-2-methoxybenzoyl)piperidin-4-yl)-1,2-dihydro-4(H)-3,1-benzoxazin-2-one

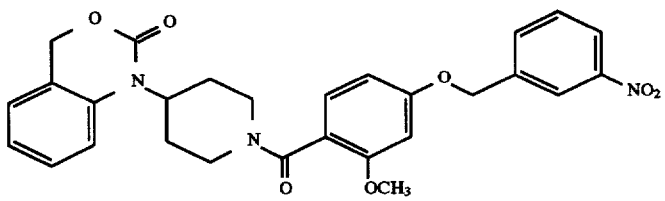

To a stirred solution of 1-(1-(4-hydroxy-2-methoxybenzoyl)-piperidin-4-yl)-1,2-dihydro-4(H)-3,1-benzoxazin-2-one from Example 214 (250 mg, 0.65 mmol) in dry DMF (10 mL) was added cesium carbonate (423 mg, 2 eq) followed by 1-nitro-3-bromomethyl benzene (300 mg, 2 eq.) and the reaction was warmed to 50° C. and stirred for 18 hours. The reaction was filtered and the solvent was removed under reduced pressure. The residue was purified by preparative reverse phase HPLC using a CH3CN:H2O gradient containing 0.1% TFA. The fractions containing

EXAMPLE 218

1-(1-(4-(2-Cyanobenzyloxy)-2-methoxybenzoyl) piperidin-4-yl)-1,2-dihydro-4(H)-3,1-benzoxazin-2-one

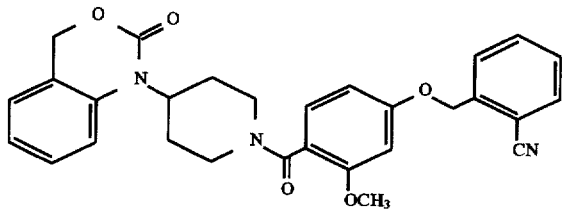

To a stirred solution of 1-(1-(4-hydroxy-2-methoxybenzoyl)-piperidin-4-yl)-1,2-dihydro-4(H)-3,1-benzoxazin-2-one from Example 214 (100 mg, 0.26 mmol) in dry DMF (4 mL) was added cesium carbonate (180 mg, 2 eq) followed by 1-cyano-2-bromomethyl benzene (103 mg, 2 eq.) and the reaction was warmed to 50° C. and stirred for 18 hours. The reaction was filtered and the solvent was removed under reduced pressure. The residue was purified by preparative reverse phase HPLC using a $CH_3CN/H_2O$ gradient containing 0.1% TFA. The fractions containing purified product were combined and the solvent removed under reduced pressure. The residue was partitioned between EtOAc (30 mL) and saturated sodium bicarbonate solution (30 mL). The organic layer was washed with water (30 mL), and brine, dried over MgSO4, and filtered. The solvent was removed under reduced pressure to give a foam which was dried in vacuo for 24 hours giving the title compound in 50% yield.

Analysis: $C_{29}H_{27}N_3O_5$ 0.45 H2O calc. C 68.88 H 5.56 N 8.31 found 68.83 5.57 8.48

TLC: Rf=0.4 (95:5 $CHCl_3$:MeOH) HPLC (method A): retention time=9.8 min, purity=96% FAB MS: m/z=498 (M+H$^+$)

EXAMPLE 219

1-(1-(4-(3-Nitro-2-pyridyloxy)-2-methoxybenzoyl) piperidin-4-yl)-1,2-dihydro-4(H)-3,1-benzoxazin-2-one

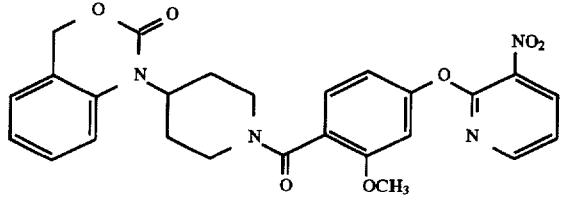

To a stirred solution of 1-(1-(4-hydroxy-2-methoxybenzoyl)-piperidin-4-yl)-1,2-dihydro-4(H)-3,1-benzoxazin-2-one from Example 214 (250 mg, 0.65 mmol) in dry DMF (10 mL) was added potassium carbonate (181 mg, 2 eq) and 2-chloro-3-nitropyridine (207 mg, 2 eq). The solution was stirred at 50° C. for 18 hours. The reaction was filtered and the solvent was removed under reduced pressure. The residue was purified by preparative reverse phase HPLC using a $CH_3CN:H_2O$ gradient containing 0.1% TFA. The fractions containing product were combined and the solvent removed under reduced pressure. The residue was partitioned between EtOAc (30 mL) and saturated sodium bicarbonate solution (30 mL). The organic layer was washed with water (30 mL), and brine, dried over MgSO4, and filtered. The solvent was removed under reduced pressure to give a foam which was dried in vacuo for 24 hours giving the title compound in 40% yield.

Analysis: $C_{26}H_{24}N_4O_7$ 0.3 EtOAc calc. C 61.53 H 5.01 N 10.55 found 61.58 5.13 10.51

TLC: Rf=0.4 (95:5 $CHCl_3$:MeOH) HPLC (method A): retention time=9.19 min, purity=99% FAB MS: m/z=505 (M+H$^+$)

EXAMPLE 220

1-(1-(4-(3-Nitrobenzyloxy)-2-methoxybenzoyl) piperidin-4-yl)-1,2-dihydro-4(H)-3,1-benzoxazin-2-one

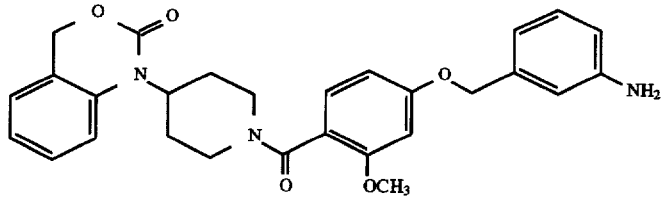

207

To a stirred solution of 1-(1-(4-(3-nitrobenzyloxy)-2-methoxybenzoyl)piperidin-4-yl)-1,2-dihydro-4(H)-3,1-benzoxazin-2-one from Example 217 (100 mg, 0.19 mmol) in dry MeOH (5 mL) was added tin dust (10 mg) and the mixture was stirred rapidly for 18 hours. The solution was filtered and the solvent removed under reduced pressure and the residue was purified by preparative reverse phase HPLC using a CH3CN:H2O gradient containing 0.1% TFA. The fractions containing product were combined and lyophilized to give the title compound as a TFA salt in 40% yield.

Analysis: $C_{28}H_{29}N_3O_5$ 1.75 TFA 0.25 H2O calc. C 54.70 H 4.55 N 6.08 found 54.72 4.57 6.31

TLC: Rf=0.35 (90:10 $CHCl_3$:MeOH) HPLC (method A): retention time=8.99 min, purity=95% FAB MS: m/z=488 (M+H$^+$)

EXAMPLE 221

1-(1-(4-(3-Carboxybenzyloxy)-2-methoxybenzoyl)piperidin-4-yl)-1,2-dihydro-4(H)-3,1-benzoxazin-2-one

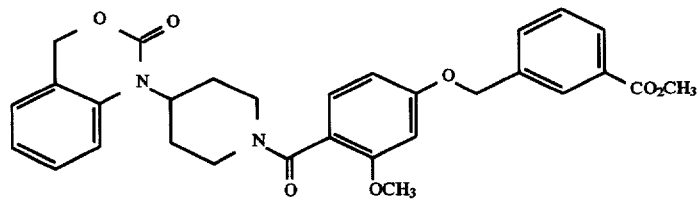

To a solution of lithium hydroxide (7 mg, 0.16 mmol in 3:1 THF:$H_2O$ (3 mL) was added 30% hydrogen peroxide (0.02 mL, 1.2 eq) and the solution was stirred for 10 min. To this solution was added 1-(1-(4-(3-methoxycarbonylbenzyloxy)-2-methoxybenzoyl) piperidin-4-yl)-1,2-dihydro-4(H)-3,1-benzoxazin-2-one from Example 216 (35 mg, 0.07 mmol) and the reaction was stirred for 24 hours. The reaction was adjusted to pH 3 with 4 N HCl and the solvent was removed under reduced pressure. The residue was purified by preparative reverse phase HPLC using a CH3CN:$H_2O$ gradient containing 0.1% TFA. The fractions containing product were combined and lyophilized to give the title compound as a TFA salt in 50% yield.

Analysis: $C_{29}H_{28}N_2O_7$ 0.75 TFA 0.25 $H_2O$ calc. C 60.39 H 4.86 N 4.62 found 60.39 4.84 4.89

208

TLC: Rf=0.15 (90:10 $CHCl_3$:MeOH)

HPLC (method A): retention time=8.97 min, purity=99%

FAB MS: m/z=517 (M+H$^+$)

EXAMPLE 222

1-(1-(4-(4-Acetyl-1-piperazinylmethyl)benzoyl) piperidin-4-yl)-1,2-dihydro-4(H)-3,1-benzoxazin-2-one

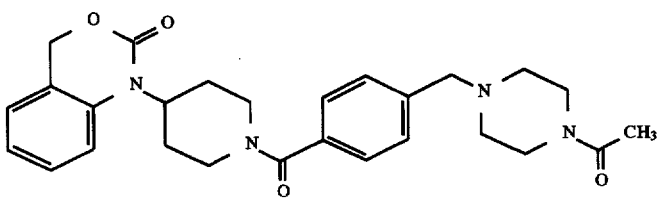

Step 1: To a stirred solution of 1-(4-piperidinyl)-1,2-dihydro-4(H)-3,1-benzoxazin-2-one hydrochloride from Step 4 of Example 1 (500 mg, 1.86 mmol) in dry DMF was added benzaldehyde 4-carboxylic acid (307 mg, 2 mmol) followed by HOBT (306 mg, 2 mmol) and EDC (382 mg, 2 mmol) and DIEA (0.35 mL, 2 mmol). The reaction was stirred for 18 hours and the solvent was removed under reduced pressure. The residue was purified by pressurized silica gel column chromatography using 3:7 EtOAc:hexanes as eluant. The fractions containing the purified product were combined and the solvent was removed under reduced pressure to give a foam which was dried in vacuo for 24 hours to give 1-(1-(4-carboxaldehydebenzoyl)pipefidin-4-yl)-1,2-dihydro-4(H)-3,1-benzoxazin-2-one in 80% yield.

Step 2: To a stirred solution of 1-(1-(4-carboxaldehydebenzoyl) piperidin-4-yl)-1,2-dihydro-4(H)-3,1-benzoxazin-2-one from Step 1 above (150 mg, 0.41 mmol) in dry MeOH ( 50 mL) under argon and at ambient temperature was added 1-tert-butyloxycarbonylpiperazine (85 mg, 1.1 eq) and glacial acetic acid (0.05 mL) followed by sodium cyanoborohydride (26 mg, 1 eq). The reaction was stirred for 18 hours. The solution was quenched with saturated sodium bicarbonate solution and the solvent was removed under reduced pressure. The residue was partitioned between methylene chloride and saturated sodium bicarbonate solution and the organic layer was washed with water and brine and dried over $MgSO_4$. The solution was filtered and the solvent was removed under reduced pressure and the residue was purified by pressurized silica gel column chromatography using 3:7 EtOAc:hexanes as eluant. The fractions containing product were combined and the solvent was removed under reduced pressure to give 1-(1-(4-(4-tertbutyloxycarbonyl-1-piperazinylmethyl)-benzoyl)piperidin-4-yl)-1,2-dihydro-4(H)-3,1-benzoxazin-2-one in 70% yield.

Step 3: 1-(1-(4-(4-tert-Butyloxycarbonyl-1-piperazinylmethyl)benzoyl)pipefidin-4-yl)-1,2-dihydro-4(H)-3,1-benzoxazin-2-one from Step 2 above (100 mg, 0.18 mmol) was dissolved in 100 mL of dry ethyl acetate under N₂ and the solution was cooled to 0° C. in an ice water bath. Anhydrous HCl gas was bubbled into the solution at 0° C. until saturation was reached. The saturated solution was stirred for 30 min at 0° C. then the ice bath was removed and N₂ was bubbled in to remove the excess HCl. Addition of hexane precipitated the HCl salt. The solid was partitioned between ethyl acetate and saturated aqueous sodium bicarbonate. The organic layer was washed with water and brine, dried over anhydrous MgSO₄, and filtered. The solvent was removed under reduced pressure to give 1-(1-(4-(1-piperazinylmethyl)-benzoyl)pipefidin-4-yl)-1,2-dihydro-4(H)-3,1-benzoxazin-2-one in 98% yield.

Step 4: To a solution of 1-(1-(4-(1-piperazinylmethyl) benzoyl) piperidin-4-yl)-1,2-dihydro-4(H)-3,1-benzoxazin-2-one from Step 3 above (50 mg, 0.1 mmol) in methylene chloride (5 mL) at ambient temperature was added acetic arthydride (0.02 mL, 2 eq.) and DIEA (0.015 mL, 1 eq) and the solution was stirred for 2 hours. The solvent was removed under reduced pressure and the residue was partitioned between methylene chloride and saturated sodium bicarbonate solution. The organic layer was washed with water and brine, dried over MgSO₄, and filtered. The solvent was removed under reduced pressure and the residue was purified by pressurized silica gel column chromatography using 1:1 EtOAc:hexanes as eluant. The fractions containing product were combined and the solvent was removed under reduced pressure to give the title compound in 90% yield.

Analysis: $C_{27}H_{32}N_4O_4$ 0.1 EtOAc 0.95 H₂O calc. C 65.48 H 6.96 N 11.15 found 65.49 6.70 11.13

TLC: Rf=0.1 (95:5 CHCl₃:MeOH)

HPLC (method A): retention time=6.21 min, purity=99%

FAB MS: m/z=477 (M+H⁺)

EXAMPLE 223

1-(1-(4-(1-tert-Butyloxycarbonyl-1,2,5,6-tetrahydropyrid-4-yl) benzoyl)piperidin-4-yl)-1,2-dihydro-4(H)-3,1-benzoxazin-2-one solvent was removed under reduced pressure to give a foam which was dried in vacuo for 18 hours. 1-(1-(4-Iodobenzoyl) piperidin-4-yl)-1,2-dihydro-4(H) -3,1-benzoxazin-2-one was obtained in 86% yield.

Step 2: To a solution of 1-tert-butyloxycarbonyl-4-piperidinone (2 g, 10 mmol) in dry THF under argon at −78° C. was added lithium hexamethyldisilazide (1.1 eq). After one hour the solution was allowed to warm to 0° C. then N-phenyltriflimide (4.29 gm, 1.2 eq) was added all at once. The temperature was allowed to warm to room temperature. After one hour the solvent was removed under reduced pressure and the residue was partitioned between EtOAc (200 mL) and 1M HCl (200 mL). The EtOAc was washed with brine and dried over Na2SO4, filtered, and the was solvent removed under reduced pressure to give 1-tert-butyloxycarbonyl-4-trifluoromethylsulfonyloxy-1,2,5,6-tetrahydropyridine as a pale yellow oil.

Step 3: 1-tert-Butyloxycarbonyl-4-trifluoromethylsulfonyloxy-1,2,5,6-tetrahydropyridine from Step 2 above (219 mg, 0.66 mmol) was dissolved in dry THF (200 mL) and hexamethyltin (216 mg, 1 eq) was added, followed by lithium chloride (168 mg, 6 eq) and bis (triphenylphosphine) palladium chloride (10 mol %). The temperature was increased to reflux. After 4 hours at reflux the solvent was removed under reduced pressure and the residue was purified by pressurized silica gel column chromatography using 15:85 EtOAc:hexanes as eluant. The fractions containing product were combined and the solvent removed under reduced pressure to give 1-tert-butyloxycarbonyl-4-trimethylstannyl-1,2,5,6-tetrahydropyridine in 95% yield.

Step 4: 1-(1-(4-Iodobenzoyl)piperidin-4-yl)-1,2-dihydro-4(H)-3,1-benzoxazin-2-one from Step 1 above (146 mg, 0.3 mmol) was dissolved in toluene (100 mL). 1-tert-Butyloxycarbonyl-4-trimethylstannyl-1,2,5,6-tetrahydropyridine from Step 3 above (109 mg, 0.3 mmol) was added followed by bis(triphenylphosphine) palladium chloride (10 mol %). The reaction was refluxed for 18 hours and the solvent was removed under reduced pressure. The residue was purified by pressurized silica gel column chromatography using 98:2 CH2Cl2:MeOH as eluant. The resulting oil was further purified by preparative reverse phase HPLC using a CH3CN:H₂O gradient with 0.1 TFA. The fractions containing product were combined and lyophilized to give the title compound as an amorphous solid.

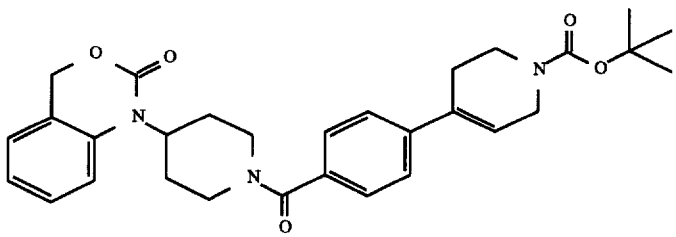

Step 1: To a stirred solution of 1-(4-piperidinyl)-1,2-dihydro-4(H)-3,1-benzoxazin-2-one hydrochloride from Step 4 of Example 1 (500 mg, 1.86 mmol) in dry CH₂Cl₂ (25 mL) at ambient temperature under argon was added 4-iodobenzoyl chloride (546 mg, 1.1 eq.) followed by DIEA (324 uL, 1.1 eq). The reaction was allowed to stir for 4 hours at which time the solvent was removed under reduced pressure and the residue purified by pressurized silica gel column chromatography using 95:5 CH2Cl2:MeOH as eluant. The fractions containing product were combined and the Analysis: $C_{30}H_{35}N_3O_5$ 0.7 TFA 0.15 H₂O calc. C 62.83 H 6.05 N 7.00 found 62.88 6.04 6.95

TLC: Rf=0.4 (95:5 CH2Cl2:MeOH)

HPLC (method A): retention time=10.99 min, purity=99%

FAB MS: m/z=518 (M+H⁺)

EXAMPLE 224

1-(1-(3-Chloromethylbenzoyl)piperidin-4-yl)-1,2-dihydro-4(H)-3,1-benzoxazin-2-one

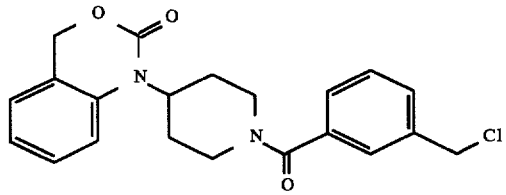

To a stirred solution of 1-(4-piperidinyl)-1,2-dihydro-4(H)-3,1-benzoxazin-2-one hydrochloride from Step 4 of Example 1 (1 g, 3.72 mmol) in dry $CH_2Cl_2$ (50 mL) at ambient temperature under argon was added 3-(chloromethyl)benzoyl chloride (770 mg, 1.1 eq) followed by DIEA (0.72 mL, 1.1 eq). The reaction was allowed to stir for 16 hours at which time the solvent was removed under reduced pressure and the residue purified by pressurized silica gel column chromatography using 3:7 EtOAc:hexanes as eluant. The fractions containing the purified product were combined and the solvent was removed under reduced pressure to give a foam which was dried in vacuo for 24 hours. The title compound was obtained in 80% yield.

Analysis: $C_{21}H_{21}N_2O_3Cl$ 0.35 EtOAc 0.05 $H_2O$ calc. C 64.57 H 5.78 N 6.72 found 64.56 5.60 6.68

TLC: Rf=0.5 (95:5 $CHCl_3$:MeOH)

HPLC (method A): retention time=9.54 min, purity=97%

FAB MS: m/z=385 (M+H$^+$)

EXAMPLE 225

1-(1-(3-Diethylaminomethylbenzoyl)piperidin-4-yl)-1,2-dihydro-4(H)-3,1-benzoxazin-2-one

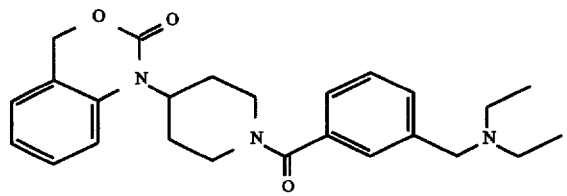

To a stirred solution of 1-(1-(3-chloromethylbenzoyl)piperidin-4-yl)-1,2-dihydro-4(H)-3,1-benzoxazin-2-one from Example 224 (100 mg, 0.24 mmol) in dry DMF (5 mL) was added diethylamine (0.1 mL, 4 eq) and the solution was stirred at 50° C. for 16 hours. The DMF was removed under reduced pressure and the residue was purified by preparative reverse phase HPLC using an H2O:CH3CN gradient containing 0.1% TFA. The fractions containing product were combined. The solvent was removed under reduced pressure and the residue was dissolved in methylene chloride (50 mL) and extracted with saturated sodium bicarbonate (3×50 mL) and brine (50 mL). The organic layer was dried over $MgSO_4$ and filtered and the solvent removed under reduced pressure to give a foam which was dried in vacuo for 24 hours. The title compound was obtained in 40% yield.

Analysis: $C_{25}H_{31}N_3O_3$ 0.85 $H_2O$ calc. C 68.73 H 7.54 N 9.62 found 68.78 7.16 9.47

TLC: Rf=0.5 (95:5 $CHCl_3$:MeOH)

HPLC (method A): retention time=5.79 min, purity=97%

FAB MS: m/z=422 (M+H$^+$)

EXAMPLE 226

1-(1-(3-(3-Ethoxycarbonyl-1-piperidinyl)benzoyl)piperidin-4-yl)-1,2-dihydro-4(H)-3,1-benzoxazin-2-one

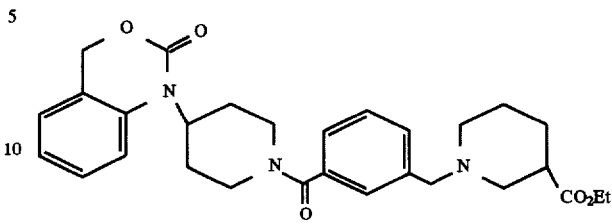

To a stirred solution of 1-(1-(3-chloromethylbenzoyl)piperidin-4-yl)-1,2-dihydro-4(H)-3,1-benzoxazin-2-one from Example 224 (100 mg, 0.25 mmol) in dry DMF (5 mL) was added ethyl nipecotate (0.05 mL, 2 eq) followed by DIEA (0.05 mL, 1 eq) and the solution was stirred at 50° C. for 16 hours. The DMF was removed under reduced pressure and the residue was purified by preparative reverse phase HPLC using an H2O:CH3CN gradient containing 0.1% TFA. The fractions containing product were combined and lyophilized to give the title compound as the TFA salt in 60% yield.

Analysis: $C_{29}H_{35}N_3O_5$ 1.3 TFA 0.25 $H_2O$ calc. C 57.64 H 5.63 N 6.38 found 57.64 5.65 6.54

TLC: Rf=0.5 (95:5 $CHCl_3$:MeOH)

HPLC (method A): retention time=6.50 min, purity=99%

FAB MS: m/z=506 (M+H$^+$)

EXAMPLE 227

1-(1-(4-Cyanomethylbenzoyl)piperidin-4-yl)-1,2-dihydro-4(H)-3, 1-benzoxazin-2-one

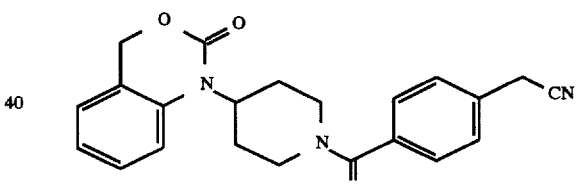

Step 1: To a stirred solution of 1-(4-piperidinyl)-1,2-dihydro-4(H)-3,1-benzoxazin-2-one hydrochloride from Step 4 of Example 1 (1 g, 3.72 mmol) in dry $CH_2Cl_2$ (50 mL) at ambient temperature under argon was added 4-(chloromethyl)benzoyl chloride (529 uL, 1.1 eq.) followed by DIEA (715 uL, 1.1 eq). The reaction was allowed to stir for 16 hours at which time the solvent was removed under reduced pressure and the residue purified by silica gel chromatography using 3:7 EtOAc:hexanes as eluant. The fractions containing 1-(1-(4-chloromethylbenzoyl)piperidin-4-yl)-1,2-dihydro-4(H)-3, 1-benzoxazin-2-one were combined and the solvent was removed under reduced pressure to give a foam which was dried in vacuo for 24 hours.

Step 2: To a solution of 1-(1-(4-chloromethylbenzoyl)piperidin-4-yl)-1,2-dihydro-4(H)-3,1-benzoxazin-2-one from Step 1 above (500 mg, 1.25 mmol) in dry DMF (50 mL) was added NaCN (150 mg, 2.5 eq) and the reaction stirred for 18 hours at 50° C. The solution was filtered and the solvent was removed under reduced pressure. The residue was purified by preparative reverse phase HPLC using an CH3CN:H2O gradient containing 0.1% TFA. The fractions containing purified product were combined and lyophilized to give the TFA salt of the title compound in 55% yield.

Analysis: $C_{22}H_{21}N_3O_3$ 0.95 TFA calc. C 59.33 H 4.57 N 8.69 found 59.31 4.58 8.90

TLC: Rf=0.3 (95:5 $CHCl_3$:MeOH)

HPLC (method A): retention time=8.59 min, purity=99%

FAB MS: m/z=376 (M+H$^+$)

EXAMPLE 228

1-(1-(4-Carboxymethylbenzoyl)piperidin-4-yl)-1,2-dihydro-4(H)-3, 1-benzoxazin-2-one

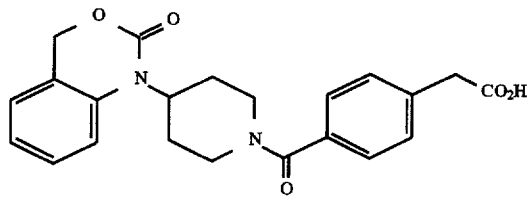

To a stirred solution of 1-(1-(4-cyanomethylbenzoyl) piperidin-4-yl)-1,2-dihydro-4(H)-3,1-benzoxazin-2-one from Example 227 (150 mg, 0.3 mmol) in MeOH (100 mL) was added 12N HCL (1 mL) and the reaction was stirred for 5 hours. The solvent was removed under reduced pressure and the residue was partitioned between $CH_2Cl_2$ and saturated sodium bicarbonate. The organic layer was washed with water and brine and dried over $MgSO_4$. Two major products were obtained which proved to be methyl ester and is carboxylic acid in a ratio of 3:2. The solution was filtered and the solvent was removed under reduced pressure and the residue was purified by preparative reverse phase HPLC using an CH3CN:H2O gradient containing 0.1% TFA. The fractions containing carboxylic acid (early fractions) were combined and lyophilized to give the title compound in 35% yield.

Analysis: $C_{22}H22N_2O_5$ 0.55 TFA 0.75 $H_2O$ calc. C 58.94 H 5.15 N 5.95 found 58.96 5.08 6.35

TLC: Rf=0.15 (95:5:05 $CHCl_3$:MeOH:HOAc)

HPLC (method A): retention time=7.75 min, purity=98%

FAB MS: m/z=395 (M+H$^+$)

EXAMPLE 229

1-(1-(4-Methoxycarbonylmethylbenzoyl)piperidin-4-yl)-1,2-dihydro-4(H)-3,1-benzoxazin-2-one

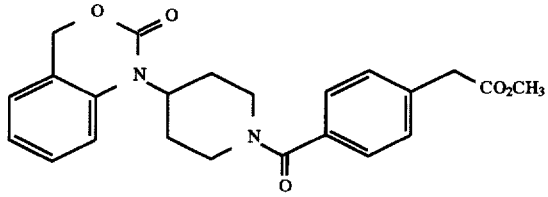

To a stirred solution of 1-(1-(4-cyanomethylbenzoyl) pipefidin-4-yl)-1,2-dihydro-4(H)-3,1-benzoxazin-2-one from Example 227 (150 mg, 0.3 mmol) in MeOH (100 mL) was added 12N HCL (1 mL) and the reaction was stirred for 5 hours. The solvent was removed under reduced pressure and the residue was partitioned between $CH_2Cl_2$ and saturated sodium bicarbonate. The organic layer was washed with water and brine and dried over $MgSO_4$. Two major products were obtained which proved to be methyl ester and is carboxylic acid in a ratio of 3:2. The solution was filtered and the solvent was removed under reduced pressure and the residue was purified by preparative reverse phase HPLC using an CH3CN:H2O gradient containing 0.1% TFA. The fractions containing purified methyl ester (later fractions) were combined and lyophilized to give the title compound in 45% yield.

Analysis: $C_{23}H_{24}N_2O_5$ 0.45 TFA 0.95 $H_2O$ calc. C 60.19 H 5.57 N 5.87 found 60.14 5.57 6.13

TLC: Rf=0.5 (95:5 $CHCl_3$:MeOH)

HPLC (method A): retention time=8.80 min, purity=99%

FAB MS: m/z=409 (M+H$^+$)

EXAMPLE 230

1-(1-(2,4-dimethoxybenzoyl)pipefidin-4-yl)-8-methoxy-1,2-dihydro-4(H)-3,1-benzoxazin-2-one

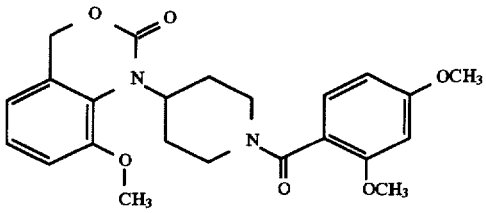

1-(Piperidin-4-yl)-8-methoxy-1,2-dihydro -4(H)-3,1-benzoxazin-2-one hydrochloride was prepared from 2-amino-3-methoxybenzoic acid according to the procedures outlined in Example 62 and 0.71 g (2.4 mmole) of this material was acylated in chloroform with 2,4-dimethoxybenzoyl chloride in the usual manner using diisopropylethylamine (2.2 equivalents) as base. The title compound was purified by flash chromatography on silica gel using EtOAc-hexane as eluant.

HPLC:>97% pure at 214 nM;

Elem. Anal. calc'd for $C_{23}H_{26}N_2O_6$•0.65EtOAc: Calc'd: C, 63.56; H, 6.50; N, 5.79. Found: C, 63.56; H, 6.22; N, 6.02.

EXAMPLE 231

1-(1-(4-(tert-butyloxycarbonyl)aminobenzoyl)piperidin-4-yl)-1,2-dihydro-4(H)-3,1-benzoxazin-2-one

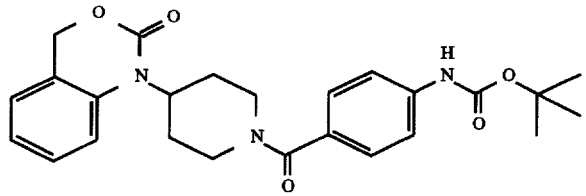

To a solution of the hydrochloride salt of 1-(4-piperidinyl)-1,2-dihydro-4(H)-3,1-benzoxazin-2-one from Step 4 of Example 1 (2.0 g, 7.4 mmol) in DMF (45 mL) was added DIEA (3 mL, 17 mmol), HOBT (1.3 mg, 9.6 mmol), EDC (1.8 g, 9.6 mmol), and 4-((1,1-dimethyl)ethyloxycarbonyl) aminobenzoic acid (2.3 g, 9.6 mmol). The reaction was stirred at ambient temperature for 24 h and the solvent was removed under reduced pressure. The residue was dissolved in EtOAc and washed with saturated aqueous $NaHCO_3$ (3×50 mL). The EtOAc layer was dried ($MgSO_4$), filtered, and the solvent was removed under reduced pressure. The residue was purified by pressurized silica gel column chromatography using a 60% ethyl acetate-hexane solvent mixture as eluant. The title compound was obtained in homogeneous form as an amorphous solid (2.4 g).

NMR: Consistent with structure;

HPLC:>99% pure at 214 nM;

Elem. Anal. calc'd for $C_{25}H_{29}N_3O_5$: Calc'd: C, 66.49; H, 6.49; N, 9.31. Found: C, 66.41; H, 6.54; N, 9.22.

EXAMPLE 232

1-(1-(4-aminobenzoyl)piperidin-4-yl)-1,2-dihydro-4(H)-3,1-benzoxazin-2-one hydrochloride

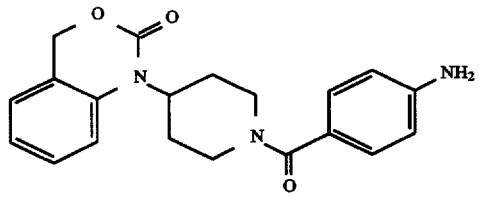

1-(1-(4-((1,1-Dimethyl)ethyloxycarbonyl)aminobenzoyl) piperidin-4-yl)-1,2-dihydro-4(H)-3,1-benzoxazin-2-one (1.0 g, 2.2 mmole) was transformed to the title compound according to the method outlined in Step 4, Example 1. In this way, 0.89 g of the analytical product was obtained.

NMR: Consistent with structure;

HPLC:>99% pure at 214 nM;

Elem. Anal. calc'd for $C_{20}H_{21}N_3O_3 \cdot HCl$: Calc'd: C, 66.49; H, 6.49; N, 9.31. Found: C, 66.41; H, 6.54; N, 9.22.

EXAMPLE 233

1-(1-(2,4-dimethoxybenzoyl)piperidin-4-yl)-5-methyl-1,2-dihydro-4(H)-3,1-benzoxazin-2-one

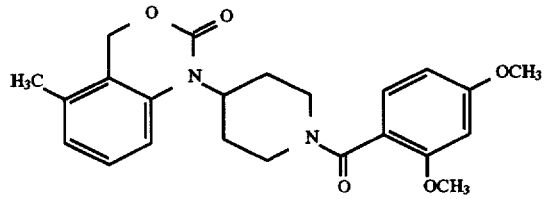

1-(Piperidin-4-yl)-5-methyl-1,2-dihydro-4(H)-3,1-benzoxazin-2-one hydrochloride (97 mg, 0.19 mmole) was acylated with acetic anhydride according the procedure given in Example 27. The crude reaction product was flash chromatographed on silica gel using a solvent mixture of 5% isopropanol-chloroform as eluant to yield 62 mg of the title compound.

NMR: Consistent with structure;

HPLC:>99% pure at 214 nM;

Elem. Anal. calc'd for $C_{29}H_{35}N_3O_6 \cdot 0.6CHCl_3 \cdot 0.6i\text{-}PrOH$: Calc'd: C, 59.93.49; H, 6.47; N, 6.68. Found: C, 59.84; H, 6.48; N, 6.80.

FAB MS: m/z 522 (M$^+$+H).

EXAMPLE 234

1-(1-(4-(4-tert-Butyloxycarbonyl-1-piperazinyl)benzoyl) piperidin-4-yl)-1,2-dihydro-4(H)-3,1-benzoxazin-2-one

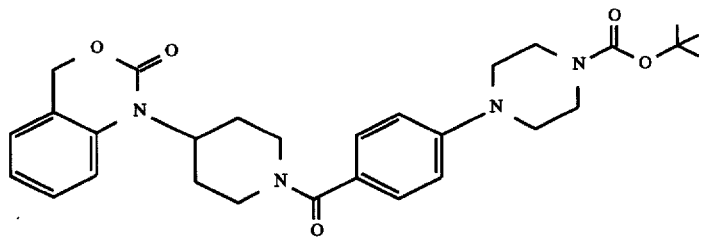

4-(4-tert-Butyloxycarbonyl)piperazin-1-yl)benzoic acid (460 mg, 1.5 mmole) and the hydrochloride salt of 1-(4-piperidinyl)-1,2-dihydro-4(H)-3,1-benzoxazin-2-one (400 mg, 1.5 mmole) from Step of Example 1 were combined with EDC (350 mg, 1.8 mmmole), HOBT (240 mg, 1.8 mmole), and DIEA (0.58 mL) in DMF according to the procedure described in Step 5, Example 1. The crude product was purified by flash chromatography on silica gel using a solvent mixture of 60% ethyl acetate in hexane.

NMR: Consistent with structure;

HPLC:>99% pure at 214 nM;

Elem. Anal. calc'd for $C_{29}H_{36}N_4O_5 \cdot 0.6CHCl_3$: Calc'd: C, 60.02; H, 6.23; N, 9.46. Found: C, 60.26; H, 6.30; N, 9.14.

EXAMPLE 235

1-(1-(4-(1-Piperazinyl)benzoyl)piperidin-4-yl)-1,2-dihydro-4(H)-3,1-benzoxazin-2-one Hydrochloride.

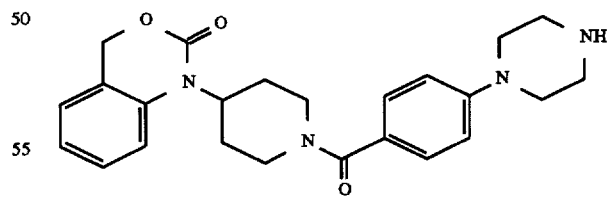

Into an ice cold solution of 1-(1-(4-(4-tert-butyloxycarbonyl)piperazin) benzoyl)piperidin-4-yl)-1,2-dihydro-4(H)-3,1-benzoxazin-2-one (290 mg, 0.56 mmole) in 25 ml of ethyl acetate was bubbled a stream of anhydrous hydrogen chloride gas for five minutes. The reaction mixture was allowed to warm to ambient temperature and the solvent was removed under reduced pressure to give 250 mg of a solid. The crude product was recrystallized from ethyl acetate/methanol/ethyl ether to give the analytical product.

NMR: Consistent with structure;
HPLC:>99% pure at 214 nM;

Elem. Anal. calc'd for C₂₄H₂₈N₄O₂•1.55HCl: Calc'd: C, 59.44; H, 6.67; N, 11.56. Found: C, 59.42; H, 6.44; N, 11.58.

EXAMPLE 236

1-(1-(4-(4-(4-Acetyl-1-piperazin)benzoyl)piperidin-4-yl)-1,2-dihydro-4(H)-3,1-benzoxazin-2-one.

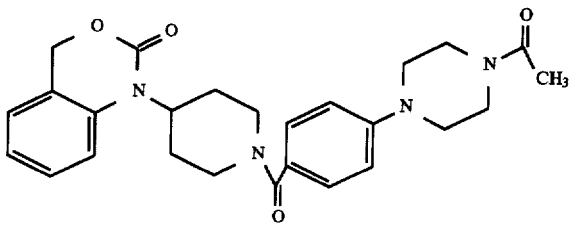

1-(1-(4-(4-Piperazin)benzoyl)piperidin-4-yl)-1,2-dihydro-4(H)-3,1-benzoxazin-2-one hydrochloride (75 mg, 0.16 mmole) was acylated with acetyl chloride and triethyl amine in in methylene chloride according to the procedure given in Example 18. Extractive workup, followed by flash chromatography on silica gel (10% isopropanol/ethyl ether elution) afforded 55 mg of the title compound compound as a white solid: m.p. 188°-191° C.

NMR: Consistent with structure; HPLC:>99% pure at 214 nM;

Elem. Anal. calc'd for C₂₆H₃₀N₄O₄•1.4H₂O: Calc'd: C, 64.02; H, 6.78; N, 11.49. Found: C, 63.97; H, 6.39; N, 11.26.

EXAMPLE 237

1-(1-(4-(4-tert-Butyloxycarbonyl-1-piperazinyl)phenylacetyl)piperidin-4-yl)-1,2-dihydro-4(H)-3,1-benzoxazin-2-one

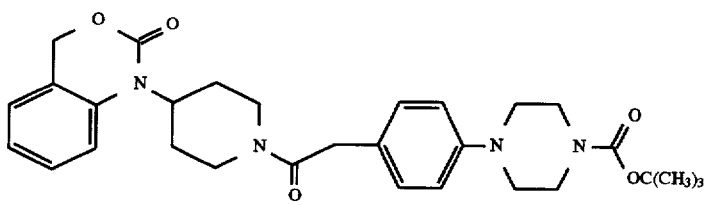

4-(4-tert-Butyloxycarbonyl)piperazin-1-yl)phenyl acetic acid (1.2 g, 3.7 mmole) and the hydrochloride salt of 1-(4-piperidinyl)-1,2-dihydro-4(H)-3,1-benzoxazin-2-one (1.0 g, 3.7 mmole) from Step 4 of Example 1 were combined with benzotriazol-1-yloxytris (dimethylamino) phosphonium hexafluorophosphate (1.7 g, 3.9 mole) and DIEA (3.9 mmole) in DMF. The reaction mixture was protected from moisture and stirred at ambient temperature for 30 minutes. The reaction mixture was concentrated in vacuo and the the residue was partitioned between ethyl acetate and water. The organic phase was washed twice with water, then brine, dried (sodium sulfate) and concentrated to give 3.8 g of a semi-solid. The crude product was purified by flash chromatography on silica gel using a solvent mixture of 85% ethyl acetate in hexane to give 2.0 g of the analytical product as a white solid: m.p. 250°-252° C.

NMR: Consistent with structure;
HPLC: 99% pure at 214 nM;
FAB MS: m/e 535 (M⁺+H);

Elem. Anal. calc'd for C₃₀H₃₈N₄O₅•1.55H₂O•0.55 ethyl acetate: Calc'd: C, 63.29; H, 7.51; N, 9.17. Found: C, 63.29; H, 6.95; N, 9.15.

EXAMPLE 238

1-(1-(4-((2-Acetamido)-α-methylbenzyloxy)benzoyl)piperidin-4-yl)-1,2-dihydro-4(H)-3,1-benzoxazin-2-one

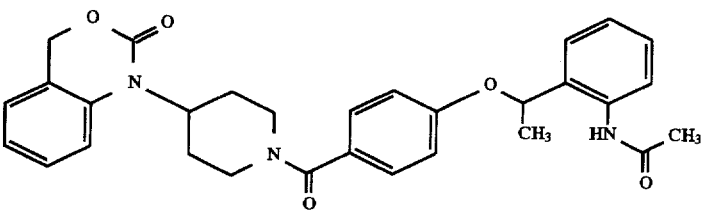

Step 1. 4-Hydroxybenzoic acid (0.26 g, 1.9 mmole) and the hydrochloride salt of 1-(4-piperidinyl)-1,2-dihydro-4(H)-3,1-benzoxazin-2-one (0.5 g, 1.9 mmole) from Step 4 of Example 1 were combined with benzotriazol-1-yloxytris (dimethylamino) phosphonium hexafluorophosphate (0.85 g, 2.0 mmmole) and DIEA (2.0 mmole) in 14 ml of DMF. The reaction mixture was protected from moisture and stirred at ambient temperature for 60 minutes. The reaction mixture was concentrated in vacuo and the the residue was partitioned between ethyl acetate and water. The organic phase was washed twice with water, then brine, dried (sodium sulfate) and concentrated to give 1.2 g of a semi-solid. The crude product was purified by flash chromatography on silica gel using a solvent mixture of 4% isopropanol in chloroform to give 0.43 g of 1-(1-(4-(hydroxy)benzoyl)piperidin-4-yl)-1,2-dihydro-4(H)-3,1-benzoxazin-2-one.

Step 2. (2-Acetamido)-α-methylbenzylalcohol (200 mg, 1.1 mmole) and 340 mg (1.3 mmole) of triphenylphosphine were dissolved in 18 ml of THF. The solution was stirred magnetically in an ice bath and treated in succession with diethylazodicarboxylate (230 mg, 1.3 mmole) and 1-(1-(4-(hydroxy)benzoyl)piperidin-4-yl)-1,2-dihydro-4(H)-3,1-benzoxazin-2-one (400 mg, 1.1 mmole). The reaction mixture was stirred for 12 hr at ambient temperature and treated with additional quantities of the following reagents: 99 mg of (2-acetamido)-α-methylbenzylalcohol, 140 mg of triphenylphosphine, 96 mg of diethylazodicarboxylate. After 36 hr, all volatiles were removed under reduced pressure and the residual material was dissolved in ethyl acetate. The organic phase was washed with 1 N sodium hydroxide solution, water, and brine, then dried (sodium sulfate) and concentrated. The crude product thus obtained was purified by flash chromatography on silica gel (ethyl acetate elution) to give 41 mg of the title compound as an amorphous solid.

NMR: Consistent with structure;

HPLC: 99% pure at 214 nM;

Elem. Anal. calc'd for $C_{30}H_{31}N_3O_5$ •0.7 ethyl acetate: Calc'd: C, 68.48; H, 6.41; N, 7.30. Found: C, 68.57; H, 6.52; N, 7.13.

EXAMPLE 239

N-[1-(4-Piperidinyl)-1,2-dihydro-4(H)-3,1-benzoxazin-2-one]-N'-[4-methoxyphenyl]urea

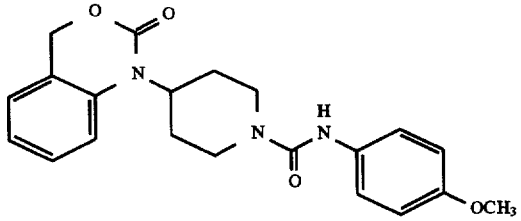

1-(4-Piperidinyl)-1,2-dihydro-4(H)-3,1-benzoxazin-2-one (100 mg, 0.43 mmole) from Step 4 of Example 1 was dissolved in 8 ml of tetrahydrofuran at 0° C. and combined with 4-methoxyphenylisocyanate (78 μL, 0.43 mmmole). The cooling bath was removed after 15 minutes and the reaction mixture was stirred at ambient temperature for 30 minutes more. All volatiles were removed under reduced pressure. The residual crude product was purified by flash chromatography on silica gel using a solvent mixture of 67% ethyl acetate in hexane to give 100 mg of the pure material. Recrystallization from ethyl acetate yielded a white solid: m.p. 180° C.

NMR: Consistent with structure;
HPLC: 98% pure at 214 nM;
FAB MS: m/e 382 (M⁺+H);

Elem. Anal. calc'd for $C_{21}H_{23}N_3O_4$•0.1CHCl₃: Calc'd: C, 64.45; H, 5.92; N, 10.69. Found: C, 64.2945 H, 6.00; N, 10.60.

EXAMPLE 240

1-(1-(2,4-dimethoxybenzoyl)piperidin-4-yl)-6-bromo-1,2-dihydro-4(H)-3,1-benzoxazin-2-one

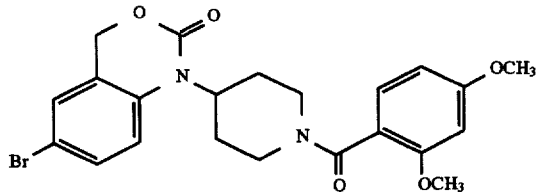

Step 1.1-((t-Butyloxycarbonyl)piperidin-4-yl)-1,2-dihydro-4(H)-3,1-benzoxazin-2-one (500 mg) was was dissolved in 15 ml of glacial acetic acid at ambient temperature and treated dropwise with 1.3 equivalents of bromine. The reaction mixture was stirred for 3 hr and quenched with 10 ml of water. The reaction mixture was then extracted with ethyl acetate and the combined organic extracts were washed with saturated sodium bicarbonate solution. The extracts were dried, concentrated, and the residual material was flash chromatographed on silica gel using a solvent mixture of hexane/ethyl acetate (3:1, v/v).This afforded 275 mg of 1-((t-butyloxy carbonyl)piperidin-4-yl)-6-bromo-1,2-dihydro-4(H)-3,1-benzoxazin-2-one.

NMR: Consistent with structure;

HPLC:>95% pure at 214 nM;

Elem. Anal. calc'd for $C_{18}H_{23}BrN_2O_4$•0.75HOAc: Calc'd: C, 51.33; H, 5.74; N, 6.14. Found: C, 51.29; H, 5.60; N, 6.19.

FAB MS: m/z 411 (M⁺+H).

Step 2.1-((t-Butyloxycarbonyl)piperidin-4-yl)-1,2-dihydro-4(H)-6-bromo-3,1-benzoxazin-2-one (600 mg) was reacted with HCl gas in ethyl acetate according to the procedure given in Step 4, Example 1. Standard work-up afforded 500 mg of 1-(4-piperidinyl)-6-bromo-1,2-dihydro-4(H)-3,1-benzoxazin-2-one hydrochloride which displayed NMR and FAB MS spectra consistent with the assigned structure.

Step 3. 1-(4-Piperidinyl)-6-bromo-1,2-dihydro-4(H)-3,1-benzoxazin-2-one hydrochloride (54 mg, 0.17 mmole) was reacted with 2,4-dimethoxybenzoic acid (38 mg, 1.9 mmole) using EDC and HOBT according to procedure described in Step 5, Example 1. In this way, the title compound was obtained in 50% yield as a solid.

NMR: Consistent with structure;

HPLC:>95% pure at 214 nM;

Elem. Anal. calc'd for $C_{22}H_{23}BrN_2O_5$•0.40 CHCl₃: Calc'd: C, 52.83; H, 4.71; N, 5.50. Found: C, 52.75; H, 5.11; N, 5.44.

FAB MS: m/z 475 (M⁺+H).

EXAMPLE 241

1-(1-(4-(4-(N-Cyanomethyl)pipefidinyloxy)-2-methoxybenzoyl) piperidin-4-yl)-1,2-dihydro-4(H)-3,1-benzoxazin-2-one

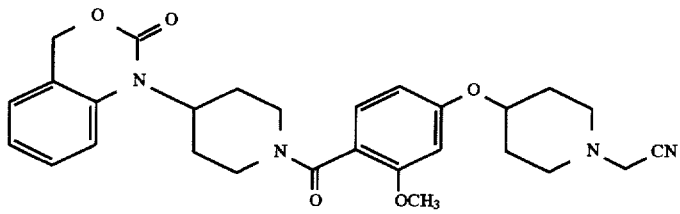

A solution of 7 ml of acetonitrile containing 500 mg (1.08 mmole) of 1-(1-(4-(4-piperidinyloxy)-2-methoxy benzoyl) piperidin-4-yl)-1,2-dihydro-4(H)-3,1-benzoxazin-2-one from Example 26 was treated with 136 μL (2.16 mmole) of chloroacetonitrile and 273 μL (1.6 mmole) of DIEA at ambient temperature. After the reaction mixture was stirred for 12 hr, more chloroacetonitrile (2 equivalents) was added and stirring was continued for 1 hr more. The reaction mixture was concentrated to dryness and the residue was dissolved in methylene choride. The organic phase was washed with 10% citric acid solution, water and brine, then dried and concentrated yielding a foam. This material was chromatographed on silica gel (chloroform-isopropanol, 98:2, v/v) to yield the title compound as a solid: m.p. 110° C.;

NMR: Consistent with structure;

HPLC:>97% pure at 214 nM;

Elem. Anal. calc'd for $C_{28}H_{32}N_4O_5 \cdot 0.15CHCl_3$: Calc'd: C, 64.71; H, 6.20; N, 10.72. Found: C, 64.86; H, 6.40; N, 10.69.

FAB MS: m/z 505 (M$^+$+H).

EXAMPLE 242

1-(1-(4-(4-(N-Aminocarbonyl)piperidinyloxy)-2-methoxybenzoyl) piperidin-4-yl)-1,2-dihydro-4(H)-3,1-benzoxazin-2-one The pH of the solution was adjusted to 3 with the addition of 50% potassium hydroxide and 208 mg (2.58 mmole) of potassium isocyanate was added. The reaction was stirred at ambient temperature overnight, then heated to 75° C. for 12 hr while maintaining the pH at approximately 3. (HC$_1$ was employed to lower the pH when required.) After 36 hr, the reaction mixture was concentrated to dryness and the residue was partitioned between chloroform and water/methanol. The organic phase was washed with water and brine, then dried and concentrated yielding 1 g of a semi-solid. This material was chromatographed on silica gel (chloroform-methanol, 96:4, v/v) to yield the title compound.

NMR: Consistent with structure;

HPLC:>99% pure at 214 nM;

Elem. Anal. calc'd for $C_{27}H_{32}N_4O_6 \cdot 0.3$ MeOH•0.3CHCl$_3$: Calc'd: C, 59.33; H, 6.24; N, 9.88. Found: C, 59.35; H, 6.22; N, 9.58.

FAB MS: m/z 509 (M$^+$+H).

EXAMPLE 243

1-(1-(4-(4-(1H-Tetrazol-5-yl)piperidinyloxy)-2-methoxybenzoyl) piperidin-4-yl)-1,2-dihydro-4(H)-3,1-benzoxazin-2-one

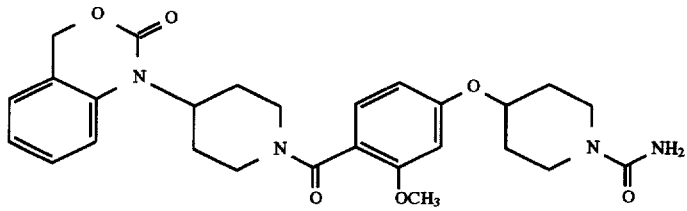

The hydrochloride salt of 1-(1-(4-(4-piperidinyloxy)-2-methoxy benzoyl)piperidin-4-yl)-1,2-dihydro-4(H)-3,1-benzoxazin-2-one (1 g, 2.15 mmole) from Example 26 was dissolved in 20 ml of water to give a solution with pH 1.7.

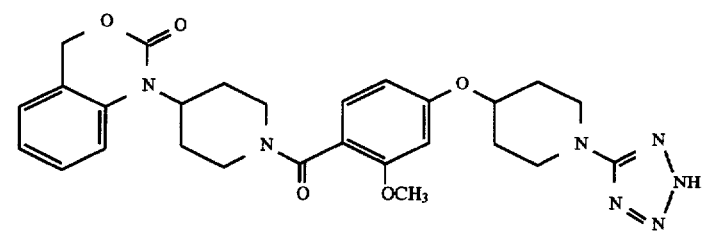

Step 1. 1-(1-(4-(4-Piperidinyloxy)-2-methoxy benzoyl) piperidin-4-yl)-1,2-dihydro-4(H)-3,1-benzoxazin-2-one (0.5 g, 0.88 mmole) from Example 26 was dissolved in 20 ml of DMF. The solution was cooled to 0° C. and solid potassium carbonate (267 mg, 1.93 mmole) and cyanogen bromide (102 mg, 0.97 mmole) were added. The reaction mixture was stirred for 0.5 hr at 0° C. and for 1.5 hr at room temperature. All volatiles were removed under reduced pressure and the residue was dissolved in ethyl acetate. The organic phase was washed with brine, dried, and concentrated to give 500 mg of 1-(1-(4-(4-(N-cyano) piperidinyloxy)-2-methoxybenzoyl) piperidin-4-yl)-1,2-dihydro-4(H)-3, 1-benzoxazin-2-one as a clear oil which solidified on standing.

Step 2. 1-(1-(4-(4-(N-Cyano)piperidinyloxy)-2-methoxybenzoyl) piperidin-4-yl)-1,2-dihydro-4(H)-3, 1-benzoxazin-2-one (180 mg, 0.367 mmole) was combined with 119 mg (1.8 mmole) of sodium azide and 96 mg of ammonium chloride in 7 ml of dry DMF. The resulting reaction mixture was heated to 100° C. for 2.5 hr. The reaction mixture was cooled and concentrated in vacuo. The residue was suspended in toluene and then concentrated once more. The crude product was subsequently purified by flash chromatography on silica gel (chloroform-methanol, 95:5, v/v) to yield the title compound as a solid: m.p. 165°–170° C.;

NMR: Consistent with structure;
HPLC:>98% pure at 214 nM;

Elem. Anal. calc'd for $C_{27}H_{31}N_7O_5 \bullet 0.15CHCl_3$: Calc'd: C, 59.13; H, 5.69; N, 17.78. Found: C, 58.81; H, 6.07; N, 18.11.

FAB MS: m/z 534 (M$^+$+H).

EXAMPLE 244

1-(1-(4-(4-(N-(N'-Cyanoamidine))piperidinyloxy)-2-methoxy benzoyl)piperidin-4-yl)-1,2-dihydro-4(H)-3,1-benzoxazin-2-one

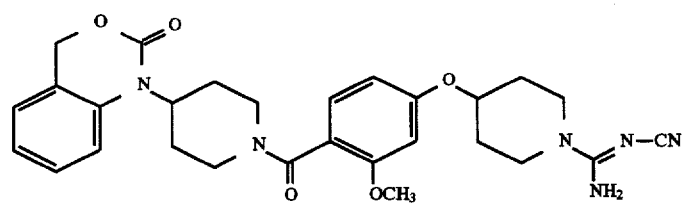

Step 1. To 10 ml of water containing 258 mg of potassium carbonate was added 10 ml of ethyl acetate containing the hydrochloride salt of 1-(1-(4-(4-piperidinyloxy)-2-methoxy benzoyl)piperidin-4-yl)-1,2-dihydro-4(H)-3,1-benzoxazin-2-one (1.0 g, 1.7 mmole) from Example 26. To this mixture was added 405 mg (1.7 mmole) of N-cyanodiphenoxyimidocarbonate. The reaction mixture was stirred for 2 hr at room temperature, diluted with ethyl acetate and the layers were separated. The organic phase was washed with water, then was dried, and concentrated to give 1.3 g of N-[1-(1-(4-(4-piperidinyloxy)-2-methoxybenzoyl) piperidin-4-yl)-1,2-dihydro-4(H)-3,1-benzoxazin-2-one]-N'-cyano-O-phenylisourea as a white amorphous solid.

Step 2. A solution of 30 ml of methanol containing 500 mg of N-[1-(1-(4-(4-piperidinyloxy)-2-methoxybenzoyl) piperidin-4-yl)-1,2-dihydro-4(H)-3,1-benzoxazin-2-one]-N'-cyano-O-phenylisourea was saturated with ammonia at 0° C. The reaction flask was capped with a septum and the reaction was allowed to stand at ambient temperature overnight. The reaction mixture was cooled and more ammonia was added. After a total reaction time of 24 hr, all volatiles were removed in vacuo and the residue was chromatographed on silica gel (chloroform-isopropanol, 98:2, v/v) to give the title compound.

NMR: Consistent with structure;

HPLC:>97% pure at 214 nM;

Elem. Anal. calc'd for $C_{28}H_{32}N_6O_5 \bullet 0.25$ IPA.0.25CHCl$_3$: Calc'd: C, 60.32; H, 5.98; N, 14.55. Found: C, 60.57; H, 5.91; N, 14.5.

FAB MS: m/z 533 (M$^+$+H).

EXAMPLE 245

1-(1-(4-(4-(N-(N'-Hydroxyamidine))piperidinyloxy)-2-methoxy benzoyl)piperidin-4-yl)-1,2-dihydro-4(H)-3,1-benzoxazin-2-one

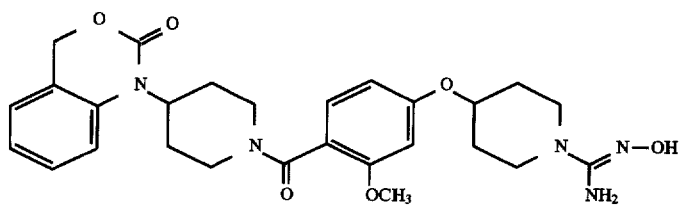

A solution of 5 ml of methanol containing 68 mg of hydroxylamine hydrochloride was treated with 1.1 ml of a 1 M solution of sodium methoxide in methanol. To this mixture was added 240 mg (0.48 mmole) of 1-(1-(4-(4-(N-Cyano)piperidinyloxy)-2-methoxybenzoyl) piperidin-4-yl)-1,2-dihydro-4(H)-3,1-benzoxazin-2-one. The resulting reaction mixture was stirred for 4 hr and concentrated. Flash chromatography of the residue on silica gel using chloroform-methanol gradient (98:2 to 95:5, v/v) yielded the title compound.

NMR: Consistent with structure;

HPLC:>95% pure at 214 nM;

Elem. Anal. calc'd for $C_{27}H_{33}N_5O_6 \cdot 0.55CHCl_3$: Calc'd: C, 58.10; H, 5.95; N, 12.39. Found: C, 58.30; H, 6.11; N, 12.36.

FAB MS: m/z 524 (M$^+$+H).

EXAMPLE 246

1-(1-(4-(4-(N-(3-Ethoxy)-1,2,5-thiadiazol-1-oxide-4-yl) piperidinyloxy)-2-methoxy benzoyl)pipeddin-4-yl)-1,2-dihydro-4(H)-3,1-benzoxazin-2-one

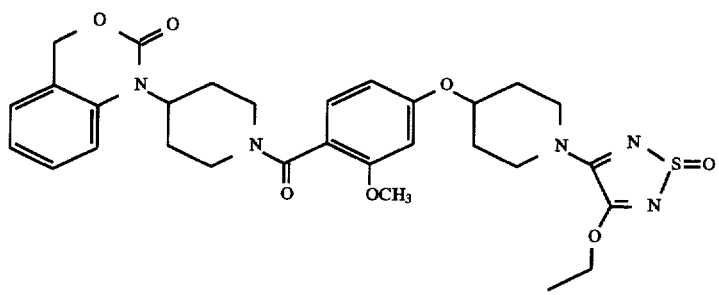

3,4-Diethoxy-1,2,5-thiadiazol-1-oxide (193 mg, 1.02 mmole) was dissolved in 10 ml of ethanol and to this solution was added mg (0.85 mmole) of 1-(1-(4-(4-piperidinyloxy)-2-methoxybenzoyl) piperidin-4-yl)-1,2-dihydro-4(H)-3,1-benzoxazin-2-one from Example 26. The resulting reaction mixture was stirred at room temperature overnight. The solids were collected and washed with cold ethanol. The filtrate was concentrated and the residual material was chromatographed on silica gel (chloroform:methanol, 95:5, v/v). The product containing fractions were concentrated and the resulting solid was combined with the previously collected precipitate giving the title compound in 92% overall yield.

NMR: Consistent with structure;

HPLC:>93% pure at 214 nM;

Elem. Anal. calc'd for $C_{30}H_{35}N_5O_7S \cdot 0.90MeOHo \cdot 0.05CHCl_3$: Calc'd: C, 57.68; H, 6.04; N, 10.87. Found: C, 57.67; H, 5.97; N, 10.67.

FAB MS: m/z 610 (M$^+$+H).

EXAMPLE 247

1-(1-(4-(4-(N-Acetyl)piperidinyloxy)-2-methoxybenzoyl)piperidin-4-yl)-tetrahydroquinolin-2-thione

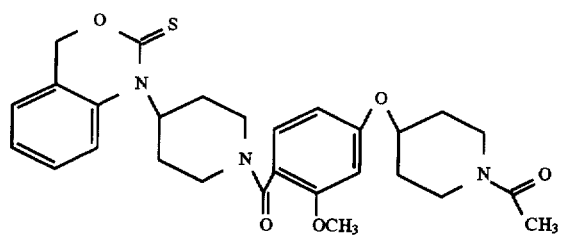

Step 1. To 40 ml of dry THF containing 1.1 g (3.3 mmole) 1-((1-t-butyloxycarbonyl)piperidin-4-yl)-tetrahydroquinolinone was added 672 mg (1.66 mmole) of [2,4-bis(methoxyphenyl)-1,3-dithia-2,4-diphosphetane-2,4-disulfide. The reaction mixture was stirred at ambient temperature for 30 minutes and then heated to reflux for 1.5 hr. All volatiles were removed under reduced pressure and the residue was applied directly to a 35 mm silica gel column. The product was eluted with hexane-ethyl acetate solution (7:1, v/v) affording 570 mg of 1-((1-t-butyloxycarbonyl) piperidin-4-yl)-tetrahydroquinolin-2-thione as an oil.

Step 2. Employing reaction conditions identical to those described in Example 1, Step 4, 570 mg of 1-((1-t-butyloxycarbonyl)piperidin-4-yl)-tetrahydroquinolin-2-thione was converted quantitatively to the hydrochloride salt of 1-(piperidin-4-yl)tetrahydroquinolin-2-thione with HCl.

Step 3. The hydrochloride salt of 1-(piperidin-4-yl) tetrahydroquinolin-2-thione (550 mg) was coupled with 702 mg of 4-(N-t-butoxycarbonyl-4-piperidinyloxy)-2-methoxybenzoic acid employing EDC and HOBT according to the procedure of Example 25, Step 4. Extractive work-up yielded 1-(1-(4-(4-(N-t-butyloxycarbonyl)piperidinyloxy)-2-methoxybenzoyl) piperidin-4-yl)tetrahydroquinolin-2-thione in essentially quantitative yield. This material was carded to the next synthetic step without further purification.

Step 4. 1-(1-(4-(4-(N-t-Butyloxycarbonyl) piperidinyloxy)-2-methoxybenzoyl)piperidin-4-yl)

tetrahydroquinolin-2-thione (1.2 g) was converted quantitatively with HCl gas to the hydrochloride salt of 1-(1-(4-(4-pipefidinyloxy)-2-methoxybenzoyl)piperidin-4-yl)-tetrahydroquinolin-2-thione according to the procedure described in Example 1, Step 4.

Step 5. 1-(1-(4-(4-Piperidinyloxy)-2-methoxybenzoyl)piperidin-4-yl)-tetrahydroquinolin-2-thione hydrochloride (1.0 g) was dissolved in 25 ml of methylene chloride containing 0.73 ml of triethylamine. To this solution was added 0.195 ml of acetyl chloride and the reaction mixture was stirred for 3 hr. The reaction mixture was diluted with methylene chloride and was washed in succession with saturated sodium bicarbonate solution and brine. Rotoevaporation of the dried organic extracts gave the crude product which was purified to homogeneity via flash chromatography on silica gel (chloroform-isopropanol, 99:1, v/v). In this way, 800 mg the title compound was obtained as an amorphous solid.

NMR: Consistent with structure;

HPLC:>99% pure at 214 nM;

Elem. Anal. calc'd for $C_{29}H_{35}N_3O_4S \cdot 0.05IPA \cdot 0.5CHCl_3$: Calc'd: C, 60.89; H, 6.55; N, 6.84. Found: C, 60.89; H, 5.56; N, 6.98.

FAB MS: m/z 522 ($M^++H$).

EXAMPLE 248

1-(1-(4-(4-(N-Acetyl)piperidinyloxy)-2-methoxybenzoyl)piperidin-4-yl)-tetrahydroqninolin-2-imine

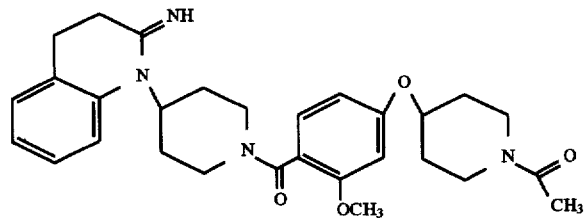

A continuous stream of dry ammonia gas was passed into an ice cold solution of 15 ml of methanol containing 130 mg (0.25 mmole) of 1-(1-(4-(4-(N-acetyl)piperidinyloxy)-2-methoxybenzoyl)piperidin-4-yl)-tetrahydroquinolin-2-thione. The reaction mixture turned black within minutes. After 15 minutes, the ammonia purge was stopped, the reaction flask was capped with a robber septum, and the reaction mixture was allowed to warm to ambient temperature on overnight stirring. The reaction mixture was filtered and concentrated. The residual material was dissolved in ethyl acetate and washed with sodium sulfide solution and brine. The organic extracts were dried and concentrated to give a semi-solid which was flash chromatographed on silica gel [initially chloroform-methanol (9:1) then chloroform-isopropanol (9:1 containing 1% concentrated ammonium hydroxide)] to yield the title compound.

NMR: Consistent with structure;

HPLC:>93% pure at 214 nM;

Elem. Anal. calc'd for $C_{29}H_{35}N_4O_4 \cdot 0.15IPA \cdot 0.25CHCl_3$: Calc'd: C, 65.76; H, 6.77; N, 10.33. Found: C, 65.83; H, 7.15; N, 10.32.

FAB MS: m/z 504 ($M^++H$).

EXAMPLE 249

N-[1-(4-Piperidinyl)-1,2-dihydro-4(H)-3,1-benzoxazin-2-one]-N'-[2,4-dimethoxyphenyl]urea

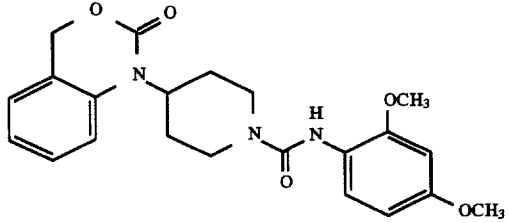

A solution of 2,4-dimethoxyaniline (200 mg, 1.3 mmole) in 8 ml of THF was stirred magnetically in an ice bath under nitrogen. To this solution was added 119 mg (0.4 mmole) of triphosgene and 0.5 ml DIEA. After addition was complete, the ice bath was removed for 15 minutes. The reaction mixture (pH=8) was recooled to 0° C. and 200 mg (0.86 mmole) of 1-(4-piperidinyl)-1,2-dihydro-4(H)-3,1-benzoxazin-2-one from Step 4 of Example 1 in 3 ml of THF was added. The reaction mixture was stirred for 1 hr and concentrated. The solids were chromatographed on silica gel (hexane-ethyl acetate, 1:1, v/v) to afford 203 mg of the title compound as an amorphous solid: m.p. 75°–77° C.;

NMR: Consistent with structure;

HPLC:>99% pure at 214 nM;

Elem. Anal. calc'd for $C_{22}H_{25}N_3O_5 \cdot 0.1EtOAc \cdot 0.65H_2O$: Calc'd: C, 62.28; H, 6.32; N, 9.73. Found: C, 62.26; H, 5.96; N, 9.73.

FAB MS: m/z 412 ($M^++H$).

EXAMPLE 250

1-(1-(2,4-Dimethoxyphenylacetyl)piperidin-4-yl)-1,2-dihydro-4(H)-3,1-benzoxazin-2-one

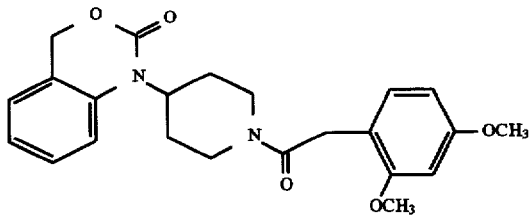

To a solution of the hydrochloride salt of 1-(4-piperidinyl)-1,2-dihydro-4(H)-3,1-benzoxazin-2-one (167 mg, 0.62 mmol) from Step 4 of Example 1 in DMF (5 mL) was added DIEA (0.238 ml, 1.36 mmol), HOBT (92 mg, 0.68 mmol), EDC (129 mg, 0.67 mmol), and 2,4-dimethoxyphenylacetic acid (128 mg, 0.65mmol). The reaction was stirred at ambient temperature for 24 h and the solvent was removed under reduced pressure. The residue was partitioned between EtOAc and saturated aqueous sodium bicarbonate solution. The EtOAc layer was washed sodium bicarbonate solution and brine, then dried ($MgSO_4$), and concentrated under reduced pressure. The residue was purified by pressurized silica gel column chromatography using chloroform-methanol (98:2, v/v). The title compound was obtained in homogeneous form as an amorphous solid.

NMR: Consistent with structure;

HPLC:>98% pure at 214 nM;

Elem. Anal. calc'd for $C_{23}H_{26}N_2O_5 \cdot .45H_2O$: Calc'd: C, 65.99; H, 6.48; N, 6.69. Found: C, 66.03; H, 6.40; N, 6.74.

FAB MS: m/z 411 (M$^+$+H).

EXAMPLE 251

1-(1-(4-(N-(2-Oxo-tetrahydrofuran-3-yl)-4-piperidinyloxy)-2-methoxybenzoyl) piperidin-4-yl)-1,2-dihydro-4(H)-3,1-benzoxazin-2-one

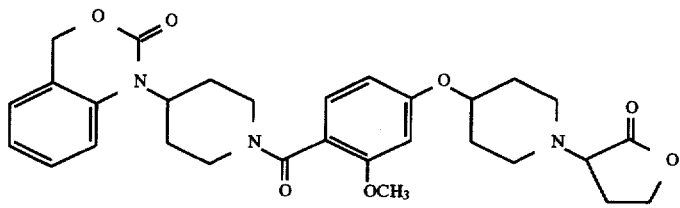

A solution of methylene chloride (4 ml) containing 186 mg (0.37 mmole) of 1-(1-(4-(4-piperidinyloxy)-2-methoxy benzoyl)piperidin-4-yl)-1,2-dihydro-4(H)-3,1-benzoxazin-2-one from Example 26 was treated with 142 gL of DIEA and 127.3 mg (0.77 mmole) of α-bromo-γ-butyrolactone at 0° C. After 1 hr the ice bath was removed and the reaction mixture was stirred for 12 hr at ambient temperature. More α-bromo-γ-butyrolactone (30 μl) was added and stirring was continued for 12 hr more. The reaction mixture was concentrated to dryness and the residue was chromatographed on silica gel (methylene chloride-methanol, 92:8, v/v) to yield the title compound as a solid: m.p. 81°–85° C.;

NMR: Consistent with structure;

HPLC:>97% pure at 214 nM;

Elem. Anal. calc'd for $C_{30}H_{35}N_3O_7 \cdot 1.5CH_2Cl_2$: Calc'd: C, 55.88; H, 5.66; N, 6.21. Found: C, 55.99; H, 5.65; N, 5.84.

FAB MS: m/z 550 (M$^+$+H).

EXAMPLE 252

1-(1-(4-(4-(N-(Methoxycarbonyl)piperidinyloxy)-2-methoxybenzoyl) piperidin-4-yl)-1,2-dihydro-4(H)-3,1-benzoxazin-2-one

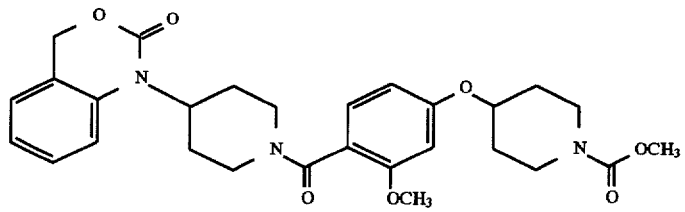

A commercial sample of methoxycarbonylisocyanate was diluted with methylene chloride to bring the concentration of the resulting solution to 1 molar. This stock solution (2 ml, 2 mmole) was then added dropwise to a solution of methylene chloride (5 ml) containing 644 mg (1.28 mmole) of 1-(1-(4-(4-piperidinyloxy)-2-methoxy benzoyl)piperidin-4-yl)-1,2-dihydro-4(H)-3,1-benzoxazin-2-one from Example 26 and 560 μL of DIEA. After 1 hr all starting material had been consumed and the reaction mixture was quenched with water. The organic phase was washed with brine, the dried, and concentrated to give an oil consisting primarily of two products. Column chromatography on silica gel (methylene chloride-methanol, 3, v/v) yielded 67 mg of the title compound as a solid: m.p. 100°–102° C.; $R_f$=0.28 (methylene chloride-methanol, 97:3, v/v);

NMR: Consistent with structure;

HPLC:>98% pure at 214 nM;

Elem. Anal. calc'd for $C_{28}H_{33}N_3O_7 \cdot 0.45H_2O$: Calc'd: C, 63.25; H, 6.43; N, 7.90. Found: C, 63.20; H, 6.49; N, 8.11.

FAB MS: m/z 524 (M$^+$+H).

EXAMPLE 253

1-(1-(4-(4-(N-Methoxyoxalyl)piperidinyloxy)-2-methoxybenzoyl) piperidin-4-yl)-1,2-dihydro-4(H)-3,1-benzoxazin-2-one

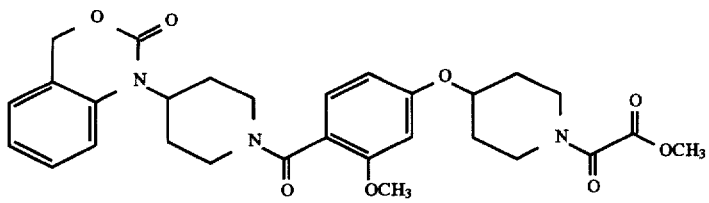

A solution of methylene chloride (8 ml) containing 239 mg (0.476 mmole) of 1-(1-(4-(4-pipefidinyloxy)-2-methoxy benzoyl)pipefidin-4-yl)-1,2-dihydro-4(H)-3,1-benzoxazin-2-one hydro chloride from Example 26 and 170 FL of DIEA was treated with methyl oxalyl chloride at 0° C. After 1 hr the reaction mixture was quenched with brine and diluted with methylene chloride. The organic phase was washed with brine, the dried, and concentrated. Column chromatography of the crude product on silica gel (methylene chloride-methanol, 97:3, v/v) yielded 220 mg of the title compound as a white solid: m.p. 108°–111° C.; Rf=0.33 (chloroform-isopropanol, 95:5, v/v);

NMR: Consistent with structure;

HPLC:>95% pure at 214 nM;

Elem. Anal. calc'd for $C_{29}H_{33}N_3O_8 \cdot 2.05H_2O \cdot 0.15 CH_2Cl_2$: Calc'd: C, 58.22; H, 6.27; N, 6.99. Found: C, 58.25; H, 6.26; N, 6.98.

FAB MS: m/z 552 (M$^+$+H).

EXAMPLE 254

1-(1-(4-(N-(Diethylphosphoryl)-4-piperidinyloxy)-2-methoxybenzoyl) piperidin-4-yl)-1,2-dihydro-4(H)-3,1-benzoxazin-2-one

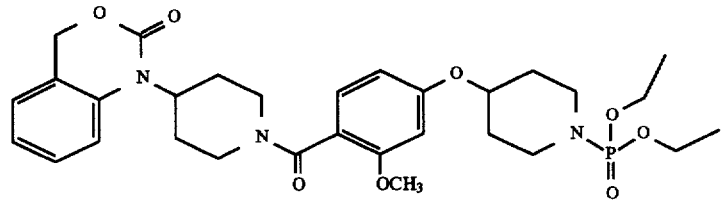

A solution of methylene chloride (5 ml) containing 147 mg (0.292 mmole) of 1-(1-(4-(4-piperidinyloxy)-2-methoxy benzoyl)piperidin-4-yl)-1,2-dihydro-4(H)-3,1-benzoxazin-2-one hydrochloride from Example 26 and 112 µL of DIEA was treated with 55.5 mg of diethyl chlorophosphate at 0° C. After 2 hr the reaction mixture was concentrated and the crude product was applied directly to a silica gel column.

Elution with methylene chloride-methanol (98:2, v/v) yielded 101 mg of the title compound as a white solid: m.p. 86°–88° C.; Rf=0.17 (chloroform-isopropanol, 95:5, v/v);

NMR: Consistent with structure;

HPLC:>98% pure at 214 nM;

Elem. Anal. calc'd for $C_{30}H_{40}N_3O_6P \cdot 0.55H_2O$: Calc'd: C, 58.92; H, 6.77; N, 6.87. Found: C, 58.93; H, 6.75; N, 7.01.

FAB MS: m/z 602 (M$^+$+H).

EXAMPLE 255

N-[1-(1-(4-(4-(Piperidinyloxy)-2-methoxybenzoyl) piperidin-4-yl)-1,2-dihydro-4(H)-3,1-benzoxazin-2-one]-N'-[ethoxycarbonylmethyl]urea

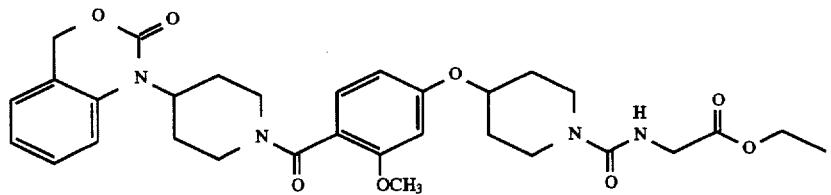

A solution of methylene chloride (4 ml) containing 288 mg (0.573 mmole) of 1-(1-(4-(4-piperidinyloxy)-2-methoxy benzoyl)piperidin-4-yl)-1,2-dihydro-4(H)-3,1-benzoxazin-2-one hydrochloride from Example 26 and 200 µL of DIEA was treated with ethyl isocyanatoacetate at 0° C. After 0.5 hr the reaction mixture was concentrated and the crude product was applied directly to a silica gel column. Elution with methylene chloride-methanol (96:4, v/v) yielded 268 mg of the title compound as a white solid: m.p. 100°–104° C.; $R_f$=0.29 (chloroform-isopropanol, 95:5, v/v);

NMR: Consistent with structure;

HPLC:>95% pure at 214 nM;

Elem. Anal. calc'd for $C_{31}H_{38}N_4O_8 \cdot 0.3CH_2Cl_2$: Calc'd: C, 60.62; H, 6.27; N, 9.04. Found: C, 60.54; H, 6.22; N, 8.96.

FAB MS: m/z 595 (M⁺+H).

EXAMPLE 256

1-(1-(4-(N-(4-Carboxybenzoyl)-4-piperidinyloxy)-2-methoxybenzoyl) piperidin-4-yl)-1,2-dihydro-4(H)-3,1-benzoxazin-2-one

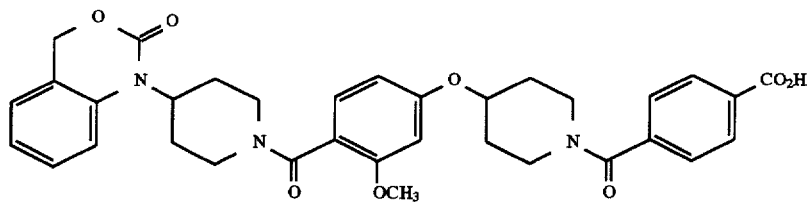

Step 1. To a solution of the hydrochloride salt of 1-(4-piperidinyl)-1,2-dihydro-4(H)-3,1-benzoxazin-2-one (655 mg, 1.32 mmol) from Step 4 of Example 1 in DMF (10 mL) was added DIEA (0.577 ml, 3.31 mmol), HOBT (201 mg, 1.48 mmol), EDC (281 mg, 1.45 mmol), and mono-methyl terephthalate (259 mg, 1.43 mmol). The reaction was protected from moisture and stirred at ambient temperature for 24 h. The solvent was removed under reduced pressure and the residue was partitioned between EtOAc and saturated aqueous sodium bicarbonate solution. The EtOAc layer was washed sodium bicarbonate solution and brine, then dried and concentrated under reduced pressure. The residue was purified by pressurized silica gel column chromatography using methylene chloride-methanol (97:3, v/v) to give 720 mg of 1-(1-(4-(4-(N-(4-(methoxycarbonyl)benzoyl) piperidinyloxy)-2-methoxy benzoyl)piperidin-4-yl)-1,2-dihydro-4(H)-3,1-benzoxazin-2-one as an oil.

Step 2. 1-(1-(4-(4-(N-(4-(Methoxycarbonyl) benzoyl) piperidinyloxy)-2-methoxy benzoyl)piperidin-4-yl)-1,2-dihydro-4(H)-3,1-benzoxazin-2-one (700 mg, 1.11 mmole) was dissolved in 10 ml of methanol and treated with 2 ml of 1N sodium hydroxide solution. The resulting reaction mixture was stirred at ambient temperature overnight. All volatiles were removed under reduced pressure and the residue was partitioned between ethyl acetate and 10% citric acid solution. The organic phase was dried and concentrated to afford 730 mg of the title compound in 93 % purity. Purification via flash chromatography on silica gel (initially chloroform-methanol elution (92:8) and then isopropanol-acetic acid (9:1)) gave a semi-solid which was treated with 6N HCl solution and then extracted with methylene chloride. In this way, 410 mg of the title compound was obtained analytically pure as an amorphous solid: m.p. 150°–155° C.; $R_f$=0.30 (chloroform-methanol, 90:10, v/v);

NMR: Consistent with structure;

HPLC:>99% pure at 214 nM;

Elem. Anal. calc'd for $C_{34}H_{35}N_3O_8 \cdot 0.3CH_2Cl_2 \cdot 0.2H_2O$: Calc'd: C, 64.09; H, 5.65; N, 6.54. Found: C, 64.08; H, 5.68; N, 6.47.

FAB MS: m/z 614 (M⁺+H).

EXAMPLE 257

1-(1-(4-(N-(Aminosulfonyl)-4-piperidinyloxy)-2-methoxybenzoyl) pipefidin-4-yl)-1,2-dihydro-4(H)-3,1-benzoxazin-2-one

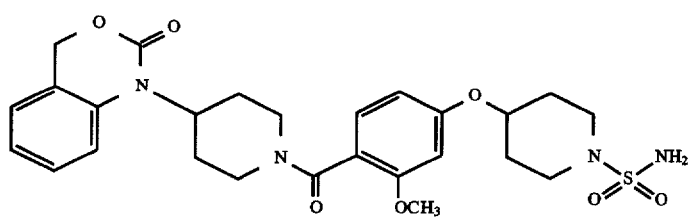

1-(1-(4-(4-Piperidinyloxy)-2-methoxy benzoyl)piperidin-4-yl)-1,2-dihydro-4(H)-3,1-benzoxazin-2-one hydrochloride (543 mg, 1.08 mmole) from Example 26 and 1.0 g of sulfamide were dissolved in ml of pyfidine under nitrogen and heated to reflux for 30 minutes. The reaction mixture was cooled and filtered. Concentration of the filtrate and chromatography of the crude product on a silica gel column (methylene chloride-methanol (95:5, v/v)) yielded 500 mg of the title compound; trituration with ethyl ether afforded the analytical sample as a white solid: m.p. 226° C.; $R_f$=0.21 (chloroform-methanol, 90:10, v/v);

NMR: Consistent with structure;

HPLC: >99% pure at 214 nM;

Elem. Anal. calc'd for $C_{26}H_{32}N_4O_7S \cdot 0.65Et_2O \cdot 0.7H_2O$: Calc'd: C, 56.73; H, 6.64; N, 9.25. Found: C, 56.74; H, 6.97; N, 9.36.

FAB MS: m/z 545 (M$^+$+H).

EXAMPLE 258

1-(1-(4-(N-(Methoxycarbonylaminosulfonyl)-4-piperidinyloxy)-2-methoxybenzoyl) piperidin-4-yl)-1,2-dihydro-4(H)-3,1-benzoxazin-2-one

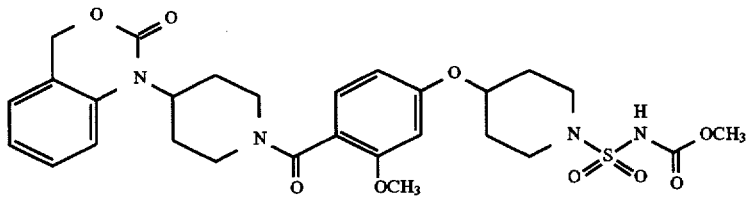

To 1 ml of ice cold methylene chloride was added 66 μL (107.3 mg, 0.758 mmole) of chlorosulfonylisocyanate and 30.5 μL (0.752 mmole) of dry methanol under nitrogen. This mixture was stirred for 1 hr and then 325 mg (0.647 mmole) of 1-(1-(4-(4-piperidinyloxy)-2-methoxy benzoyl)piperidin-4-yl)-1,2-dihydro-4(H)-3,1-benzoxazin-2-one hydrochloride from Example 26 in 1 ml of methylene chloride was added, followed by the addition of 250 μL of DIEA. The reaction mixture was stirred at ambient temperature overnight. Concentration of the reaction mixture in vacuo and chromatography of the residual material on a silica gel column (methylene chloride-methanol (97:3, v/v)) yielded 100 mg of the title compound as a white solid: m.p. 117°–120° C.; $R_f$=0.17 (methylene chloride-methanol, 97:3, v/v);

NMR: Consistent with structure;

HPLC: >97% pure at 214 nM;

Elem. Anal. calc'd for $C_{28}H_{34}N_4O_9S \cdot 0.5CH_2Cl_2 \cdot 0.15H_2O$: Calc'd: C, 52.83; H, 5.49; N, 8.65. Found: C, 52.81; H, 5.49; N, 8.94.

FAB MS: m/z 603 (M$^+$+H).

EXAMPLE 259

1-(1-(4-(N-(3-Nitrophenylsulfonyl)-4-piperidinyloxy)-2-methoxybenzoyl) piperidin-4-yl)-1,2-dihydro-4(H)-3,1-benzoxazin-2-one

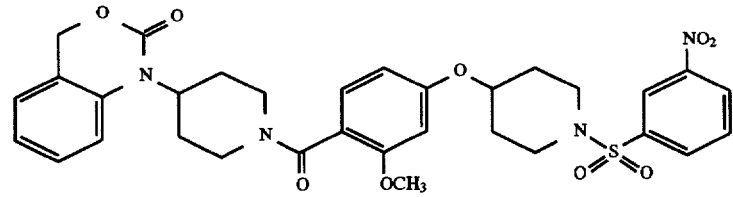

A solution of methylene chloride (8 ml) containing 424mg (0.844 mmole) of 1-(1-(4-(4-piperidinyloxy)-2-methoxy benzoyl)piperidin-4-yl)-1,2-dihydro-4(H)-3,1-benzoxazin-2-one hydrochloride from Example 26 and 295 μL (1.69 mmole) of DIEA was treated at 0° C. with 2 ml of THF containing 212 mg (0.956 mmole) of 3-nitrophenylsulfonyl chloride. After 0.5 hr the reaction mixture was quenched with water and concentrated in vacuo. The crude product was applied directly to a silica gel column. Elution with methylene chloride-methanol (96:4, v/v) yielded 505 mg of the title compound as a whim solid: m.p. 105°–109° C.; $R_f$=0.32 (EtOAc);

NMR: Consistent with structure;

HPLC: >95% pure at 214 nM;

Elem. Anal. calc'd for $C_{32}H_{34}N_4O_9S \cdot 0.1H_2O \cdot 0.45CH_2Cl_2$: Calc'd: C, 56.42; H, 5.12; N, 8.11. Found: C, 56.41; H, 5.10; N, 8.20.

FAB MS: m/z 651 (M$^+$+H).

EXAMPLE 260

1-(1-(4-(N-(N,N-Diethylaminoethylaminosulfonyl)-4-piperidinyloxy)-2-methoxybenzoyl)piperidin-4-yl)-1,2-dihydro-4(H)-3, 1-benzoxazin-2-one

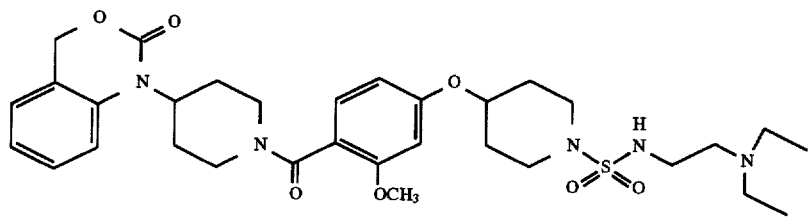

Step 1. A solution of methylene chloride (30 ml) was cooled to −78° C. and treated with fluorosulfonylchloride (3.2 g, 27 mmole). To this solution was then added dropwise over 10 minutes a solution of methylene chloride (30 ml) containing 1.195 g (2.567 mmole) of 1-(1-(4-(4-piperidinyloxy)-2-methoxy benzoyl)piperidin-4-yl)-1,2-dihydro-4(H)-3,1-benzoxazin-2-one from Example 26 and 2 ml (11.5 mmole) of DIEA. After 0.5 hr, the pH of the reaction mixture is was estimated to be 1 (moist pH paper) and more DIEA (1 ml) was added. Stirring was continued for 0.5 hr and all volatiles were rotoevaporated. The residual material was applied directly to a silica gel column and eluted with methylene chloride-methanol (98:2, v/v) to give 630 mg of 1-(1-(4-(4-(N-(fluorosulfonyl)piperidinyloxy)-2-methoxybenzoyl)piperidin-4-yl)-1,2-dihydro-4(H)-3,1-benzoxazin-2-one as an oil. This material was used in the next step without further purification.

Step 2. A solution of methylene chloride (4 ml) containing 135 mg (0.246 mmole) of 1-(1-(4-(4-(N-(fluorosulfonyl) piperidinyloxy)-2-methoxy benzoyl)piperidin-4-yl)-1,2-dihydro-4(H)-3, 1-benzoxazin-2-one was treated at ambient temperature with 124 mg (1.06 mmole) of N,N-diethylethylenediamine. The reaction mixture was stirred for overnight and concentrated. The crude product was applied directly to a silica gel column. Elution with methylene chloride-methanol (98:2, v/v) yielded 145 mg of the title compound as a white solid: m.p. 90°–93° C.; R$_f$=0.13 (chloroform-isopropanol, 90:10).

NMR: Consistent with structure;

HPLC:>99% pure at 214 nM;

Elem. Anal. calc'd for C$_{32}$H$_{45}$N$_5$O$_7$S•0.25CH$_2$Cl$_2$: Calc'd: C, 58.24; H, 6.90; N, 10.53. Found: C, 58.47; H, 7.00; N, 10.17.

FAB MS: m/z 644 (M$^+$+H).

EXAMPLE 261

1-(1-(4-(N-(tert-Butyloxycarbonyl)piperidin-4-yloxy)-2-methoxy benzoyl)piperidin-4-yl)-1,2-dihydro-4(H)-3,1-pyridoxazin-2-one

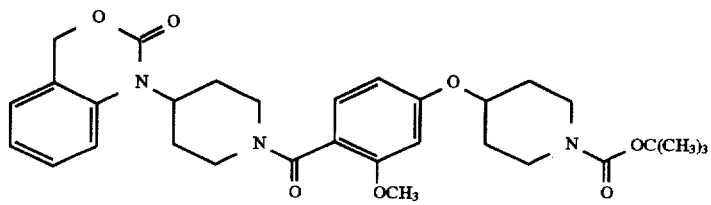

Step 1. The methyl ester of 2-amino nicotinic acid is reduced with lithium aluminium hydride in a solvent such as THF to give 2-amino-3-hydroxymethylpyridine.

Step 2. The product from Step 1 and 1-(tert-butyloxycarbonyl)piperidin-4-one are heated together in a solvent such as THF or methanol. The cooled mixture is treated with sodium cyanpborohydride to give 1-(tert-butyloxycarbonyl)-4-(3-hydroxymethyl-2-pyridylamino) piperidine.

Step 3. The product from Step 2 is treated with phosgene and triethylamine in a solvent such as THF or toluene to give 1-(1-(tert-butyloxycarbonyl)piperidin-4-yl)-1,2-dihydro-4 (H)-3,1-pyridoxazin-2-one.

Step 4. The product from Step 3 is treated with HCl gas in a solvent such as EtOAc or dioxane to give the hydrochloride salt of 1-(1-(tert-butyloxycarbonyl)piperidin-4-yl)-1,2-dihydro-4(H)-3,1-pyridoxazin-2-one.

Step 5. The product from Step 4 is acylated with 4-(1-(tert-butyloxycarbonyl)piperidin-4-yl)-2-methoxybenzoic acid using conditions such as those given in Step 4 of Example 25 to give the title compound.

EXAMPLE 262

1-(1-(6-(N-(tert-Butyloxycarbonyl)piperidin-4-yloxy) nicotinoyl)piperidin-4-yl)-1,2-dihydro-4(H)-3,1-benzoxazin-2-one

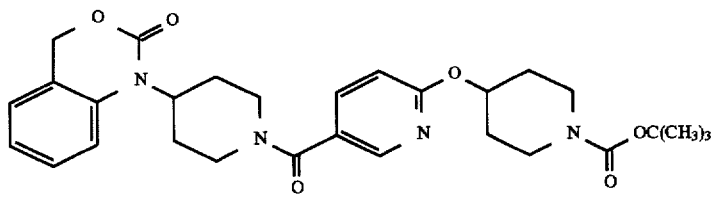

Step 1. 1-(tert-Butyloxycarbonyl)-4-piperidinol is treated with sodium hydride in a solvent such as THF or DMF to make the alkoxide. Addition of the methyl ester of 6-chloronicotinic acid to the alkoxide gives methyl 6-(1-(tert-butyloxycarbonyl)piperidin-4-yloxy) nicotinate.

Step 2. The product from Step 1 is saponified with NaOH in water-methanol to give 6-(1-(tert-butyloxycarbonyl) piperidin-4-yloxy) nicotinic acid.

Step 3. The product from Step 3 is coupled to 1-(piperidin-4-yl)-1,2-dihydro-4(H)-3,1-benzoxazin-2-one hydrochloride from Step 4 of Example 1 using EDC and HOBT in DMF to give the title compound.

EXAMPLE 263

1-(1-(4-(N-(Imidazolecarbonyl)piperidin-4-yloxy)-2-methoxy benzoyl)pipefidin-4-yl)-1,2-dihydro-4(H)-3,1-benzoxazin-2-one

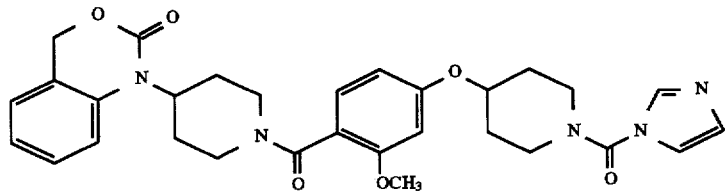

1-(1-(4-(4-Piperidinyloxy)-2-methoxybenzoyl)piperidin-4-yl)-1,2-dihydro-4(H)-3, 1-benzoxazin-2-one (660 mg, 1.41 mmole) from Example 26 was dissolved in 20 mL of THF at room temperature and treated with 230 mg (1.41 mmole) of carbonyldiimidazole. After 0.5 hr the reaction mixture was poured into 50 ml of water and extracted with ethyl acetate. The combined organic extracts were washed with water and brine, then dried and concentrated to give a solid. Trituration of this material with ether afforded the title compound in analytical form: m.p. 123°–126° C.

TLC $R_f$=0.32 (chloroform-methanol, 90:10);

NMR: Consistent with structure;

HPLC:>96% pure at 214 nM;

Elem. Anal. calc'd for $C_{30}H_{33}N_5O_6 \cdot 0.3CHCl_3$: Calc'd: C, 61.11; H, 5.64; N, 11.76. Found: C, 61.09; H, 5.80; N, 11.38.

FAB MS: m/z 560 (M$^+$+H).

EXAMPLE 264

1-(1-(4-(N-(Carboxamidino)piperidin-4-yloxy)-2-methoxybenzoyl) piperidin-4-yl)-3,4-dihydro-2(1H)-quinolinone

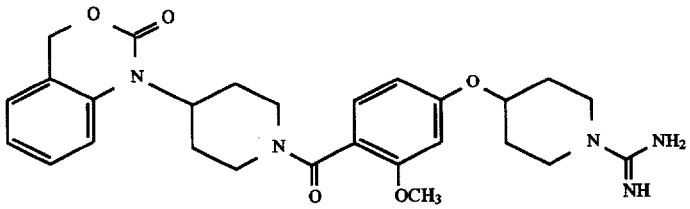

1-(1-(4-(4-Piperidinyloxy)-2-methoxybenzoyl)piperidin-4-yl)-3,4-dihydro-2(1H)-quinolinone from Example 190 (230 mg, 0.497 mmole) was dissolved in 3 ml of dry DMF containing 0.346 mL of triethylamine and treated with 500 mg of 2,3-dimethylpyrazole-1-carboxamidine (2.48 mmole) at room temperature. The reaction mixture was stirred for 12 hr and more 2,3-dimethylpyrazole-1-carboxamidine (2.48 mmole) and triethylamine (346 gL) were added. The reaction mixture stirred for 2 hr more and then was concentrated under high vacuum. The residue was flash chromatographed on silica gel (chloroform-methanol-concentrated ammonium hydroxide, 90:10:1, v/v) to afford 528 mg of the title compound as a solid. The TFA salt of the title compound was obtained via preparative reverse phase HPLC utilizing a water-acetonitrile gradient containing 0.1% TFA: m.p. 105°–108° C.; TLC $R_f$=0.3 (chloroform-methanol-concentrated ammonium hydroxide, 70:30:3);

HPLC:>99% pure at 214 nM;

Elem. Anal. calc'd for $C_{28}H_{35}N_5O_4$•1.75TFA•0.55CHCl$_3$: Calc'd: C, 49.84; H, 4.88; N, 9.09. Found: C, 49.96; H, 4.67; N, 9.11.

FAB MS: m/z 506 (M$^+$+H).

EXAMPLE 265

1-(1-(4-(N-(Acetamido)piperidin-4-yloxy)-2-methoxybenzoyl)piperidin-4-yl)-3,4-dihydro-2(1H)-quinolinone

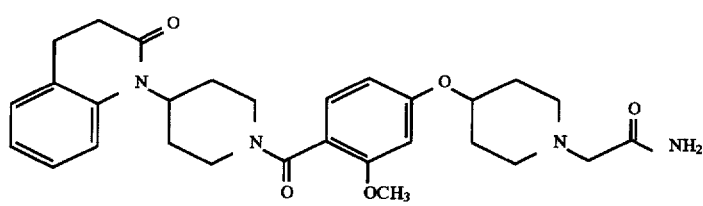

Step 1. 1-(1-(4-(4-Piperidinyloxy)-2-methoxybenzoyl) piperidin-4-yl)-3,4-dihydro-2(1H)-quinolinone hydrochloride from Example 190 (500 mg, 1.00 mmole) was dissolved in 7 ml of dry DMF containing 303 mg (2.19 mmole) of potassium carbonate. The suspension was cooled to 0° C. and 90 gL (1.42 mmole) of chloroacetonitrile was added neat with stirring. The cooling bath was removed after 10 minutes and the reaction was continued at room temperature for 4 hr. All volatiles were rotoevaporated and the residue was partitioned between ethyl acetate and brine. The combined organic extracts were dried and concentrated to yield 430 mg of 1-(1-(4-(N-cyanomethyl)piperidin-4-yloxy)-2-methoxybenzoyl) piperidin-4-yl)-3,4-dihydro-2(1H)-quinolinone as an oil.

Step 2. 1-(1-(4-(N-cyanomethyl)piperidin-4-yloxy)-2-methoxybenzoyl)piperidin-4-yl)-3,4-dihydro-2(1H)-quinolinone (79 mg, 0.157 mole) from Step 1 above was added to a rapidly stirred heterogeneous mixture of 90 μL (0.475 mmole) of 30% hydrogen peroxide solution, 431 μL of 2 M sodium hydroxide solution, and 2 ml of ethanol. The reaction mixture was stirred for 3 hr and all volatiles were removed under reduced pressure. The residue partitioned between ethyl acetate and water. The combined organic extracts were dried and concentrated to give 64 mg of the crude product. Chromatography on silica gel (chloroform-methanol, 92:8, v/v), followed by trituration of the chromatographed product with ether afforded 15 mg of the title compound as a solid: m.p. 116°–119° C.; $R_f$=0.21 (chloroform-methanol, 90:10);

NMR: Consistent with structure;

HPLC:>94% pure at 214 nM;

Elem. Anal. calc'd for $C_{29}H_{36}N_4O_5$•0.5Et$_2$O•0.45CHCl$_3$: Calc'd: C, 61.78; H, 6.83; N, 9.16. Found: C, 61.71; H, 7.23; N, 9.40.

FAB MS: m/z 521 (M$^+$+H).

EXAMPLE 266

1-(1-(4-(N-(Cyano)piperidin-4-yloxy)-2-methoxybenzoyl) pipeddin-4-yl)-3,4-dihydro-2(1H)-quinolinone

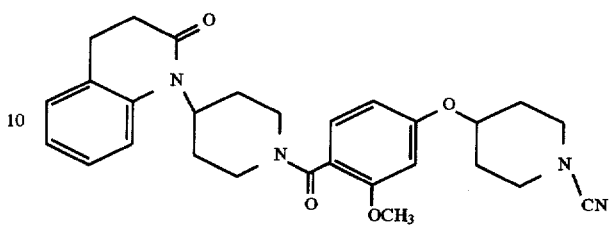

1-(1-(4-(4-Piperidinyloxy)-2-methoxybenzoyl)piperidin-4-yl)-3,4-dihydro-2(1H)-quinolinone hydrochloride (523 mg, 1.05 mmole) from Example 190 was dissolved in 7 ml of DMF. The solution was cooled to 0° C. and solid potassium carbonate (318 mg, 2.20 mmole) and cyanogen bromide (122 mg, 1.15 mmole) were added. The reaction mixture was stirred for 0.5 hr at 0° C. and for 1.5 hr at room temperature. All volalIies were removed under reduced pressure and the residue was dissolved in ethyl acetate. The organic phase was washed with brine, dried, and concentrated. Chromatography of the residual material on silica gel using chloroform-methanol (85–15, v/v) gave 520 mg of the title compound as a solid: m.p. 103°–105° C.; $R_f$=0.12 (ethyla acetate-hexane, 4:1);

NMR: Consistent with structure;

HPLC:>99% pure at 214 nM;

Elem. Anal. calc'd for $C_{28}H_{32}N_4O_4$•0.5CHCl$_3$: Calc'd: C, 62.43; H, 5.98; N, 10.22. Found: C, 62.42; H, 5.99; N, 10.04.

FAB MS: m/z 489 (M$^+$+H).

EXAMPLE 267

1-(1-(4-(1H-Tetrazol-5-yl)piperidin-4-yloxy)-2-methoxybenzoyl) piperidin-4-yl)-3,4-dihydro-2(1H)-quinolinone

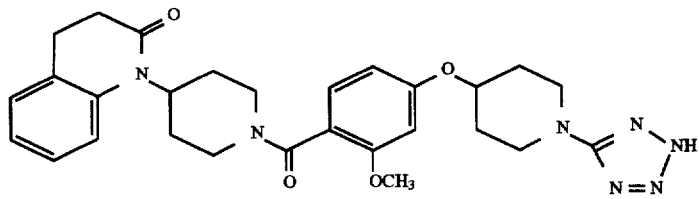

1-(1-(4-(N-Cyano)-iperidin-4-yloxy)-2-methoxybenzoyl) piperidin-4-yl)-3,4-dihydro-2(1H)-quinolinone (200 mg, 0.409 mmole) from Example 266 was combined with 133 mg (2.04 mmole) of sodium azide and 109 mg of ammonium chloride in 5 ml of dry DMF. The resulting reaction mixture was heated to 100° C. for 2 hr. The reaction mixture was cooled and diluted with 50 ml of ethyl acetate. The reaction mixture was then filtered and the filtrate was concentrated in vacuo. The residue was suspended in toluene and then concentrated once more. The crude product was subsequently purified by flash chromatography on silica gel (chloroform-methanol, 99:1 to 90:10 gradient, v/v) to yield 180 mg of the title compound as a solid: m.p. 142°–145° C.; $R_f$=0.32 (chloroform-methanol, 85:15);

NMR: Consistent with structure;

HPLC:>99% pure at 214 nM;

Elem. Anal. calc'd for $C_{28}H_{33}N_7O_4 \cdot 1.05CHCl_3$: Calc'd: C, 53.11; H, 5.22; N, 14.93. Found: C, 53.18; H, 532; N, 14.54.

FAB MS: m/z 532 (M$^+$+H).

EXAMPLE 268

1-(1-(4-(N-((N'-Hydroxy) carboxyamidino)piperidin-4-yloxy)-2-methoxybenzoyl) piperidin-4-yl)-3,4-dihydro-2 (1H)-quinolinone

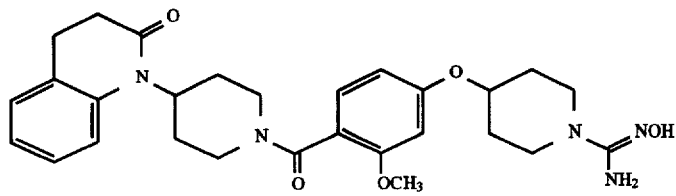

1-(1-(4-(N-Cyano)piperidin-4-yloxy)-2-methoxybenzoyl)piperidin-4-yl)-3,4-dihydro-2(1H)-quinolinone (69 mg, 0.15 mmole) from Example 266 was combined with 13 mg (0.18 mmole) of hydroxylamine hydrochloride in 5 ml of ethanol containing 0.18 mmole of sodium ethoxide. The resulting reaction mixture was stirred at ambient temperature for 12 hr; more hydroxylamine hydrochloride (10 mg) and sodium ethoxide (0.14 mmole) were added and stirring was continued for 2 hr. The reaction mixture was concentrated in vacuo and the residue was applied directly to a silica gel column and eluted with chloroform-methanol (98:2 to 84:16 gradient, v/v). The product containing fractions were combined and concentrated to yield 14 mg of the title compound as a solid: m.p. 124°–127° C.; $R_f$=0.27 (chloroform-methanol, 80:20);

NMR: Consistent with structure;

HPLC:>97% pure at 214 nM;

Elem. Anal. calc'd for $C_{27}H_{33}N_5O_4 \cdot 1.15CHCl_3$: Calc'd: C, 53.76; H, 5.47; N, 11.14. Found: C, 53.82; H, 5.57; N, 11.09.

FAB MS:m/z 492 (M$^+$+H).

EXAMPLE 269

1-(1-(4-(N-(4H-1,2,4-Oxadiazolon-5-yl)piperidin-4-yloxy)-2-methoxy benzoyl)piperidin-4-yl)-3,4-dihydro-2 (1H)-quinolinone

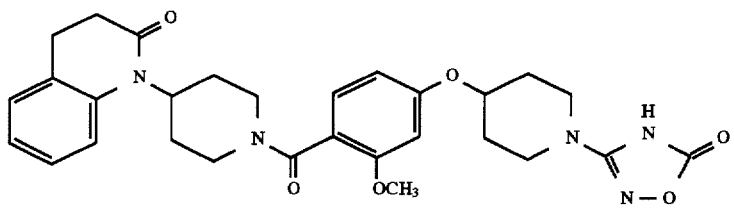

1-(1-(4-(N-((N'-Hydroxy)carboxyamidino)piperidin-4-yloxy)-2-methoxybenzoyl)pipeddin-4-yl)-3,4-dihydro-2(1H)-quinolinone (92 mg, 0.176 mmole) from Example 268 was combined with 33 mg (0.204 mmole) of carbonyldiimidazole in 7 ml of THF at room temperature. The resulting reaction mixture was stirred at for 12 hr. The reaction mixture was concentrated in vacuo and the residue was partitioned between ethyl acetate and 59% brine. The organic extracts were dried and concentrated and the crude product was purified by silica gel chromatography using chloroform-methanol (97:3 to 90:10 gradient, v/v). The product containing fractions were combined and purified further by preparative thick plate chromatography on pre-coated E. Merck silica gel plates (chloroform-methanol, 88:12) to yield 39 mg of the title compound as a solid: m.p. 164°–167° C.; $R_f$=0.48 (chloroform-methanol, 85:15);

NMR: Consistent with structure;

HPLC:>99% pure at 214 nM;

Elem. Anal. calc'd for $C_{29}H_{33}N_5O_6 \cdot 1.1CHCl_3$: Calc'd: C, 53.25; H, 5.06; N, 10.32. Found: C, 53.18; H, 5.22; N, 10.21.

FAB MS: m/z 548 (M⁺+H).

EXAMPLE 270

1-(1-(4-(N-(3-Ethoxy-3-cyclobutene-1,2-dion-4-yl) piperidin-4-yloxy)-2-methoxy benzoyl)piperidin-4-yl)-1,2-dihydro-4(H)-3,1-benzoxazin-2-one

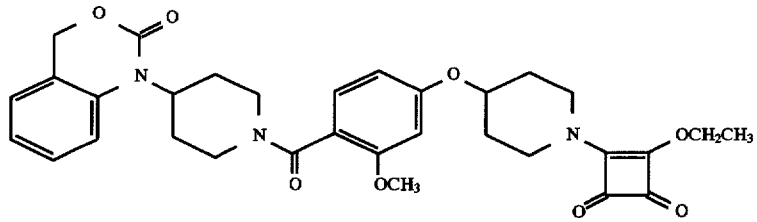

A solution of 6 ml of ethanol containing 1-(1-(4-(4-piperidinyloxy)-2-methoxybenzoyl)piperidin-4-yl)-1,2-dihydro-4(H)-3,1 -benzoxazin-2-one (606 mg, 1.3 mmole) from Example 26 was treated with 2 ml of ethanol containing 222 mg (1.3 mmole) of 3,4-diethoxy-3-cyclobutene-1,2-dione at room temperature. The reaction mixture was stirred for 3 hr and concentrated. The resulting semi-solid was triturated with 5 ml of methanol to give 255 mg of the title compound in analytical form: m.p. 207°–209° C.; TLC $R_f$=0.46 (chloroform-methanol, 90:10);

NMR: Consistent with structure;

HPLC:>96% pure at 214 nM;

Elem. Anal. calc'd for $C_{32}H_{35}N_3O_8 \cdot 0.6H_2O$: Calc'd: C, 64.00; H, 6.08; N, 7.00. Found: C, 64.04; H, 5.98; N, 7.14.

FAB MS: m/z 590 (M⁺+H).

EXAMPLE 271

1-(1-(4-(N-(3-Hydroxy-3-cyclobutene-1,2-dion-4-yl) piperidin-4-yloxy)-2-methoxy benzoyl)piperidin-4-yl)-1,2-dihydro-4(H)-3,1-benzoxazin-2-one

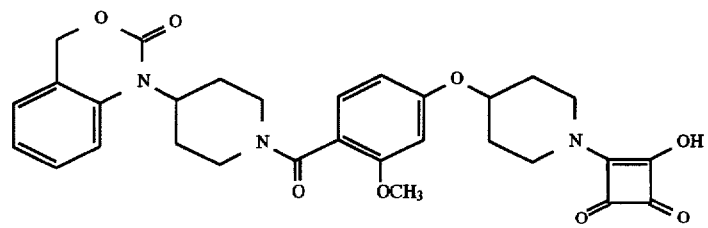

To a solution of 8 ml of ethanol containing 255 mg (0.432 mmole) of 1-(1-(4-(N-(3-Ethoxy-3-cyclobutene-1,2-dion-4-yl) piperidin-4-yloxy)-2-methoxy benzoyl)piperidin-4-yl)-1,2-dihydro-4(H)-3,1-benzoxazin-2-one from Example 270 was added 432 μL (0.432 mmole) of a 1 M sodium hydroxide solution. The milky reaction mixture was stirred at ambient temperature overnight and concentrated. The residual material was applied directly to five pre-coated E. Merck silica gel semi-preparative plates (0.5 mm thickness) and eluted with chloroform-methanol-acetic acid (85:15:5, v/v) to yield 166 mg of the title compound as a solid: m.p. 144°–148° C.; R$_f$=0.29 (chloroform-methanol-acetic acid, 90:10:1);

NMR: Consistent with structure;
HPLC:>97% pure at 214 nM;

Elem. Anal. calc'd for $C_{30}H_{31}N_3O_8 \bullet 1.45CHCl_3$: Calc'd: C, 51.41; H, 4.45; N, 5.72. Found: C, 51.57; H, 4.83; N, 5.55.

FAB MS: m/z 584 (M$^+$+Na).

EXAMPLE 272

1-(1-(4-(N-(N,N-Diethylaminoethyl-3-amino-3-cyclobutene-1,2-dion-4-yl) piperidin-4-yloxy)-2-methoxy benzoyl)piperidin-4-yl)-1,2-dihydro-4(H)-3,1-benzoxazin-2-one

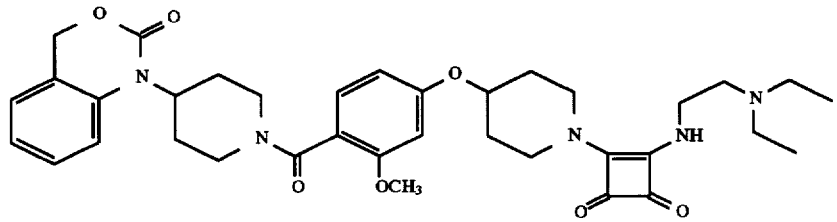

1-(1-(4-(N-(3-Ethoxy-3-cyclobutene-1,2-dion-4-yl) piperidin-4-yloxy)-2-methoxy benzoyl)piperidin-4-yl)-1,2-dihydro-4(H)-3,1-benzoxazin-2-one (305 mg, 0.517 mmole) from Example 270 was suspended in 8 ml of ethanol and treated with N,N-diethylethylenediamine (101 μL, 0.724 mmole). The milky reaction mixture was stirred at ambient temperature overnight and then at 45° C. for 20 minutes. The homogeneous reaction mixture was concentrated and the residue was azeotropically dried with toluene. The residual amorphous solid was applied directly to six pre-coated E. Merck silica gel semi-preparative plates (0.5 mm thickness) and eluted with chloroform-methanol (85:15, v/v) to yield 283 mg of the title compound as a solid: m.p. 147°–150° C.;

TLC R$_f$=0.11 (chloroform-methanol, 90:10);

NMR: Consistent with structure;

HPLC:>98% pure at 214 nM;

Elem. Anal. calc'd for $C_{36}H_{45}N_5O_7 \bullet 1.25CHCl_3$: Calc'd: C, 55.30; H, 5.76; N, 8.66. Found: C, 55.39; H, 5.90; N, 8.75.

FAB MS: m/z 660 (M$^+$+Na).

EXAMPLE 273

1-(1-(4-(N-(N'-Methylsulfonyl)carboxyamidino) piperidin-4-yloxy)-2-methoxy benzoyl)piperidin-4-yl)-1,2-dihydro-4(H)-3,1-benzoxazin-2-one

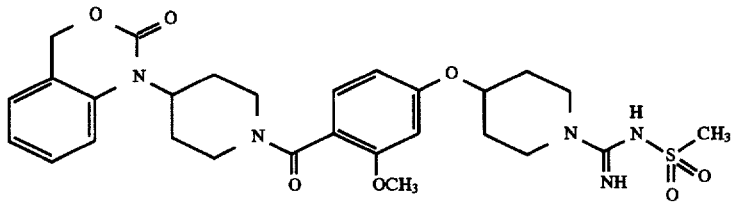

1-(1-(4-(4-Piperidinyloxy)-2-methoxybenzoyl)piperidin-4-yl)-1,2-dihydro-4(H)-3, 1-benzoxazin-2-one (188 mg, 0.404 mmole) from Example 26 was dissolved in 4 ml of methanol and treated portionwise with N-methylsulfonyldithioimido carbonate (3×80 mg, 0.404 mmole). The resulting reaction mixture was stirred at ambient temperature for 60 hr. The reaction mixture was then cooled to 0° C. and a stream of ammonia was passed through the stirred solution for 15 minutes. The reaction flask was capped with rubber septum, the cooling bath was removed, and the reaction mixture was allowed to warm to room temperature over a 2 hr period. The reaction mixture was rotoevaporated and the residual material was applied directly to four pre-coated E. Merck silica gel semi-preparative plates (0.5 mm thickness) and eluted with chloroform-methanol (92:8, v/v) to yield 69. mg of the title compound as a solid: m.p. 148°–151° C.;

TLC $R_f$=0.22 (chloroform-methanol, 90:10);
NMR: Consistent with structure;
HPLC:>99% pure at 214 nM;

Elem. Anal. calc'd for $C_{28}H_{35}N_5O_7S \cdot 0.25$ EtOH$\cdot$1.05CHCl$_3$: Calc'd: C, 49.12; H, 5.24; N, 9.69. Found: C, 49.28; H, 5.19; N, 9.70.

FAB MS: m/z 586 (M$^+$+Na).

EXAMPLE 274

1-(1-(4-(1-(1-Amino-2-nitro)ethenyl)piperidin-4-yloxy)-2-methoxybenzoyl)piperidin-4-yl)-1,2-dihydro-4(H)-3,1-benzoxazin-2-one

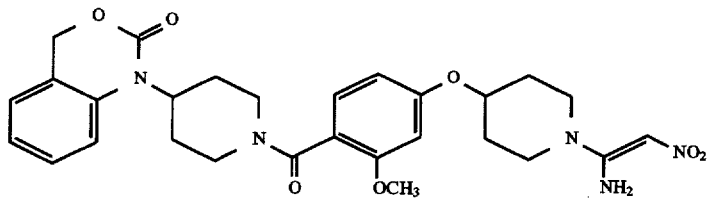

1-(1-(4-(4-Piperidinyloxy)-2-methoxybenzoyl)piperidin-4-yl)-1,2-dihydro-4(H)-3,1-benzoxazin-2-one (445 mg, 0.956 mmole) from Example 26 was dissolved in 10 ml of absolute ethanol and treated portionwise with 1,1-bis (methylthio)-2-nitroethylene (3×60 mg and 158 mg, 0.956 mmole). The resulting reaction mixture was stirred at ambient temperature for 6 hr and then at the refluxing temperature of ethanol for 12 hr. The reaction mixture was then cooled to 0° C. and a stream of ammonia was passed through the stirred solution for 20 minutes. The reaction flask was capped with rubber septum, the cooling bath was removed, and the reaction mixture was allowed to warm to room temperature over a 1 hr period. The reaction mixture was rotoevaporated and the residual material was applied directly to four pre-coated E. Merck silica gel semi-preparative plates (0.5 mm thickness) and eluted with chloroform-methanol (92:8, v/v) to yield 118 mg of the title compound as a solid: m.p. 178°–182° C.; $R_f$=0.13 (chloroform-methanol, 90:10);

NMR: Consistent with structure;

HPLC:>99% pure at 214 nM;

Elem. Anal. calc'd for $C_{28}H_{33}N_5O_7 \cdot 1.4CHCl_3$: Calc'd: C, 49.13; H, 4.82; N, 9.74. Found: C, 49.12; H, 4.79; N, 9.61.

FAB MS: m/z 552 (M$^+$+Na).

EXAMPLE 275

1-(1-(4-(N-(Guanidinocarbonyl)piperidin-4-yloxy)-2-methoxy benzoyl)piperidin-4-yl)-1,2-dihydro-4(H)-3,1-benzoxazin-2-one

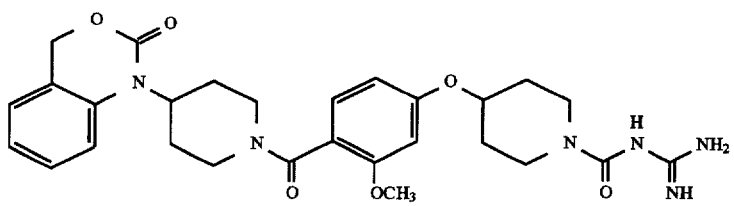

Step 1. An ice cold solution of dry THF containing 180 mg (0.387 mmole) of 1-(1-(4-(4-piperidinyloxy)-2-methoxybenzoyl)piperidin-4-yl)-1,2-dihydro-4(H)-3,1-benzoxazin-2-one from Example 26 was treated in succession with 107 μL (0.772 mmole) of triethylamine and 38 mg (0.129 mmole) of triphosgene. The milky suspension was stirred at 0° C. for 10 minutes and at ambient temperature for 10 minutes. The reaction mixture was then diluted with 100 ml of ethyl acetate and the organic phase was washed with water and brine. The organic extracts were dried and rotoevaporated to give a semi-solid which was further dried azeotropically with toluene to give 230 mg of 1-(1-(4-(N-(chlorocarbonyl)piperidin-4-yloxy)-2-methoxy benzoyl) piperidin-4-yl)-1,2-dihydro-4(H)-3, 1-benzoxazin-2-one as a foam.

Step 2. Sodium methoxide (0.697 mmole) in methanol was added to 67 mg (0.697 mmole) guanidine hydrochloride in 2 ml of methanol. The thick, milky suspension was stirred at room temperature for 1 hr. All volatiles were removed under reduced pressure. The residue was dissolved in 5 ml of THF/toluene (1:1) and rotoevaporated to give guanidine as a free base. The latter was treated with 3 ml of a DMSO solution containing 230 mg of 1-(1-(4-(N-(chlorocarbonyl) piperidin-4-yloxy)-2-methoxy benzoyl)piperidin-4-yl)-1,2-dihydro-4(H)-3,1-benzoxazin-2-one from Step 1 above. This mixture was stirred for 1.5 hr at ambient temperature. The reaction mixture was poured into 100 ml of 50% brine and extracted with ethyl acetate (3×100 ml) and chloroform (2×100 ml). The combined organic extracts were dried and concentrated to give 282 mg of crude product. The analytical material was obtained by precipitating the product from a chloroform solution with ethyl ether: m.p. 169°–173° C.; $R_f$=0.19 (chloroform-methanol, 85:15);

NMR: Consistent with structure;

HPLC:>99% pure at 214 nM;

Elem. Anal. calc'd for $C_{28}H_{34}N_6O_6 \cdot 1.15\ CHCl_3$: Calc'd: C, 50.89; H, 5.15; N, 12.22. Found: C, 51.07; H, 5.29; N, 12.05.

FAB MS: m/z 551 (M$^+$+Na).

EXAMPLE 276

1-(1-{2-methoxy-4-[1-(2-methyl-N-oxido-pyridin-3-ylmethyl)piperidin-4-yloxy]-benzoyl}-piperidin-4-yl)-1,4-dihydro-benzo[1,3]oxazin-2-one

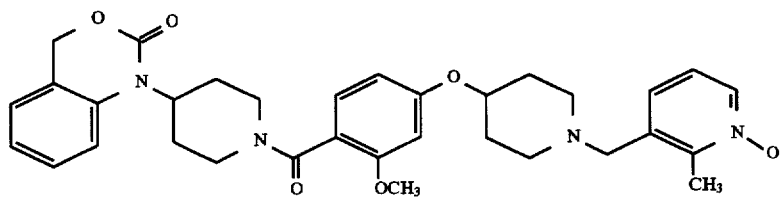

To a stirred solution of 1-(1-{4-[piperidin-4-yloxy]-2-methoxy-benzoyl}-piperidin-4-yl)-1,4-dihydro-benzo[1,3]oxazin-2-one hydrochloride from Example 26 (125 mg, 0.249 mmol) in DMF (5 mL) was added 3-chloromethyl-2-methylpyridine N-oxide (39 mg, 0.260 mmol) and DIEA (96.5 mg, 0.13 mL, 0.747 mmol). The solution was stirred at 50° C. for 48 hours. The solvent was removed under reduced pressure. The residue was partitioned between aqueous saturated NaHCO$_3$ (10 mL) and methylene chloride. The organic phase was dried (MgSO$_4$), filtered, and the solvent was removed under reduced pressure. The residue was purified by pressurized silica gel column chromatography using 95:5:0.5 methylene chloride:methanol:NH$_4$OH as eluant. The title compound was further purified by preparative reverse-phase HPLC using a water-acetonitrile gradient containing 0.1% TFA. The product-containing fractions were combined and lyophilized to give the TFA salt of the title compound as an amorphous solid.

Analysis calculated for $C_{33}H_{38}N_4O_6$, 1.8 TFA, 0.35 H$_2$O C, 55.07; H, 5.11; N, 7.02 Found C, 55.05; H, 5.13; N, 7.03

TLC: R$_f$=0.26 in 96:4:0.4 methylene chloride:methanol:NH$_4$OH

HPLC (Method A) retention time 5.96 min

FAB MS m/z 587 (M$^+$+H)

EXAMPLE 277

1-(1-(4-(1-(3-Methyl-2-pyridylmethyl)-4-piperidinyloxy)-2-methoxyphenylacetyl)piperidin-4-yl)-1,2-dihydro-4(1H)-3,1-benzoxazin-2-one To a solution of 1-(1-(4-(4-piperidinyloxy)-2-methoxyphenylacetyl)piperidin-4-yl)-1,2-dihydro-4(1H)-3,1-benzoxazin-2-one (200 mg, 0.34 mmol) from Example 123 in dry degassed DMF (5 mL) was added 2-methyl-3-chloromethylpyridine hydrochloride (100 mg, 0.68 mmol) and DIEA (0.10 mL, 0.66 mmol) and the reaction was warmed to 50° C. for 24 hours. The solvent was removed under reduced pressure and the residue was purified by pressurized silica gel column chromatography using 98:2 CH$_2$Cl2:MeOH as eluant. The product-containing fractions were combined and the solvent was removed under reduced pressure. The residue was lyophilized from acetonitrile-water containing 2 equivalents of 1 N aqueous HCl to give the hydrochloride salt of the title compound as an amorphous solid.

Analysis: $C_{34}H_{40}N_4O_5$, 2.0 HCl, 1.45 H$_2$O calc. C 59.72 H 6.62 N 9.19 found 59.70 6.63 8.24

TLC: R$_f$=0.30 (97:3 CH$_2$Cl$_2$:MeOH)

HPLC (method A): retention time=6.00 min,

FAB MS: m/z=585 (M+H$^+$)

EXAMPLE 278

RADIOLIGAND BINDING ASSAYS

The high affinity binding of [$^3$H]Oxytocin (OT)([tyrosyl, 3,5-[$^3$H]OT; 30–60 Ci/mmol; New England Nuclear, Boston, Mass.) to uterine OT receptors was based on an assay (Fuchs, A-R; Fuchs, F; Soloff, MS. 1985 *J. Clin. Endocrinol. Metab.* 60:37) using a crude membrane preparation of uteri taken from diethylstilbestrol dipropionate (DES)-treated (0.3 mg/kg, ip; 18–24) rats. Competition studies were conducted at equilibrium (60 minutes; 22° C.) using 1 nM[$^3$H]OT in the following assay buffer: 50 mM Tris-HCl, 5 mM MgCl$_2$, and 0.1% BSA, pH 7.4. Nonspecific binding (10% of the total binding) was determined using 1 μM unlabeled OT and the binding reaction was terminated by filtration through glass fiber filters using a cell harvester (model 7019, Skatron, Inc., Sterling, Va.). IC$_{50}$ values (the concentration of tested compound that inhibits 50% of OT) were reported.

The measurement of [$^3$H]Vasopressin (AVP) ([phenylalanyl-3,4,5-$^3$H]AVP; 80–90 Ci/mmol; New England Nuclear) binding to a crude membrane preparation of male rat liver (AVP-V$_1$ sites) or kidney medulla (AVP-V$_2$ sites) was determined according to the method of Butlen, et al. (Butlen, D; Guillon, G; Rajerison, R. M.; Jard, S; Sawyer, W. H.; Manning, M. 1978 Mol Pharmacol 14:1006).

Competition assays were conducted at equilibrium (30 minutes at 30° C.) using 1 nM [$^3$H]AVP (liver) or 2 nM

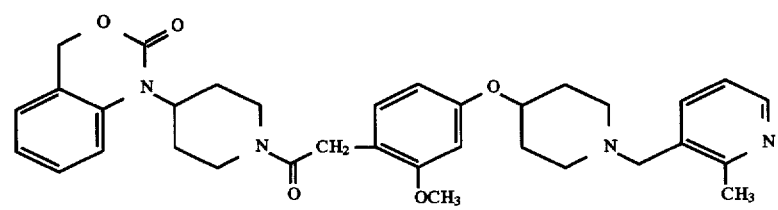

[3H]AVP (kidney) in the following assay buffer: 100 mM Tris-HCl, 5 mM MgCl$_2$, 0.1% BSA, 50 mM phenylmethylsulfonylfluoride, and 50 mg/ml bacitracin, pH 8.0. Nonspecific binding (5–10% of the total binding) was determined using 10 μM unlabeled AVP, and the binding reaction was terminated by filtration as described above for the [3H]OT binding assay.

IC$_{50}$ values were determined for the [3H]OT and [3H]AVP binding assays by linear regression of the relation log concentration of compound vs. percent inhibition of specific binding. Data is either reported as a given percentage of inhibition at a specified concentration, or if an IC$_{50}$ was calculated, as a nanomolar concentration. Representative IC$_{50}$ values of the compounds of the instant invention are given below.

| Example | Result For [3H]OT |
|---------|-------------------|
| 1 | 61% inhib. at 10,000 nM |
| 3 | 40% inhib. at 10,000 nM |
| 4 | 78% inhib. at 10,000 nM |
| 7 | 6,200 nM |
| 9 | 280 nM |
| 12 | 410 nM |
| 14 | 74 nM |
| 15 | 56 nM |
| 17 | 81 nM |
| 22 | 260 nM |
| 24 | 550 nM |
| 27 | 46 nM |
| 30 | 69 nM |
| 32 | 78% inhib. at 10,000 nM |
| 34 | 320 nM |
| 36 | 48% inhib. at 10,000 nM |
| 39 | 46% inhib. at 1,000 nM |
| 41 | 42% inhib. at 1,000 nM |
| 43 | 59% inhib. at 1,000 nM |
| 44 | 5,000 nM |
| 45 | 44 nM |
| 46 | 23 nM |
| 47 | 76 nM |
| 48 | 340 nM |
| 49 | 72% inhib. at 1,000 nM |
| 52 | 4,300 nM |
| 55 | 6,200 nM |
| 57 | 54% inhib. at 10,000 nM |
| 60 | 70% inhib. at 10,000 nM |
| 61 | 64% inhib. at 10,000 nM |
| 63 | 590 nM |
| 66 | 25 nM |
| 147 | 54 nM |

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth hereinabove may be applicable as a consequence of variations in the responsiveness of the mammal being treated for prevention of preterm labor, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula

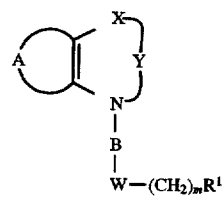

wherein

Y is CH$_2$, C=O, C=S, C=N—H or C=N—CHH$_3$;

X is selected from the group consisting of —CH$_2$—O—, —C(R$^8$)$_2$—O—, —C(R$^8$)$_2$—CH$_2$—, —CH(R$^{11}$)—O—, —CH(R$^{11}$)—CH$_2$, —C(O)—CH$_2$—, —CH$_2$—NH—, —CH$_2$—NR$^8$—, —O—CH$_2$—, —C(R$^8$)=N—, —N=C(R$^8$)—, —NH—CH$_2$—, —NR$^8$—CH$_2$—, —CH$_2$'—CH$_2$, —CH=CH—, —C(OH)=CH—, and —S(O)$_m$—CH$_2$—;

"A" represents a fused aromatic or heteroaromatic ring such that the bicyclic ring system containing the A ring is selected from the group consisting of

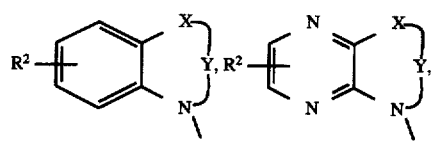

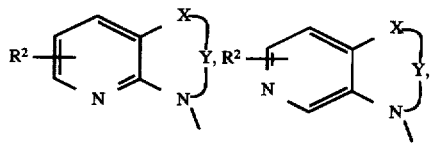

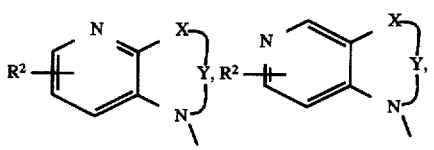

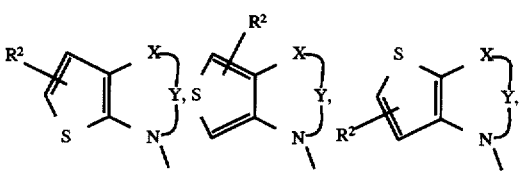

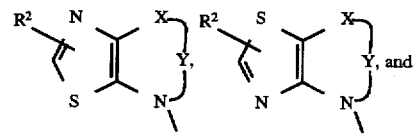

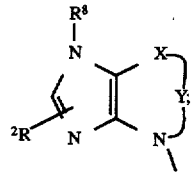

B is a heterocyclic or heterobicyclic ring selected from the group consisting of

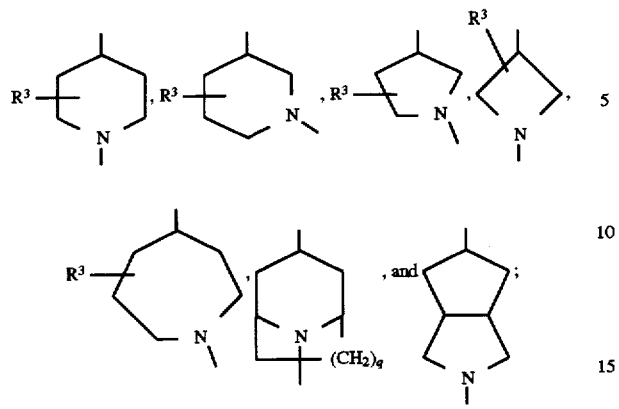

W is —CO—, —COO—, —CONRS—, —C(=NR⁸)—, —C(O)—CH(R¹⁰)—, —C(=NCH₂Ph)— or —SO₂—;

R¹ is selected from the group consisting of camphor-10-yl, $C_{1-5}$ alkoxyl, styryl, hydroxystyryl, furyl, thienyl, pyrrolyl, naphthyl, indolyl, tetrahydronaphthyl, unsubstituted, mono- or di-substituted pyridyl where said substituent on said pyridyl are each independently selected from $C_{1-5}$ alkyl, $C_{1-5}$ alkoxy, halogen, hydroxyl or $R^7$, pyrazinyl, quinolinyl, substituted thienyl where said substituent is selected from the group consisting of $C_{1-5}$ alkoxycarbonyl, $C_{1-5}$ alkylcarbonyl, carboxyl and pyridyl, $C_{1-5}$ alkyl-substituted pyrrolyl, unsubstituted or substituted cyclohexyl where said substituent is $R^4$, and unsubstituted or substituted phenyl where said substituents are one or more of $R^5$, $R^6$ or $R^7$;

R² is selected from the group consisting of hydrogen, hydroxyl, $C_{1-5}$ alkoxyl, $C_{1-5}$ alkyl, amino, $C_{1-5}$ alkylcarbonylamino, nitro, methanesulfonylamino, trifluoromethyl and halogen;

R³ is selected from the group consisting of hydrogen, amino, $C_{1-5}$ alkyl, $C_{1-5}$ alkoxycarbonyl, hydroxy-$C_{1-10}$ alkyl, methylthio-$C_{1-10}$ alkyl, methylsulfonyl-$C_{1-10}$ alkyl, methylsulfonyl, cyano, carbamoyl and carboxy;

R⁴ is independently one or two members of the group consisting of hydrogen, oxo, hydroxyl, $C_{1-5}$ alkoxyl, $C_{1-5}$ alkoxy-carbonylamino-$C_{1-5}$ alkyl and amino-$C_{1-5}$ alkyl;

R⁵ and R⁶ are each independently selected from the group consisting of hydrogen, halogen, phenyl, hydroxyphenyl, phenoxy, hydroxyphenoxy, phenyl-$C_{1-5}$ alkyl, $C_{1-10}$ alkyl, trifluoromethyl, $C_{3-6}$ cycloalkyl, cyano, carboxy-$C_{1-5}$ alkyl, $C_{1-10}$ alkoxy-$C_{1-5}$ alkyl, $C_{1-10}$ alkoxycarbonyl-$C_{1-5}$ alkyl, $C_{1-10}$ alkoxycarbonyl-$C_{2-6}$ alkenyl, mono- or di-$C_{1-10}$ alkylamino-$C_{1-5}$ alkyl, cyano-$C_{1-5}$ alkyl, halo-$C_{1-5}$ alkyl, —S(O)ₘ—CH₃, —NO₂, hydroxyl, hydroxy-$C_{1-5}$ alkyl, $C_{1-10}$ alkoxyl, substituted $C_{1-5}$ alkoxy in which the alkyl group of said alkyloxy substitutent is substituted with a $C_{2-6}$ alkenyl group, substituted $C_{1-5}$ alkoxy in which the alkyl group of said alkyloxy substitutent is substituted with a $C_{2-6}$ alkynyl group, $C_{3-6}$ cycloalkyloxy, $C_{3-6}$ cycloalkyl-$C_{1-5}$ alkoxy, trifluoromethoxy, carboxy, $C_{1-10}$ alkoxycarbonyl, $C_{1-10}$ alkylcarbonyl, —N(R¹³)₂ and —NH—COR¹⁴;

R⁷ is selected from the group consisting of hydrogen, $C_{1-5}$ alkoxy, carboxyl, amino-$C_{2-5}$ alkoxy, —CO—R¹⁶,

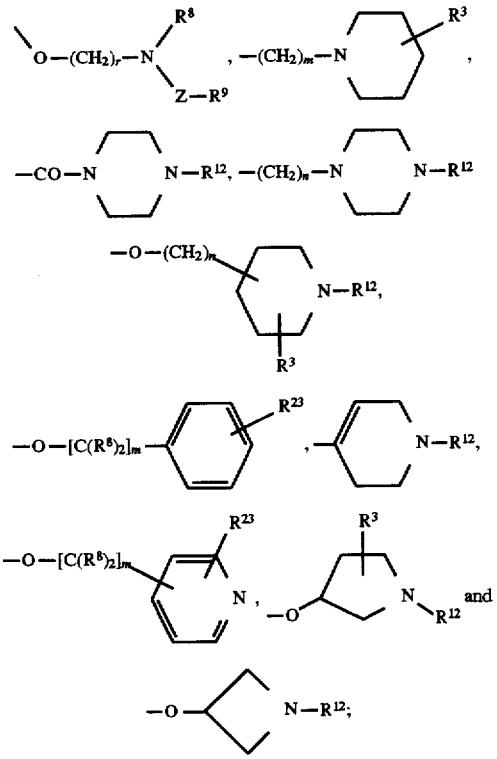

R⁸ is independently selected from hydrogen or $C_{1-5}$ alkyl;

R⁹ is selected from the group consisting of Het, amino, —N(R⁸)—(CH₂)_q—CO—R¹⁴, $C_{1-5}$ alkoxyl, mono- or di-$C_{1-10}$ alkylamino-$C_{1-5}$ alkyl, mono- or di-$C_{1-10}$ alkylamino-$C_{2-6}$ alkylamino, unsubstituted $C_{1-5}$ alkyl and substituted $C_{1-5}$ alkyl where said substitutent is selected from the group consisting of carboxyl, hydroxyl, amino, methylsulfonyl, —N(R⁸)₂, —NHR⁸, $C_{1-5}$ alkoxycarbonyl, $C_{1-10}$ alkoxycarbonylamino and Het;

R¹⁰ is selected from the group consisting of hydrogen, hydroxyl, $C_{1-5}$ alkoxycarbonyl, $C_{1-5}$ alkoxycarbonylamino, hydroxy-$C_{1-5}$ alkyl, amino, —N(R⁸)₂, —NHR⁸, cyano, $C_{1-5}$ alkyl and $C_{1-5}$ alkoxy;

R¹¹ is selected from the group consisting of $C_{1-5}$ alkyl, trifluoromethyl and unsubstituted, mono-, di- or tri-substituted phenyl wherein said substituents on said phenyl are independently selected from the group consisting of $C_{1-5}$ alkyl, $C_{1-10}$ alkoxyl, halogen and trifluoromethyl;

R¹² is selected from the group consisting of hydrogen, $C_{1-10}$ alkyl, $C_{3-6}$ cycloalkyl, $C_{3-6}$ cycloalkyl-$C_{1-5}$ alkyl, $C_{2-6}$ alkenyl, $C_{2-6}$ alkynyl, $C_{1-10}$ alkoxycarbonyl, $C_{1-5}$ alkylcarbonyl, tetrazolyl, cyano, 4-tetrahydropyranyl, 4-tetrahydrothiopyranyl, 4-piperidinyl, N-($C_{1-10}$ alkoxy-carbonyl)-4-piperidinyl, N-($C_{1-5}$ alkyl)-4-piperidinyl, 2-pyrimidinyl optionally substituted with one to two members of the group consisting of halogen, carbamoyl, carboxyl, cyano, 5-tetrazolyl, aminothiocarbonyl, —C(NHR¹⁸)=NR¹⁷, amino-$C_{1-5}$- alkyl, and mono- or di- $C_{1-10}$-alkylamino-$C_{1-5}$-alkyl,

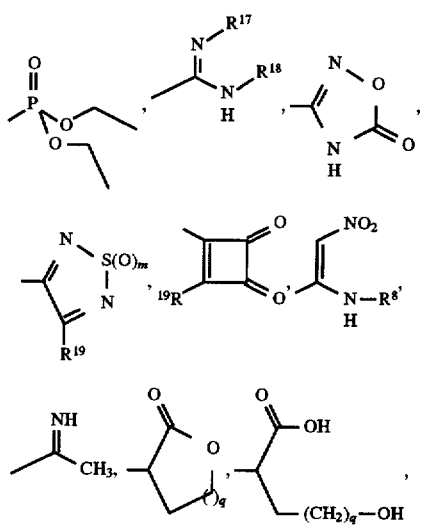

—SO$_2$—R$^{15}$, —CO—R$^{16}$, unsubstituted or substituted pyridyl wherein said substituent on said pyridyl is selected from hydrogen, halogen, C$_{1-10}$ alkoxycarbonyl, carboxy, nitro or amino, and mono- or di-substituted C$_{1-10}$ alkyl wherein said substituents on said C$_{1-10}$ alkyl are independently selected from the group consisting of hydroxyl, C$_{1-10}$ alkoxycarbonyl, carboxyl, hydroxyl, C$_{1-5}$ alkoxyl, cyano, methylsulfonyl, aminocarbonyl, imidazolyl, tetrazolyl, morpholinyl, piperazinyl, benzodioxanyl, quinolinyl, isoquinolinyl, furyl, furopyridyl, thienyl, 5-halo-2-thienyl, 3,5-dimethyl-4-isoxazolyl, pyrazinyl, C$_{1-5}$ akyl-substituted pyrazinyl, pyrimidinyl, pyridazinyl, thiazolyl, C$_{1-10}$ alkyl-substituted thiazolyl, oxadiazolyl, phenyl-substituted oxadiazolyl, chlorophenyl-substituted thiazolyl, benzimidazolyl, thienopyridyl, mono or dichlorothienopyridyl, furopyridyl, uracil, tinsubstituted, mono-, or di-substituted pyridyl wherein said substituents on said pyridyl are independently selected from hydrogen, halogen, C$_{1-10}$ alkoxy, C$_{1-10}$ alkyl, amino-C$_{1-5}$ alkyl, mono or di-C$_{1-5}$ alkylamino-C$_{1-5}$ alkyl, C$_{1-10}$ alkyl-carbonyl, C$_{1-10}$ alkoxycarbonyl, carboxy, nitro, hydroxy, hydroxy C$_{1-5}$ alkyl, C$_{1-5}$ alkoxy-C$_{1-5}$ alkyl or amino, mono-, or di-substituted pyridyl-N-oxide wherein said substituents on said pyridyl-N-oxide are independently selected from hydrogen, halogen, C$_{1-10}$ alkoxy, C$_{1-10}$ alkyl, amino-C$_{1-5}$ alkyl, mono or di-C$_{1-5}$ alkyl-amino-C$_{1-5}$ alkyl, C$_{1-10}$ alkylcarbonyl, C$_{1-10}$ alkoxy-carbonyl, carboxy, nitro, hydroxy, hydroxy C$_{1-5}$ alkyl, C$_{1-5}$ alkoxy-C$_{1-5}$ alkyl or amino, and unsubstituted, mono- or di-substituted phenyl wherein said substituents on said phenyl are independently selected from hydrogen, halogen, hydroxyl, C$_{1-10}$ alkoxyl, C$_{1-10}$ alkoxycarbonyl, cyano or carboxyl;

R$^{13}$ is independently selected from the group consisting of hydrogen, C$_{1-5}$ alkyl and C$_{1-5}$ alkylsulfonyl;

R$^{14}$ is selected from the group consisting of C$_{1-5}$ alkyl, C$_{1-5}$ alkoxyl, amino-C$_{1-5}$ alkyl, phenyl and benzimidazolyl;

R$^{15}$ is selected from the group consisting of amino, C$_{1-10}$ alkoxy-carbonylamino, amino-C$_{2-10}$ alkylamino, mono- or di- C$_{1-10}$ alkylamino-C$_{2-10}$ alkylamino, 3-azetidinyl, 1-benzyl-3-azetidinyl, 1-(C$_{1-10}$ alkyl)-3-azetidinyl, unsubstituted or 1-substituted piperidinyl in which said substituent on said piperidinyl is selected from the group consisting of benzyl, C$_{1-5}$ alkoxycarbonyl, C$_{1-5}$ alkyl, hydroxy-C$_{2-5}$ alkyl, C$_{1-5}$ alkoxy-C$_{2-5}$ alkyl, pyridylmethyl, or C$_{1-5}$ alkylpyridylmethyl, unsubstituted or 1-substituted 3-pyrrolidinyl in which said substituent on said pyrrolidinyl is selected from the group consisting of benzyl, C$_{1-5}$ alkoxycarbonyl, C$_{1-5}$ alkyl, hydroxy-C$_{2-5}$ alkyl, C$_{1-5}$ alkoxy-C$_{2-5}$ alkyl, pyridylmethyl, or C$_{1-5}$ alkylpyridylmethyl, unsubstituted or 4-substituted 1-piperazinyl in which said substituent on said piperazinyl is selected from the group consisting of benzyl, C$_{1-5}$ alkoxycarbonyl, C$_{1-5}$ alkyl, hydroxy-C$_{2-5}$ alkyl, C$_{1-5}$ alkoxy-C$_{2-5}$ alkyl, pyridylmethyl, or C$_{1-5}$ alkylpyridylmethyl, 1-(C$_{3-6}$ cycloalkyl)-4-piperazinyl, mono- or di-C$_{1-10}$ alkylamino-C$_{2-10}$ alkylamino, vinyl, pyridyl, unsubstituted or substituted phenyl wherein said substitutent on said phenyl is selected from C$_{1-5}$ alkyl, nitro, amino, C$_{1-10}$ alkoxycarbonyl or carboxy, and unsubstituted or substituted C$_{1-10}$ alkyl wherein said substituent on said alkyl is selected from halogen, R$^{20}$, carboxy, cyano, C$_{1-10}$ alkoxycarbonyl, azido, acetamidinyl, guanido, morpholino, pyrrolidinyl, piperidinyl, 2,2,6,6-tetramethyl-1-piperidinyl, hydroxy-pyrrolidinyl, tetrazolyl, piperazinyl, C$_{1-5}$ alkoxy-C$_{1-5}$ alkyl-substituted 1-pyrrolidinyl, 3-(C$_{1-5}$ alkoxy)-1-pyrrolidinyl, 4-(C$_{1-5}$ alkoxy-C$_{2-5}$ alkyl)-1-piperazinyl, 1-(C$_{1-10}$ alkyl)-4-piperazinyl, N-tetrahydroisoquinolinyl, aza-cycloheptyl, mono- or di-substituted 1-piperidinyl wherein said substitutents on said piperidinyl are independently selected from C$_{1-5}$ alkyl, hydroxyl, C$_{1-5}$ alkoxy, cyano, phenyl, 1-piperidinyl, trihalomethyl, spiro-cyclopropyl, or spiro-cyclopentyl, mono- or di-substituted 1-pyrrolidinyl wherein said substitutents on said pyrrolidinyl are independently selected from C$_{1-5}$ alkyl, trihalomethyl, spiro-cyclopropyl, or spiro-cyclopentyl, C$_{3-8}$ cycloalkyl wherein said cycloalkyl is optionally substituted with carboxy, nitro, amino, mono- or di-C$_{1-5}$ alkylamino, R$^{20}$, 1-pyrrolidinyl, 4-morpholinyl, 1-piperidinyl, 4-(C$_{1-5}$ alkyl)-1-piperidinyl, or 4,4-di-(C$_{1-5}$ alkyl)-1-piperidinyl, and unsubstituted, mono- or di-substituted amino wherein said substituents on said amino are independently selected from benzyl, C$_{1-10}$ alkyl, hydroxy-C$_{2-10}$ alkyl, C$_{1-10}$ alkoxy-C$_{2-10}$ alkyl, C$_{3-8}$ cycloalkyl, carboxy-C$_{1-10}$ alkyl, C$_{1-10}$ alkoxycarbonyl-C$_{1-10}$ alkyl, C$_{3}$-6 cycloalkyl-substituted-C$_{1-10}$ alkyl or allyl;

R$^{16}$ is selected from the group consisting of hydrogen, Het, 1-(C$_{1-10}$ alkoxycarbonyl)-4-piperidinyl, imidazolyl, unsubstituted or 1-substituted piperidinyl in which said substituent on said piperidinyl is selected from the group consisting of benzyl, C$_{1-5}$ alkoxycarbonyl, C$_{1-5}$ alkyl, hydroxy-C$_{2-5}$ alkyl, C$_{1-5}$ alkoxy-C$_{2-5}$ alkyl, pyridylmethyl, or C$_{1-5}$ alkylpyridylmethyl, unsubstituted or 1-substituted 3-pyrrolidinyl in which said substituent on said pyrrolidinyl is selected from the group consisting of benzyl, C$_{1-5}$ alkoxycarbonyl, C$_{1-5}$ alkyl, hydroxy-C$_{2-5}$ alkyl, C$_{1-5}$ alkoxy-C$_{2-5}$ alkyl, pyridylmethyl, or C$_{1-5}$ alkylpyridylmethyl, unsubstituted or 4-substituted 1-piperazinyl in which said substituent on said piperazinyl is selected from the group consisting of benzyl, C$_{1-5}$ alkoxycarbonyl, C$_{1-5}$ alkyl, hydroxy-C$_{2-5}$ alkyl, C$_{1-5}$ alkoxy-C$_{2-5}$ alkyl, pyridylmethyl, or C$_{1-5}$ alkylpyridylmethyl, pyridyl, 1-(C$_{3-6}$ cycloalkyl)-4-piperazinyl, trihalomethyl, C$_{1-10}$ alkoxycarbonyl, carboxyl, phenylamino, vinyl, C$_{1-10}$ alkoxycarbonylamino, methylsulfonylamino, trihalomethyl-sulfonylamino, amino, guanido, propargylamino, mono- or di-$C_{1-10}$ alkylamino-$C_{2-10}$ alkylamino, $C_{1-10}$ alkylamino, cyanoamino, $C_{1-10}$ alkoxycarbonyl-$C_{1-10}$ alkylamino, $C_{1-10}$ alkoxycarbonyl-$C_{1-10}$ alkylamino-$C_{1-10}$ alkyl, carboxy-$C_{1-10}$ alkylamino-$C_{1-10}$ alkyl, unsubstituted, mono- or di- substituted phenyl wherein said substituents on said phenyl are independently selected from halogen, amino-$C_{1-10}$ alkyl, mono- or di-$C_{1-10}$ alkylamino-$C_{2-10}$ alkyl-amino, $C_{1-10}$ alkoxycarbonyl, carboxyl, $C_{1-10}$ alkoxyl, 1-($C_{1-10}$ alkoxycarbonyl)-4-piperidinyloxy or 4-piperidinyloxy, and mono- or di-substituted $C_{1-10}$ alkyl wherein said substituents on said alkyl are independently selected from halogen, $R^{20}$, azido, guanido, acetamidinyl, $C_{1-10}$ alkoxycarbonyl, carboxy, carboxymethoxy, carboxy-$C_{1-10}$ alkylcyclopentyl, $C_{1-10}$ alkoxycarbonyl-amino, amino, cyano, methylsulfonyl, imidazolyl, morpholinyl, azetidinyl, pyrrolidinyl, piperazinyl, piperidinyl, 2,2,6,6-tetramethyl-1-piperidinyl, 3-hydroxy-1-pyrrolidinyl, $C_{1-5}$ alkoxy-$C_{1-5}$ alkyl-substituted 1-pyrrolidinyl, 1-($C_{1-10}$ alkyl)-4-piperazinyl, piperidinyl, N-tetrahydroisoquinolinyl, aza-cycloheptyl, mono- or di- substituted 1-piperidinyl wherein said substitutents on said piperidinyl are independently selected from $C_{1-5}$ alkyl, hydroxyl, $C_{1-5}$ alkoxyl, cyano, or spirocyclopentyl, $C_{3-8}$ cycloalkyl wherein said cycloalkyl is optionally substituted with nitro, amino, tri- or di-$C_{1-5}$ alkyl-amino, $R^{20}$, 1-pyrrolidinyl, or 1-piperidinyl, unsubstituted, mono- or di-substituted amino wherein said substituents on said amino are independently selected from benzyl, $C_{1-10}$ alkyl, hydroxy-$C_{2-10}$ alkyl, $C_{1-10}$ alkoxy-$C_{2-10}$ alkyl, $C_{3-6}$ cycloalkyl, $C_{1-5}$ alkoxycarbonyl-$C_{1-10}$ alkyl, carboxy-$C_{1-10}$ alkyl or $C_{3-8}$ cycloalkyl-substituted $C_{1-10}$ alkyl, $C_{1-10}$ alkoxycarbonyl, carboxy, carboxymethoxy, carboxy-$C_{1-10}$ alkylcyclopentyl, $C_{1-10}$ alkoxycarbonylamino, cyano, methylsulfonyl, imidazolyl, morpholinyl, azetidinyl, or 1-($C_{1-10}$ alkyl)-4-piperazinyl;

$R^{17}$ is selected from the group consisting of hydrogen, hydroxyl, cyano, $C_{1-10}$ alkylsulfonyl, trihalomethylsulfonyl, $C_{1-10}$ alkylcarbonyl and trihalomethylcarbonyl;

$R^{18}$ is selected from the group consisting of hydrogen, $C_{1-10}$ alkyl, mono- or di-$C_{1-10}$ alkylamino-$C_{2-10}$ alkyl and $C_{3-6}$ cycloalkyl;

$R^{19}$ is selected from the group consisting of $C_{1-10}$ alkoxy, hydroxyl, mono- or di-$C_{1-10}$ alkylamino-$C_{2-10}$ alkylamino and di-$C_{1-10}$ alkylamino —$C_{1-10}$ alkyl;

$R^{20}$ is

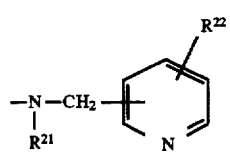

$R^{21}$ is selected from the group consisting of hydrogen, $C_{1-10}$ alkyl, and $C_{3-8}$ cycloalkyl;

$R^{22}$ is independently one to two members from the group consisting of hydrogen, $C_{1-5}$ alkyl, halogen, $C_{1-5}$ alkoxylcarbonyl, $C_{1-5}$ alkoxy, and carboxy;

$R^{23}$ is selected from the group consisting of hydrogen, cyano, amino, $C_{1-5}$ alkylcarbonylamino, halogen, halomethyl, —CHO, nitro, carboxy, $C_{1-5}$ alkoxycarbonyl, and unsubstituted or substituted $C_{1-5}$ alkyl wherein said substituent on said alkyl is selected from amino, mono- or di-$C_{1-5}$ alkylamino, cyano, $C_{1-5}$ alkoxycarbonyl, carboxy, piperazinyl, 4-[$C_{1-5}$ alkoxycarbonyl]-1-piperazinyl, 4-($C_{1-5}$ alkylcarbonyl)-1-piperazinyl, piperidinyl or substituted piperidinyl wherein said substituent on said piperidine is selected from hydroxyl, $C_{1-5}$ alkoxycarbonyl or carboxyl; and Het is selected from the group consisting of imidazolyl, piperidinyl, $C_{1-5}$ alkyl-substituted piperidinyl, piperazinyl, $C_{1-5}$ alkyl-substituted piperizinyl, $C_{1-5}$ alkoxycarbonyl-substituted piperazinyl, morpholinyl, tetrazolyl, $C_{1-5}$ alkylcarbonyl-substituted piperidinyl, $C_{1-5}$ alkoxy-carbonyl-substituted piperidinyl, pyrrolidinyl, $C_{1-5}$ alkyl-substituted pyrrolidinyl, and pyridyl;

Z is —CO— or —$SO_2$—;

m is an integer of from 0 to 2;

n is an integer of from 0 to 3;

p is an integer of from 1 to 4;

q is an integer from 1 to 2; and r is an integer of from 2 to 4;

provided that when the A containing bicyclic ring system is

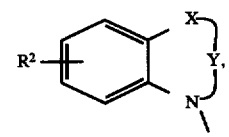

and Y is —C=O, and X is —$(CH_2)_2$—, —CH=CH—, —$C(R^8)_2$—$CH_2$—, —CH($R^{11}$)—$CH_2$ or —C(OH)=CH—, then $R^1$ is substituted phenyl wherein $R^7$ is

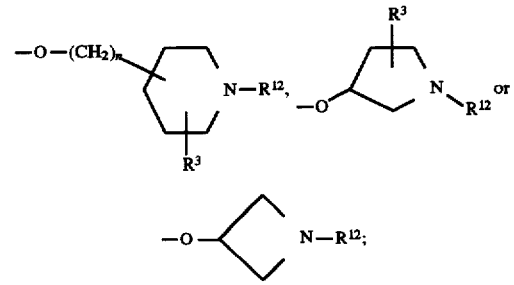

and the pharmaceutically acceptable salts thereof.

2. The compound of claim 1, wherein

X is selected from the group consisting of —$CH_2$—O, —$C(R^8)_2$—O—, —CH($R^{11}$)—O—, —C(O)—$CH_2$—, —O—$CH_2$—, —$CH_2$—$CH_2$—, —CH=CH— and— S(O)$_m$—$CH_2$—;

A represents a fused aromatic ring such that the bicyclic ring system containing the A ring is

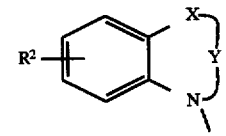

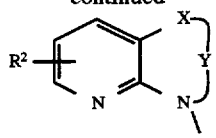

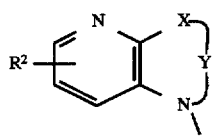

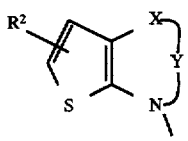

and,

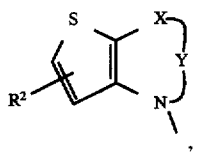

W is selected from —CO—, —CONR$^8$—, —C(=NR$^8$)—, —C(O)—CH(R$^{10}$)— or —SO$_2$—;

R$^1$ is selected from the group consisting of camphor-10-yl, C$_{1-5}$ alkoxyl, styryl, hydroxystyryl, furyl, thienyl, indolyl, tetrahydronaphthyl, unsubstituted, mono- or di-substituted pyridyl where said substituent on said pyridyl are each independently selected from C$_{1-5}$ alkyl, C$_{1-5}$ alkoxy, halogen, hydroxyl or R$^7$, pyrazinyl, substituted thienyl where said substituent on said thienyl is selected from C$_{1-5}$ alkoxycarbonyl, carboxy or pyridyl, C$_{1-5}$ alkyl-substituted pyrrolyl, unsubstituted or substituted cyclohexyl where said substituent is R$^4$, and unsubstituted or substituted phenyl where said substituents are one or more of R$^5$, R$^6$ or R$^7$;

R$^2$ is selected from the group consisting of hydrogen, C$_{1-5}$ alkoxyl, C$_{1-5}$ alkyl, amino, C$_{1-5}$ alkylcarbonylamino, nitro and halogen;

R$^3$ is selected from the group consisting of hydrogen, C$_{1-5}$ alkoxycarbonyl, cyano and carbamoyl;

R$^5$ and R$^6$ are each independently selected from the group consisting of hydrogen, halogen, hydroxyphenyl, hydroxyphenoxy, phenyl-C$_{1-5}$ alkyl, C$_{1-5}$ alkyl, cyano, C$_{1-5}$ alkoxy-C$_{1-5}$ alkyl, C$_{1-5}$ alkoxycarbonyl-C$_{1-5}$ alkyl, C$_{1-10}$ alkoxycarbonyl-C$_{2-6}$ alkenyl, mono- or di-C$_{1-10}$ alkylamino-C$_{1-5}$ alkyl, cyano-C$_{1-5}$ alkyl, halo-C$_{1-5}$ alkyl, —S(O)$_m$—CH$_3$, —NO$_2$, hydroxyl, hydroxy-C$_{1-5}$ alkyl, C$_{1-5}$ alkoxyl, substituted C$_{1-5}$ alkoxy in which the alkyl group of said alkyloxy substituent is substituted with a C$_{2-6}$ alkenyl group, substituted C$_{1-5}$ alkoxy in which the alkyl group of said alkyloxy substituent is substituted with a C$_{2-6}$ alkynyl group, C$_{3-6}$ cyloalkyl-C$_{1-5}$ alkoxy, trifluoromethoxy, carboxy, C$_{1-5}$ alkoxycarbonyl, C$_{1-5}$ alkylcarbonyl, —N(R$^{13}$)$_2$ and —NH—COR$^{14}$;

R$^7$ is selected from the group consisting of hydrogen, C$_{1-5}$ alkoxy, amino-C$_{2-5}$ alkoxy,-CO—R$^{16}$.

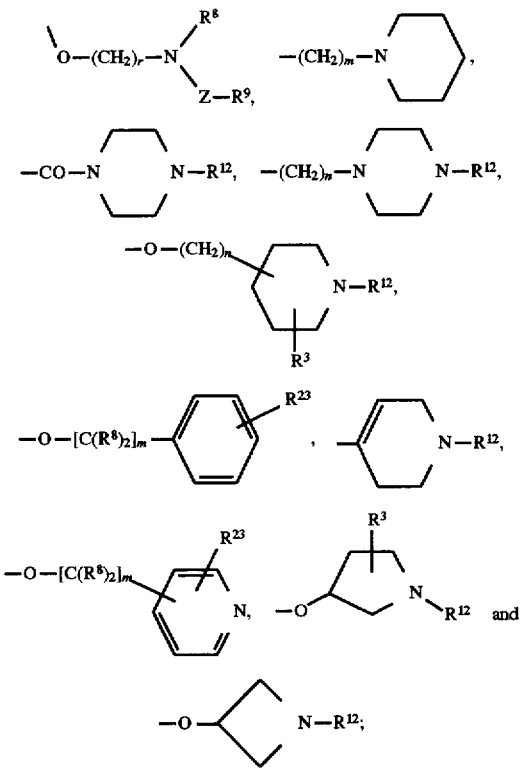

R$^9$ is selected from the group consisting of Het, —N(R$^8$)—(CH$_2$)$_q$—CO—R$^{14}$, C$_{1-5}$ alkoxyl, unsubstituted C$_{1-5}$ alkyl and substituted C$_{1-5}$ alkyl where said substitutent is selected from the group consisting of amino, C$_{1-10}$ alkoxycarbonylamino and Het;

R$^{10}$ is selected from the group consisting of hydroxyl, C$_{1-5}$ alkoxycarbonylamino, hydroxy-C$_{1-5}$ alkyl, amino and C$_{1-5}$ alkoxyl;

R$^{11}$ is selected from the group consisting of C$_{1-5}$ alkyl and unsubstituted phenyl;

R$^{12}$ is selected from the group consisting of hydrogen, C$_{1-10}$ alkyl, C$_{3-6}$ cycloalkyl-substituted C$_{1-5}$ alkyl, C$_{1-5}$ alkoxycarbonyl, C$_{1-5}$ alkylcarbonyl, tetrazolyl, cyano, 4-tetrahydropyranyl, 4-tetrahydrothiopyranyl, 2-pyrimidinyl optionally substituted with one to two members of the group consisting of halogen, carbamoyl, carboxyl, cyano, 5-tetrazolyl, aminothiocarbonyl, —C(NHR$^{18}$)=NR$^{17}$, amino-C$_{1-5}$-alkyl, and mono- or di- C$_{1-10}$-alkylamino-C$_{1-5}$-alkyl,

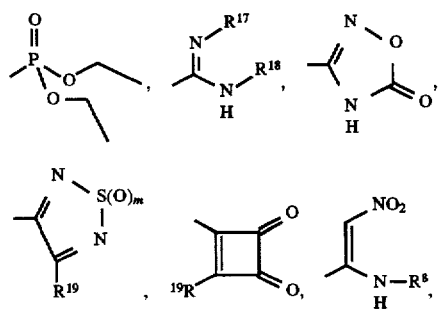

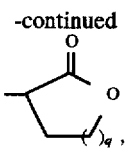

—$SO_2$—$R^{15}$, —CO—$R^{16}$, unsubstituted or substituted 2-pyridyl wherein said substituent on said pyridyl is selected from halogen, $C_{1-5}$ alkoxycarbonyl, carboxy, nitro or amino, and mono-substituted $C_{1-5}$ alkyl wherein the substituent on said alkyl is selected from the group consisting of $C_{1-10}$ alkoxycarbonyl, carboxy, cyano, methylsulfonyl, aminocarbonyl, imidazolyl, benzodioxanyl, quinolinyl, furyl, furopyridinyl, thienyl, 5-halo-2-thienyl, 3,5-dimethyl-4-isoxazolyl, pyrazinyl, $C_{1-5}$ alkyl-substituted pyrazinyl, thiazolyl, $C_{1-5}$ alkyl-substituted thiazolyl, oxadiazolyl, phenyl-substituted oxadiazolyl, chlorophenyl-substituted thiazolyl, benzimidazolyl, uracil, unsubstituted, mono-, or disubstituted pyridyl in which said substituents on said pyridyl are independently selected from hydrogen, halogen, $C_{1-10}$ alkoxyl, $C_{1-10}$ alkyl, amino-$C_{1-5}$ alkyl, mono- or di-$C_{1-5}$ alkylamino-$C_{1-5}$ alkyl, $C_{1-10}$ alkyl-carbonyl, $C_{1-10}$ alkoxycarbonyl, carboxy, hydroxy, hydroxy-$C_{1-5}$ alkyl, $C_{1-5}$ alkoxy-$C_{1-5}$ alkyl or amino, mono-, or disubstituted pyridyl-N-oxide in which said substituents on said pyridyl-N-oxide are independently selected from hydrogen, halogen, $C_{1-10}$ alkoxyl, $C_{1-10}$ alkyl, amino-$C_{1-5}$ alkyl, mono- or di-$C_{1-5}$ alkyl-amino-$C_{1-5}$ alkyl, $C_{1-10}$ alkylcarbonyl, $C_{1-10}$ alkoxycarbonyl, carboxy, hydroxy, hydroxy-$C_{1-5}$ alkyl, $C_{1-5}$ alkoxy-$C_{1-5}$ alkyl or amino, and unsubstituted, mono- or di-substituted phenyl wherein said substituents on said phenyl are independently selected from halogen, hydroxy, $C_{1-10}$ alkoxy, $C_{1-10}$ alkoxycarbonyl, cyano or carboxy;

$R^{13}$ is selected from hydrogen or $C_{1-5}$ alkylsulfonyl;

$R^{14}$ is selected from the group consisting of $C_{1-5}$ alkyl, $C_{1-5}$ alkoxy, amino-$C_{1-5}$ alkyl and benzimidazolyl;

$R^{15}$ is selected from the group consisting of amino, $C_{1-10}$ alkoxy-carbonylamino, unsubstituted or 1-substituted piperidinyl in which said substituent on said piperidinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, unsubstituted or 1-substituted 3-pyrrolidinyl in which said substituent on said pyrrolidinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, unsubstituted or 4-substituted 1-piperazinyl in which said substituent on said piperazinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkyl-pyridylmethyl, 1-($C_{3-6}$ cycloalkyl)-4-piperazinyl, mono- or di-$C_{1-10}$ alkylamino-$C_{2-10}$ alkylamino, vinyl, unsubstituted or substituted phenyl wherein said substitutent on said phenyl is selected from $C_{1-5}$ alkyl, nitro, amino or $C_{1-10}$ alkoxycarbonyl, and unsubstituted or substituted $C_{1-10}$ alkyl wherein said substituent on said alkyl is selected from the group consisting of halogen, $R^{20}$, carboxy, $C_{1-10}$ alkoxycarbonyl, azido, acetamidinyl, guanido, morpholino, pyrrolidinyl, piperidinyl, 2,2,6,6-tetramethyl-1-piperidinyl, 3-hydroxy-1-pyrrolidinyl, $C_{1-5}$ alkoxy-$C_{1-5}$ alkyl-substituted 1-pyrrolidinyl, 3-($C_{1-5}$ alkoxy)-1-pyrrolidinyl, -($C_{1-5}$ alkoxy-$C_{2-5}$ alkyl)-1-piperazinyl, 1-($C_{1-10}$ alkyl)-4piperazinyl, N-tetrahydroisoquinolinyl, aza-cycloheptyl, mono- or di-substituted 1-piperidinyl wherein said substitutents on said piperidinyl are independently selected from $C_{1-5}$ alkyl, hydroxyl, $C_{1-5}$ alkoxyl, cyano, phenyl, 1-piperidinyl, spiro-cyclopropyl or spiro-cyclopentyl, $C_{3-8}$ cycloalkyl wherein said cycloalkyl is optionally substituted with nitro, amino, mono- or di-$C_{1-5}$ alkylamino, $R^{20}$, 1-pyrrolidinyl, or 1-piperidinyl, and unsubstituted, mono- or di-substituted amino wherein said substituents on said amino are independently selected from benzyl, $C_{1-10}$ alkyl, hydroxy-$C_{2-10}$ alkyl, $C_{1-10}$ alkoxy-$C_{2-10}$ alkyl, $C_{3-8}$ cycloalkyl, $C_{1-5}$ alkoxycarbonyl-$C_{1-10}$ alkyl, carboxy-$C_{1-10}$ alkyl or $C_3$-6 cycloalkyl-substituted $C_{1-10}$ alkyl;

$R^{16}$ is selected from the group consisting of hydrogen, unsubstituted or 1-substituted piperidinyl in which said substituent on said piperidinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, unsubstituted or 1-substituted 3-pyrrolidinyl in which said substituent on said pyrrolidinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, imidazolyl, $C_{1-10}$ alkoxy-carbonyl, carboxyl, 1-($C_{1-10}$ alkyl)-4-piperidinyl, phenylamino, vinyl, $C_{1-10}$ alkoxycarbonylamino, amino, guanidino, propargylamino, mono- or di-$C_{1-10}$ alkyl-amino-$C_{2-10}$ alkylamino, $C_{1-10}$ alkylamino, $C_{1-10}$ alkoxy-carbonyl-$C_{1-10}$ alkylamino, unsubstituted, mono- or di- substituted phenyl wherein said substituents on said phenyl are independently selected from $C_{1-10}$ alkoxycarbonyl, carboxyl, $C_{1-10}$ alkoxy, 1-($C_{1-10}$ alkoxycarbonyl)-4-piperidinyloxy or 4-piperidinyloxy, and mono- or di-substituted $C_{1-10}$ alkyl wherein said substituents on said alkyl are independently selected from halogen, $R^{20}$, azido, guanido, acetamidinyl, $C_{1-10}$ alkoxy-carbonyl, carboxy, carboxymethoxy, carboxy-$C_{1-10}$ alkylcyclopentyl, $C_{1-10}$ alkoxycarbonylamino, amino, cyano, methylsulfonyl, imidazolyl, morpholinyl, azetidinyl, pyrrolidinyl, piperidinyl, 2,2,6,6-tetramethyl-1-piperidinyl, 3-hydroxy-1-pyrrolidinyl, $C_{1-5}$ alkoxy-$C_{1-5}$ alkyl-substituted 1-pyrrolidinyl, 1-($C_{1-10}$ alkyl)-4-piperazinyl, N-tetrahydroisoquinolinyl, aza-cycloheptyl, mono- or di-substituted 1-piperidinyl wherein said substitutents on said piperidinyl are independently selected from $C_{1-5}$ alkyl, hydroxyl, $C_{1-5}$ alkoxyl, cyano, or spiro-cyclopentyl, $C_{3-8}$ cycloalkyl wherein said cycloalkyl is optionally substituted with nitro, amino, mono- or di-$C_{1-5}$ alkylamino, $R^{20}$, 1-pyrrolidinyl, or 1-piperidinyl, tinsubstituted, mono- or di-substituted amino wherein said substituents on said amino are independently selected from benzyl, $C_{1-10}$ alkyl, hydroxy-$C_{2-10}$ alkyl, $C_{1-10}$ alkoxy-$C_{2-10}$ alkyl, $C_{3-6}$ cycloalkyl, $C_{1-5}$ alkoxycarbonyl-$C_{1-10}$ alkyl, carboxy-$C_{1-10}$ alkyl or $C_{3-8}$ cycloalkyl-substituted $C_{1-10}$ alkyl, $C_{1-10}$ alkoxycarbonyl, carboxy, carboxy-methoxy, carboxy-$C_{1-10}$ alkylcyclopentyl, $C_{1-10}$ alkoxycarbonylamino, cyano, methylsulfonyl, imidazolyl, morpholinyl, azetidinyl, or 1-($C_{1-10}$ alkyl)-4-piperazinyl;

$R^{17}$ is selected from the group consisting of hydrogen, hydroxyl, cyano, $C_{1-10}$ alkylsulfonyl and trihalomethylcarbonyl;

$R^{18}$ is selected from the group consisting of hydrogen, $C_{1-10}$ alkyl and mono- or di-$C_{1-10}$ alkylamino-$C_{2-10}$ alkyl;

$R^{19}$ is selected from the group consisting of $C_{1-10}$ alkoxy, hydroxyl and mono- or di-$C_{1-10}$ alkylamino-$C_{2-10}$ alkylamino;

$R^{21}$ is hydrogen;

$R^{22}$ is $C_{1-5}$ alkyl; and

Het is selected from the group consisting of imidazolyl, piperidinyl, piperazinyl, $C_{1-5}$ alkoxycarbonyl-substituted piperazinyl and $C_{1-5}$ alkylcarbonyl-substituted piperidinyl.

3. The compound of claim 2, wherein

A represents a fused aromatic ring such that the bicyclic ring system containing the A ring is

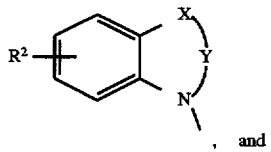
, and

B is a heterocyclic or heterobicyclic ring selected from the group consisting of

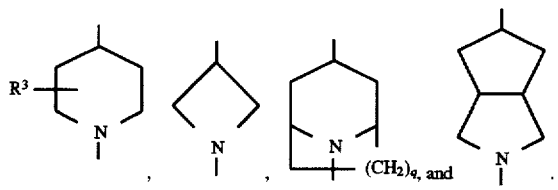

4. The compound of claim 3 of the formula

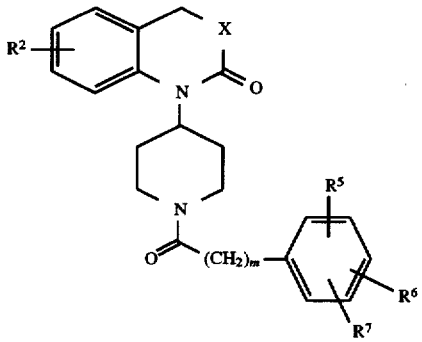

wherein

X is —CH$_2$— or —O—;

m is an integer from 0 to 1;

$R^2$ is selected from the group consisting of hydrogen, $C_{1-5}$ alkyl and halogen;

$R^5$ and $R^6$ are each independently selected from the group consisting of hydrogen, halogen, $C_{1-5}$ alkyl, hydroxyl and $C_{1-5}$ alkoxyl;

$R^7$ is selected from

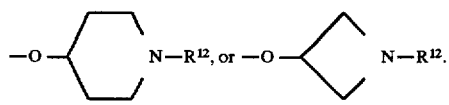

5. The compound of claim 4 of the formula

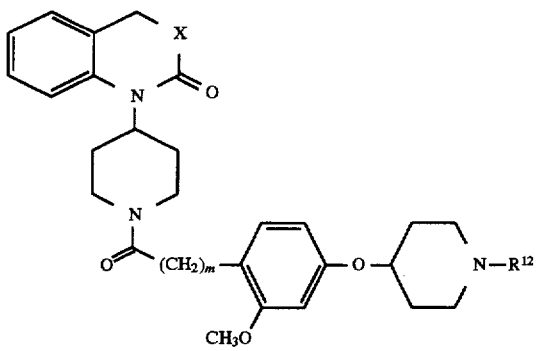

wherein

X is —CH$_2$— or —O—;

m is an integer from 0 to 1;

$R^{12}$ is hydrogen, unsubstituted $C_{1-10}$ alkyl, —SO$_2$—$R^{15}$ and substituted $C_{1-5}$ alkyl wherein the substituent on said alkyl is selected from the group consisting of hydroxyl, $C_{1-5}$ alkoxyl, imidazolyl, benzodioxanyl, quinolinyl, furyl, furopyridinyl, thienyl, 5-halo-2-thienyl, 3,5-dimethyl-4-isoxazolyl, pyrazinyl, $C_{1-5}$ alkyl-substituted pyrazinyl, thiazolyl, $C_{1-5}$ alkyl-substituted thiazolyl, oxadiazolyl, phenyl-substituted oxadiazolyl, pyrazinyl, pyrimidinyl, chlorophenyl-substituted thiazolyl, benzimidazolyl, uracil, unsubstituted, mono-, or disubstituted pyridyl in which said substituents on said pyridyl are independently selected from hydrogen, halogen, $C_{1-10}$ alkoxyl, $C_{1-10}$ alkyl, amino-$C_{1-5}$ alkyl, mono- or di-$C_{1-5}$ alkylamino-$C_{1-5}$ alkyl, $C_{1-10}$ alkylcarbonyl, $C_{1-10}$ alkoxycarbonyl, carboxy, amino, hydroxy, hydroxy-$C_{1-5}$ alkyl, or $C_{1-5}$ alkoxy-$C_{1-5}$ alkyl, mono-, or disubstituted pyridyl-N-oxide in which said substituents on said pyridyl-N-oxide are independently selected from hydrogen, halogen, $C_{1-10}$ alkoxyl, $C_{1-10}$ alkyl, amino —$C_{1-5}$ alkyl, mono- or di-$C_{1-5}$ alkylamino-$C_{1-5}$ alkyl, $C_{1-10}$ alkylcarbonyl, $C_{1-10}$ alkoxycarbonyl, carboxy, amino, hydroxy, hydroxy-$C_{1-5}$ alkyl, or $C_{1-5}$ alkoxy-$C_{1-5}$ alkyl, and unsubstituted, mono-, or di-substituted phenyl wherein said substituents on said phenyl are independently selected from halogen, cyano, $C_{1-10}$ alkoxy, hydroxy, $C_{1-10}$ alkoxycarbonyl or carboxy;

$R^{15}$ is selected from the group consisting of unsubstituted or 1-substituted 3-pyrrolidinyl in which said substituent on said pyrrolidinyl is selected from the group consisting of benzyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, unsubstituted or 4-substituted 1-piperazinyl in which said substituent on said piperazinyl is selected from the group consisting of benzyl, $C_{1-5}$ alkoxycarbonyl, $C_{1-5}$ alkyl, hydroxy-$C_{2-5}$ alkyl, $C_{1-5}$ alkoxy-$C_{2-5}$ alkyl, pyridylmethyl, or $C_{1-5}$ alkylpyridylmethyl, mono- or di- $C_{1-10}$ alkylamino-$C_{2-10}$ alkylamino, and substituted $C_{1-10}$ alkyl wherein said substituent on said alkyl is selected from the group consisting of $R^{20}$, carboxy, $C_{1-10}$ alkoxycarbonyl, guanido, acetamidinyl, morpholino, pyrrolidinyl, piperidinyl, 2,2,6,6-tetramethyl-1-piperidinyl, 3-hydroxy-1-pyrrolidinyl, $C_{1-5}$ alkoxy-$C_{1-5}$ alkyl-substituted 1-pyrrolidinyl, 3-($C_{1-5}$ alkoxy)-1-pyrrolidinyl, 4-($C_{1-5}$ alkoxy-$C_{2-5}$ alkyl)-1-piperazinyl, 1-($C_{1-10}$ alkyl)-4-piperazinyl, N-tetrahydroisoquinolinyl, aza-cycloheptyl, mono- or di-substituted 1-piperidinyl wherein said substitutents on said piperidinyl are independently selected from $C_{1-5}$ alkyl, hydroxyl, $C_{1-5}$ alkoxyl, cyano, phenyl, 1-piperidinyl, spiro-cyclopropyl or spiro-cyclopentyl, $C_{3-8}$ cycloalkyl wherein said cycloalkyl is substituted with amino, mono- or di- $C_{1-5}$ alkylamino, 1-pyrrolidinyl, 1-piperidinyl, or $R^{20}$, and unsubstituted, mono- or di-substituted amino wherein said substituents on said amino are independently selected from $C_{1-10}$ alkyl, hydroxy-$C_{2-10}$ alkyl, $C_{1-10}$ alkoxy-$C_{2-10}$ alkyl, $C_{3-8}$ cycloalkyl, $C_{1-5}$ alkoxycarbonyl-$C_{1-10}$ alkyl, carboxy-$C_{1-10}$ alkyl or $C_{3-6}$ cycloalkyl-substituted $C_{1-10}$ alkyl.

6. The compound of claim 5, selected from the group consisting of

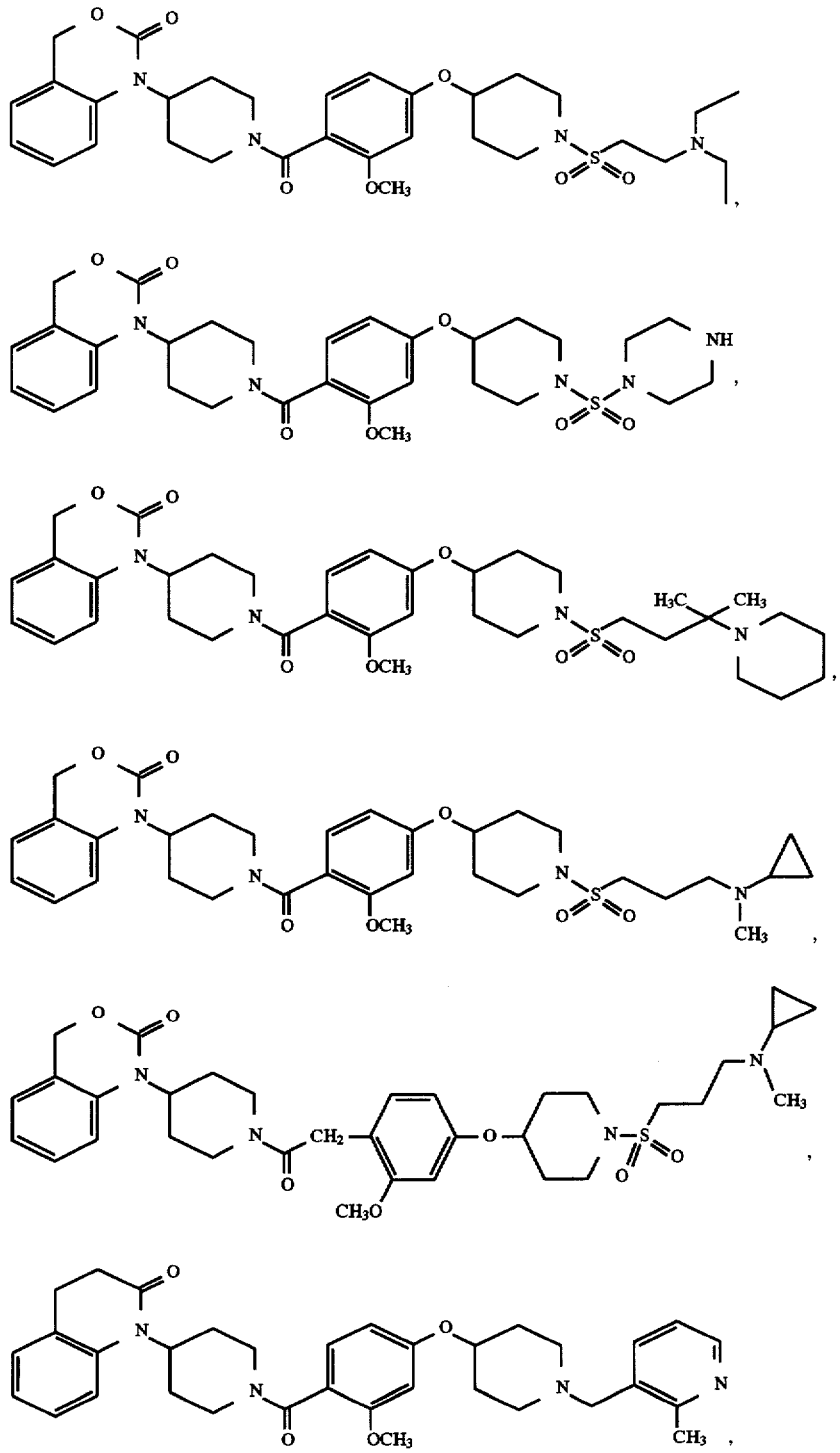

-continued

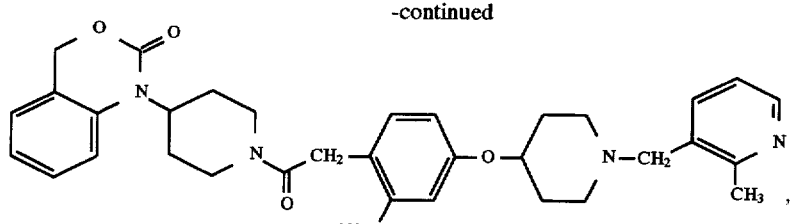

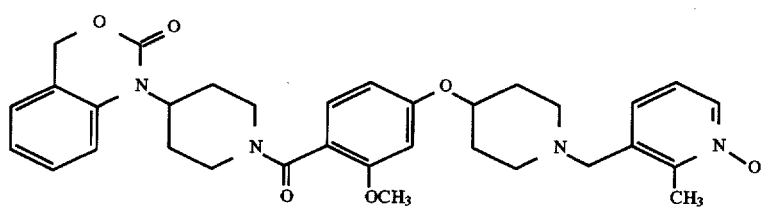

and

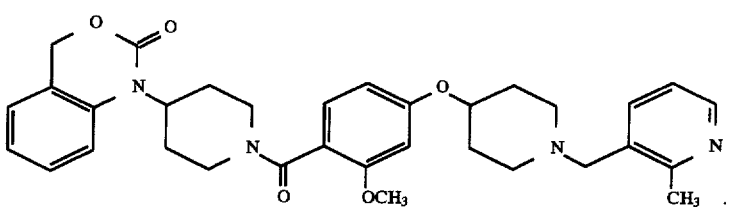

7. The compound of claim 6, selected from the group consisting of

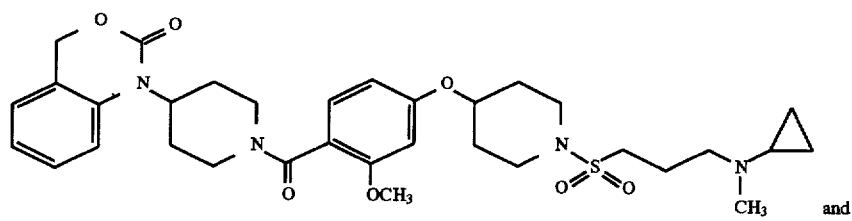

and

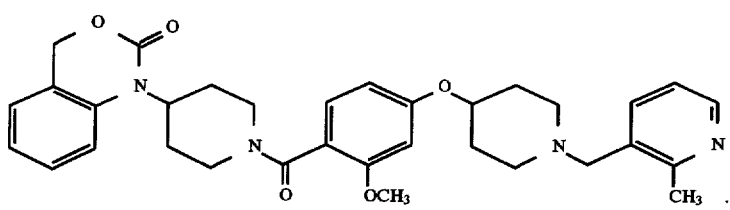

8. A pharmaceutically acceptable salt of the compound of claim 7 wherein the salt is selected from the group consisting of hydrochloride, tartrate and sulfate.

9. A pharmaceutical composition comprising a pharmaceutically acceptable carrier and a pharmacologically effective amount of the compound as claimed in claim 1 sufficient to prevent preterm labor in a mammal in need thereof.

10. A method of antagonizing oxytocin from binding to its receptor site in a mammal, comprising the step of administering to said mammal a pharmacologically effective amount of the compound as claimed in claim 1.

11. A method of preventing preterm labor in a mammal in need thereof, comprising the step of administering to said mammal a pharmacologically effective amount of the compound as claimed in claim 1.

12. A method of stopping labor preparatory to cesarian delivery in a mammal in need thereof, comprising the step of administering to said mammal a pharmacologically effective amount of the compound as claimed in claim 1.

13. A method of treating dysmenorrhea in a mammal in need thereof, comprising the step of administering to said mammal a pharmacologically effective amount of the compound as claimed in claim 1.

14. A method of antagonizing vasopressin from binding to its receptor site in a mammal, comprising the step of administering to said mammal a pharmacologically effective amount of the compound as claimed in claim 1.

15. A method of inducing vasodilation in a mammal in need thereof, comprising the step of administering to said mammal a pharmacologically effective amount of the compound as claimed in claim 1.

16. A method of treating hypertension in a mammal in need thereof, comprising the step of administering to said mammal a pharmacologically effective amount of the compound as claimed in claim 1.

17. A method of inducing diuresis in a mammal in need thereof, comprising the step of administering to said mammal a pharmacologically effective amount of the compound as claimed in claim 1.

18. A method of inhibiting platelet agglutination in a mammal in need thereof, comprising the step of administering to said mammal a pharmacologically effective amount of the compound as claimed in claim 1.

19. A method of improving fertility rates in a farm animal, comprising the step of administering to the farm animal a pharmacologically effective amount of the compound as claimed in claim 1.

20. A compound of the formula

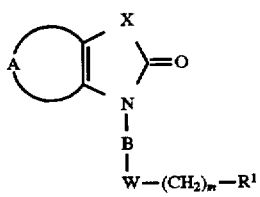

wherein

X is selected from the group consisting of $CH_2$—O, —$C(R^8)_2$—O—, —$CH(R^{14})$—O—, —$CH_2$—NH—, —$CH_2$—$NR^8$—, —O—$CH_2$—, —$C(R^8)$=N—, —N=C($R^8$)—, —NH—$CH_2$—, —$NR^8$—$CH_2$—, —C(OH)=CH—, —$CH(CF_3)$—O—, —S—$CH_2$—, —S(O)—$CH_2$—, and —$S(O)_2$—$CH_2$—;

"A" represents an aromatic or heteroaromatic ring such that the bicyclic ring system containing the A ring is selected from the group consisting of

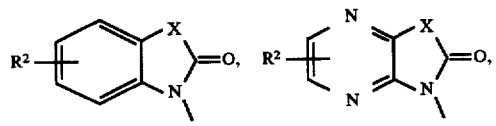

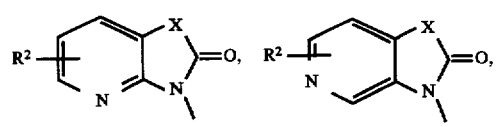

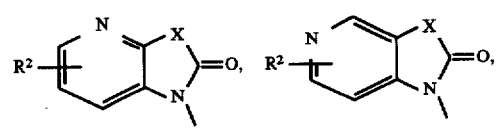

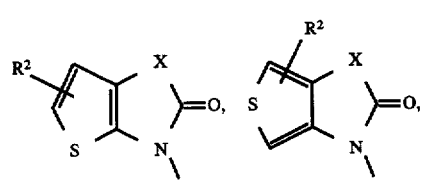

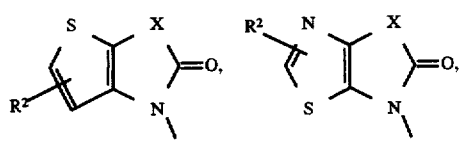

-continued

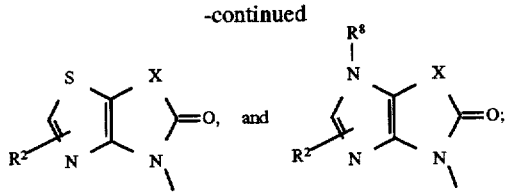

B is a heterocyclic or heterobicyclic ring selected from the group consisting of

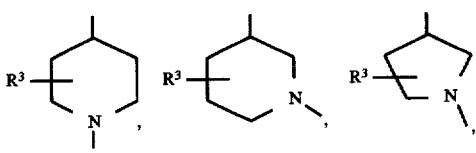

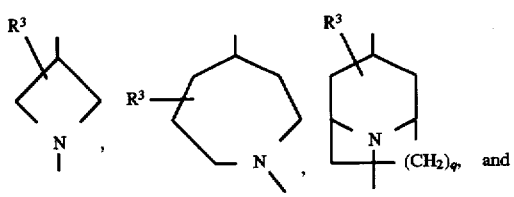

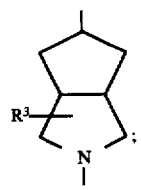

W is —CO—, —COO—, —$CONR^8$—, —C(=$NR^8$)—, —C(=$NCH_2Ph$)—, or —$SO_2$—;

$R^1$ is selected from the group consisting of camphor-10-yl, lower alkoxyl, styryl, furyl, thienyl, pyrrolyl, naphthyl, indolyl, tetrahydronaphthyl, pyridyl, quinolinyl, unsubstituted or substituted cyclohexyl where said substituent is $R^4$, and unsubstituted or substituted phenyl where said substituents are one or more of $R^5$, $R^6$ or $R^7$;

$R^2$ is selected from the group consisting of hydrogen, hydroxy, lower alkoxy, lower alkyl, nitro, methanesulfonylamino, trifluoromethyl, and halogen;

$R^3$ is selected from the group consisting of hydrogen, lower alkyl, hydroxyalkyl, methylthioalkyl, methylsulfonylalkyl, methylsulfonyl, cyano, carbamoyl, —$(CH_2)_n$—$CO_2H$, —$(CH_2)_p$—$R^{10}$, and —$(CH_2)_p$—$COR^{10}$;

$R^4$ is selected from the group consisting of hydrogen, keto, hydroxyl and lower alkoxy.

$R^5$ and $R^6$ are independently selected from the group consisting of hydrogen, lower alkyl, lower alkoxy, trifluoromethoxy, 2,2,2-trifluoroethoxy, allyloxy, propargyloxy, trifluoromethyl, cycloalkyloxy, cylopropylmethoxy, hydroxy, hydroxyalkyl, cyano, nitro, amino, halogen, —$(CH_2)_n$—CO—$R^{10}$, —$O(CH_2)_n$—CO—$R^{10}$, —$(CH_2)_n$—$R^{10}$, —$OCH_2(CH_2)_q$—$R^{10}$, —$OCH_2(CH_2)_q$—$N(R^8)$—Z—$R^{11}$ and —$(CH_2)_n$—N ($R^8$)—Z—$R^{11}$;

$R^7$ is selected from the group consisting of hydrogen, lower alkyl, halogenated lower alkyl, phenyl, phenyl lower alkyl, amino lower alkoxy, lower alkoxy, carboxyl, carboxy lower alkyl, lower alkoxycarbonyl, halogen, hydroxyl,

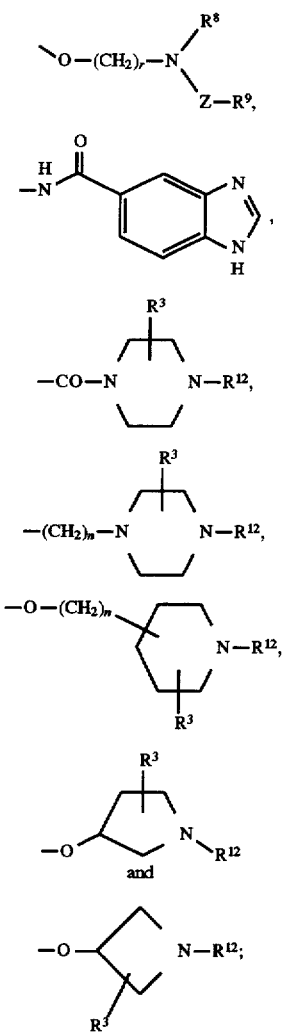

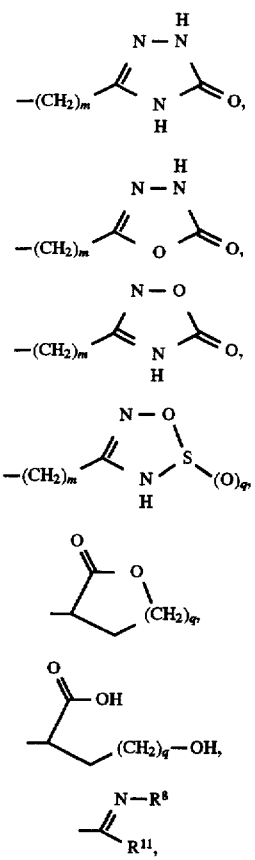

and substituted alkyl wherein the substituent is selected from the group consisting of hydroxy, alkoxy, alkoxycarbonyl, carboxy, —SO$_2$NH$_2$, amino, —N(R$^8$)$_2$, —NHR$^8$, 1-piperazinyl, 4-methyl-1-piperazinyl, pyridinyl, quinolinyl, 4-morpholinyl, 1-pyrrolidinyl, imidazolyl, 4-piperidinyl, 1-methyl-4-piperidinyl, 1-piperidinyl, 5-tetrazolyl, and phenyl optionally substituted with one to three members from the group consisting of halogen, lower alkoxy, alkylenedioxy, lower alkyl, alkoxycarbonyl, carboxy, trifluoromethyl, SO$_2$CH$_3$, and SO$_2$NH$_2$;

R$^8$ is selected from the group consisting of hydrogen and lower alkyl;

R$^9$ is selected from the group consisting of Het, lower alkoxyl, unsubstituted lower alkyl and substituted lower alkyl where said substitutent is selected from the group consisting of carboxyl, hydroxyl, amino, amino lower alkyl, —N(R$^8$)$_2$, —NHR$^8$, alkoxycarbonylamino, alkoxycarbonylamino lower alkyl and Het;

R$^{10}$ is hydroxy, lower alkoxy, amino, —N(R$^8$)$_2$, —NHR$^8$, 1-piperazinyl, 4-methyl-1-piperazinyl, pyridinyl, 4-morpholinyl, 1-pyrrolidinyl and 1-piperidinyl;

R$^{11}$ is lower alkyl and phenyl;

R$^{12}$ is selected from the group consisting of hydrogen, lower alkoxycarbonyl, lower alkylcarbonyl, lower alkyl, allyl, 5-tetrazolyl, 2-pyrimidinyl, 2-pyrazinyl, 2-pyridyl, 4-pyridyl, 4-piperidinyl, 1-methyl-4-piperidinyl, 4-tetrahydropyranyl, —CO—NH—COR$^{15}$, —CO—NH—SO$_2$R$^{15}$, —SO$_2$—NH—COR$^{15}$, Z—R$^{13}$, R$^{13}$ is selected from the group consisting of alkyl, alkoxy, amino, carboxy, phenyl, vinyl, morpholinyl, piperidinyl, pyrrolidinyl, pyridinyl, piperazinyl, 1-methyl-4-piperazinyl, 1-alkoxycarbonyl-4-piperidinyl, —NCR$^8$)—(CH$_2$)$_r$—R$^{10}$, substituted phenyl wherein the substituent is selected from the group consisting of nitro, alkoxy, amino, monoalkylamino, dialkylamino, halogen, 1-piperazinyl, 4-piperidinyloxy, 4-methyl-1-piperazinyl, alkoxycarbonyl, carboxy, aminoalkyl, monoalkylaminoalkyl, dialkylaminoalkyl, 4-morpholinylalkyl, 1-piperazinylalkyl, and 4-methyl-1-piperazinylalkyl; and substituted lower alkyl wherein the substituent is selected from the group consisting of phenyl, hydroxy, alkoxy, alkoxycarbonyl, carboxy, halogen, amino, —N(R$^8$)$_2$, —NHR$^8$, 1-piperazinyl, 1-methyl-4-piperazinyl, pyridinyl, 4-morpholinyl, pyrrolidinyl, imidazolyl, 5-tetrazolyl, azetidinyl, piperidinyl, and substituted phenyl wherein the substituent is selected from the group consisting of nitro, alkoxy, amino, monoalkylamino, dialkylamino, halogen, l-piperazinyl, 4-piperidinyloxy, 4-methyl-1-piperazinyl, alkoxycarbonyl, carboxy, aminoalkyl, monoalkylaminoalkyl, dialkylaminoalkyl, 4-morpholinylalkyl, 1-piperazinylalkyl, and 4-methyl-1-piperazinylalkyl;

$R^{14}$ is selected from the group consisting of trifluoromethyl and phenyl optionally substituted with one to three members of the group consisting of lower alkyl, alkoxy, halogen, and trifluoromethyl;

$R^{15}$ is selected from the group consisting of alkyl, trifluoromethyl and phenyl optionally substituted with one to three members of the group consisting of lower alkyl, alkoxy, halogen, and trifluoromethyl;

Het is selected from the group consisting of imidazolyl, piperidinyl, lower alkyl substituted piperidinyl, piperazinyl, lower alkyl substituted piperizinyl, morpholinyl, tetrazolyl, lower alkylcarbonyl piperidinyl, lower alkoxycarbonyl piperidinyl, pyrrolidinyl, lower alkyl substituted pyrrolidinyl, and pyridinyl;

Z is —CO— or —SO$_2$—;

m is an integer of from 0 to 1;

n is an integer of from 0 to 3;

p is an integer of from 1 to 3;

q is an integer from 1 to 2; and r is an integer of from 2 to 4;

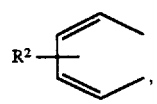

with the proviso that when A is and when B is

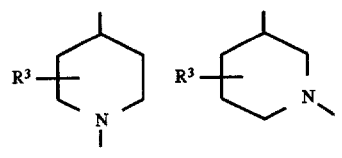

and when W is —CO—, and when $R^1$ is phenyl, and when m is 0 and when X is —(CH$_2$)$_2$— or —CH=CH—, then $R^7$ cannot be

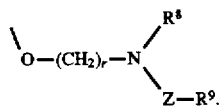

* * * * *